US007923602B2

(12) United States Patent
Carozzi et al.

(10) Patent No.: US 7,923,602 B2
(45) Date of Patent: Apr. 12, 2011

(54) AXMI-031, AXMI-039, AXMI-040 AND AXMI-049, A FAMILY OF NOVEL DELTA ENDOTOXIN GENES AND METHODS FOR THEIR USE

(75) Inventors: Nadine Carozzi, Raleigh, NC (US); Nicholas Duck, Apex, NC (US); Theodore Kahn, Apex, NC (US); Nalini Desai, Chapel Hill, NC (US)

(73) Assignee: Athenix Corp., Morrisville, NC (US)

( * ) Notice: Subject to any disclaimer, the term of this patent is extended or adjusted under 35 U.S.C. 154(b) by 340 days.

(21) Appl. No.: 11/762,886

(22) Filed: Jun. 14, 2007

(65) Prior Publication Data

US 2007/0294787 A1    Dec. 20, 2007

Related U.S. Application Data

(60) Provisional application No. 60/813,774, filed on Jun. 14, 2006.

(51) Int. Cl.
*A01H 5/00* (2006.01)
*A01H 5/10* (2006.01)
*C12N 15/82* (2006.01)
*C12N 15/32* (2006.01)
*C12N 1/21* (2006.01)

(52) U.S. Cl. .................. 800/302; 536/23.71; 435/320.1; 435/252.3; 435/418; 424/93.2; 800/279

(58) Field of Classification Search .......................... None
See application file for complete search history.

(56) References Cited

U.S. PATENT DOCUMENTS

| 5,281,530 | A | * | 1/1994 | Sick et al. ................. 435/252.3 |
| 5,589,382 | A | | 12/1996 | Payne et al. |
| 5,959,080 | A | * | 9/1999 | Payne et al. ................. 530/350 |
| 6,166,195 | A | | 12/2000 | Schnepf et al. |
| 6,632,792 | B2 | | 10/2003 | Schnepf et al. |

FOREIGN PATENT DOCUMENTS

WO    WO 2005/021585 A1    3/2005
WO    WO 2005/038032 A2    4/2005

OTHER PUBLICATIONS de Maagd et al, 1999, Appl. Environ. Microbiol. 65:4369-4374.*
Tounsi et al, 2003, J. Appl. Microbiol. 95:23-28.*
Aaronson et al (2001, FEMS Microbiol. Lett. 195:1-8.*
De Maagd et al (2001, Trends Genet. 17:193-199).*
Guo et al (2004, Proc. Natl. Acad. Sci. USA 101: 9205-9210).*
Atkinson et al, 2003, Annu. Rev. Phytopathol. 41:615-639.*
Wei, J-Z et al., "Bacillus thuringiensis Crystal Proteins that Target Nematodes," *PNAS*, Mar. 4, 2003, pp. 2760-2765, vol. 100, No. 5.
Li, X-Q., et al., "Resistance to Root-knot Nematode in Tomato Roots Expressing a Nematicidal *Bacillus thuringiensis* Crystal Protein," *Plant Biotechnology Journal*, 2007, pp. 455-464, vol. 9.
NCBI Database Report for Accession No. BAC6484, direct submission on Jul. 19, 2002.
NCBI Database Report for Accession No. Q45710, submitted on Mar. 15, 2005.
NCBI Database Report for Accession No. Q45712, submitted on Mar. 15, 2005.

* cited by examiner

*Primary Examiner* — Anne Kubelik
(74) *Attorney, Agent, or Firm* — Destiny M. Davenport

(57) ABSTRACT

Compositions and methods for conferring pesticidal activity to bacteria, plants, plant cells, tissues and seeds are provided. Compositions comprising a coding sequence for a delta-endotoxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated delta-endotoxin nucleic acid molecules are provided. Additionally, amino acid sequences corresponding to the polynucleotides are encompassed, and antibodies specifically binding to those amino acid sequences. In particular, the present invention provides for isolated nucleic acid molecules comprising nucleotide sequences encoding the amino acid sequence shown in SEQ ID NO:2, 4, 6, 8, 10, 12, 15, 17, 19, 21, 23, 25, 27, 29, 31, 33, 35, or 38, or the nucleotide sequence set forth in SEQ ID NO: 1, 3, 5, 7, 9, 11, 14, 16, 18, 20, 22, 24, 26, 28, 30, 32, 34, or 37, as well as variants and fragments thereof.

14 Claims, No Drawings

AXMI-031, AXMI-039, AXMI-040 AND AXMI-049, A FAMILY OF NOVEL DELTA ENDOTOXIN GENES AND METHODS FOR THEIR USE

CROSS REFERENCE TO RELATED APPLICATION

This application claims the benefit of U.S. Provisional Application Ser. No. 60/813,774, filed Jun. 14, 2006, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "329212_SequenceListing.txt", created on Jun. 12, 2007, and having a size of 347 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against *Hymenoptera, Homoptera, Phthiraptera, Mallophaga*, and *Acari* pest orders, as well as other invertebrate orders such as *Nemathelminthes, Platyhelminthes*, and *Sarcomastigorphora* (Feitelson (1993) The Bacillus Thuringiensis family tree. In *Advanced Engineered Pesticides*, Marcel Dekker, Inc., New York, N.Y.) These proteins were originally classified as CryI to CryV based primarily on their insecticidal activity. The major classes were *Lepidoptera*-specific (I), *Lepidoptera*- and *Diptera*-specific (TI), *Coleoptera*-specific (III), *Diptera*-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer there is a continual need to discover new forms of *Bacillus thuringiensis* delta-endotoxins.

SUMMARY OF INVENTION

Compositions and methods for conferring pest resistance to bacteria, plants, plant cells, tissues and seeds are provided. Compositions include nucleic acid molecules encoding sequences for delta-endotoxin polypeptides, vectors comprising those nucleic acid molecules, and host cells comprising the vectors. Compositions also include the polypeptide sequences of the endotoxin, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules corresponding to delta-endotoxin nucleic acid sequences are provided. Additionally, amino acid sequences corresponding to the polynucleotides are encompassed. In particular, the present invention provides for an isolated nucleic acid molecule comprising a nucleotide sequence encoding the amino acid sequence shown in SEQ ID NO:2, 4, 6, 8, 10, 12, 15, 17, 19, 21, 23, 25, 27, 29, 31, 33, 35, or 38, a nucleotide sequence set forth in SEQ ID NO:1, 3, 5, 7, 9, 11, 14, 16, 18, 20, 22, 24, 26, 28, 30, 32, 34, or 37, or the delta-endotoxin nucleotide sequences deposited in bacterial hosts as Accession Nos. B-30935, B-30936, B-30937, and B-50046, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran or coleopteran pest. Methods and kits for detecting the nucleic acids and polypeptides of the invention in a sample are also included.

Methods for controlling or killing a nematode pest population are further provided. The methods comprise introducing into a plant a polynucleotide encoding a nematode-active polypeptide with a molecular size greater than 22 kDa. These nematode-active polypeptides are useful for controlling or killing plant-parasitic nematodes, particularly cyst nematodes.

The compositions and methods of the invention are useful for the production of organisms with pesticide resistance, specifically bacteria and plants. These organisms and compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

DETAILED DESCRIPTION

The present invention is drawn to compositions and methods for regulating pest resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered pesticidal proteins by methods known in the art, such as domain swapping or DNA shuffling. The proteins find use in controlling or killing lepidopteran, coleopteran, and nematode pest populations, and for producing compositions with pesticidal activity.

Plasmids containing the nucleotide sequences of the invention were deposited in the permanent collection of the Agricultural Research Service Culture Collection, Northern Regional Research Laboratory (NRRL), 1815 North University Street, Peoria, Ill. 61604, United States of America, on Jun. 9, 2006, and assigned Accession Nos. NRRL B-30935 (for axmi-031), NRRL B-30936 (for axmi-039), and NRRL B-30937 (for axmi-040); and on May 29, 2007 and assigned NRRL B-50046 (axmi-049). These deposits will be maintained under the terms of the Budapest Treaty on the International Recognition of the Deposit of Microorganisms for the Purposes of Patent Procedure. Access to this deposit will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposit with the NRRL. These deposits were made merely as a convenience for those of skill in the art and are not an admission that a deposit is required under 35 U.S.C. §112.

By "delta-endotoxin" is intended a toxin from *Bacillus thuringiensis* that has toxic activity against one or more pests, including, but not limited to, members of the *Lepidoptera, Diptera*, and *Coleoptera* orders or members of the *Nematoda* phylum, or a protein that has homology to such a protein. In some cases, delta-endotoxin proteins have been isolated from other organisms, including *Clostridium bifermentans* and *Paenibacillus popilliae*. Delta-endotoxin proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Provided herein are novel isolated nucleotide sequences that confer pesticidal activity. Also provided are the amino acid sequences of the delta-endotoxin proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:1, 3, 5, 34, and 37, the delta endotoxin nucleotide sequences deposited in bacterial hosts as Accession Nos. NRRL B-30935, B-30936, B-30937, and B-50046, and variants, fragments, and complements thereof (for example, SEQ ID NO:7, 9, 11, 14, 16, 18, 20, 22, 24, 26, 28, 30, and 32). By "complement" is intended a nucleotide sequence that is sufficiently complementary to a given nucleotide sequence such that it can hybridize to the given nucleotide sequence to thereby form a stable duplex. The corresponding amino acid sequence for the delta-endotoxin protein encoded by this nucleotide sequence are set forth in SEQ ID NO:2, 4, 6, 8, 10, 12, 14, 16, 18, 20, 22, 24, 26, 28, 30, 32, 34, and 37.

Nucleic acid molecules that are fragments of these delta-endotoxin encoding nucleotide sequences are also encompassed by the present invention (for example, SEQ ID NO:9, 11, 14, 18, 20, 22, and 24). By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 50, 100, 200, 300, 400, 500, 600, 700, 800, 900, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350 contiguous nucleotides, or up to the number of nucleotides present in a full-length delta-endotoxin encoding nucleotide sequence disclosed herein (for example, 3558 nucleotides for SEQ ID NO:1, 3984 nucleotides for SEQ ID NO:3, 3720 nucleotides for SEQ ID NO:5, and 3669 nucleotides for SEQ ID NO:34) depending upon the intended use. By "contiguous" nucleotides is intended nucleotide residues that are immediately adjacent to one another. Fragments of the nucleotide sequences of the present invention will encode protein fragments that retain the biological activity of the delta-endotoxin protein and, hence, retain pesticidal activity. By "retains activity" is intended that the fragment will have at least about 30%, at least about 50%, at least about 70%, 80%, 90%, 95% or higher of the pesticidal activity of the delta-endotoxin protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, 600, 650, 700, 750, 800, 850, 900, 950, 1000, 1050, 1100 contiguous amino acids, or up to the total number of amino acids present in a full-length delta-endotoxin protein of the invention (for example, 1185 amino acids for SEQ ID NO:2, 1327 amino acids for SEQ ID NO:4, 1239 amino acids for SEQ ID NO:6, and 1223 amino acids for SEQ ID NO:35).

Preferred delta-endotoxin proteins of the present invention are encoded by a nucleotide sequence sufficiently identical to the nucleotide sequence of SEQ ID NO:1, 3, 5, 7, 9, 11, 14, 16, 18, 20, 22, 24, 26, 28, 30, 32, 34, or 37. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to delta-endotoxin-like nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules (for example, SEQ ID NO:7, 9, 11, 16, 18, 22, 24, 26, 28, 30, and 32). "Variants" of the delta-endotoxin encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J of Economic Entomology* 78:290-293; and U.S. Pat. No. 5,743, 477, all of which are herein incorporated by reference in their entirety.

The skilled artisan will further appreciate that changes can be introduced by mutation of the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of the amino acid sequences of the present invention and known delta-endotoxin sequences. Examples of residues that are conserved but that may allow conservative amino acid substitutions and still retain activity include, for example, residues that have only conservative substitutions between all proteins contained in an alignment of the amino acid sequences of the present invention and known delta-endotoxin sequences. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer delta-endotoxin activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook and Russell (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, N.Y.).

In a hybridization method, all or part of the delta-endotoxin nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known delta-endotoxin-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of delta-endotoxin encoding nucleotide sequence of the invention or a fragment or variant thereof. Methods for the preparation of probes for hybridization are generally known in the art and are disclosed in Sambrook and Russell, 2001, supra herein incorporated by reference.

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the Tm can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NO:2, 4, 6, 8, 10, 12, 15, 17, 19, 21, 23, 25, 27, 29, 31, 33, 35, or 38. Fragments, biologically active portions, and variants thereof are also provided, and may be used to practice the methods of the present invention.

"Fragments" or "biologically active portions" include polypeptide fragments comprising amino acid sequences sufficiently identical to the amino acid sequence set forth in SEQ ID NO:2, 4, 6, 8, 10, 12, 16, 17, 19, 21, 23, 25, 27, 29, 31, 33, 35, or 38 and that exhibit pesticidal activity (for example, SEQ ID NO:15, 19, 21, 23, or 25). A biologically active portion of a delta-endotoxin protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2, 4, 6, 8, 10, 12, 15, 17, 19, 21, 23, 25, 27, 29, 31, 33, 35, or 38. The invention encompasses other fragments, however, such as any fragment in the protein greater than about 10, 20, 30, 50, 100, 150, 200, 250, 300, 350, 400, 400, 450, 500, 550, 600, 650, 700, 750, 800, 850, 900, 950, 1000, 1050, 1100, 1150, 1200, 1250, or 1300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO:2, 4, 6, 8, 10, 12, 16, 17, 19, 21, 23, 25, 27, 29, 31, 33, 35, or 38 (e.g., SEQ ID NO:10, 12, 17, 19, 23, 25, 27, 29, 31, or 33). Variants also include polypeptides encoded by a nucleic acid molecule that hybridizes to the nucleic acid molecule of SEQ ID NO:1, 3, 5, 7, 9, 11, 14, 16, 18, 20, 22, 24, 26, 28, 30, 32, 34, or 37, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi-031, axmi-039, axmi-040, and axmi-049 genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. These delta-endotoxin proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a delta-endotoxin may be altered by various methods, and that these alterations may result in DNA sequences encoding proteins with amino acid sequences different than that encoded by a delta-endotoxin of the present invention. This protein may be altered in various ways including amino acid substitutions, deletions, truncations, and insertions of one or more amino acids of SEQ ID NO:2, 4, 6, 8, 10, 12, 15, 17, 19, 21, 23, 25, 27, 29, 31, 33, 35, or 38,including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of a delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a delta-endotoxin to confer pesticidal activity may be improved by the use of such techniques upon the compositions of this invention. For example, one may express a delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem*.265:20923-20930; Rang et al. 91999) *Appl. Environ. Microbiol.* 65:2918-2925).

Vectors

A delta-endotoxin sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" (i.e., SEQ ID NO:9, 11, 28, 30, and 32) to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence (i.e., SEQ ID NO:10, 12, 29, 31, and 33) sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-45 1). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe etal. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the delta-endotoxin is targeted to the chloroplast for expression. In this manner, where the delta-endotoxin is not directly inserted into the chloroplast, the expression cassette will additionally contain a nucleic acid encoding a transit peptide to direct the delta-endotoxin to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196: 1414-1421; and Shah et al. (1986) *Science* 233:478-481.

The delta-endotoxin gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The delta-endotoxin gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the delta-endotoxin are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of Agrobacterium strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Led1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or Agrobacterium vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the delta-endotoxin is then tested by hybridizing the filter to a radioactive probe derived from a delta-endotoxin, by methods known in the art (Sambrook and Russell, 2001, supra).

Western blot, biochemical assays and the like may be carried out on the transgenic plants to confirm the presence of protein encoded by the delta-endotoxin gene by standard procedures (Sambrook and Russell, 2001, supra) using antibodies that bind to one or more epitopes present on the delta-endotoxin protein.

Pesticidal Activity in Plants

In another aspect of the invention, one may generate transgenic plants expressing a delta-endotoxin that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a delta-endotoxin may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pest Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a delta-endotoxin gene into a cellular host. Expression of the delta-endotoxin gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

Nematode Control

Plant-parasitic nematodes, including cyst nematodes, root knot nematodes, and other nematodes, cause billions of dollars in damage to crops every year. Plant-parasitic nematodes pierce plant cell walls with their stylet, which is formed by some of the mouth and esophagus parts, and pump up the plant cell just into their digestive system. Numerous publications in the art conclude that sedentary plant parasitic nematodes do not ingest molecules larger than about 23-28 kDa in vivo. This has led to the widespread belief that the feeding tube produced by these nematodes acts as a molecular sieve, restricting the size of molecules that can be ingested. Böckenhoff and Grundler ((1994) *Parasitology* 109:249-254) injected fluorescently labeled dextrans into syncytia that were being fed upon by *Heterodera schachtii*. They found that the nematodes ingested 22 kDa dextrans, but not 40 kDa dextrans. Urwin et al. ((1998) *Planta* 204:472-479) found that a 23 kDa fusion protein expressed in transgenic *Arabidopsis* could not be ingested by *H. Schachtii*, although a protein of about 11 kDa could be ingested. Similarly, Unwin et al. ((1997) *Molecular Plant-Microbe Interactions* 10:394-400) found that 28 kDa green fluorescent protein (GFP) expressed in transgenic *Arabidopsis* could not be ingested by *H. schachtii*. Thus, it was not previously recognized or demonstrated that nematodes could be controlled by expressing a protein greater than 22 kDa in a plant since it was understood that nematodes would not ingest such a protein.

Provided herein are methods and compositions for conferring resistance to nematodes in plants. The methods comprise introducing into a plant at least one nucleotide sequence encoding a nematode-active polypeptide and growing the plant in a field containing nematodes. By "nematode-active polypeptide" is intended a polypeptide that, when ingested by the nematode, results in the death or stunting of growth or proliferation of at least one nematode. In one embodiment, the nematode-active polypeptide has a molecular weight greater than about 22 kDa, about 23 kDa, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80 kDa, or greater.

In another embodiment, the nematode-active polypeptide has activity against plant-parasitic nematodes. Expression of the nematode-active polypeptide in a plant reduces the ability of nematodes to infest or feed on roots of the plant. Examples of plant-parasitic nematodes sensitive to the compositions of the present invention include root knot nematodes (*Meloidogyne* sp.), stunt nematode (*Tylenchorhynchus* sp.), lance nematode (*Hoplolaimus* sp.), spiral nematode (*Helicotylenchus* sp.), lesion nematode (*Pratylenchus* sp.), cyst nematode (*Heterodera* sp. and *Globodera* sp.), and ring nematode (*Criconema* sp.).

Pesticidal Compositions

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, coleopteran, or nematode pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleriodea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; zygogramma exclamationis, sunflower beetle; *Bothyrus gibbosus*, carrot beetle; *Neolasioptera murtfeldtiana*, sunflower seed midge; Cotton: *Heliothis virescens*, cotton budworm; *Heli-* coverpa zea, cotton bollworm; *Spodoptera exigua*, beet armyworm; *Pectinophora gossypiella*, pink bollworm; *Anthonomus grandis*, boll weevil; *Aphis gossypli*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise introducing into a plant or plant cell a polynucleotide comprising a pesticidal sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing a pesticidal protein disclosed herein. Expression of the pesticidal protein results in a reduced ability of a pest to infest or feed on the plant, thus improving plant yield.

The following examples are offered by way of illustration and not by way of limitation.

EXPERIMENTAL

Example 1

Growth of ATX9387, and Preparation of Extracts

Strain ATX9387, identified as a member of the *Bacillus cereus/Bacillus thuringiensis* group by MIDI analysis, was grown in T3 medium at 30 degrees for times ranging from 16 hours to 5 days. Cultures were centrifuged and the supernatants were passed through 0.2 micron filters, resulting in sterile supernatants Example 2

C. elegans bioassay

*Caenorhabitis elegans* ("*C. elegans*") hermaphrodites were reared as known in the art, to generate populations of healthy animals for bioassay. General procedures for growth, harvesting, and genetic manipulation of C elegans including growth media, etc. may be found in the art, for example, in Wood, ed. (1988) *The Nematode Caenorhabditis elegans* (Cold Spring Harbor Laboratory Press, Cold Spring Harbor, N.Y.).

Sterile supernatants from strain ATX9387 were tested for activity on *C. elegans*. Bioassays were performed in 96-well plates. Five to ten nematodes were added to 80 µl of S medium (Wood, supra) and were mixed with 20 µl of sterile supernatant, 0.5 µl of concentrated HB101 (prepared as described in Wood, supra) and rifampicin (final concentration of 0.1 µg/µl). Assays were allowed to proceed at room temperature for 3 days and nematodes were quantitated. Negative control samples (T3 medium or sterile supernatants from inactive strains) contained hundreds of active nematodes, while test samples (containing ATX9387 supernatant) contained 5 to 10 nematodes that were sluggish or dead. The results of the bioassay of ATX9387 extracts on *C. elegans* are shown in Table 1.

TABLE 1

Activity of ATX9387 extracts on *C. elegans*

| Growth Time | ATX9387 | Control |
|---|---|---|
| 16 hours | – | – |
| 1 day | – | – |
| 2 days | – | – |
| 3 days | ++ | – |
| 4 days | ++ | – |
| 5 days | ++ | – |

Example 3

Activity of ATX9387 on Soybean Cyst Nematodes

A sterile supernatant of a 5-day culture of ATX9387 was concentrated 40-fold and fed to SCN J2 nematodes. Nematodes feeding on sterile supernatant were reproducibly observed to be sluggish, and exhibited higher motility than nematodes fed extract of a negative control concentrated to the same extent.

Example 4

Anti-nematode Activity from ATX9387 is Conferred by a Protein

To identify the anti-nematode activity in ATX9387, the following tests were performed. First, the ability of the activity to be destroyed by heating was tested by heating samples of sterile supernatant from ATX9387 to 100° C. for 10 minutes, then assaying heated material in a nematode bioassay. Heat treatment of sterile supernatants from ATX9387 resulted in a loss of anti-nematode activity. Next, active samples were treated with pronase to degrade proteins. This treatment resulted in loss of activity. Sterile supernatants from ATX9387 were passed through a 3 kDa molecular weight cut-off ("MWCO") concentration unit. The active ingredient was retained by the 3 kDa MWCO filter while the flow-through showed no activity. This indicates that the active molecule was larger than 3 kDa in size.

Example 5

Fractionation of Activity from ATX9387

The sterile supernatant of a 4-day culture of ATX9387 was fractionated by liquid chromatography on an anion exchange column in 20 mM Tris pH 8, using a gradient from 0 M to 1 M NaCl. Several consecutive fractions were active. The most active fraction was subjected to SDS-PAGE, and two prominent bands of approximately 130 kd and approximately 70 kd were observed.

In another experiment strain ATX9387 was grown for 5 days in T3 medium at 30° C. The culture was centrifuged at 8,000×g for 10 minutes, and the supernatant was passed through a 0.2 µm filter. The filtered supernatant was dialyzed against 20 mM Tris pH 8 using Spectra/Por 1 dialysis tubing (6-8,000 MWCO), and was then fractionated on an anion exchange column (Mono Q) using a gradient from 0 to 1 M NaCl over 20 bed volumes. The fractions were dialyzed against 20 mM Tris pH 8 using Slide-A-Lyzer (Pierce Biotechnology, Rockford, Ill.) mini dialysis units (7,000 MWCO), and bioassayed on C. elegans using 20 µl of sample in a 100 µl bioassay volume, as described herein. Fractions 12 and 13 were found to be active, and were pooled and then concentrated 7-fold using an Amicon Ultra-4 5,000 MWCO concentrator. The concentrated material was fractionated on a gel filtration column (Superdex 200) in 50 mM sodium phosphate, 150 mM NaCl, pH 7. Fractions were concentrated 10-fold using Centricon YM-3 concentrators, and were bioassayed on C. elegans as above. Fractions 5 and 6 were the most active, and fraction 7 was somewhat active. SDS-PAGE of the fractions showed that fractions 5-7 shared several proteins: a protein at about 130 kDa, a doublet at about 75 kDa, and a protein at about 53 kDa. The most prominent bands were subjected to N-terminal protein sequencing by Edman degradation. The 130 kDa protein and the 70 kDa protein had very similar N-terminal sequences (cysteine could not be detected by the method used), and thus are likely to result from the same initial protein. This protein was designated as AXMI-031 (SEQ ID NO:2).

TABLE 2

N-terminal sequence of the ~130 kDa protein from ATX9387

| 1 | A, S + S', M |
| 2 | D, Q |
| 3 | ?, P, N |
| 4 | N |
| 5 | L |
| 6 | Q |
| 7 | S |
| 8 | Q |
| 9 | ?, Q |
| 10 | N |
| 11 | I |
| 12 | P |
| 13 | Y |
| 14 | N |
| 15 | V |

TABLE 3

N-terminal sequence of the about ~70 kDa protein from ATX9387

| 1 | A, G, S + S' |
| 2 | F |
| 3 | P |
| 4 | N |
| 5 | L |
| 6 | Q |
| 7 | V? |
| 8 | Q |
| 9 | ? |
| 10 | N?, V? |
| 11 | I |
| 12 | P |
| 13 | Y, Q |
| 14 | ?, N |
| 15 | ?, V |

A search of protein databases with the N-terminal sequences of the ~130 kDa protein and the ~70 kDa protein demonstrated that the N-terminal amino acids of the AXMI-031 proteins have significant similarity to the N-terminus of the endotoxin Cry14Aa (SEQ ID NO:13).

N-terminal sequence of Cry14A: MDCN-LQSQQNIPYNV (amino acid residues 1 through 15 of SEQ ID NO:13).

Example 6

Cloning of the axmi-031 Coding Region from ATX9387

A random fragment library of ATX9387 was generated, and a DNA clone (pAX031) containing the DNA sequence encoding the N-terminus of axmi-031 was identified. A second clone, pAX032, was identified as containing the C-terminus of axmi-031. Clones pAX031 and pAX032 overlap substantially, such that it is clear to one skilled in the art that both clones together comprise the entire axmi-031 coding region.

To confirm the nature of the AXMI-031, a genomic clone was amplified using a high fidelity polymerase PFU ULTRA™ (Stratagene) from total DNA using primers designed to the ends of the axmi-031 open reading frame. The resulting PCR product was cloned into the PCR-TOPOII-Blunt vector (Invitrogen) to create pAX980. The DNA sequence pAX980 was determined and found to contain the same open reading frame as in the random fragment library clones pAX031 and pAX032. Translation of this open reading frame generates a protein sequence consistent with the N-terminal sequence obtained from the purified AXMI-031 protein. Thus, this open reading frame was designated axmi-031 (SEQ ID NO:1). The plasmid clone pAX2515, containing axmi-031 was deposited on Jun. 9, 2006 and assigned the accession number NRRL B-30935.

Example 7

Comparison of AXMI-031 to Other Known Endotoxins

Database searches using the AXMI-031 protein sequence demonstrate that AXMI-031 is a member of the delta-endotoxin class of insecticidal proteins. AXMI-031 is most similar to the cry14Aa1 endotoxin. The amino acid sequence of AXMI-031 is 86.6% identical to CRY14Aa1 (SEQ ID NO:13).

Example 8

Expression of the AXMI-031 Polypeptide in E. coli

For soluble expression in E. coli, primers were designed to include the translation start and stop codons from the axmi-031 ORF. The primers added an optimal RBS and Gateway attB recombination sites. Stratagene Pfu I polymerase was used to consistently amplify the ORF from the pAX980, and recombined with pDONR221 (Invitrogen, Carlsbad, Calif.) to create the entry vector pAX2515 (as per protocols from Invitrogen). The clone was sequenced for verification. A further recombination was performed to introduce the ORF into pDEST17 to be expressed by the T7 promoter, yielding pAX2530. The presence and orientation of the inserted axmi-031 fragment were verified by restriction digest, and transformed into E. coli BL21 (DE3) cells. This vector produces a translational fusion of 26 amino acids (3.17 kDa), including a 6×His tag, on the N-terminus of AXMI-031.

His-AXMI-031 was expressed from pAX2530 in BL21* (DE3) cells as follows. A starter culture of pAX2530 was grown overnight at 37° C. in LB with 50 µg/ml carbenicillin. The following day the saturated culture was diluted 1:100 into fresh medium, and the fresh culture grown at 37° to an OD of 0.4, at which time the culture was placed at room temperature with shaking overnight. As a control, an expression vector carrying the axmi-004 gene (pAX2530) was constructed as for axmi-031, and the AXMI-004 protein (U.S. patent application Ser. No. 10/782,020) was expressed from pAX2504 in the same E. coli host. Whole cultures were analyzed by SDS-PAGE. Cultures containing pAX2530 produced a prominent protein band at approximately 135 kDa, the expected size for His-AXMI-031 protein, while cultures containing pAX2504 did not.

Example 9

Antibodies to AXMI-031

To generate anti-AXMI-031 antibodies, affinity purified AXMI-031 (SEQ ID NO:2) protein was inoculated into rabbits, and antisera to AXMI-031 isolated and titered as known in the art. The selected antisera were found to also react with SYNAXMI-031 protein (SEQ ID NO:8).

Example 10

Activity of AXMI-031 on C. elegans

Cultures of E. coli containing pAX2530, were prepared, and found to produce a 135 kDa protein not present in control strains, suggesting the expression of AXMI-031 in pAX2530 containing strains. These cultures were tested for activity on C. elegans and were active against C. elegans, while control cultures showed no activity against C. elegans.

Example 11

Expression of AXMI-031 in Bacillus

The insecticidal gene axmi-031 is amplified by PCR from pAX980, and the PCR product is cloned into the Bacillus expression vector pAX916, or another suitable vector, by methods well known in the art. The resulting Bacillus strain, containing the vector with axmi-031 is cultured on a conventional growth media, such as CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared, and AXMI-031 protein was tested for activity in bioassays against C. elegans, and found to have activity.

Example 12 synaxmi-031, synaxmi-031(apo) and synaxmi-031 (ER)

In one aspect of the invention, synthetic axmi-031 sequences are generated, for example synaxmi-031 (SEQ ID NO:7). These synthetic sequences have an altered DNA sequence relative to the axmi-031 sequence, and encode a protein that is collinear with the original AXMI-031 protein, but lacks the C-terminal "crystal domain" present in AXMI-031. The synaxmi-031 gene sequence encodes SYNAXMI-031 protein (SEQ ID NO:8), which comprises the first 685 amino acids of the AXMI-031 protein.

In another aspect of the invention, modified versions of synaxmi-031 are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin Lupinus albus (Genebank ID GI:14276838; Miller et al. (2001) Plant Physiology 127: 594-606) is known in the art to result in endoplasmic reticulum targeting of heterologous proteins. If the resulting fusion protein also contains an endoplasmic retention sequence comprising the peptide N-terminus-lysine-aspartic acid-glutamic acid-leucine (i.e. the "KDEL" motif (SEQ ID NO:36) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, the synaxmi-031ER gene (SEQ ID NO: 11) encodes a fusion protein that contains the N-terminal thirty-one amino acids of the acid phosphatase gene from the White Lupin Lupinus albus fused to the N-terminus of SYNAXMI-031, as well as the KDEL sequence at the C-terminus. Thus, the resulting protein AXMI-031ER (SEQ ID NO:12), is predicted to be targeted the plant endoplasmic reticulum upon expression in a plant cell.

The synaxmi-031(apo) gene (SEQ ID NO:9) encodes a fusion protein that contains the N-terminal thirty-one amino acids of the acid phosphatase gene from the White Lupin Lupinus albus fused to the N-terminus of SYNAXMI-031, but lacks the KDEL (SEQ ID NO:36) sequence at the C-terminus. Thus, the resulting protein AXMI-031 (APO) (SEQ ID NO:10), is predicted to be targeted to the plant apoplast upon expression in a plant cell.

Example 13

Truncations of synaxmi-031 to Yield Alternate AXMI-031 Proteins

DNA constructs that resulted in expression of variants of AXMI-031 protein were developed and expressed, in addition to synthetic sequences encoding AXMI-031 and variants and fragments thereof (SEQ ID NO:15-27). A subset of these genes were tested for nematode activity in vitro.

TABLE 4

Nematicidal Activity of AXMI-031 variants in vitro

| Protein | Nucleotide SEQ ID NO: | Amino acid SEQ ID NO: | Active on C. elegans? |
|---|---|---|---|
| Bacterial Expression | | | |
| AXMI-031-truncated | 14 | 15 | Yes |
| AXMI-031(ml) | 16 | 17 | Yes |
| AXMI-031(ml)-truncated | 18 | 19 | Yes |
| AXMI-031(A-D) | 20 | 21 | Yes |
| SYNAXMI-031 (A-D) | 26 | 27 | NT |
| AXMI-031(B-C) | 22 | 23 | Yes |
| AXMI-031(B-D) | 24 | 25 | Yes |

NT = not tested

Example 14

Truncations and Addition of Cellular Targeting Domain(s) for Plant Expression

In another aspect of the invention, modified versions of the synaxmi-031 sequences are designed such that the resulting peptide is targeted to a plant organelle, such as the endoplasmic reticulum or the apoplast.

In another aspect of the invention, the genes are truncated such that the resulting peptide is a truncated version of AXMI-031, which may or may not be further modified for targeting to plant organelles, such as the apoplast or the endoplasmic reticulum.

In another aspect of the invention, modified versions are developed that result in expression of truncated variants that contain domains designed to target the resulting protein to plant organelles.

The following variant nucleotide sequences were designed:
aposynaxmi-031(A-D) (SEQ ID NO:28) encodes the APOAXMI-031(A-D) protein (SEQ ID NO:29). apoSyn2axmi-031(A-D) (SEQ ID NO:30) encodes the APOSYN2AXMI-31(A-D) protein (SEQ ID NO:31). aposynaxmi-031(fl) (SEQ ID NO:37) encodes the APOSYN-AXMI-031(FL) protein (SEQ ID NO:38). Synaxmi031(fl)-ER (SEQ ID NO:32) encodes the SYNAXMI-031(FL)-ER protein (SEQ ID NO:33).

Example 15

Extraction of Plasmid DNA from Strains ATX16538, ATX16093 and ATX21049

Strains ATX16538, ATX16093, and ATX21049 were selected for analysis. Pure cultures of each strain were grown in large quantities of rich media. The cultures were centrifuged to harvest the cell pellet. The cell pellet was then prepared by treatment with SDS by methods known in the art, resulting in breakage of the cell wall and release of DNA. Proteins and large genomic DNA was then precipitated by a high salt concentration. The plasmid DNA was then precipitated with ethanol. In several instances, the plasmid DNA was separated from any remaining chromosomal DNA by high-speed centrifugation through a cesium chloride gradient. Alternatively, the plasmid DNA was purified by binding to a resin, as known in the art. For each strain, the quality of the DNA was checked by visualization on an agarose gel by methods known in the art.

Example 16

Cloning of Genes from Strains ATX16538, ATX16093 and ATX21049

DNA libraries were prepared from the plasmid DNA or each strain. This may be achieved in many ways as known in the art. For, example, the purified plasmid DNA can be sheared into 5-10 kb sized fragments and the 5' and 3' single stranded overhangs repaired using T4 DNA polymerase and Klenow fragment in the presence of all four dNTPs, as known in the art. Phosphates can then be attached to the 5' ends by treatment with T4 polynucleotide kinase, as known in the art. The repaired DNA fragments can then be ligated overnight into a standard high copy vector (i.e. pBLUESCRIPT® SK+), suitably prepared to accept the inserts as known in the art (for example by digestion with a restriction enzyme producing blunt ends).

The quality of the resulting DNA libraries was analyzed by digesting a subset of clones with a restriction enzyme known to have a cleavage site flanking the cloning site. A high percentage of clones were determined to contain inserts, usually with an average insert size of 5-6 kb.

Example 17

High Throughput Sequencing of Library Plates

Once the DNA library quality was checked and confirmed, colonies were grown in a rich broth in 2 ml 96-well blocks overnight at 37° C., typically at a shaking speed of 350 rpm. The blocks were centrifuged to collect the cells at the bottom of the block. The blocks were then prepared by standard alkaline lysis prep in a high throughput format.

The end sequences of clones from this library were then determined for a large number of clones from each block in the following manner: The DNA sequence of each clone chosen for analysis was determined using the fluorescent dye terminator sequencing technique (Applied Biosystems), by methods known in the art using an automated DNA sequencing machine, and standard oligonucleotide primers that anneal to the plasmid vector in the region flanking the insert.

Example 18

Assembly and Screening of Sequencing Data

DNA sequences obtained were compiled into an assembly project and aligned together to form contigs. This can be done efficiently using a computer program, such as Vector NTi, or alternatively by using the Pred/Phrap suite of DNA alignment and analysis programs as described elsewhere herein. These contigs, along with any individual read that may not have been added to a contig, were compared to a compiled database of all classes of known pesticidal genes. Contigs or individual reads identified as having identity to a known endotoxin or pesticidal gene were analyzed further.

From strain ATX16538, pAX2579 was found to contain an open reading frame with homology to "cry" type delta-endotoxins. This open reading frame was designated as axmi-039 (SEQ ID NO:3), and the encoded protein was designated AXMI-039 (SEQ ID NO:4). The axmi-039 ORF and flanking sequence (151 bp upstream of the start codon and 29 bp downstream of the stop codon) was PCR amplified, cloned into pRSF1B and sequenced to yield pAX2579. pAX2579 was deposited with the ARS Patent Strain Collection on Jun. 9, 2006, and assigned NRRL B-30936. AXMI-039 is 43.9% amino acid sequence identity to Cry5Ba1, which is the closest homolog identified.

From strain ATX16093, pAX4313 was found to contain an open reading frame with homology to "cry" type delta-endotoxins. This open reading frame was designated as axmi-040 (SEQ ID NO:5), and the encoded protein was designated AXMI-040 (SEQ ID NO:6). pAX4313 was deposited with the ARS Patent Strain Collection on Jun. 9, 2006, and assigned NRRL B-30937. AXMI-040 is 42.9% amino acid sequence identity to Cry21Ba1, which is the closest homolog identified.

From strain ATX21049, an open reading frame was identified that exhibited homology to "cry" type delta-endotoxins. This open reading frame was designated as axmi-049 (SEQ ID NO:34), and the encoded protein was designated AXMI-049 (SEQ ID NO:35). This open reading frame was amplified by PCR and cloned into a vector to yield pAX5039. pAX5039 was deposited with the ARS Patent Strain Collection on May 29, 2007, and assigned NRRL B-50046. AXMI-049 has 46.1% amino acid sequence identity to Cry21Ba1, which is the closest homology identified.

Example 19

Vectoring of the Pesticidal Genes of the Invention for Plant Expression

Each of the coding regions of the genes of the invention are connected independently with appropriate promoter and terminator sequences for expression in plants. Such sequences are well known in the art and may include the rice actin promoter or maize ubiquitin promoter for expression in monocots, the Arabidopsis UBQ3 promoter or CaMV 35S promoter for expression in dicots, and the nos or PinII terminators. Techniques for producing and confirming promoter—gene—terminator constructs also are well known in the art.

Example 20

Transformation of the Genes of the Invention into Plant Cells by Agrobacterium-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an Agrobacterium strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

Example 21

Transgenic Plants Expressing AXMI-031 and Variants

The plant expression cassettes described herein are combined with an appropriate plant selectable marker to aid in the selections of transformed cells and tissues, and ligated into plant transformation vectors. These may include binary vectors from Agrobacterium-mediated transformation or simple plasmid vectors for aerosol or biolistic transformation. synaxmi-031 (apo) was cloned into a plant expression vector, and this vector was introduced into Agrobacterium tumefaciens as known in the art. The synaxmi-031 (apo) coding region under control of the Arabidopsis UBQ3 promoter (Norris et al. (1993) *J. Plant Mol. Biol.* 21:895-906) was introduced into Arabidopsis thaliana by floral dip method as known in the art, and transgenic plants were selected. The presence of synaxmi-031(apo) in the transgenic Ti population was confirmed by PCR analysis as known in the art, using oligonucleotide primers derived from the sequence of synaxmi-031, which also anneal to synaxmi-031 (apo).

Leaf and root tissue from transgenic synaxmi-031 (apo) containing plants was prepared and separated on polyacrylamide gels alongside non-transgenic controls and dilutions of AXMI-031 protein, and transferred to a membrane as known in the art. The samples were tested for the presence of the expression product of synaxmi-031(apo) by Western blot analysis as known in the art, using anti-AXMI-031 antibodies described herein. The expression product of synaxmi-031 (apo) of the expected size was detected in samples of both leaf and root tissue from transgenic synaxmi-031(apo)-containing plants, but not detected in non-transgenic controls.

TABLE 5

Antibody detection of SYNAXMI-031(APO) in transgenic plants

| Source of Tissue | Detection of SYNAXMI-031(APO) |
|---|---|
| Non-transformed control | – |
| synaxmi-031 (apo) containing plant 'A' | +++ |
| synaxmi-031(apo) containing plant 'B' | +++ |

Example 22

Reduced Cyst Formation by AXMI-031 Expressing Plants

Transgenic plants expressing synaxmi-031 (apo) were tested for ability to resist infestation by *Heterodera schachtii* compared to control plants. Transgenic plants, as well as control plants transformed with vector alone, were infested with approximately 100 J2 hatchlings, and the number of nematodes entering the roots, as well as the number of cyst formed, was measured. Transgenic plants expressing SYN-AXMI-031 (APO) were found to consistently have reduced numbers of nematodes entering the roots, and reduced numbers of cysts formed relative to controls.

TABLE 6

Reduced cyst formation in AXMI-031 expressing plants

| | Cyst formation |
|---|---|
| Control plant | ++ |
| Plants expressing AXMI-031(APO) | + |

Example 23

Additional Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*. CRC, Boca Raton, FL. Alternatively, assays are commonly described in the journals "Arthropod Management Tests" and "Journal of Economic Entomology" or by discussion with members of the Entomological Society of America (ESA).

Example 24

Transformation of Maize Cells with the Pesticidal Genes of the Invention

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/mL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240,842).

DNA constructs designed to express the genes of the invention in plant cells are accelerated into plant tissue using an aerosol beam accelerator, using conditions essentially as described in PCT Publication No. WO/01385 14. After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | per liter | Source |
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000 × Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3g/L, and autoclave. After cooling to 50° C., add 2 ml/L of a 5 mg/ml stock solution of Silver Nitrate (Phytotechnology Labs). Recipe yields about 20 plates.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A recombinant nucleic acid molecule comprising a nucleotide sequence selected from the group consisting of:
   a) the nucleotide sequence of SEQ ID NO:1, 7, 9, 11, 14, 16, 18, 20, 22, 24, 26, 28, 30, 32, or 37, or a complement thereof;
   b) a nucleotide sequence that encodes a polypeptide comprising the amino acid sequence of SEQ ID NO:2, 8, 10, 12, 15, 17, 19, 21, 23, 25, 27, 29, 31, 33, or 38;
   c) a nucleotide sequence that encodes a polypeptide comprising an amino acid sequence having at least 95% sequence identity to the amino acid sequence of SEQ ID NO:2, 8, 10, 12, 15, 17, 19, 21, 23, 25, 27, 29, 31, 33, or 38, wherein said amino acid sequence has pesticidal activity against a lepidopteran or a nematode pest; and,
   d) the delta endotoxin nucleotide sequence of the DNA insert of the plasmid deposited at the Northern Regional Research Laboratory (NRRL) as Accession No. B-30935 or a complement thereof.

2. The recombinant nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. A host cell that contains the vector of claim 3.

6. The host cell of claim 5 that is a bacterial host cell.

7. The host cell of claim 5 that is a plant cell.

8. A transgenic plant comprising the host cell of claim 7.

9. The transgenic plant of claim 8, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

10. A transgenic seed comprising the nucleic acid molecule of claim 1.

11. A plant having stably incorporated into its genome a DNA construct comprising a nucleotide sequence that encodes a protein having pesticidal activity, wherein said nucleotide sequence is selected from the group consisting of:
   a) the nucleotide sequence of SEQ ID NO:1, 7, 9, 11, 14, 16, 18, 20, 22, 24, 26, 28, 30, 32, or 37, or a complement thereof;
   b) a nucleotide sequence that encodes a polypeptide comprising the amino acid sequence of SEQ ID NO:2, 8, 10, 12, 15, 17, 19, 21, 23, 25, 27, 29, 31, 33, or 38;
   c) a nucleotide sequence that encodes a polypeptide comprising an amino acid sequence having at least 95% sequence identity to the amino acid sequence of SEQ ID NO:2, 8, 10, 12, 15, 17, 19, 21, 23, 25, 27, 29, 31, 33, or 38, wherein said amino acid sequence has pesticidal activity against a lepidopteran or a nematode pest; and,
   d) the delta endotoxin nucleotide sequence of the DNA insert of the plasmid deposited at the NRRL as Accession Nos. B-30935 or a complement thereof;
   wherein said nucleotide sequence is operably linked to a promoter that drives expression of a coding sequence in a plant cell.

12. The plant of claim 11, wherein said plant is a plant cell.

13. A method for protecting a plant from a pest, said method comprising introducing into said plant or cell thereof at least one expression vector comprising a nucleotide sequence that encodes a pesticidal polypeptide, wherein said nucleotide sequence is selected from the group consisting of:
   a) the nucleotide sequence of SEQ ID NO:1, 7, 9, 11, 14, 16, 18, 20, 22, 24, 26, 28, 30, 32, or 37, or a complement thereof;

b) a nucleotide sequence that encodes a polypeptide comprising the amino acid sequence of SEQ ID NO:2, 8, 10, 12, 15, 17, 19, 21, 23, 25, 27, 29, 31, 33, or 38;
c) a nucleotide sequence that encodes a polypeptide comprising an amino acid sequence having at least 95% sequence identity to the amino acid sequence of SEQ ID NO:2, 8, 10, 12, 15, 17, 19, 21, 23, 25, 27, 29, 31, 33, or 38, wherein said amino acid sequence has pesticidal activity against a lepidopteran or a nematode pest; and,
d) the delta endotoxin nucleotide sequence of the DNA insert of the plasmid deposited at the NRRL as Accession Nos. B-30935 or a complement thereof.

14. The recombinant nucleic acid sequence of claim 1, wherein said nucleic acid sequence is operably linked to a promoter that drives expression of said nucleic acid sequence in a plant cell.

* * * * *

SEQUENCE LISTING

<160> NUMBER OF SEQ ID NOS: 38

<210> SEQ ID NO 1
<211> LENGTH: 3558
<212> TYPE: DNA
<213> ORGANISM: Bacillus cereus/Bacillus thuringiensis
<220> FEATURE:
<221> NAME/KEY: CDS
<222> LOCATION: (1)...(3558)

<400> SEQUENCE: 1

| | | | | | | | | | | | | | | | | |
|---|---|---|---|---|---|---|---|---|---|---|---|---|---|---|---|---|
| atg | gat | tgt | aat | tta | caa | tca | caa | caa | aat | att | cca | tat | aat | gta | tta | 48 |
| Met | Asp | Cys | Asn | Leu | Gln | Ser | Gln | Gln | Asn | Ile | Pro | Tyr | Asn | Val | Leu | |
| 1 | | | | 5 | | | | | 10 | | | | | 15 | | |
| gca | ata | cca | gta | tct | aat | gtt | aat | tcg | ttg | act | gat | aca | gtt | gga | gat | 96 |
| Ala | Ile | Pro | Val | Ser | Asn | Val | Asn | Ser | Leu | Thr | Asp | Thr | Val | Gly | Asp | |
| | | | 20 | | | | | 25 | | | | | 30 | | | |
| tta | aaa | aaa | gca | tgg | gaa | gaa | ttt | caa | aaa | act | ggt | tct | ttt | tca | tta | 144 |
| Leu | Lys | Lys | Ala | Trp | Glu | Glu | Phe | Gln | Lys | Thr | Gly | Ser | Phe | Ser | Leu | |
| | 35 | | | | | 40 | | | | | 45 | | | | | |
| aca | gct | tta | caa | caa | gga | ttt | tct | gct | tca | caa | gga | gga | aca | ttc | aat | 192 |
| Thr | Ala | Leu | Gln | Gln | Gly | Phe | Ser | Ala | Ser | Gln | Gly | Gly | Thr | Phe | Asn | |
| 50 | | | | | 55 | | | | | 60 | | | | | | |
| tat | tta | aca | tta | cta | caa | tca | gga | ata | tca | tta | gct | ggt | tct | ttt | gtt | 240 |
| Tyr | Leu | Thr | Leu | Leu | Gln | Ser | Gly | Ile | Ser | Leu | Ala | Gly | Ser | Phe | Val | |
| 65 | | | | | 70 | | | | | 75 | | | | | 80 | |
| cct | gga | ggt | act | ttt | gta | gca | cct | att | att | aat | atg | gtt | att | ggt | tgg | 288 |
| Pro | Gly | Gly | Thr | Phe | Val | Ala | Pro | Ile | Ile | Asn | Met | Val | Ile | Gly | Trp | |
| | | | | 85 | | | | | 90 | | | | | 95 | | |
| tta | tgg | cca | cat | aaa | aac | aaa | aat | gcg | gat | aca | gaa | aat | tta | ata | aat | 336 |
| Leu | Trp | Pro | His | Lys | Asn | Lys | Asn | Ala | Asp | Thr | Glu | Asn | Leu | Ile | Asn | |
| | | | 100 | | | | | 105 | | | | | 110 | | | |
| tta | att | gat | tca | gaa | att | caa | aaa | caa | tta | aac | aaa | gct | tta | tta | gat | 384 |
| Leu | Ile | Asp | Ser | Glu | Ile | Gln | Lys | Gln | Leu | Asn | Lys | Ala | Leu | Leu | Asp | |
| | 115 | | | | | 120 | | | | | 125 | | | | | |
| gca | gat | aga | aat | gag | tgg | agc | tct | tat | tta | gaa | tct | ata | ttt | gat | tct | 432 |
| Ala | Asp | Arg | Asn | Glu | Trp | Ser | Ser | Tyr | Leu | Glu | Ser | Ile | Phe | Asp | Ser | |
| 130 | | | | | 135 | | | | | 140 | | | | | | |
| tca | aat | aac | cta | aat | ggt | gca | att | gta | gat | gca | cag | tgg | tca | ggc | act | 480 |
| Ser | Asn | Asn | Leu | Asn | Gly | Ala | Ile | Val | Asp | Ala | Gln | Trp | Ser | Gly | Thr | |
| 145 | | | | | 150 | | | | | 155 | | | | | 160 | |
| gta | aat | act | aca | aat | aga | aca | cta | aga | aat | cca | aca | gaa | tca | gat | tat | 528 |
| Val | Asn | Thr | Thr | Asn | Arg | Thr | Leu | Arg | Asn | Pro | Thr | Glu | Ser | Asp | Tyr | |
| | | | | 165 | | | | | 170 | | | | | 175 | | |
| aca | aat | gtt | gtt | aca | aat | ttt | att | gca | gcg | gat | ggt | gac | att | gca | aat | 576 |
| Thr | Asn | Val | Val | Thr | Asn | Phe | Ile | Ala | Ala | Asp | Gly | Asp | Ile | Ala | Asn | |
| | | | 180 | | | | | 185 | | | | | 190 | | | |
| aat | gaa | aat | cac | ata | atg | aat | ggc | aac | ttt | gac | gta | gct | gca | gca | cct | 624 |
| Asn | Glu | Asn | His | Ile | Met | Asn | Gly | Asn | Phe | Asp | Val | Ala | Ala | Ala | Pro | |
| | 195 | | | | | 200 | | | | | 205 | | | | | |
| tat | ttt | gtt | ata | gga | gca | aca | gca | cgt | ttt | gca | gca | atg | caa | tct | tat | 672 |
| Tyr | Phe | Val | Ile | Gly | Ala | Thr | Ala | Arg | Phe | Ala | Ala | Met | Gln | Ser | Tyr | |
| 210 | | | | | 215 | | | | | 220 | | | | | | |
| att | aaa | ttt | tgt | aat | gct | tgg | att | gat | aaa | gtt | gga | ttg | agt | gac | gca | 720 |
| Ile | Lys | Phe | Cys | Asn | Ala | Trp | Ile | Asp | Lys | Val | Gly | Leu | Ser | Asp | Ala | |
| 225 | | | | | 230 | | | | | 235 | | | | | 240 | |
| cag | ctt | act | aca | caa | aag | gct | aat | tta | gat | cgc | acg | aaa | caa | aat | atg | 768 |
| Gln | Leu | Thr | Thr | Gln | Lys | Ala | Asn | Leu | Asp | Arg | Thr | Lys | Gln | Asn | Met | |
| | | | | 245 | | | | | 250 | | | | | 255 | | |
| cgt | aat | gca | att | ctt | aac | tat | aca | caa | caa | gtt | atg | aaa | gtt | ttt | aaa | 816 |

|     |     |     |     |     |     |     |     |     |     |     |     |     |     |     |
|-----|-----|-----|-----|-----|-----|-----|-----|-----|-----|-----|-----|-----|-----|-----|
| Arg | Asn | Ala | Ile | Leu | Asn | Tyr | Thr | Gln | Gln | Val | Met | Lys | Val | Phe | Lys |
|     |     |     | 260 |     |     |     |     | 265 |     |     |     |     | 270 |     |     |

```
gat tcc aaa aat atg cct aca ata ggt act aat aaa ttt agt gtt gat      864
Asp Ser Lys Asn Met Pro Thr Ile Gly Thr Asn Lys Phe Ser Val Asp
        275                 280                 285 acc tat aat gta tat att aaa gga atg aca tta aat gtt tta gat att      912
Thr Tyr Asn Val Tyr Ile Lys Gly Met Thr Leu Asn Val Leu Asp Ile
    290                 295                 300 gta gca ata tgg cct tca tta tat cca gat gat tat act tca caa aca      960
Val Ala Ile Trp Pro Ser Leu Tyr Pro Asp Asp Tyr Thr Ser Gln Thr
305                 310                 315                 320 gcc tta gaa caa aca cgt gtc act ttt tca aat atg gtt ggc caa gaa     1008
Ala Leu Glu Gln Thr Arg Val Thr Phe Ser Asn Met Val Gly Gln Glu
                325                 330                 335 gaa ggt aca gat gga agc cta aga att tac aat act ttt gat tct ttt     1056
Glu Gly Thr Asp Gly Ser Leu Arg Ile Tyr Asn Thr Phe Asp Ser Phe
            340                 345                 350 agt tat caa cat agt cca ata cct aat aat aat gtt aat tta att tct     1104
Ser Tyr Gln His Ser Pro Ile Pro Asn Asn Asn Val Asn Leu Ile Ser
        355                 360                 365 tat tat aat gat gaa tta caa aat cta gaa tta gga gta tat acc cct     1152
Tyr Tyr Asn Asp Glu Leu Gln Asn Leu Glu Leu Gly Val Tyr Thr Pro
    370                 375                 380 cct aaa aaa gga agt gga tac tct tat cct tat gga ttt gtt tta aat     1200
Pro Lys Lys Gly Ser Gly Tyr Ser Tyr Pro Tyr Gly Phe Val Leu Asn
385                 390                 395                 400 tat gca aac agt aaa tat aaa tat ggt gat agc aat gat cca gaa tct     1248
Tyr Ala Asn Ser Lys Tyr Lys Tyr Gly Asp Ser Asn Asp Pro Glu Ser
                405                 410                 415 cta gga gga tta tct aca cta tct gca cct ata caa caa gtt aat gca     1296
Leu Gly Gly Leu Ser Thr Leu Ser Ala Pro Ile Gln Gln Val Asn Ala
            420                 425                 430 gca act caa aac agt aaa tat cta gat gga gaa atc cta aat gga ata     1344
Ala Thr Gln Asn Ser Lys Tyr Leu Asp Gly Glu Ile Leu Asn Gly Ile
        435                 440                 445 gga gca tcc tta cct ggt tat tgt act aca gga tgt tca cca aca gaa     1392
Gly Ala Ser Leu Pro Gly Tyr Cys Thr Thr Gly Cys Ser Pro Thr Glu
    450                 455                 460 cca cct ttt agt tgt act tct acc gct aat ggc tat aaa gca agc tgt     1440
Pro Pro Phe Ser Cys Thr Ser Thr Ala Asn Gly Tyr Lys Ala Ser Cys
465                 470                 475                 480 aat cct tca gat aca aat caa aaa att aac gct tta tat cct ttt aca     1488
Asn Pro Ser Asp Thr Asn Gln Lys Ile Asn Ala Leu Tyr Pro Phe Thr
                485                 490                 495 caa gct aat gta aag gga aac aca gga aaa tta gga gta ctg gca agt     1536
Gln Ala Asn Val Lys Gly Asn Thr Gly Lys Leu Gly Val Leu Ala Ser
            500                 505                 510 ctt gtt tca tat gat tta aat cct aaa aat gta ttt ggt gaa tta gat     1584
Leu Val Ser Tyr Asp Leu Asn Pro Lys Asn Val Phe Gly Glu Leu Asp
        515                 520                 525 tca gat aca aat aat gtt atc tta aaa gga att cct gca gaa aaa gga     1632
Ser Asp Thr Asn Asn Val Ile Leu Lys Gly Ile Pro Ala Glu Lys Gly
    530                 535                 540 tat ttt cct aat aat gcg cgt cct act gtt gta aaa gaa tgg att aat     1680
Tyr Phe Pro Asn Asn Ala Arg Pro Thr Val Val Lys Glu Trp Ile Asn
545                 550                 555                 560 ggt gca agt gct gta cca ctt gat tca gga aat acc tta ttt atg acg     1728
Gly Ala Ser Ala Val Pro Leu Asp Ser Gly Asn Thr Leu Phe Met Thr
                565                 570                 575 gct acg aat tta aca gct act caa tat aga att aga ata cgt tat gca     1776
```

```
Ala Thr Asn Leu Thr Ala Thr Gln Tyr Arg Ile Arg Ile Arg Tyr Ala
            580                 585                 590 aat cca aat tca aat act caa atc ggt gta cga att aca caa aat ggt      1824
Asn Pro Asn Ser Asn Thr Gln Ile Gly Val Arg Ile Thr Gln Asn Gly
            595                 600                 605 tct cta att tcc agt agt aat cta aca ctt tat agt act act gat atg      1872
Ser Leu Ile Ser Ser Ser Asn Leu Thr Leu Tyr Ser Thr Thr Asp Met
            610                 615                 620 aat aat act tta cca cta aat gta tat gta ata gga gaa aat gga aat      1920
Asn Asn Thr Leu Pro Leu Asn Val Tyr Val Ile Gly Glu Asn Gly Asn
625                 630                 635                 640 tat aca ctt caa gat tta tat aat act act aat gtt tta tca aca gga      1968
Tyr Thr Leu Gln Asp Leu Tyr Asn Thr Thr Asn Val Leu Ser Thr Gly
                645                 650                 655 gat att aca tta caa att aca gga gga gat caa aaa ata ttt att gat      2016
Asp Ile Thr Leu Gln Ile Thr Gly Gly Asp Gln Lys Ile Phe Ile Asp
                660                 665                 670 cga ata gaa ttt gtt cct act atg cct gta cct ggt aat act aac aac      2064
Arg Ile Glu Phe Val Pro Thr Met Pro Val Pro Gly Asn Thr Asn Asn
                675                 680                 685 aat aac ggt aat aat aac ggt aat aat aat ccc cca cac cac gtt tgt      2112
Asn Asn Gly Asn Asn Asn Gly Asn Asn Asn Pro Pro His His Val Cys
690                 695                 700 gca ata gct ggt aca caa caa tct tgt tct gga ccg ccc aaa ttt gaa      2160
Ala Ile Ala Gly Thr Gln Gln Ser Cys Ser Gly Pro Pro Lys Phe Glu
705                 710                 715                 720 caa gta agt gat tta gaa aaa att aca aca caa gta tat atg tta ttc      2208
Gln Val Ser Asp Leu Glu Lys Ile Thr Thr Gln Val Tyr Met Leu Phe
                725                 730                 735 aaa tct tct ccg tat gaa gaa tta gct cta gaa gtt tcc agc tat caa      2256
Lys Ser Ser Pro Tyr Glu Glu Leu Ala Leu Glu Val Ser Ser Tyr Gln
                740                 745                 750 att agt caa gta gca tta aaa gtt atg gca tta tct gat gaa cta ttt      2304
Ile Ser Gln Val Ala Leu Lys Val Met Ala Leu Ser Asp Glu Leu Phe
                755                 760                 765 tgt gaa gaa aaa aac gta tta cga aaa tta gtc aat aaa gca aaa caa      2352
Cys Glu Glu Lys Asn Val Leu Arg Lys Leu Val Asn Lys Ala Lys Gln
770                 775                 780 tta tta gaa gca agt aac tta cta gta ggt gga aat ttt gaa aca act      2400
Leu Leu Glu Ala Ser Asn Leu Leu Val Gly Gly Asn Phe Glu Thr Thr
785                 790                 795                 800 caa aat tgg gta ctt gga aca aat gct tat ata aat tat gat tcg ttt      2448
Gln Asn Trp Val Leu Gly Thr Asn Ala Tyr Ile Asn Tyr Asp Ser Phe
                805                 810                 815 tta ttt aat gga aat tat tta tct tta caa cca gca agt gga ttt ttc      2496
Leu Phe Asn Gly Asn Tyr Leu Ser Leu Gln Pro Ala Ser Gly Phe Phe
                820                 825                 830 aca tct tat gct tat caa aaa ata gat gag tca aca tta aaa cca tat      2544
Thr Ser Tyr Ala Tyr Gln Lys Ile Asp Glu Ser Thr Leu Lys Pro Tyr
                835                 840                 845 aca cga tat aaa gtt tct ggg ttc att ggg caa agt aat caa gta gaa      2592
Thr Arg Tyr Lys Val Ser Gly Phe Ile Gly Gln Ser Asn Gln Val Glu
850                 855                 860 ctt att att tct cgt tat gga aaa gaa att gat aaa ata tta aat gtt      2640
Leu Ile Ile Ser Arg Tyr Gly Lys Glu Ile Asp Lys Ile Leu Asn Val
865                 870                 875                 880 cca tat gca gga cct ctt cct atc act gct gat gca tca ata act tgt      2688
Pro Tyr Ala Gly Pro Leu Pro Ile Thr Ala Asp Ala Ser Ile Thr Cys
                885                 890                 895 tgt gca cca gaa ata ggc caa tgt gat ggg gaa caa tct gat tct cat      2736
```

```
Cys Ala Pro Glu Ile Gly Gln Cys Asp Gly Glu Gln Ser Asp Ser His
        900                 905                 910 ttc ttt aac tat agc atc gat gta ggt gca ctt cac cca gaa tta aac      2784
Phe Phe Asn Tyr Ser Ile Asp Val Gly Ala Leu His Pro Glu Leu Asn
            915                 920                 925 cct ggc att gaa att ggt ctt aaa att gtg caa tca aat ggt tat ata      2832
Pro Gly Ile Glu Ile Gly Leu Lys Ile Val Gln Ser Asn Gly Tyr Ile
        930                 935                 940 aca att agt aat cta gaa att att gaa gaa cgt cca ctt aca gaa atg      2880
Thr Ile Ser Asn Leu Glu Ile Ile Glu Glu Arg Pro Leu Thr Glu Met
945                 950                 955                 960 gaa att caa gca gtc aat cga aaa aat caa aaa tgg gaa aga gaa aaa      2928
Glu Ile Gln Ala Val Asn Arg Lys Asn Gln Lys Trp Glu Arg Glu Lys
            965                 970                 975 ctt cta gaa tgt gca agt att agt gaa ctt tta caa cca att att aat      2976
Leu Leu Glu Cys Ala Ser Ile Ser Glu Leu Leu Gln Pro Ile Ile Asn
        980                 985                 990 caa atc gat tca ttg ttt aaa gat gga aac tgg tat aat gat att ctt      3024
Gln Ile Asp Ser Leu Phe Lys Asp Gly Asn Trp Tyr Asn Asp Ile Leu
            995                 1000                1005 cct cat gtc aca tat caa gat tta aaa aat att ata ata ccc gag tta      3072
Pro His Val Thr Tyr Gln Asp Leu Lys Asn Ile Ile Ile Pro Glu Leu
    1010                1015                1020 cca aaa tta aaa cat tgg ttc ata gag aat ctc cca ggt gaa tat cat      3120
Pro Lys Leu Lys His Trp Phe Ile Glu Asn Leu Pro Gly Glu Tyr His
1025                1030                1035                1040 gaa att gaa caa aaa atg aaa gaa gct cta aaa tat gca ttt aca caa      3168
Glu Ile Glu Gln Lys Met Lys Glu Ala Leu Lys Tyr Ala Phe Thr Gln
                1045                1050                1055 tta gac gag aaa aat tta atc cac aat ggt cac ttt aca act aac tta      3216
Leu Asp Glu Lys Asn Leu Ile His Asn Gly His Phe Thr Thr Asn Leu
            1060                1065                1070 ata gat tgg caa gta gaa ggt gat gct caa atg aaa gta tta gaa aat      3264
Ile Asp Trp Gln Val Glu Gly Asp Ala Gln Met Lys Val Leu Glu Asn
        1075                1080                1085 gat gct ctt gca tta caa ctt ttc aac tgg gat gct agt gct tca caa      3312
Asp Ala Leu Ala Leu Gln Leu Phe Asn Trp Asp Ala Ser Ala Ser Gln
    1090                1095                1100 tct ata aat ata tta gaa ttt gat gaa gat aag gca tat aaa ctt cgc      3360
Ser Ile Asn Ile Leu Glu Phe Asp Glu Asp Lys Ala Tyr Lys Leu Arg
1105                1110                1115                1120 gta tat gct caa gga agc gga aca atc caa ttt gga aac tgt gaa gat      3408
Val Tyr Ala Gln Gly Ser Gly Thr Ile Gln Phe Gly Asn Cys Glu Asp
                1125                1130                1135 gaa gct atc caa ttt aat aca aac tca ttc ata tat caa gaa aaa ata      3456
Glu Ala Ile Gln Phe Asn Thr Asn Ser Phe Ile Tyr Gln Glu Lys Ile
            1140                1145                1150 gtc tat ttc gat acc cca tca gtt aat tta cac ata caa tca gaa ggt      3504
Val Tyr Phe Asp Thr Pro Ser Val Asn Leu His Ile Gln Ser Glu Gly
        1155                1160                1165 tct gaa ttt att gta agt agt atc gat cta att gaa tta tca gac gac      3552
Ser Glu Phe Ile Val Ser Ser Ile Asp Leu Ile Glu Leu Ser Asp Asp
    1170                1175                1180 caa taa                                                              3558
Gln *
1185

<210> SEQ ID NO 2
<211> LENGTH: 1185
<212> TYPE: PRT
<213> ORGANISM: Bacillus cereus/Bacillus thuringiensis
```

```
<400> SEQUENCE: 2

Met Asp Cys Asn Leu Gln Ser Gln Gln Asn Ile Pro Tyr Asn Val Leu
  1               5                  10                  15

Ala Ile Pro Val Ser Asn Val Asn Ser Leu Thr Asp Thr Val Gly Asp
             20                  25                  30

Leu Lys Lys Ala Trp Glu Glu Phe Gln Lys Thr Gly Ser Phe Ser Leu
         35                  40                  45

Thr Ala Leu Gln Gln Gly Phe Ser Ala Ser Gln Gly Gly Thr Phe Asn
     50                  55                  60

Tyr Leu Thr Leu Leu Gln Ser Gly Ile Ser Leu Ala Gly Ser Phe Val
 65                  70                  75                  80

Pro Gly Gly Thr Phe Val Ala Pro Ile Ile Asn Met Val Ile Gly Trp
                 85                  90                  95

Leu Trp Pro His Lys Asn Lys Asn Ala Asp Thr Glu Asn Leu Ile Asn
             100                 105                 110

Leu Ile Asp Ser Glu Ile Gln Lys Gln Leu Asn Lys Ala Leu Leu Asp
             115                 120                 125

Ala Asp Arg Asn Glu Trp Ser Ser Tyr Leu Glu Ser Ile Phe Asp Ser
130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                 165                 170                 175

Thr Asn Val Val Thr Asn Phe Ile Ala Ala Asp Gly Asp Ile Ala Asn
             180                 185                 190

Asn Glu Asn His Ile Met Asn Gly Asn Phe Asp Val Ala Ala Ala Pro
         195                 200                 205

Tyr Phe Val Ile Gly Ala Thr Ala Arg Phe Ala Ala Met Gln Ser Tyr
     210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                 245                 250                 255

Arg Asn Ala Ile Leu Asn Tyr Thr Gln Gln Val Met Lys Val Phe Lys
             260                 265                 270

Asp Ser Lys Asn Met Pro Thr Ile Gly Thr Asn Lys Phe Ser Val Asp
         275                 280                 285

Thr Tyr Asn Val Tyr Ile Lys Gly Met Thr Leu Asn Val Leu Asp Ile
     290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                 325                 330                 335

Glu Gly Thr Asp Gly Ser Leu Arg Ile Tyr Asn Thr Phe Asp Ser Phe
             340                 345                 350

Ser Tyr Gln His Ser Pro Ile Pro Asn Asn Val Asn Leu Ile Ser
         355                 360                 365

Tyr Tyr Asn Asp Glu Leu Gln Asn Leu Glu Leu Gly Val Tyr Thr Pro
     370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                 405                 410                 415
```

```
Leu Gly Gly Leu Ser Thr Leu Ser Ala Pro Ile Gln Val Asn Ala
            420                 425                 430

Ala Thr Gln Asn Ser Lys Tyr Leu Asp Gly Glu Ile Leu Asn Gly Ile
        435                 440                 445

Gly Ala Ser Leu Pro Gly Tyr Cys Thr Gly Cys Ser Pro Thr Glu
    450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
                485                 490                 495

Gln Ala Asn Val Lys Gly Asn Thr Gly Lys Leu Gly Val Leu Ala Ser
                500                 505                 510

Leu Val Ser Tyr Asp Leu Asn Pro Lys Asn Val Phe Gly Glu Leu Asp
            515                 520                 525

Ser Asp Thr Asn Asn Val Ile Leu Lys Gly Ile Pro Ala Glu Lys Gly
    530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575

Ala Thr Asn Leu Thr Ala Thr Gln Tyr Arg Ile Arg Ile Arg Tyr Ala
            580                 585                 590

Asn Pro Asn Ser Asn Thr Gln Ile Gly Val Arg Ile Thr Gln Asn Gly
        595                 600                 605

Ser Leu Ile Ser Ser Ser Asn Leu Thr Leu Tyr Ser Thr Thr Asp Met
    610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Thr Asn Val Leu Ser Thr Gly
                645                 650                 655

Asp Ile Thr Leu Gln Ile Thr Gly Gly Asp Gln Lys Ile Phe Ile Asp
            660                 665                 670

Arg Ile Glu Phe Val Pro Thr Met Pro Val Pro Gly Asn Thr Asn Asn
        675                 680                 685

Asn Asn Gly Asn Asn Gly Asn Asn Pro His His Val Cys
    690                 695                 700

Ala Ile Ala Gly Thr Gln Gln Ser Cys Ser Gly Pro Pro Lys Phe Glu
705                 710                 715                 720

Gln Val Ser Asp Leu Glu Lys Ile Thr Thr Gln Val Tyr Met Leu Phe
                725                 730                 735

Lys Ser Ser Pro Tyr Glu Glu Leu Ala Leu Glu Val Ser Ser Tyr Gln
            740                 745                 750

Ile Ser Gln Val Ala Leu Lys Val Met Ala Leu Ser Asp Glu Leu Phe
        755                 760                 765

Cys Glu Glu Lys Asn Val Leu Arg Lys Leu Val Asn Lys Ala Lys Gln
    770                 775                 780

Leu Leu Glu Ala Ser Asn Leu Leu Val Gly Gly Asn Phe Glu Thr Thr
785                 790                 795                 800

Gln Asn Trp Val Leu Gly Thr Asn Ala Tyr Ile Asn Tyr Asp Ser Phe
                805                 810                 815

Leu Phe Asn Gly Asn Tyr Leu Ser Leu Gln Pro Ala Ser Gly Phe Phe
            820                 825                 830

Thr Ser Tyr Ala Tyr Gln Lys Ile Asp Glu Ser Thr Leu Lys Pro Tyr
```

```
                    835                 840                 845
Thr Arg Tyr Lys Val Ser Gly Phe Ile Gly Gln Ser Asn Gln Val Glu
850                 855                 860
Leu Ile Ile Ser Arg Tyr Gly Lys Glu Ile Asp Lys Ile Leu Asn Val
865                 870                 875                 880
Pro Tyr Ala Gly Pro Leu Pro Ile Thr Ala Asp Ala Ser Ile Thr Cys
                885                 890                 895
Cys Ala Pro Glu Ile Gly Gln Cys Asp Gly Glu Gln Ser Asp Ser His
            900                 905                 910
Phe Phe Asn Tyr Ser Ile Asp Val Gly Ala Leu His Pro Glu Leu Asn
        915                 920                 925
Pro Gly Ile Glu Ile Gly Leu Lys Ile Val Gln Ser Asn Gly Tyr Ile
    930                 935                 940
Thr Ile Ser Asn Leu Glu Ile Ile Glu Glu Arg Pro Leu Thr Glu Met
945                 950                 955                 960
Glu Ile Gln Ala Val Asn Arg Lys Asn Gln Lys Trp Glu Arg Glu Lys
                965                 970                 975
Leu Leu Glu Cys Ala Ser Ile Ser Glu Leu Leu Gln Pro Ile Ile Asn
            980                 985                 990
Gln Ile Asp Ser Leu Phe Lys Asp Gly Asn Trp Tyr Asn Asp Ile Leu
        995                 1000                1005
Pro His Val Thr Tyr Gln Asp Leu Lys Asn Ile Ile Pro Glu Leu
    1010                1015                1020
Pro Lys Leu Lys His Trp Phe Ile Glu Asn Leu Pro Gly Glu Tyr His
1025                1030                1035                1040
Glu Ile Glu Gln Lys Met Lys Glu Ala Leu Lys Tyr Ala Phe Thr Gln
                1045                1050                1055
Leu Asp Glu Lys Asn Leu Ile His Asn Gly His Phe Thr Thr Asn Leu
            1060                1065                1070
Ile Asp Trp Gln Val Glu Gly Asp Ala Gln Met Lys Val Leu Glu Asn
        1075                1080                1085
Asp Ala Leu Ala Leu Gln Leu Phe Asn Trp Asp Ala Ser Ala Ser Gln
    1090                1095                1100
Ser Ile Asn Ile Leu Glu Phe Asp Glu Asp Lys Ala Tyr Lys Leu Arg
1105                1110                1115                1120
Val Tyr Ala Gln Gly Ser Gly Thr Ile Gln Phe Gly Asn Cys Glu Asp
                1125                1130                1135
Glu Ala Ile Gln Phe Asn Thr Asn Ser Phe Ile Tyr Gln Glu Lys Ile
            1140                1145                1150
Val Tyr Phe Asp Thr Pro Ser Val Asn Leu His Ile Gln Ser Glu Gly
        1155                1160                1165
Ser Glu Phe Ile Val Ser Ser Ile Asp Leu Ile Glu Leu Ser Asp Asp
    1170                1175                1180
Gln
1185

<210> SEQ ID NO 3
<211> LENGTH: 3984
<212> TYPE: DNA
<213> ORGANISM: Unknown
<220> FEATURE:
<223> OTHER INFORMATION: Isolated from soil sample
<220> FEATURE:
<221> NAME/KEY: CDS
<222> LOCATION: (1)...(3984)

<400> SEQUENCE: 3
```

```
atg gca aca ctt aat aat atg ttt tca gtt cct tat aat gta cta gct        48
Met Ala Thr Leu Asn Asn Met Phe Ser Val Pro Tyr Asn Val Leu Ala
1               5                   10                  15 cta ccc att atc ccc aat tct atc tta act ttt gaa gat aat cga aaa        96
Leu Pro Ile Ile Pro Asn Ser Ile Leu Thr Phe Glu Asp Asn Arg Lys
            20                  25                  30 aaa ata gaa gag ggt att aaa gag ttt gaa aag act gga cgt ata aaa       144
Lys Ile Glu Glu Gly Ile Lys Glu Phe Glu Lys Thr Gly Arg Ile Lys
        35                  40                  45 ccc ctt aaa gat tta ata gag ctc ata ttc aaa ggg tat agt gac gat       192
Pro Leu Lys Asp Leu Ile Glu Leu Ile Phe Lys Gly Tyr Ser Asp Asp
    50                  55                  60 gaa tct tct tac gca gca tta gtt caa act atg ctt gtc gtt att ccc       240
Glu Ser Ser Tyr Ala Ala Leu Val Gln Thr Met Leu Val Val Ile Pro
65              70                  75                  80 ttg gcg ttc cct gaa tta gcc cca gtt ctt cca att att ggc gta gta       288
Leu Ala Phe Pro Glu Leu Ala Pro Val Leu Pro Ile Ile Gly Val Val
            85                  90                  95 att aat ttc gtt ttt cca ggt ttg aag ggt tct gct aaa tca acc tat       336
Ile Asn Phe Val Phe Pro Gly Leu Lys Gly Ser Ala Lys Ser Thr Tyr
        100                 105                 110 aca atg att aca gag atg gtt gat aaa gcc att aac caa tca ttc acg       384
Thr Met Ile Thr Glu Met Val Asp Lys Ala Ile Asn Gln Ser Phe Thr
    115                 120                 125 gcc cag att aca aat ata tta aca aac aat att act ggt ata caa aat       432
Ala Gln Ile Thr Asn Ile Leu Thr Asn Asn Ile Thr Gly Ile Gln Asn
130                 135                 140 aat ata caa tct gtt tac gac gca atg agc aat gcc att gga aca aat       480
Asn Ile Gln Ser Val Tyr Asp Ala Met Ser Asn Ala Ile Gly Thr Asn
145                 150                 155                 160 gac aca att cat aat ttc atc aga aat aat gat aca aca cct tgc tct       528
Asp Thr Ile His Asn Phe Ile Arg Asn Asn Asp Thr Thr Pro Cys Ser
            165                 170                 175 caa aac aat cag cca gct tgt cct tgt cct cca aat aat caa tgt tta       576
Gln Asn Asn Gln Pro Ala Cys Pro Cys Pro Pro Asn Asn Gln Cys Leu
        180                 185                 190 caa aaa gtt gtt gat gaa tat act aaa gca ata gct aat atc gat ctc       624
Gln Lys Val Val Asp Glu Tyr Thr Lys Ala Ile Ala Asn Ile Asp Leu
    195                 200                 205 att atc cct caa ttt cat gat cca ctt act ggt gta att tcc gat tta       672
Ile Ile Pro Gln Phe His Asp Pro Leu Thr Gly Val Ile Ser Asp Leu
210                 215                 220 gct act gca aac atg tat att tta cct tta tac gct caa act gtt aat       720
Ala Thr Ala Asn Met Tyr Ile Leu Pro Leu Tyr Ala Gln Thr Val Asn
225                 230                 235                 240 tta aaa tta att ttg cgt cag agt ttc att gaa ttt atg gag aaa tat       768
Leu Lys Leu Ile Leu Arg Gln Ser Phe Ile Glu Phe Met Glu Lys Tyr
            245                 250                 255 aaa tat gat gaa aaa gaa act gtt ttt cag gct ttt att aat gct gat       816
Lys Tyr Asp Glu Lys Glu Thr Val Phe Gln Ala Phe Ile Asn Ala Asp
        260                 265                 270 att cca gaa caa att aaa aaa ctt cgt caa gat att atc acg tat aca       864
Ile Pro Glu Gln Ile Lys Lys Leu Arg Gln Asp Ile Ile Thr Tyr Thr
    275                 280                 285 aaa gat att tat atg caa ttt gaa gct cac gct ccc tac ccg act tat       912
Lys Asp Ile Tyr Met Gln Phe Glu Ala His Ala Pro Tyr Pro Thr Tyr
290                 295                 300 aat tca aaa aaa caa cta aat gac tat atc cgt tat aca aga att atc       960
Asn Ser Lys Lys Gln Leu Asn Asp Tyr Ile Arg Tyr Thr Arg Ile Ile
305                 310                 315                 320
```

```
caa gta tat tgt ttg gat tta gta gca atg tgg cct acg ctt gat cga    1008
Gln Val Tyr Cys Leu Asp Leu Val Ala Met Trp Pro Thr Leu Asp Arg
                325                 330                 335 gtg aat tat gca tta cct gtc caa caa aat atg aca cgc att ata ttt    1056
Val Asn Tyr Ala Leu Pro Val Gln Gln Asn Met Thr Arg Ile Ile Phe
            340                 345                 350 gga gat ctt att ggc cct gta gaa act gtg cct cag gtt ccc cgc caa    1104
Gly Asp Leu Ile Gly Pro Val Glu Thr Val Pro Gln Val Pro Arg Gln
        355                 360                 365 aat tca gat aac ttt cat ttt aat ttg tct gat gtt tat aga aac ccc    1152
Asn Ser Asp Asn Phe His Phe Asn Leu Ser Asp Val Tyr Arg Asn Pro
    370                 375                 380 tta cct aat aat gat att ttt aat tac cgt tat ggc ggg ctt caa att    1200
Leu Pro Asn Asn Asp Ile Phe Asn Tyr Arg Tyr Gly Gly Leu Gln Ile
385                 390                 395                 400 tct aaa gcg caa ttt atg aca tat tat aaa aaa ttc gga gct ttc agt    1248
Ser Lys Ala Gln Phe Met Thr Tyr Tyr Lys Lys Phe Gly Ala Phe Ser
                405                 410                 415 acc cat gat gaa tat tat tat gta gat ggg cat cgc cta agt ttt aat    1296
Thr His Asp Glu Tyr Tyr Tyr Val Asp Gly His Arg Leu Ser Phe Asn
            420                 425                 430 act tca gat aaa aaa aca att gaa atc aat gct cat caa aat tct cat    1344
Thr Ser Asp Lys Lys Thr Ile Glu Ile Asn Ala His Gln Asn Ser His
        435                 440                 445 gat act att gaa aag gat gta ata gat caa cta ggc ggc tat gtt aca    1392
Asp Thr Ile Glu Lys Asp Val Ile Asp Gln Leu Gly Gly Tyr Val Thr
    450                 455                 460 cgt atg aat atg gta agt caa gaa atc ggt agt ggc agt ata ttg ggt    1440
Arg Met Asn Met Val Ser Gln Glu Ile Gly Ser Gly Ser Ile Leu Gly
465                 470                 475                 480 gga aat gcc ata gat cga act gcc ctt act acc agt aca ggt gat aaa    1488
Gly Asn Ala Ile Asp Arg Thr Ala Leu Thr Thr Ser Thr Gly Asp Lys
                485                 490                 495 gac ata ctt gct gca gga ttt aac gcg ata aat aat gga aat tac aag    1536
Asp Ile Leu Ala Ala Gly Phe Asn Ala Ile Asn Asn Gly Asn Tyr Lys
            500                 505                 510 aca gaa ggt cgc ggt gcc tcc cat aat cag gat gtt cca aat cat aaa    1584
Thr Glu Gly Arg Gly Ala Ser His Asn Gln Asp Val Pro Asn His Lys
        515                 520                 525 gtt caa gcg att tat cct gtt caa ccg aat aaa tat gaa tat gac gat    1632
Val Gln Ala Ile Tyr Pro Val Gln Pro Asn Lys Tyr Glu Tyr Asp Asp
    530                 535                 540 tat gga tct gaa gaa aag tat gga tac ctt tat act tta att cca atg    1680
Tyr Gly Ser Glu Glu Lys Tyr Gly Tyr Leu Tyr Thr Leu Ile Pro Met
545                 550                 555                 560 gat gtg agt ttc att ccc caa ctc aat gca gaa gat gta att act act    1728
Asp Val Ser Phe Ile Pro Gln Leu Asn Ala Glu Asp Val Ile Thr Thr
                565                 570                 575 att cct gca gaa caa gca gtc aaa att aat ggt caa tct gta ata gat    1776
Ile Pro Ala Glu Gln Ala Val Lys Ile Asn Gly Gln Ser Val Ile Asp
            580                 585                 590 act gta aac acc aat tct tta ttg gaa ttt gtt aat ggt gca aat gca    1824
Thr Val Asn Thr Asn Ser Leu Leu Glu Phe Val Asn Gly Ala Asn Ala
        595                 600                 605 att aaa cta tct cct ggc gaa aca gca caa tac act atg att aat ccc    1872
Ile Lys Leu Ser Pro Gly Glu Thr Ala Gln Tyr Thr Met Ile Asn Pro
    610                 615                 620 gtc aat cgt tcc tac cag gtt aga gtt cgg gtt gct act gaa gga gaa    1920
Val Asn Arg Ser Tyr Gln Val Arg Val Arg Val Ala Thr Glu Gly Glu
625                 630                 635                 640
```

|     |     |     |     |     |     |     |     |     |     |     |     |     |     |     |     | |
|---|---|---|---|---|---|---|---|---|---|---|---|---|---|---|---|---|
| acc | caa | tta | gat | att | ata | gca | ccc | gtt | gat | agc | aat | acc | ctt | aat | ctt | 1968 |
| Thr | Gln | Leu | Asp | Ile | Ile | Ala | Pro | Val | Asp | Ser | Asn | Thr | Leu | Asn | Leu | |
|     |     |     |     | 645 |     |     |     |     | 650 |     |     |     |     | 655 |     | |
| tca | aac | aca | aaa | aca | aca | gca | aat | gat | caa | aat | ggg | ata | tta | ggt | aaa | 2016 |
| Ser | Asn | Thr | Lys | Thr | Thr | Ala | Asn | Asp | Gln | Asn | Gly | Ile | Leu | Gly | Lys | |
|     |     |     | 660 |     |     |     |     | 665 |     |     |     |     | 670 |     |     | |
| caa | ggt | aat | tat | ata | gta | ttt | cca | cag | cca | aac | att | gat | act | gtc | aca | 2064 |
| Gln | Gly | Asn | Tyr | Ile | Val | Phe | Pro | Gln | Pro | Asn | Ile | Asp | Thr | Val | Thr | |
|     |     |     | 675 |     |     |     |     | 680 |     |     |     |     | 685 |     |     | |
| ggc | acc | agt | tta | cct | cct | acc | gaa | aac | att | atg | aat | ttt | cca | gta | gga | 2112 |
| Gly | Thr | Ser | Leu | Pro | Pro | Thr | Glu | Asn | Ile | Met | Asn | Phe | Pro | Val | Gly | |
|     | 690 |     |     |     |     | 695 |     |     |     |     | 700 |     |     |     |     | |
| aca | ttt | gat | ttt | acc | att | gta | aat | tct | gga | aac | tca | gat | act | att | tta | 2160 |
| Thr | Phe | Asp | Phe | Thr | Ile | Val | Asn | Ser | Gly | Asn | Ser | Asp | Thr | Ile | Leu | |
| 705 |     |     |     |     | 710 |     |     |     |     | 715 |     |     |     |     | 720 | |
| gat | cga | att | gaa | ttt | gtt | cct | att | gta | act | tct | aat | aaa | att | caa | caa | 2208 |
| Asp | Arg | Ile | Glu | Phe | Val | Pro | Ile | Val | Thr | Ser | Asn | Lys | Ile | Gln | Gln | |
|     |     |     |     | 725 |     |     |     |     | 730 |     |     |     |     | 735 |     | |
| gat | ttc | act | att | tct | cct | gga | aca | agt | caa | gta | att | tgg | acc | gga | aat | 2256 |
| Asp | Phe | Thr | Ile | Ser | Pro | Gly | Thr | Ser | Gln | Val | Ile | Trp | Thr | Gly | Asn | |
|     |     |     | 740 |     |     |     |     | 745 |     |     |     |     | 750 |     |     | |
| tca | gct | aac | act | ata | gat | att | aca | att | att | gac | aac | gta | gat | aca | agc | 2304 |
| Ser | Ala | Asn | Thr | Ile | Asp | Ile | Thr | Ile | Ile | Asp | Asn | Val | Asp | Thr | Ser | |
|     |     |     | 755 |     |     |     |     | 760 |     |     |     |     | 765 |     |     | |
| ggt | tta | ttc | gtt | caa | att | ttc | caa | aaa | ggt | aag | caa | ctg | cat | gga | gaa | 2352 |
| Gly | Leu | Phe | Val | Gln | Ile | Phe | Gln | Lys | Gly | Lys | Gln | Leu | His | Gly | Glu | |
|     | 770 |     |     |     |     | 775 |     |     |     |     | 780 |     |     |     |     | |
| cta | act | ttg | att | gat | ccc | gct | cat | att | caa | cgt | aca | ttc | tct | gaa | aaa | 2400 |
| Leu | Thr | Leu | Ile | Asp | Pro | Ala | His | Ile | Gln | Arg | Thr | Phe | Ser | Glu | Lys | |
| 785 |     |     |     |     | 790 |     |     |     |     | 795 |     |     |     |     | 800 | |
| ttt | gat | caa | att | gtt | ttg | tat | aac | cca | ggt | tat | aat | agt | tct | ata | tct | 2448 |
| Phe | Asp | Gln | Ile | Val | Leu | Tyr | Asn | Pro | Gly | Tyr | Asn | Ser | Ser | Ile | Ser | |
|     |     |     |     | 805 |     |     |     |     | 810 |     |     |     |     | 815 |     | |
| ggt | aca | gtg | agt | ggt | tca | gta | agc | tct | att | cct | aag | aaa | ttc | gaa | tta | 2496 |
| Gly | Thr | Val | Ser | Gly | Ser | Val | Ser | Ser | Ile | Pro | Lys | Lys | Phe | Glu | Leu | |
|     |     |     | 820 |     |     |     |     | 825 |     |     |     |     | 830 |     |     | |
| tct | agc | gac | tta | caa | aat | atc | aca | aac | caa | gtt | aat | aac | tta | ttt | gca | 2544 |
| Ser | Ser | Asp | Leu | Gln | Asn | Ile | Thr | Asn | Gln | Val | Asn | Asn | Leu | Phe | Ala | |
|     |     |     | 835 |     |     |     |     | 840 |     |     |     |     | 845 |     |     | |
| tcg | agc | gaa | cat | gat | aca | ctt | gcc | aca | gat | gta | agt | gat | tat | gat | att | 2592 |
| Ser | Ser | Glu | His | Asp | Thr | Leu | Ala | Thr | Asp | Val | Ser | Asp | Tyr | Asp | Ile | |
|     | 850 |     |     |     |     | 855 |     |     |     |     | 860 |     |     |     |     | |
| gaa | gaa | gtg | att | cta | aaa | gta | gat | gca | tta | tct | gat | gaa | gtg | ttt | gga | 2640 |
| Glu | Glu | Val | Ile | Leu | Lys | Val | Asp | Ala | Leu | Ser | Asp | Glu | Val | Phe | Gly | |
| 865 |     |     |     |     | 870 |     |     |     |     | 875 |     |     |     |     | 880 | |
| aaa | gag | aaa | aaa | gca | cta | cgt | aaa | ttg | gta | aat | caa | gcg | aag | cgt | tta | 2688 |
| Lys | Glu | Lys | Lys | Ala | Leu | Arg | Lys | Leu | Val | Asn | Gln | Ala | Lys | Arg | Leu | |
|     |     |     |     | 885 |     |     |     |     | 890 |     |     |     |     | 895 |     | |
| agt | aaa | gcg | cgt | aat | ctt | ctc | cta | gga | gga | agt | ttt | gat | aat | ttg | gat | 2736 |
| Ser | Lys | Ala | Arg | Asn | Leu | Leu | Leu | Gly | Gly | Ser | Phe | Asp | Asn | Leu | Asp | |
|     |     |     | 900 |     |     |     |     | 905 |     |     |     |     | 910 |     |     | |
| gct | tgg | tat | agg | gga | cga | aat | gta | gta | act | gta | tct | gat | cat | gaa | ctg | 2784 |
| Ala | Trp | Tyr | Arg | Gly | Arg | Asn | Val | Val | Thr | Val | Ser | Asp | His | Glu | Leu | |
|     |     |     | 915 |     |     |     |     | 920 |     |     |     |     | 925 |     |     | |
| ttt | aaa | agt | gat | cat | ata | tta | tta | cca | cta | cca | aca | aca | ttg | tat | cca | 2832 |
| Phe | Lys | Ser | Asp | His | Ile | Leu | Leu | Pro | Leu | Pro | Thr | Thr | Leu | Tyr | Pro | |
|     |     |     | 930 |     |     |     |     | 935 |     |     |     |     | 940 |     |     | |
| tct | tat | ctt | ttc | caa | aaa | gta | gag | gaa | tct | aaa | tta | aaa | gca | aat | aca | 2880 |
| Ser | Tyr | Leu | Phe | Gln | Lys | Val | Glu | Glu | Ser | Lys | Leu | Lys | Ala | Asn | Thr | |
| 945 |     |     |     |     | 950 |     |     |     |     | 955 |     |     |     |     | 960 | |

```
cgt tat act gtc tct ggt ttc atc gcg cat gca gag gat tta gaa att    2928
Arg Tyr Thr Val Ser Gly Phe Ile Ala His Ala Glu Asp Leu Glu Ile
                965                 970                 975 gtt gtt tct cgt tat ggg caa gaa ata aag aaa gtg gtg caa gtt cca    2976
Val Val Ser Arg Tyr Gly Gln Glu Ile Lys Lys Val Val Gln Val Pro
            980                 985                 990 tat ggt gaa gca ttc cca ttg aca tcg agc gga cca att tgt tgt aga    3024
Tyr Gly Glu Ala Phe Pro Leu Thr Ser Ser Gly Pro Ile Cys Cys Arg
        995                 1000                1005 cca cgt tct aga gta aat ggt aaa cct gct gat cca cat ttc ttt agt    3072
Pro Arg Ser Arg Val Asn Gly Lys Pro Ala Asp Pro His Phe Phe Ser
    1010                1015                1020 tac agc att gat gta ggt gca tta gat gtg gaa gca aat cct ggt att    3120
Tyr Ser Ile Asp Val Gly Ala Leu Asp Val Glu Ala Asn Pro Gly Ile
1025                1030                1035                1040 gaa tta ggg ttt cgt att gta gag cca act gga atg gca cgt gta agt    3168
Glu Leu Gly Phe Arg Ile Val Glu Pro Thr Gly Met Ala Arg Val Ser
                1045                1050                1055 aac tta gaa att cgt gag gat cgc cca tta acg gca aat gaa ata cgt    3216
Asn Leu Glu Ile Arg Glu Asp Arg Pro Leu Thr Ala Asn Glu Ile Arg
            1060                1065                1070 aag gtg caa cgt gct gct aga gat tgg aaa caa aag tat gat caa gag    3264
Lys Val Gln Arg Ala Ala Arg Asp Trp Lys Gln Lys Tyr Asp Gln Glu
        1075                1080                1085 cgt gcg gaa gta aga gcc ctg att caa cct gtt tta aat caa atc aat    3312
Arg Ala Glu Val Arg Ala Leu Ile Gln Pro Val Leu Asn Gln Ile Asn
    1090                1095                1100 gcg ttg tat gaa aat gaa gat tgg aat gga gca att cgt tct gga gtt    3360
Ala Leu Tyr Glu Asn Glu Asp Trp Asn Gly Ala Ile Arg Ser Gly Val
1105                1110                1115                1120 tct tat cat gac tta gaa gca att gtt tta cca aca tta cca aaa tta    3408
Ser Tyr His Asp Leu Glu Ala Ile Val Leu Pro Thr Leu Pro Lys Leu
                1125                1130                1135 aat cat tgg ttt atg tcc gat atg tta ggg gaa caa ggt tcc att tta    3456
Asn His Trp Phe Met Ser Asp Met Leu Gly Glu Gln Gly Ser Ile Leu
            1140                1145                1150 gct caa ttc caa gaa gca tta aat cgt gcg tat acg caa ctc gaa gga    3504
Ala Gln Phe Gln Glu Ala Leu Asn Arg Ala Tyr Thr Gln Leu Glu Gly
        1155                1160                1165 agt aca att ctg cat aat ggc cat ttc aca aca gat gca gca aat tgg    3552
Ser Thr Ile Leu His Asn Gly His Phe Thr Thr Asp Ala Ala Asn Trp
    1170                1175                1180 acg ata gaa ggc gat gca cat cag gta gta tta gaa gat ggt aga cgt    3600
Thr Ile Glu Gly Asp Ala His Gln Val Val Leu Glu Asp Gly Arg Arg
1185                1190                1195                1200 gta tta cga ttg cca gat tgg tct tcg agt ttg tct caa acg att gaa    3648
Val Leu Arg Leu Pro Asp Trp Ser Ser Ser Leu Ser Gln Thr Ile Glu
                1205                1210                1215 atc gag aat ttt gat cca gat aaa gaa tat caa tta gta ttt cat ggg    3696
Ile Glu Asn Phe Asp Pro Asp Lys Glu Tyr Gln Leu Val Phe His Gly
            1220                1225                1230 caa gga gaa gga acg gtt acg ttg gag cat ggt gaa gaa gga gaa tat    3744
Gln Gly Glu Gly Thr Val Thr Leu Glu His Gly Glu Glu Gly Glu Tyr
        1235                1240                1245 gtg gaa aca cac ccg cat aag ttt gcg aat ttt aca act tct caa cgt    3792
Val Glu Thr His Pro His Lys Phe Ala Asn Phe Thr Thr Ser Gln Arg
    1250                1255                1260 caa gga att acg ttt gaa tca aat aaa gtg aca gtg act att tct tca    3840
Gln Gly Ile Thr Phe Glu Ser Asn Lys Val Thr Val Thr Ile Ser Ser
1265                1270                1275                1280
```

-continued

```
gaa gat gga gaa ttc tta gcg gat aat att gca att gtg gaa gtt cct    3888
Glu Asp Gly Glu Phe Leu Ala Asp Asn Ile Ala Ile Val Glu Val Pro
            1285                1290                1295 atg ttt aac aag aat caa atg gtc aat gaa aat aga ggt gta aat ata    3936
Met Phe Asn Lys Asn Gln Met Val Asn Glu Asn Arg Gly Val Asn Ile
        1300                1305                1310 aat agc aat aca aat atg aat agt agc aat aac agc aat aac caa taa    3984
Asn Ser Asn Thr Asn Met Asn Ser Ser Asn Asn Ser Asn Asn Gln *
        1315                1320                1325
```

<210> SEQ ID NO 4
<211> LENGTH: 1327
<212> TYPE: PRT
<213> ORGANISM: Unknown
<220> FEATURE:
<223> OTHER INFORMATION: Isolated from soil sample

<400> SEQUENCE: 4

```
Met Ala Thr Leu Asn Asn Met Phe Ser Val Pro Tyr Asn Val Leu Ala
  1               5                  10                  15

Leu Pro Ile Ile Pro Asn Ser Ile Leu Thr Phe Glu Asp Asn Arg Lys
             20                  25                  30

Lys Ile Glu Glu Gly Ile Lys Glu Phe Glu Lys Thr Gly Arg Ile Lys
         35                  40                  45

Pro Leu Lys Asp Leu Ile Glu Leu Ile Phe Lys Gly Tyr Ser Asp Asp
     50                  55                  60

Glu Ser Ser Tyr Ala Ala Leu Val Gln Thr Met Leu Val Val Ile Pro
 65                  70                  75                  80

Leu Ala Phe Pro Glu Leu Ala Pro Val Leu Pro Ile Ile Gly Val Val
                 85                  90                  95

Ile Asn Phe Val Phe Pro Gly Leu Lys Gly Ser Ala Lys Ser Thr Tyr
            100                 105                 110

Thr Met Ile Thr Glu Met Val Asp Lys Ala Ile Asn Gln Ser Phe Thr
        115                 120                 125

Ala Gln Ile Thr Asn Ile Leu Thr Asn Asn Ile Thr Gly Ile Gln Asn
    130                 135                 140

Asn Ile Gln Ser Val Tyr Asp Ala Met Ser Asn Ala Ile Gly Thr Asn
145                 150                 155                 160

Asp Thr Ile His Asn Phe Ile Arg Asn Asn Asp Thr Thr Pro Cys Ser
                165                 170                 175

Gln Asn Asn Gln Pro Ala Cys Pro Cys Pro Asn Asn Gln Cys Leu
            180                 185                 190

Gln Lys Val Val Asp Glu Tyr Thr Lys Ala Ile Ala Asn Ile Asp Leu
        195                 200                 205

Ile Ile Pro Gln Phe His Asp Pro Leu Thr Gly Val Ile Ser Asp Leu
    210                 215                 220

Ala Thr Ala Asn Met Tyr Ile Leu Pro Leu Tyr Ala Gln Thr Val Asn
225                 230                 235                 240

Leu Lys Leu Ile Leu Arg Gln Ser Phe Ile Glu Phe Met Glu Lys Tyr
                245                 250                 255

Lys Tyr Asp Glu Lys Glu Thr Val Phe Gln Ala Phe Ile Asn Ala Asp
            260                 265                 270

Ile Pro Glu Gln Ile Lys Lys Leu Arg Gln Asp Ile Thr Tyr Thr
        275                 280                 285

Lys Asp Ile Tyr Met Gln Phe Glu Ala His Ala Pro Tyr Pro Thr Tyr
    290                 295                 300
```

```
Asn Ser Lys Lys Gln Leu Asn Asp Tyr Ile Arg Tyr Thr Arg Ile Ile
305                 310                 315                 320

Gln Val Tyr Cys Leu Asp Leu Val Ala Met Trp Pro Thr Leu Asp Arg
            325                 330                 335

Val Asn Tyr Ala Leu Pro Val Gln Gln Asn Met Thr Arg Ile Ile Phe
                340                 345                 350

Gly Asp Leu Ile Gly Pro Val Glu Thr Val Pro Gln Val Pro Arg Gln
            355                 360                 365

Asn Ser Asp Asn Phe His Phe Asn Leu Ser Asp Val Tyr Arg Asn Pro
        370                 375                 380

Leu Pro Asn Asn Asp Ile Phe Asn Tyr Arg Tyr Gly Gly Leu Gln Ile
385                 390                 395                 400

Ser Lys Ala Gln Phe Met Thr Tyr Tyr Lys Lys Phe Gly Ala Phe Ser
                405                 410                 415

Thr His Asp Glu Tyr Tyr Val Asp Gly His Arg Leu Ser Phe Asn
                420                 425                 430

Thr Ser Asp Lys Lys Thr Ile Glu Ile Asn Ala His Gln Asn Ser His
            435                 440                 445

Asp Thr Ile Glu Lys Asp Val Ile Asp Gln Leu Gly Gly Tyr Val Thr
        450                 455                 460

Arg Met Asn Met Val Ser Gln Glu Ile Gly Ser Gly Ser Ile Leu Gly
465                 470                 475                 480

Gly Asn Ala Ile Asp Arg Thr Ala Leu Thr Thr Ser Thr Gly Asp Lys
                485                 490                 495

Asp Ile Leu Ala Ala Gly Phe Asn Ala Ile Asn Asn Gly Asn Tyr Lys
            500                 505                 510

Thr Glu Gly Arg Gly Ala Ser His Asn Gln Asp Val Pro Asn His Lys
        515                 520                 525

Val Gln Ala Ile Tyr Pro Val Gln Pro Asn Lys Tyr Glu Tyr Asp Asp
        530                 535                 540

Tyr Gly Ser Glu Glu Lys Tyr Gly Tyr Leu Tyr Thr Leu Ile Pro Met
545                 550                 555                 560

Asp Val Ser Phe Ile Pro Gln Leu Asn Ala Glu Asp Val Ile Thr Thr
                565                 570                 575

Ile Pro Ala Glu Gln Ala Val Lys Ile Asn Gly Gln Ser Val Ile Asp
            580                 585                 590

Thr Val Asn Thr Asn Ser Leu Leu Glu Phe Val Asn Gly Ala Asn Ala
        595                 600                 605

Ile Lys Leu Ser Pro Gly Glu Thr Ala Gln Tyr Thr Met Ile Asn Pro
        610                 615                 620

Val Asn Arg Ser Tyr Gln Val Arg Val Arg Val Ala Thr Glu Gly Glu
625                 630                 635                 640

Thr Gln Leu Asp Ile Ile Ala Pro Val Asp Ser Asn Thr Leu Asn Leu
                645                 650                 655

Ser Asn Thr Lys Thr Thr Ala Asn Asp Gln Asn Gly Ile Leu Gly Lys
            660                 665                 670

Gln Gly Asn Tyr Ile Val Phe Pro Gln Pro Asn Ile Asp Thr Val Thr
        675                 680                 685

Gly Thr Ser Leu Pro Pro Thr Glu Asn Ile Met Asn Phe Pro Val Gly
690                 695                 700

Thr Phe Asp Phe Thr Ile Val Asn Ser Gly Asn Ser Asp Thr Ile Leu
705                 710                 715                 720

Asp Arg Ile Glu Phe Val Pro Ile Val Thr Ser Asn Lys Ile Gln Gln
                725                 730                 735
```

-continued

```
Asp Phe Thr Ile Ser Pro Gly Thr Ser Gln Val Ile Trp Thr Gly Asn
            740                 745                 750
Ser Ala Asn Thr Ile Asp Ile Thr Ile Ile Asp Asn Val Asp Thr Ser
            755                 760                 765
Gly Leu Phe Val Gln Ile Phe Gln Lys Gly Lys Gln Leu His Gly Glu
            770                 775                 780
Leu Thr Leu Ile Asp Pro Ala His Ile Gln Arg Thr Phe Ser Glu Lys
785                 790                 795                 800
Phe Asp Gln Ile Val Leu Tyr Asn Pro Gly Tyr Asn Ser Ser Ile Ser
                805                 810                 815
Gly Thr Val Ser Gly Ser Val Ser Ile Pro Lys Lys Phe Glu Leu
            820                 825                 830
Ser Ser Asp Leu Gln Asn Ile Thr Asn Gln Val Asn Asn Leu Phe Ala
            835                 840                 845
Ser Ser Glu His Asp Thr Leu Ala Thr Asp Val Ser Asp Tyr Asp Ile
            850                 855                 860
Glu Val Ile Leu Lys Val Asp Ala Leu Ser Asp Glu Val Phe Gly
865                 870                 875                 880
Lys Glu Lys Lys Ala Leu Arg Lys Leu Val Asn Gln Ala Lys Arg Leu
                885                 890                 895
Ser Lys Ala Arg Asn Leu Leu Leu Gly Gly Ser Phe Asp Asn Leu Asp
            900                 905                 910
Ala Trp Tyr Arg Gly Arg Asn Val Val Thr Val Ser Asp His Glu Leu
            915                 920                 925
Phe Lys Ser Asp His Ile Leu Leu Pro Leu Pro Thr Thr Leu Tyr Pro
            930                 935                 940
Ser Tyr Leu Phe Gln Lys Val Glu Glu Ser Lys Leu Lys Ala Asn Thr
945                 950                 955                 960
Arg Tyr Thr Val Ser Gly Phe Ile Ala His Ala Glu Asp Leu Glu Ile
                965                 970                 975
Val Val Ser Arg Tyr Gly Gln Glu Ile Lys Lys Val Val Gln Val Pro
            980                 985                 990
Tyr Gly Glu Ala Phe Pro Leu Thr Ser Ser Gly Pro Ile Cys Cys Arg
            995                 1000                1005
Pro Arg Ser Arg Val Asn Gly Lys Pro Ala Asp Pro His Phe Phe Ser
            1010                1015                1020
Tyr Ser Ile Asp Val Gly Ala Leu Asp Val Glu Ala Asn Pro Gly Ile
1025                1030                1035                1040
Glu Leu Gly Phe Arg Ile Val Glu Pro Thr Gly Met Ala Arg Val Ser
                1045                1050                1055
Asn Leu Glu Ile Arg Glu Asp Arg Pro Leu Thr Ala Asn Glu Ile Arg
            1060                1065                1070
Lys Val Gln Arg Ala Ala Arg Asp Trp Lys Gln Lys Tyr Asp Gln Glu
            1075                1080                1085
Arg Ala Glu Val Arg Ala Leu Ile Gln Pro Val Leu Asn Gln Ile Asn
            1090                1095                1100
Ala Leu Tyr Glu Asn Glu Asp Trp Asn Gly Ala Ile Arg Ser Gly Val
1105                1110                1115                1120
Ser Tyr His Asp Leu Glu Ala Ile Val Leu Pro Thr Leu Pro Lys Leu
                1125                1130                1135
Asn His Trp Phe Met Ser Asp Met Leu Gly Glu Gln Gly Ser Ile Leu
            1140                1145                1150
Ala Gln Phe Gln Glu Ala Leu Asn Arg Ala Tyr Thr Gln Leu Glu Gly
```

```
                1155                1160                1165
Ser Thr Ile Leu His Asn Gly His Phe Thr Asp Ala Ala Asn Trp
    1170                1175                1180

Thr Ile Glu Gly Asp Ala His Gln Val Val Leu Glu Asp Gly Arg Arg
1185                1190                1195                1200

Val Leu Arg Leu Pro Asp Trp Ser Ser Leu Ser Gln Thr Ile Glu
                1205                1210                1215

Ile Glu Asn Phe Asp Pro Asp Lys Glu Tyr Gln Leu Val Phe His Gly
        1220                1225                1230

Gln Gly Glu Gly Thr Val Thr Leu Glu His Gly Glu Gly Glu Tyr
            1235                1240                1245

Val Glu Thr His Pro His Lys Phe Ala Asn Phe Thr Thr Ser Gln Arg
    1250                1255                1260

Gln Gly Ile Thr Phe Glu Ser Asn Lys Val Thr Val Thr Ile Ser Ser
1265                1270                1275                1280

Glu Asp Gly Glu Phe Leu Ala Asp Asn Ile Ala Ile Val Glu Val Pro
                1285                1290                1295

Met Phe Asn Lys Asn Gln Met Val Asn Glu Asn Arg Gly Val Asn Ile
            1300                1305                1310

Asn Ser Asn Thr Asn Met Asn Ser Ser Asn Asn Ser Asn Asn Gln
        1315                1320                1325

<210> SEQ ID NO 5
<211> LENGTH: 3720
<212> TYPE: DNA
<213> ORGANISM: Unknown
<220> FEATURE:
<223> OTHER INFORMATION: Isolated from soil sample
<220> FEATURE:
<221> NAME/KEY: CDS
<222> LOCATION: (1)...(3720)

<400> SEQUENCE: 5 atg aat gat atg aca aat tta tct aaa tta tat tca cct gta cca tac     48
Met Asn Asp Met Thr Asn Leu Ser Lys Leu Tyr Ser Pro Val Pro Tyr
  1               5                  10                  15 aat gtg tta gca act cca aat gtc tta gca aca aac aaa caa cca cta     96
Asn Val Leu Ala Thr Pro Asn Val Leu Ala Thr Asn Lys Gln Pro Leu
             20                  25                  30 gca gat aca gat gca tta aat aaa ttt tac aac gat ttg caa att gga    144
Ala Asp Thr Asp Ala Leu Asn Lys Phe Tyr Asn Asp Leu Gln Ile Gly
         35                  40                  45 aaa gtt tca gct ttt aca att gat gca tta tgg agc ctt atg aca acc    192
Lys Val Ser Ala Phe Thr Ile Asp Ala Leu Trp Ser Leu Met Thr Thr
     50                  55                  60 gga aaa tat gac tgg tcg tca att gct aaa ttt tgt tgg tct ctt gga    240
Gly Lys Tyr Asp Trp Ser Ser Ile Ala Lys Phe Cys Trp Ser Leu Gly
 65                  70                  75                  80 act ggt gta aca cct ctg tta ggt ata ttt tca cct att ata gat ata    288
Thr Gly Val Thr Pro Leu Leu Gly Ile Phe Ser Pro Ile Ile Asp Ile
                 85                  90                  95 att ttc cct gct tta ttc ggt ggt aac aaa cta agt cta ttt gaa caa    336
Ile Phe Pro Ala Leu Phe Gly Gly Asn Lys Leu Ser Leu Phe Glu Gln
            100                 105                 110 cta aaa cct caa ata gaa aaa ctg att att gaa aaa tta aca gat gaa    384
Leu Lys Pro Gln Ile Glu Lys Leu Ile Ile Glu Lys Leu Thr Asp Glu
        115                 120                 125 gaa aaa aat ttc tta gct caa aaa act agt gat att caa tcc tat tta    432
Glu Lys Asn Phe Leu Ala Gln Lys Thr Ser Asp Ile Gln Ser Tyr Leu
    130                 135                 140
```

```
aat gat tat aaa agt gca gtt tct aaa att aat aat cca aat gtt ata      480
Asn Asp Tyr Lys Ser Ala Val Ser Lys Ile Asn Asn Pro Asn Val Ile
145                 150                 155                 160 gat agc gat ttt gaa tct tta cat gca aca att aat cta aca tta tca      528
Asp Ser Asp Phe Glu Ser Leu His Ala Thr Ile Asn Leu Thr Leu Ser
                165                 170                 175 aaa ata aaa gga tca tta tct tat ttc tct atc ttt aac cag cca gat      576
Lys Ile Lys Gly Ser Leu Ser Tyr Phe Ser Ile Phe Asn Gln Pro Asp
            180                 185                 190 gat aga aaa cca att tat aca ata cta ggt tta cct tat tat acc ctt      624
Asp Arg Lys Pro Ile Tyr Thr Ile Leu Gly Leu Pro Tyr Tyr Thr Leu
        195                 200                 205 atg gcc act atg tat tta aca tta tta cga gac gtt att tta aat aca      672
Met Ala Thr Met Tyr Leu Thr Leu Leu Arg Asp Val Ile Leu Asn Thr
    210                 215                 220 aca aaa tgg aaa ata tca cca gct tct aat att tcc tat cgt caa caa      720
Thr Lys Trp Lys Ile Ser Pro Ala Ser Asn Ile Ser Tyr Arg Gln Gln
225                 230                 235                 240 ttt aaa caa aac atg aat tca ttt gtt ctt aca att aaa aat aat tat      768
Phe Lys Gln Asn Met Asn Ser Phe Val Leu Thr Ile Lys Asn Asn Tyr
                245                 250                 255 caa act ggt ttt aat tat ata aca aat gaa gct tac aaa gca cat cct      816
Gln Thr Gly Phe Asn Tyr Ile Thr Asn Glu Ala Tyr Lys Ala His Pro
            260                 265                 270 aca aat cct tca aag act ata ctt cca ttt gaa aat aaa atg aca ttg      864
Thr Asn Pro Ser Lys Thr Ile Leu Pro Phe Glu Asn Lys Met Thr Leu
        275                 280                 285 gac tgt ttt gac tat gtt gca atg tgg ccc act tta tat cca gat gat      912
Asp Cys Phe Asp Tyr Val Ala Met Trp Pro Thr Leu Tyr Pro Asp Asp
    290                 295                 300 tat tat act gaa aaa aca aat ttg caa aaa act cgc tta tta ttt tcc      960
Tyr Tyr Thr Glu Lys Thr Asn Leu Gln Lys Thr Arg Leu Leu Phe Ser
305                 310                 315                 320 cca ata tta ggt cgt atg cca gat tct cga agt caa tgg ctt cat agt     1008
Pro Ile Leu Gly Arg Met Pro Asp Ser Arg Ser Gln Trp Leu His Ser
                325                 330                 335 aaa cct tat tcc tgg gat agt aat aaa act ttt acg ttc gat cac tat     1056
Lys Pro Tyr Ser Trp Asp Ser Asn Lys Thr Phe Thr Phe Asp His Tyr
            340                 345                 350 tat atg gct gaa ctc aca cac att gac act aaa gaa ttt gat cga gta     1104
Tyr Met Ala Glu Leu Thr His Ile Asp Thr Lys Glu Phe Asp Arg Val
        355                 360                 365 gac aga atc cgt cag att tat caa gaa gga tat caa aaa gaa caa caa     1152
Asp Arg Ile Arg Gln Ile Tyr Gln Glu Gly Tyr Gln Lys Glu Gln Gln
    370                 375                 380 acg tat gat gat tat tac act tat ggc gga gat tct gct caa aat act     1200
Thr Tyr Asp Asp Tyr Tyr Thr Tyr Gly Gly Asp Ser Ala Gln Asn Thr
385                 390                 395                 400 tct ttt aca aca gat aat cca ctt gca atc atg tat cct act cga ggt     1248
Ser Phe Thr Thr Asp Asn Pro Leu Ala Ile Met Tyr Pro Thr Arg Gly
                405                 410                 415 ggt aat tat gta ggt acc gct att aaa tgg ttt gat gac aca gtg caa     1296
Gly Asn Tyr Val Gly Thr Ala Ile Lys Trp Phe Asp Asp Thr Val Gln
            420                 425                 430 ggt ggt cga tct tca gga tat aca act cca tat tct gga gac cct gat     1344
Gly Gly Arg Ser Ser Gly Tyr Thr Thr Pro Tyr Ser Gly Asp Pro Asp
        435                 440                 445 cct ata ata act cct gat gat cat aaa gtt aat ttt ctc tat aca gta     1392
Pro Ile Ile Thr Pro Asp Asp His Lys Val Asn Phe Leu Tyr Thr Val
    450                 455                 460
```

```
aaa gat gaa tta aaa gga att gat gca tgg gtc aat tca tgg gtt ccc      1440
Lys Asp Glu Leu Lys Gly Ile Asp Ala Trp Val Asn Ser Trp Val Pro
465             470                 475                 480 att tat aca act gtt cca aat ata att gaa aat gaa atg ttc ctc act      1488
Ile Tyr Thr Thr Val Pro Asn Ile Ile Glu Asn Glu Met Phe Leu Thr
                485                 490                 495 aca cta ggt ttt cct ttt gaa aaa gga ata att gat aca ggc gga gct      1536
Thr Leu Gly Phe Pro Phe Glu Lys Gly Ile Ile Asp Thr Gly Gly Ala
            500                 505                 510 ggt gga gat aaa ata tat caa cta gaa cga tta aat gga tcc atg gct      1584
Gly Gly Asp Lys Ile Tyr Gln Leu Glu Arg Leu Asn Gly Ser Met Ala
        515                 520                 525 atc aac tta aaa ttt aaa caa ata att aaa tta cca ttt aca aat cta      1632
Ile Asn Leu Lys Phe Lys Gln Ile Ile Lys Leu Pro Phe Thr Asn Leu
530                 535                 540 aca acc ggt aat tat cta att cgt tta cgt tat gca agt cat tcg gat      1680
Thr Thr Gly Asn Tyr Leu Ile Arg Leu Arg Tyr Ala Ser His Ser Asp
545                 550                 555                 560 ata aat gca ttt act cac att cac tct gaa aat gga gct gat atc agc      1728
Ile Asn Ala Phe Thr His Ile His Ser Glu Asn Gly Ala Asp Ile Ser
                565                 570                 575 agt act cct tta gga aat att act ctt cct aac acg caa aat ttc act      1776
Ser Thr Pro Leu Gly Asn Ile Thr Leu Pro Asn Thr Gln Asn Phe Thr
            580                 585                 590 ttt cct act aac gat gaa tac caa ccc aat caa ccc caa tat acg acc      1824
Phe Pro Thr Asn Asp Glu Tyr Gln Pro Asn Gln Pro Gln Tyr Thr Thr
        595                 600                 605 tat ata gag gga aat gct ggt aaa tat gct tta tat caa ttt aca caa      1872
Tyr Ile Glu Gly Asn Ala Gly Lys Tyr Ala Leu Tyr Gln Phe Thr Gln
610                 615                 620 aat atc tcg ctc aca tct gga caa tat act ttc tat att caa aat aat      1920
Asn Ile Ser Leu Thr Ser Gly Gln Tyr Thr Phe Tyr Ile Gln Asn Asn
625                 630                 635                 640 agt aat act gat ctc ttt tta gat cgg att gaa ttt gtt cct atg ccg      1968
Ser Asn Thr Asp Leu Phe Leu Asp Arg Ile Glu Phe Val Pro Met Pro
                645                 650                 655 cct tct tca ata tca tta cct gat att gaa ata act aac aca gat tat      2016
Pro Ser Ser Ile Ser Leu Pro Asp Ile Glu Ile Thr Asn Thr Asp Tyr
            660                 665                 670 gaa att tgg aaa agt gat cgt cca tat ggc cat tct ata aat gga ata      2064
Glu Ile Trp Lys Ser Asp Arg Pro Tyr Gly His Ser Ile Asn Gly Ile
        675                 680                 685 ttc ata gtc agc gtg cca ttt gga aac cag aca gat act gta act ata      2112
Phe Ile Val Ser Val Pro Phe Gly Asn Gln Thr Asp Thr Val Thr Ile
690                 695                 700 aca tat tgg aat aat ggg gaa aaa gtc cat aca gac tct caa aca ttt      2160
Thr Tyr Trp Asn Asn Gly Glu Lys Val His Thr Asp Ser Gln Thr Phe
705                 710                 715                 720 gat atg gca aga ttc caa ggt caa gat ctt aca caa tgg caa gga gct      2208
Asp Met Ala Arg Phe Gln Gly Gln Asp Leu Thr Gln Trp Gln Gly Ala
                725                 730                 735 ttt gat cgt gta act att cgt aga act cat tct gat ggt aca ttg tca      2256
Phe Asp Arg Val Thr Ile Arg Arg Thr His Ser Asp Gly Thr Leu Ser
            740                 745                 750 tta aca agt gca acc cta tac ttt gtt atc cca aaa tca tcc ttt agt      2304
Leu Thr Ser Ala Thr Leu Tyr Phe Val Ile Pro Lys Ser Ser Phe Ser
        755                 760                 765 acc cca gaa gat tta gaa aaa atc aca aac caa gtc aat cag tta ttt      2352
Thr Pro Glu Asp Leu Glu Lys Ile Thr Asn Gln Val Asn Gln Leu Phe
770                 775                 780
```

```
act tcc tca tcc caa aca gaa tta gct aac acc gta acc gat tac gga     2400
Thr Ser Ser Ser Gln Thr Glu Leu Ala Asn Thr Val Thr Asp Tyr Gly
785                 790                 795                 800 att gat caa gtt ttg atg aaa gta gat gcg tta tca gac gat gta ttt     2448
Ile Asp Gln Val Leu Met Lys Val Asp Ala Leu Ser Asp Asp Val Phe
            805                 810                 815 ggg gta gag aaa aaa gca tta cgt aaa ctt gtc aat cag gcc aaa caa     2496
Gly Val Glu Lys Lys Ala Leu Arg Lys Leu Val Asn Gln Ala Lys Gln
        820                 825                 830 ctg agt aaa gca cgc aat gta tta gtc ggt gga aac ttt gaa gga aat     2544
Leu Ser Lys Ala Arg Asn Val Leu Val Gly Gly Asn Phe Glu Gly Asn
    835                 840                 845 cat gaa tgg gta ctc ggt cgt aaa gcg gtc atg gtc gca aat gat gag     2592
His Glu Trp Val Leu Gly Arg Lys Ala Val Met Val Ala Asn Asp Glu
850                 855                 860 tta ttt aaa ggc aat cat tta tta tta cca cct cca agt cta tat cca     2640
Leu Phe Lys Gly Asn His Leu Leu Leu Pro Pro Pro Ser Leu Tyr Pro
865                 870                 875                 880 tcg tat gcg tat caa aaa gtg gat gaa tcc aaa tta aaa ccg aat aca     2688
Ser Tyr Ala Tyr Gln Lys Val Asp Glu Ser Lys Leu Lys Pro Asn Thr
            885                 890                 895 cga tat acc gtt tct ggt ttt gtg gcg caa agt gaa caa tta gaa gtc     2736
Arg Tyr Thr Val Ser Gly Phe Val Ala Gln Ser Glu Gln Leu Glu Val
        900                 905                 910 gtt gtt tcc cgt tat ggt aaa gaa gta cat gac atg tta aat gtt cct     2784
Val Val Ser Arg Tyr Gly Lys Glu Val His Asp Met Leu Asn Val Pro
    915                 920                 925 tat gaa gaa gcg tta ccg att tct tca aat gaa aag tca aat tgt tgt     2832
Tyr Glu Glu Ala Leu Pro Ile Ser Ser Asn Glu Lys Ser Asn Cys Cys
930                 935                 940 aaa ccg gct act tgc aac tat aca tct tgt gag ggg aaa gaa cca gat     2880
Lys Pro Ala Thr Cys Asn Tyr Thr Ser Cys Glu Gly Lys Glu Pro Asp
945                 950                 955                 960 tct cat ttc ttc cgt tat agt atc gat gtc ggt gct tta caa cca gaa     2928
Ser His Phe Phe Arg Tyr Ser Ile Asp Val Gly Ala Leu Gln Pro Glu
            965                 970                 975 gca aat cta gga att gaa ttc ggt ctt cgt att gtg aaa tca aat gga     2976
Ala Asn Leu Gly Ile Glu Phe Gly Leu Arg Ile Val Lys Ser Asn Gly
        980                 985                 990 ttt gca aaa atc agt aat tta gaa atc aaa gaa gat cgt cca tta aca     3024
Phe Ala Lys Ile Ser Asn Leu Glu Ile Lys Glu Asp Arg Pro Leu Thr
    995                 1000                1005 gac caa gaa att aaa aaa gta caa cac aaa gaa caa aag tgg aaa aaa     3072
Asp Gln Glu Ile Lys Lys Val Gln His Lys Glu Gln Lys Trp Lys Lys
1010                1015                1020 gca ttt aac aaa gaa caa gca gag tta acg gca aca ctc caa cca aca     3120
Ala Phe Asn Lys Glu Gln Ala Glu Leu Thr Ala Thr Leu Gln Pro Thr
1025                1030                1035                1040 ctg aat caa atc aat gcc ttg tat caa cag gaa gat tgg aat ggt tcg     3168
Leu Asn Gln Ile Asn Ala Leu Tyr Gln Gln Glu Asp Trp Asn Gly Ser
            1045                1050                1055 att cat cct cat gtg acg tat caa cat ctg tct gat gtt gtc tta cca     3216
Ile His Pro His Val Thr Tyr Gln His Leu Ser Asp Val Val Leu Pro
        1060                1065                1070 acg tta cca aaa caa aca cat tgg ttt atg gaa aat cga gaa ggc gaa     3264
Thr Leu Pro Lys Gln Thr His Trp Phe Met Glu Asn Arg Glu Gly Glu
    1075                1080                1085 cat gtt gtt ctg acg caa caa ttc caa caa gca tta gat cgt gct ttc     3312
His Val Val Leu Thr Gln Gln Phe Gln Gln Ala Leu Asp Arg Ala Phe
1090                1095                1100
```

-continued

| | | |
|---|---|---|
| caa caa atc gaa gaa caa aac ttg atc cac aat ggt agc ttt aca agt<br>Gln Gln Ile Glu Glu Gln Asn Leu Ile His Asn Gly Ser Phe Thr Ser<br>1105                      1110                   1115                    1120 | 3360 |
| gga tta aca gat tgg act gta aca gga gat gca cag att act atc tat<br>Gly Leu Thr Asp Trp Thr Val Thr Gly Asp Ala Gln Ile Thr Ile Tyr<br>                     1125                    1130                   1135 | 3408 |
| gat gaa gat cca gta tta gaa cta gca cat tgg gat gca agc gtc tct<br>Asp Glu Asp Pro Val Leu Glu Leu Ala His Trp Asp Ala Ser Val Ser<br>                    1140                    1145                    1150 | 3456 |
| caa acg att gag att act gat ttt gaa gaa gaa aaa gaa tac aaa ctt<br>Gln Thr Ile Glu Ile Thr Asp Phe Glu Glu Glu Lys Glu Tyr Lys Leu<br>1155                      1160                    1165 | 3504 |
| cgt gta cgc gga aaa ggc aaa gga acg gtt acc gtt caa cat gaa gaa<br>Arg Val Arg Gly Lys Gly Lys Gly Thr Val Thr Val Gln His Glu Glu<br>1170                      1175                    1180 | 3552 |
| gag tta gaa aca atg aca ttt aac aca act agt ttt aca acg aaa gaa<br>Glu Leu Glu Thr Met Thr Phe Asn Thr Thr Ser Phe Thr Thr Lys Glu<br>1185                      1190                    1195                    1200 | 3600 |
| caa acc ttc tat ttc gaa gga aat aca ata gat gta cac gtt caa tca<br>Gln Thr Phe Tyr Phe Glu Gly Asn Thr Ile Asp Val His Val Gln Ser<br>                     1205                    1210                    1215 | 3648 |
| gag aat aat gca ttc ctt gta gac agt gtg gaa ctc att gaa gtt gta<br>Glu Asn Asn Ala Phe Leu Val Asp Ser Val Glu Leu Ile Glu Val Val<br>                    1220                    1225                    1230 | 3696 |
| aaa gaa caa gaa gaa aaa caa taa<br>Lys Glu Gln Glu Glu Lys Gln *<br>            1235 | 3720 |

<210> SEQ ID NO 6
<211> LENGTH: 1239
<212> TYPE: PRT
<213> ORGANISM: Unknown
<220> FEATURE:
<223> OTHER INFORMATION: Isolated from soil sample

<400> SEQUENCE: 6

Met Asn Asp Met Thr Asn Leu Ser Lys Leu Tyr Ser Pro Val Pro Tyr
1               5                   10                  15

Asn Val Leu Ala Thr Pro Asn Val Leu Ala Thr Asn Lys Gln Pro Leu
            20                  25                  30

Ala Asp Thr Asp Ala Leu Asn Lys Phe Tyr Asn Asp Leu Gln Ile Gly
        35                  40                  45

Lys Val Ser Ala Phe Thr Ile Asp Ala Leu Trp Ser Leu Met Thr Thr
50                  55                  60

Gly Lys Tyr Asp Trp Ser Ser Ile Ala Lys Phe Cys Trp Ser Leu Gly
65                  70                  75                  80

Thr Gly Val Thr Pro Leu Leu Gly Ile Phe Ser Pro Ile Ile Asp Ile
                85                  90                  95

Ile Phe Pro Ala Leu Phe Gly Gly Asn Lys Leu Ser Leu Phe Glu Gln
            100                 105                 110

Leu Lys Pro Gln Ile Glu Lys Leu Ile Glu Lys Leu Thr Asp Glu
        115                 120                 125

Glu Lys Asn Phe Leu Ala Gln Lys Thr Ser Asp Ile Gln Ser Tyr Leu
    130                 135                 140

Asn Asp Tyr Lys Ser Ala Val Ser Lys Ile Asn Asn Pro Asn Val Ile
145                 150                 155                 160

Asp Ser Asp Phe Glu Ser Leu His Ala Thr Ile Asn Leu Thr Leu Ser
                165                 170                 175

-continued

```
Lys Ile Lys Gly Ser Leu Ser Tyr Phe Ser Ile Phe Asn Gln Pro Asp
            180                 185                 190
Asp Arg Lys Pro Ile Tyr Thr Ile Leu Gly Leu Pro Tyr Tyr Thr Leu
        195                 200                 205
Met Ala Thr Met Tyr Leu Thr Leu Leu Arg Asp Val Ile Leu Asn Thr
    210                 215                 220
Thr Lys Trp Lys Ile Ser Pro Ala Ser Asn Ile Ser Tyr Arg Gln Gln
225                 230                 235                 240
Phe Lys Gln Asn Met Asn Ser Phe Val Leu Thr Ile Lys Asn Asn Tyr
                245                 250                 255
Gln Thr Gly Phe Asn Tyr Ile Thr Asn Glu Ala Tyr Lys Ala His Pro
            260                 265                 270
Thr Asn Pro Ser Lys Thr Ile Leu Pro Phe Glu Asn Lys Met Thr Leu
        275                 280                 285
Asp Cys Phe Asp Tyr Val Ala Met Trp Pro Thr Leu Tyr Pro Asp Asp
    290                 295                 300
Tyr Tyr Thr Glu Lys Thr Asn Leu Gln Lys Thr Arg Leu Leu Phe Ser
305                 310                 315                 320
Pro Ile Leu Gly Arg Met Pro Asp Ser Arg Ser Gln Trp Leu His Ser
                325                 330                 335
Lys Pro Tyr Ser Trp Asp Ser Asn Lys Thr Phe Thr Phe Asp His Tyr
            340                 345                 350
Tyr Met Ala Glu Leu Thr His Ile Asp Thr Lys Glu Phe Asp Arg Val
        355                 360                 365
Asp Arg Ile Arg Gln Ile Tyr Gln Glu Gly Tyr Gln Lys Glu Gln Gln
    370                 375                 380
Thr Tyr Asp Asp Tyr Tyr Thr Tyr Gly Gly Asp Ser Ala Gln Asn Thr
385                 390                 395                 400
Ser Phe Thr Thr Asp Asn Pro Leu Ala Ile Met Tyr Pro Thr Arg Gly
                405                 410                 415
Gly Asn Tyr Val Gly Thr Ala Ile Lys Trp Phe Asp Asp Thr Val Gln
            420                 425                 430
Gly Gly Arg Ser Ser Gly Tyr Thr Thr Pro Tyr Ser Gly Asp Pro Asp
        435                 440                 445
Pro Ile Ile Thr Pro Asp Asp His Lys Val Asn Phe Leu Tyr Thr Val
    450                 455                 460
Lys Asp Glu Leu Lys Gly Ile Asp Ala Trp Val Asn Ser Trp Val Pro
465                 470                 475                 480
Ile Tyr Thr Thr Val Pro Asn Ile Ile Glu Asn Glu Met Phe Leu Thr
                485                 490                 495
Thr Leu Gly Phe Pro Phe Glu Lys Gly Ile Ile Asp Thr Gly Gly Ala
            500                 505                 510
Gly Gly Asp Lys Ile Tyr Gln Leu Glu Arg Leu Asn Gly Ser Met Ala
        515                 520                 525
Ile Asn Leu Lys Phe Lys Gln Ile Lys Leu Pro Phe Thr Asn Leu
    530                 535                 540
Thr Thr Gly Asn Tyr Leu Ile Arg Leu Arg Tyr Ala Ser His Ser Asp
545                 550                 555                 560
Ile Asn Ala Phe Thr His Ile His Ser Glu Asn Gly Ala Asp Ile Ser
                565                 570                 575
Ser Thr Pro Leu Gly Asn Ile Thr Leu Pro Asn Thr Gln Asn Phe Thr
            580                 585                 590
Phe Pro Thr Asn Asp Glu Tyr Gln Pro Asn Gln Pro Tyr Thr Thr
        595                 600                 605
```

Tyr Ile Glu Gly Asn Ala Gly Lys Tyr Ala Leu Tyr Gln Phe Thr Gln
            610                 615                 620

Asn Ile Ser Leu Thr Ser Gly Gln Tyr Thr Phe Tyr Ile Gln Asn Asn
625                 630                 635                 640

Ser Asn Thr Asp Leu Phe Leu Asp Arg Ile Glu Phe Val Pro Met Pro
            645                 650                 655

Pro Ser Ser Ile Ser Leu Pro Asp Ile Glu Ile Thr Asn Thr Asp Tyr
            660                 665                 670

Glu Ile Trp Lys Ser Asp Arg Pro Tyr Gly His Ser Ile Asn Gly Ile
            675                 680                 685

Phe Ile Val Ser Val Pro Phe Gly Asn Gln Thr Asp Thr Val Thr Ile
            690                 695                 700

Thr Tyr Trp Asn Asn Gly Glu Lys Val His Thr Asp Ser Gln Thr Phe
705                 710                 715                 720

Asp Met Ala Arg Phe Gln Gly Gln Asp Leu Thr Gln Trp Gln Gly Ala
            725                 730                 735

Phe Asp Arg Val Thr Ile Arg Arg Thr His Ser Asp Gly Thr Leu Ser
            740                 745                 750

Leu Thr Ser Ala Thr Leu Tyr Phe Val Ile Pro Lys Ser Ser Phe Ser
            755                 760                 765

Thr Pro Glu Asp Leu Glu Lys Ile Thr Asn Gln Val Asn Gln Leu Phe
            770                 775                 780

Thr Ser Ser Ser Gln Thr Glu Leu Ala Asn Thr Val Thr Asp Tyr Gly
785                 790                 795                 800

Ile Asp Gln Val Leu Met Lys Val Asp Ala Leu Ser Asp Asp Val Phe
            805                 810                 815

Gly Val Glu Lys Lys Ala Leu Arg Lys Leu Val Asn Gln Ala Lys Gln
            820                 825                 830

Leu Ser Lys Ala Arg Asn Val Leu Val Gly Gly Asn Phe Glu Gly Asn
            835                 840                 845

His Glu Trp Val Leu Gly Arg Lys Ala Val Met Val Ala Asn Asp Glu
850                 855                 860

Leu Phe Lys Gly Asn His Leu Leu Pro Pro Pro Ser Leu Tyr Pro
865                 870                 875                 880

Ser Tyr Ala Tyr Gln Lys Val Asp Glu Ser Lys Leu Lys Pro Asn Thr
            885                 890                 895

Arg Tyr Thr Val Ser Gly Phe Val Ala Gln Ser Glu Gln Leu Glu Val
            900                 905                 910

Val Val Ser Arg Tyr Gly Lys Glu Val His Asp Met Leu Asn Val Pro
            915                 920                 925

Tyr Glu Glu Ala Leu Pro Ile Ser Ser Asn Glu Lys Ser Asn Cys Cys
            930                 935                 940

Lys Pro Ala Thr Cys Asn Tyr Thr Ser Cys Glu Gly Lys Glu Pro Asp
945                 950                 955                 960

Ser His Phe Phe Arg Tyr Ser Ile Asp Val Gly Ala Leu Gln Pro Glu
            965                 970                 975

Ala Asn Leu Gly Ile Glu Phe Gly Leu Arg Ile Val Lys Ser Asn Gly
            980                 985                 990

Phe Ala Lys Ile Ser Asn Leu Glu Ile Lys Glu Asp Arg Pro Leu Thr
            995                 1000                1005

Asp Gln Glu Ile Lys Lys Val Gln His Lys Glu Gln Lys Trp Lys Lys
            1010                1015                1020

Ala Phe Asn Lys Glu Gln Ala Glu Leu Thr Ala Thr Leu Gln Pro Thr

-continued

```
                1025                1030                1035                1040
Leu Asn Gln Ile Asn Ala Leu Tyr Gln Gln Glu Asp Trp Asn Gly Ser
                    1045                1050                1055

Ile His Pro His Val Thr Tyr Gln His Leu Ser Asp Val Val Leu Pro
                    1060                1065                1070

Thr Leu Pro Lys Gln Thr His Trp Phe Met Glu Asn Arg Glu Gly Glu
            1075                1080                1085

His Val Val Leu Thr Gln Gln Phe Gln Gln Ala Leu Asp Arg Ala Phe
        1090                1095                1100

Gln Gln Ile Glu Glu Gln Asn Leu Ile His Asn Gly Ser Phe Thr Ser
1105                1110                1115                1120

Gly Leu Thr Asp Trp Thr Val Thr Gly Asp Ala Gln Ile Thr Ile Tyr
            1125                1130                1135

Asp Glu Asp Pro Val Leu Glu Leu Ala His Trp Asp Ala Ser Val Ser
                1140                1145                1150

Gln Thr Ile Glu Ile Thr Asp Phe Glu Glu Lys Glu Tyr Lys Leu
            1155                1160                1165

Arg Val Arg Gly Lys Gly Lys Gly Thr Val Thr Val Gln His Glu Glu
        1170                1175                1180

Glu Leu Glu Thr Met Thr Phe Asn Thr Thr Ser Phe Thr Lys Glu
1185                1190                1195                1200

Gln Thr Phe Tyr Phe Glu Gly Asn Thr Ile Asp Val His Val Gln Ser
                1205                1210                1215

Glu Asn Asn Ala Phe Leu Val Asp Ser Val Glu Leu Ile Glu Val Val
            1220                1225                1230

Lys Glu Gln Glu Glu Lys Gln
        1235

<210> SEQ ID NO 7
<211> LENGTH: 2059
<212> TYPE: DNA
<213> ORGANISM: Artificial Sequence
<220> FEATURE:
<223> OTHER INFORMATION: synaxmi-031
<220> FEATURE:
<221> NAME/KEY: CDS
<222> LOCATION: (1)...(2058)

<400> SEQUENCE: 7 atg gat tgc aat ctc cag agc cag cag aat atc cca tac aat gtg ctt      48
Met Asp Cys Asn Leu Gln Ser Gln Gln Asn Ile Pro Tyr Asn Val Leu
 1               5                  10                  15 gct atc cct gtt agc aat gtt aat agc ctt acg gat acg gtt ggc gat      96
Ala Ile Pro Val Ser Asn Val Asn Ser Leu Thr Asp Thr Val Gly Asp
             20                  25                  30 cta aag aag gca tgg gaa gag ttc cag aag acg ggc agc ttc tcc ctt     144
Leu Lys Lys Ala Trp Glu Glu Phe Gln Lys Thr Gly Ser Phe Ser Leu
         35                  40                  45 acc gca ctc cag cag ggc ttc agc gct tcc cag ggc ggg acg ttc aat     192
Thr Ala Leu Gln Gln Gly Phe Ser Ala Ser Gln Gly Gly Thr Phe Asn
     50                  55                  60 tac ctc acc ctc ctc cag tcc ggg atc tcc ctg gct ggc agc ttc gtg     240
Tyr Leu Thr Leu Leu Gln Ser Gly Ile Ser Leu Ala Gly Ser Phe Val
 65                  70                  75                  80 cct ggc ggc acc ttc gtt gct cca atc atc aat atg gtg atc ggc tgg     288
Pro Gly Gly Thr Phe Val Ala Pro Ile Ile Asn Met Val Ile Gly Trp
                 85                  90                  95 ctc tgg cct cat aag aat aag aat gca gat acg gaa aat ctg atc aat     336
Leu Trp Pro His Lys Asn Lys Asn Ala Asp Thr Glu Asn Leu Ile Asn
```

|  |  |  |  |  |  |  |  |  |  |  |  |  |  |  |  |
|---|---|---|---|---|---|---|---|---|---|---|---|---|---|---|---|
|  | 100 |  |  |  | 105 |  |  |  | 110 |  |  |  |  |  |  |
| ctg | atc | gat | tca | gaa | atc | cag | aag | cag | ctg | aat | aag | gct | ctg | ctg | gat | 384
| Leu | Ile | Asp | Ser | Glu | Ile | Gln | Lys | Gln | Leu | Asn | Lys | Ala | Leu | Leu | Asp |
|  |  |  | 115 |  |  |  |  | 120 |  |  |  |  | 125 |  |  |
| gct | gat | cgc | aat | gaa | tgg | agc | agc | tac | ctc | gag | tcc | atc | ttc | gat | agc | 432
| Ala | Asp | Arg | Asn | Glu | Trp | Ser | Ser | Tyr | Leu | Glu | Ser | Ile | Phe | Asp | Ser |
|  | 130 |  |  |  |  | 135 |  |  |  |  | 140 |  |  |  |  |
| agc | aat | aat | ctg | aat | ggc | gca | atc | gtt | gat | gct | cag | tgg | tcc | ggc | acc | 480
| Ser | Asn | Asn | Leu | Asn | Gly | Ala | Ile | Val | Asp | Ala | Gln | Trp | Ser | Gly | Thr |
| 145 |  |  |  |  | 150 |  |  |  |  | 155 |  |  |  |  | 160 |
| gtg | aat | acg | acc | aat | cgt | acg | ctt | cgt | aat | cct | acg | gaa | tca | gat | tac | 528
| Val | Asn | Thr | Thr | Asn | Arg | Thr | Leu | Arg | Asn | Pro | Thr | Glu | Ser | Asp | Tyr |
|  |  |  |  | 165 |  |  |  |  | 170 |  |  |  |  | 175 |  |
| acc | aat | gtg | gtg | acg | aat | ttc | atc | gca | gca | gat | ggg | gat | atc | gct | aat | 576
| Thr | Asn | Val | Val | Thr | Asn | Phe | Ile | Ala | Ala | Asp | Gly | Asp | Ile | Ala | Asn |
|  |  |  | 180 |  |  |  |  | 185 |  |  |  |  | 190 |  |  |
| aat | gaa | aat | cat | atc | atg | aat | ggg | aat | ttc | gat | gtg | gca | gca | gct | cca | 624
| Asn | Glu | Asn | His | Ile | Met | Asn | Gly | Asn | Phe | Asp | Val | Ala | Ala | Ala | Pro |
|  | 195 |  |  |  |  | 200 |  |  |  |  | 205 |  |  |  |  |
| tac | ttc | gtt | atc | ggg | gct | acc | gct | aga | ttc | gca | gct | atg | cag | tcc | tac | 672
| Tyr | Phe | Val | Ile | Gly | Ala | Thr | Ala | Arg | Phe | Ala | Ala | Met | Gln | Ser | Tyr |
| 210 |  |  |  |  | 215 |  |  |  |  | 220 |  |  |  |  |  |
| atc | aag | ttc | tgc | aat | gca | tgg | atc | gat | aag | gtt | ggg | ctg | tca | gat | gct | 720
| Ile | Lys | Phe | Cys | Asn | Ala | Trp | Ile | Asp | Lys | Val | Gly | Leu | Ser | Asp | Ala |
| 225 |  |  |  | 230 |  |  |  |  | 235 |  |  |  |  | 240 |  |
| cag | ctg | acc | acg | cag | aag | gct | aat | ctg | gat | aga | acg | aag | cag | aat | atg | 768
| Gln | Leu | Thr | Thr | Gln | Lys | Ala | Asn | Leu | Asp | Arg | Thr | Lys | Gln | Asn | Met |
|  |  |  | 245 |  |  |  |  | 250 |  |  |  |  | 255 |  |  |
| cgt | aat | gct | atc | ctt | aat | tac | acc | cag | cag | gtt | atg | aag | gtt | ttc | aag | 816
| Arg | Asn | Ala | Ile | Leu | Asn | Tyr | Thr | Gln | Gln | Val | Met | Lys | Val | Phe | Lys |
|  | 260 |  |  |  |  | 265 |  |  |  |  | 270 |  |  |  |  |
| gat | tcc | aag | aat | atg | cca | acg | atc | ggc | acg | aat | aag | ttc | agc | gtt | gat | 864
| Asp | Ser | Lys | Asn | Met | Pro | Thr | Ile | Gly | Thr | Asn | Lys | Phe | Ser | Val | Asp |
|  |  | 275 |  |  |  |  | 280 |  |  |  |  | 285 |  |  |  |
| acc | tac | aat | gtt | tac | atc | aag | ggg | atg | acg | ctt | aat | gtg | ctt | gat | atc | 912
| Thr | Tyr | Asn | Val | Tyr | Ile | Lys | Gly | Met | Thr | Leu | Asn | Val | Leu | Asp | Ile |
|  | 290 |  |  |  |  | 295 |  |  |  |  | 300 |  |  |  |  |
| gtt | gct | atc | tgg | cca | agc | ctg | tac | cca | gat | gat | tac | acg | tca | cag | acg | 960
| Val | Ala | Ile | Trp | Pro | Ser | Leu | Tyr | Pro | Asp | Asp | Tyr | Thr | Ser | Gln | Thr |
| 305 |  |  |  |  | 310 |  |  |  |  | 315 |  |  |  |  | 320 |
| gct | ctg | gaa | cag | acc | cgc | gtg | acg | ttc | tcc | aat | atg | gtg | ggg | cag | gaa | 1008
| Ala | Leu | Glu | Gln | Thr | Arg | Val | Thr | Phe | Ser | Asn | Met | Val | Gly | Gln | Glu |
|  |  |  |  | 325 |  |  |  |  | 330 |  |  |  |  | 335 |  |
| gaa | ggc | acg | gat | ggc | agc | ctc | aga | atc | tac | aat | acc | ttc | gat | agc | ttc | 1056
| Glu | Gly | Thr | Asp | Gly | Ser | Leu | Arg | Ile | Tyr | Asn | Thr | Phe | Asp | Ser | Phe |
|  |  |  | 340 |  |  |  |  | 345 |  |  |  |  | 350 |  |  |
| tcc | tac | cag | cat | agc | cct | atc | cct | aat | aat | aat | gtg | aat | ctc | atc | agc | 1104
| Ser | Tyr | Gln | His | Ser | Pro | Ile | Pro | Asn | Asn | Asn | Val | Asn | Leu | Ile | Ser |
|  |  | 355 |  |  |  |  | 360 |  |  |  |  | 365 |  |  |  |
| tac | tac | aat | gat | gaa | ctt | cag | aat | ctg | gaa | ctc | ggg | gtt | tac | acc | cca | 1152
| Tyr | Tyr | Asn | Asp | Glu | Leu | Gln | Asn | Leu | Glu | Leu | Gly | Val | Tyr | Thr | Pro |
|  | 370 |  |  |  |  | 375 |  |  |  |  | 380 |  |  |  |  |
| cca | aag | aag | ggc | tca | ggc | tac | agc | tac | cca | tac | ggg | ttc | gtg | ctg | aat | 1200
| Pro | Lys | Lys | Gly | Ser | Gly | Tyr | Ser | Tyr | Pro | Tyr | Gly | Phe | Val | Leu | Asn |
| 385 |  |  |  |  | 390 |  |  |  |  | 395 |  |  |  |  | 400 |
| tac | gca | aat | agc | aag | tac | aag | tac | ggc | gat | tcc | aat | gat | cca | gaa | tcc | 1248
| Tyr | Ala | Asn | Ser | Lys | Tyr | Lys | Tyr | Gly | Asp | Ser | Asn | Asp | Pro | Glu | Ser |
|  |  |  |  | 405 |  |  |  |  | 410 |  |  |  |  | 415 |  |
| ctc | ggc | ggg | ctt | tcc | acc | ctt | agc | gct | cca | atc | caa | cag | gtt | aat | gct | 1296
| Leu | Gly | Gly | Leu | Ser | Thr | Leu | Ser | Ala | Pro | Ile | Gln | Gln | Val | Asn | Ala |

```
                       420                 425                 430
gct acc cag aat agc aag tac ctt gat ggc gaa atc ctg aat ggg atc        1344
Ala Thr Gln Asn Ser Lys Tyr Leu Asp Gly Glu Ile Leu Asn Gly Ile
            435                 440                 445 ggc gca agc ctg cct ggc tac tgc acg acc ggg tgc tca cct acc gaa        1392
Gly Ala Ser Leu Pro Gly Tyr Cys Thr Thr Gly Cys Ser Pro Thr Glu
    450                 455                 460 cca cca ttc agc tgc acg agc acg gca aat ggg tac aag gca agc tgc        1440
Pro Pro Phe Ser Cys Thr Ser Thr Ala Asn Gly Tyr Lys Ala Ser Cys
465                 470                 475                 480 aat cca agc gat acc aat cag aag atc aat gct ctc tac cca ttc acg        1488
Asn Pro Ser Asp Thr Asn Gln Lys Ile Asn Ala Leu Tyr Pro Phe Thr
                485                 490                 495 cag gca aat gtg aag ggg aat acc ggg aag ctg ggc gtt ctc gca agc        1536
Gln Ala Asn Val Lys Gly Asn Thr Gly Lys Leu Gly Val Leu Ala Ser
            500                 505                 510 ctt gtt agc tac gat ctg aat cct aag aat gtt ttc ggg gaa ctc gat        1584
Leu Val Ser Tyr Asp Leu Asn Pro Lys Asn Val Phe Gly Glu Leu Asp
        515                 520                 525 tca gat acc aat aat gtt atc ctt aag ggc atc cca gca gaa aag ggc        1632
Ser Asp Thr Asn Asn Val Ile Leu Lys Gly Ile Pro Ala Glu Lys Gly
530                 535                 540 tac ttc cca aat aat gca aga cca acc gtt gtg aag gaa tgg atc aat        1680
Tyr Phe Pro Asn Asn Ala Arg Pro Thr Val Val Lys Glu Trp Ile Asn
545                 550                 555                 560 ggg gct tcc gca gtt cca ctt gat tcc ggc aat acc ctg ttc atg acg        1728
Gly Ala Ser Ala Val Pro Leu Asp Ser Gly Asn Thr Leu Phe Met Thr
                565                 570                 575 gct acg aac ctg acg gct acc cag tac aga atc cgc atc cgt tac gct        1776
Ala Thr Asn Leu Thr Ala Thr Gln Tyr Arg Ile Arg Ile Arg Tyr Ala
            580                 585                 590 aac cca aac tca aac acg cag atc ggc gtt aga atc acg cag aac ggg        1824
Asn Pro Asn Ser Asn Thr Gln Ile Gly Val Arg Ile Thr Gln Asn Gly
        595                 600                 605 agc ctc atc tcc tcc tcc aac ctc acg ctg tac tca acc acc gat atg        1872
Ser Leu Ile Ser Ser Ser Asn Leu Thr Leu Tyr Ser Thr Thr Asp Met
    610                 615                 620 aac aac acc ctg cca ctg aac gtt tac gtg atc ggg gaa aac ggg aac        1920
Asn Asn Thr Leu Pro Leu Asn Val Tyr Val Ile Gly Glu Asn Gly Asn
625                 630                 635                 640 tac acc ctc cag gat ctc tac aac acg acg aac gtt ctg tcc acg ggc        1968
Tyr Thr Leu Gln Asp Leu Tyr Asn Thr Thr Asn Val Leu Ser Thr Gly
                645                 650                 655 gat atc acc ctg cag atc acc ggc ggg gat cag aag ata ttc atc gat        2016
Asp Ile Thr Leu Gln Ile Thr Gly Gly Asp Gln Lys Ile Phe Ile Asp
            660                 665                 670 cgc atc gag ttc gtg cct acg atg cca gtg cca ggc aac taa                2058
Arg Ile Glu Phe Val Pro Thr Met Pro Val Pro Gly Asn *
        675                 680                 685 a                                                                       2059

<210> SEQ ID NO 8
<211> LENGTH: 685
<212> TYPE: PRT
<213> ORGANISM: Artificial Sequence
<220> FEATURE:
<223> OTHER INFORMATION: SYNAXMI-031

<400> SEQUENCE: 8

Met Asp Cys Asn Leu Gln Ser Gln Gln Asn Ile Pro Tyr Asn Val Leu
1               5                   10                  15
```

```
Ala Ile Pro Val Ser Asn Val Asn Ser Leu Thr Asp Thr Val Gly Asp
             20                  25                  30

Leu Lys Lys Ala Trp Glu Glu Phe Gln Lys Thr Gly Ser Phe Ser Leu
         35                  40                  45

Thr Ala Leu Gln Gln Gly Phe Ser Ala Ser Gln Gly Gly Thr Phe Asn
     50                  55                  60

Tyr Leu Thr Leu Leu Gln Ser Gly Ile Ser Leu Ala Gly Ser Phe Val
 65                  70                  75                  80

Pro Gly Gly Thr Phe Val Ala Pro Ile Ile Asn Met Val Ile Gly Trp
                 85                  90                  95

Leu Trp Pro His Lys Asn Lys Asn Ala Asp Thr Glu Asn Leu Ile Asn
             100                 105                 110

Leu Ile Asp Ser Glu Ile Gln Lys Gln Leu Asn Lys Ala Leu Leu Asp
             115                 120                 125

Ala Asp Arg Asn Glu Trp Ser Ser Tyr Leu Glu Ser Ile Phe Asp Ser
        130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Val Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
            245                 250                 255

Arg Asn Ala Ile Leu Asn Tyr Thr Gln Gln Val Met Lys Val Phe Lys
        260                 265                 270

Asp Ser Lys Asn Met Pro Thr Ile Gly Thr Asn Lys Phe Ser Val Asp
    275                 280                 285

Thr Tyr Asn Val Tyr Ile Lys Gly Met Thr Leu Asn Val Leu Asp Ile
290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
            325                 330                 335

Glu Gly Thr Asp Gly Ser Leu Arg Ile Tyr Asn Thr Phe Asp Ser Phe
        340                 345                 350

Ser Tyr Gln His Ser Pro Ile Pro Asn Asn Val Asn Leu Ile Ser
    355                 360                 365

Tyr Tyr Asn Asp Glu Leu Gln Asn Leu Glu Leu Gly Val Tyr Thr Pro
370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Gln Val Asn Ala
        420                 425                 430

Ala Thr Gln Asn Ser Lys Tyr Leu Asp Gly Glu Ile Leu Asn Gly Ile
```

```
                435              440              445
Gly Ala Ser Leu Pro Gly Tyr Cys Thr Thr Gly Cys Ser Pro Thr Glu
    450                  455                  460

Pro Pro Phe Ser Cys Thr Ser Thr Ala Asn Gly Tyr Lys Ala Ser Cys
465                  470                  475                  480

Asn Pro Ser Asp Thr Asn Gln Lys Ile Asn Ala Leu Tyr Pro Phe Thr
                485                  490                  495

Gln Ala Asn Val Lys Gly Asn Thr Gly Lys Leu Gly Val Leu Ala Ser
            500                  505                  510

Leu Val Ser Tyr Asp Leu Asn Pro Lys Asn Val Phe Gly Glu Leu Asp
        515                  520                  525

Ser Asp Thr Asn Asn Val Ile Leu Lys Gly Ile Pro Ala Glu Lys Gly
    530                  535                  540

Tyr Phe Pro Asn Asn Ala Arg Pro Thr Val Val Lys Glu Trp Ile Asn
545                  550                  555                  560

Gly Ala Ser Ala Val Pro Leu Asp Ser Gly Asn Thr Leu Phe Met Thr
                565                  570                  575

Ala Thr Asn Leu Thr Ala Thr Gln Tyr Arg Ile Arg Ile Arg Tyr Ala
            580                  585                  590

Asn Pro Asn Ser Asn Thr Gln Ile Gly Val Arg Ile Thr Gln Asn Gly
        595                  600                  605

Ser Leu Ile Ser Ser Ser Asn Leu Thr Leu Tyr Ser Thr Thr Asp Met
    610                  615                  620

Asn Asn Thr Leu Pro Leu Asn Val Tyr Val Ile Gly Glu Asn Gly Asn
625                  630                  635                  640

Tyr Thr Leu Gln Asp Leu Tyr Asn Thr Asn Val Leu Ser Thr Gly
                645                  650                  655

Asp Ile Thr Leu Gln Ile Thr Gly Gly Asp Gln Lys Ile Phe Ile Asp
            660                  665                  670

Arg Ile Glu Phe Val Pro Thr Met Pro Val Pro Gly Asn
        675                  680                  685

<210> SEQ ID NO 9
<211> LENGTH: 2148
<212> TYPE: DNA
<213> ORGANISM: Artificial Sequence
<220> FEATURE:
<223> OTHER INFORMATION: synaxmi-031(apo)
<220> FEATURE:
<221> NAME/KEY: CDS
<222> LOCATION: (1)...(2148)

<400> SEQUENCE: 9 atg ggg tac tcc agc ttc gtt gct atc gct ctt ctt atg agc gtg gtt      48
Met Gly Tyr Ser Ser Phe Val Ala Ile Ala Leu Leu Met Ser Val Val
1               5                   10                  15 gtt gtt tgc aat ggg ggc aag acg tcc acc tac gtg cgt aat ctg gat      96
Val Val Cys Asn Gly Gly Lys Thr Ser Thr Tyr Val Arg Asn Leu Asp
            20                  25                  30 tgc aat ctc cag agc cag cag aat atc cca tac aat gtg ctt gct atc    144
Cys Asn Leu Gln Ser Gln Gln Asn Ile Pro Tyr Asn Val Leu Ala Ile
        35                  40                  45 cct gtt agc aat gtt aat agc ctt acg gat acg gtt ggc gat cta aag    192
Pro Val Ser Asn Val Asn Ser Leu Thr Asp Thr Val Gly Asp Leu Lys
    50                  55                  60 aag gca tgg gaa gag ttc cag aag acg ggc agc ttc tcc ctt acc gca    240
Lys Ala Trp Glu Glu Phe Gln Lys Thr Gly Ser Phe Ser Leu Thr Ala
65                  70                  75                  80
```

```
ctc cag cag ggc ttc agc gct tcc cag ggc ggg acg ttc aat tac ctc       288
Leu Gln Gln Gly Phe Ser Ala Ser Gln Gly Gly Thr Phe Asn Tyr Leu
                85                  90                  95 acc ctc ctc cag tcc ggg atc tcc ctg gct ggc agc ttc gtg cct ggc       336
Thr Leu Leu Gln Ser Gly Ile Ser Leu Ala Gly Ser Phe Val Pro Gly
                100                 105                 110 ggc acc ttc gtt gct cca atc atc aat atg gtg atc ggc tgg ctc tgg       384
Gly Thr Phe Val Ala Pro Ile Ile Asn Met Val Ile Gly Trp Leu Trp
            115                 120                 125 cct cat aag aat aag aat gca gat acg gaa aat ctg atc aat ctg atc       432
Pro His Lys Asn Lys Asn Ala Asp Thr Glu Asn Leu Ile Asn Leu Ile
        130                 135                 140 gat tca gaa atc cag aag cag ctg aat aag gct ctg ctg gat gct gat       480
Asp Ser Glu Ile Gln Lys Gln Leu Asn Lys Ala Leu Leu Asp Ala Asp
145                 150                 155                 160 cgc aat gaa tgg agc agc tac ctc gag tcc atc ttc gat agc agc aat       528
Arg Asn Glu Trp Ser Ser Tyr Leu Glu Ser Ile Phe Asp Ser Ser Asn
                165                 170                 175 aat ctg aat ggc gca atc gtt gat gct cag tgg tcc ggc acc gtg aat       576
Asn Leu Asn Gly Ala Ile Val Asp Ala Gln Trp Ser Gly Thr Val Asn
                180                 185                 190 acg acc aat cgt acg ctt cgt aat cct acg gaa tca gat tac acc aat       624
Thr Thr Asn Arg Thr Leu Arg Asn Pro Thr Glu Ser Asp Tyr Thr Asn
            195                 200                 205 gtg gtg acg aat ttc atc gca gca gat ggg gat atc gct aat aat gaa       672
Val Val Thr Asn Phe Ile Ala Ala Asp Gly Asp Ile Ala Asn Asn Glu
        210                 215                 220 aat cat atc atg aat ggg aat ttc gat gtg gca gca gct cca tac ttc       720
Asn His Ile Met Asn Gly Asn Phe Asp Val Ala Ala Ala Pro Tyr Phe
225                 230                 235                 240 gtt atc ggg gct acc gct aga ttc gca gct atg cag tcc tac atc aag       768
Val Ile Gly Ala Thr Ala Arg Phe Ala Ala Met Gln Ser Tyr Ile Lys
                245                 250                 255 ttc tgc aat gca tgg atc gat aag gtt ggg ctg tca gat gct cag ctg       816
Phe Cys Asn Ala Trp Ile Asp Lys Val Gly Leu Ser Asp Ala Gln Leu
                260                 265                 270 acc acg cag aag gct aat ctg gat aga acg aag cag aat atg cgt aat       864
Thr Thr Gln Lys Ala Asn Leu Asp Arg Thr Lys Gln Asn Met Arg Asn
            275                 280                 285 gct atc ctt aat tac acc cag cag gtt atg aag gtt ttc aag gat tcc       912
Ala Ile Leu Asn Tyr Thr Gln Gln Val Met Lys Val Phe Lys Asp Ser
        290                 295                 300 aag aat atg cca acg atc ggc acg aat aag ttc agc gtt gat acc tac       960
Lys Asn Met Pro Thr Ile Gly Thr Asn Lys Phe Ser Val Asp Thr Tyr
305                 310                 315                 320 aat gtt tac atc aag ggg atg acg ctt aat gtg ctt gat atc gtt gct      1008
Asn Val Tyr Ile Lys Gly Met Thr Leu Asn Val Leu Asp Ile Val Ala
                325                 330                 335 atc tgg cca agc ctg tac cca gat gat tac acg tca cag acg gct ctg      1056
Ile Trp Pro Ser Leu Tyr Pro Asp Asp Tyr Thr Ser Gln Thr Ala Leu
            340                 345                 350 gaa cag acc cgc gtg acg ttc tcc aat atg gtg ggg cag gaa gaa ggc      1104
Glu Gln Thr Arg Val Thr Phe Ser Asn Met Val Gly Gln Glu Glu Gly
        355                 360                 365 acg gat ggc agc ctc aga atc tac aat acc ttc gat agc ttc tcc tac      1152
Thr Asp Gly Ser Leu Arg Ile Tyr Asn Thr Phe Asp Ser Phe Ser Tyr
370                 375                 380 cag cat agc cct atc cct aat aat aat gtg aat ctc atc agc tac tac      1200
Gln His Ser Pro Ile Pro Asn Asn Asn Val Asn Leu Ile Ser Tyr Tyr
                385                 390                 395                 400
```

```
aat gat gaa ctt cag aat ctg gaa ctc ggg gtt tac acc cca cca aag      1248
Asn Asp Glu Leu Gln Asn Leu Glu Leu Gly Val Tyr Thr Pro Pro Lys
            405                 410                 415 aag ggc tca ggc tac agc tac cca tac ggg ttc gtg ctg aat tac gca      1296
Lys Gly Ser Gly Tyr Ser Tyr Pro Tyr Gly Phe Val Leu Asn Tyr Ala
                420                 425                 430 aat agc aag tac aag tac ggc gat tcc aat gat cca gaa tcc ctc ggc      1344
Asn Ser Lys Tyr Lys Tyr Gly Asp Ser Asn Asp Pro Glu Ser Leu Gly
            435                 440                 445 ggg ctt tcc acc ctt agc gct cca atc caa cag gtt aat gct gct acc      1392
Gly Leu Ser Thr Leu Ser Ala Pro Ile Gln Gln Val Asn Ala Ala Thr
        450                 455                 460 cag aat agc aag tac ctt gat ggc gaa atc ctg aat ggg atc ggc gca      1440
Gln Asn Ser Lys Tyr Leu Asp Gly Glu Ile Leu Asn Gly Ile Gly Ala
465                 470                 475                 480 agc ctg cct ggc tac tgc acg acc ggg tgc tca cct acc gaa cca cca      1488
Ser Leu Pro Gly Tyr Cys Thr Thr Gly Cys Ser Pro Thr Glu Pro Pro
                485                 490                 495 ttc agc tgc acg agc acg gca aat ggg tac aag gca agc tgc aat cca      1536
Phe Ser Cys Thr Ser Thr Ala Asn Gly Tyr Lys Ala Ser Cys Asn Pro
            500                 505                 510 agc gat acc aat cag aag atc aat gct ctc tac cca ttc acg cag gca      1584
Ser Asp Thr Asn Gln Lys Ile Asn Ala Leu Tyr Pro Phe Thr Gln Ala
        515                 520                 525 aat gtg aag ggg aat acc ggg aag ctg ggc gtt ctc gca agc ctt gtt      1632
Asn Val Lys Gly Asn Thr Gly Lys Leu Gly Val Leu Ala Ser Leu Val
    530                 535                 540 agc tac gat ctg aat cct aag aat gtt ttc ggg gaa ctc gat tca gat      1680
Ser Tyr Asp Leu Asn Pro Lys Asn Val Phe Gly Glu Leu Asp Ser Asp
545                 550                 555                 560 acc aat aat gtt atc ctt aag ggc atc cca gca gaa aag ggc tac ttc      1728
Thr Asn Asn Val Ile Leu Lys Gly Ile Pro Ala Glu Lys Gly Tyr Phe
                565                 570                 575 cca aat aat gca aga cca acc gtt gtg aag gaa tgg atc aat ggg gct      1776
Pro Asn Asn Ala Arg Pro Thr Val Val Lys Glu Trp Ile Asn Gly Ala
            580                 585                 590 tcc gca gtt cca ctt gat tcc ggc aat acc ctg ttc atg acg gct acg      1824
Ser Ala Val Pro Leu Asp Ser Gly Asn Thr Leu Phe Met Thr Ala Thr
        595                 600                 605 aac ctg acg gct acc cag tac aga atc cgc atc cgt tac gct aac cca      1872
Asn Leu Thr Ala Thr Gln Tyr Arg Ile Arg Ile Arg Tyr Ala Asn Pro
    610                 615                 620 aac tca aac acg cag atc ggc gtt aga atc acg cag aac ggg agc ctc      1920
Asn Ser Asn Thr Gln Ile Gly Val Arg Ile Thr Gln Asn Gly Ser Leu
625                 630                 635                 640 atc tcc tcc tcc aac ctc acg ctg tac tca acc acc gat atg aac aac      1968
Ile Ser Ser Ser Asn Leu Thr Leu Tyr Ser Thr Thr Asp Met Asn Asn
                645                 650                 655 acc ctg cca ctg aac gtt tac gtg atc ggg gaa aac ggg aac tac acc      2016
Thr Leu Pro Leu Asn Val Tyr Val Ile Gly Glu Asn Gly Asn Tyr Thr
            660                 665                 670 ctc cag gat ctc tac aac acg acg aac gtt ctg tcc acg ggc gat atc      2064
Leu Gln Asp Leu Tyr Asn Thr Thr Asn Val Leu Ser Thr Gly Asp Ile
        675                 680                 685 acc ctg cag atc acc ggc ggg gat cag aag ata ttc atc gat cgc atc      2112
Thr Leu Gln Ile Thr Gly Gly Asp Gln Lys Ile Phe Ile Asp Arg Ile
    690                 695                 700 gag ttc gtg cct acg atg cca gtg cca ggc aac taa                      2148
Glu Phe Val Pro Thr Met Pro Val Pro Gly Asn  *
705                 710                 715
```

<210> SEQ ID NO 10
<211> LENGTH: 715
<212> TYPE: PRT
<213> ORGANISM: Artificial Sequence
<220> FEATURE:
<223> OTHER INFORMATION: SYNAXMI-031(APO)

<400> SEQUENCE: 10

```
Met Gly Tyr Ser Ser Phe Val Ala Ile Ala Leu Leu Met Ser Val Val
 1               5                  10                  15

Val Val Cys Asn Gly Gly Lys Thr Ser Thr Tyr Val Arg Asn Leu Asp
             20                  25                  30

Cys Asn Leu Gln Ser Gln Gln Asn Ile Pro Tyr Asn Val Leu Ala Ile
         35                  40                  45

Pro Val Ser Asn Val Asn Ser Leu Thr Asp Thr Val Gly Asp Leu Lys
     50                  55                  60

Lys Ala Trp Glu Glu Phe Gln Lys Thr Gly Ser Phe Ser Leu Thr Ala
 65                  70                  75                  80

Leu Gln Gln Gly Phe Ser Ala Ser Gln Gly Gly Thr Phe Asn Tyr Leu
                 85                  90                  95

Thr Leu Leu Gln Ser Gly Ile Ser Leu Ala Gly Ser Phe Val Pro Gly
            100                 105                 110

Gly Thr Phe Val Ala Pro Ile Ile Asn Met Val Ile Gly Trp Leu Trp
        115                 120                 125

Pro His Lys Asn Lys Asn Ala Asp Thr Glu Asn Leu Ile Asn Leu Ile
    130                 135                 140

Asp Ser Glu Ile Gln Lys Gln Leu Asn Lys Ala Leu Leu Asp Ala Asp
145                 150                 155                 160

Arg Asn Glu Trp Ser Ser Tyr Leu Glu Ser Ile Phe Asp Ser Ser Asn
                165                 170                 175

Asn Leu Asn Gly Ala Ile Val Asp Ala Gln Trp Ser Gly Thr Val Asn
            180                 185                 190

Thr Thr Asn Arg Thr Leu Arg Asn Pro Thr Glu Ser Asp Tyr Thr Asn
        195                 200                 205

Val Val Thr Asn Phe Ile Ala Ala Asp Gly Asp Ile Ala Asn Asn Glu
    210                 215                 220

Asn His Ile Met Asn Gly Asn Phe Asp Val Ala Ala Pro Tyr Phe
225                 230                 235                 240

Val Ile Gly Ala Thr Ala Arg Phe Ala Ala Met Gln Ser Tyr Ile Lys
                245                 250                 255

Phe Cys Asn Ala Trp Ile Asp Lys Val Gly Leu Ser Asp Ala Gln Leu
            260                 265                 270

Thr Thr Gln Lys Ala Asn Leu Asp Arg Thr Lys Gln Asn Met Arg Asn
        275                 280                 285

Ala Ile Leu Asn Tyr Thr Gln Gln Val Met Lys Val Phe Lys Asp Ser
    290                 295                 300

Lys Asn Met Pro Thr Ile Gly Thr Asn Lys Phe Ser Val Asp Thr Tyr
305                 310                 315                 320

Asn Val Tyr Ile Lys Gly Met Thr Leu Asn Val Leu Asp Ile Val Ala
                325                 330                 335

Ile Trp Pro Ser Leu Tyr Pro Asp Asp Tyr Thr Ser Gln Thr Ala Leu
            340                 345                 350

Glu Gln Thr Arg Val Thr Phe Ser Asn Met Val Gly Gln Glu Glu Gly
        355                 360                 365

Thr Asp Gly Ser Leu Arg Ile Tyr Asn Thr Phe Asp Ser Phe Ser Tyr
```

| | | 370 | | | 375 | | | 380 | | | |
|---|---|---|---|---|---|---|---|---|---|---|---|

Gln His Ser Pro Ile Pro Asn Asn Val Asn Leu Ile Ser Tyr Tyr
385     390     395     400

Asn Asp Glu Leu Gln Asn Leu Glu Leu Gly Val Tyr Thr Pro Pro Lys
     405     410     415

Lys Gly Ser Gly Tyr Ser Tyr Pro Tyr Gly Phe Val Leu Asn Tyr Ala
    420     425     430

Asn Ser Lys Tyr Lys Tyr Gly Asp Ser Asn Asp Pro Glu Ser Leu Gly
   435     440     445

Gly Leu Ser Thr Leu Ser Ala Pro Ile Gln Gln Val Asn Ala Ala Thr
450     455     460

Gln Asn Ser Lys Tyr Leu Asp Gly Glu Ile Leu Asn Gly Ile Gly Ala
465     470     475     480

Ser Leu Pro Gly Tyr Cys Thr Thr Gly Cys Ser Pro Thr Glu Pro Pro
    485     490     495

Phe Ser Cys Thr Ser Thr Ala Asn Gly Tyr Lys Ala Ser Cys Asn Pro
   500     505     510

Ser Asp Thr Asn Gln Lys Ile Asn Ala Leu Tyr Pro Phe Thr Gln Ala
  515     520     525

Asn Val Lys Gly Asn Thr Gly Lys Leu Gly Val Leu Ala Ser Leu Val
530     535     540

Ser Tyr Asp Leu Asn Pro Lys Asn Val Phe Gly Glu Leu Asp Ser Asp
545     550     555     560

Thr Asn Asn Val Ile Leu Lys Gly Ile Pro Ala Glu Lys Gly Tyr Phe
    565     570     575

Pro Asn Asn Ala Arg Pro Thr Val Val Lys Glu Trp Ile Asn Gly Ala
   580     585     590

Ser Ala Val Pro Leu Asp Ser Gly Asn Thr Leu Phe Met Thr Ala Thr
  595     600     605

Asn Leu Thr Ala Thr Gln Tyr Arg Ile Arg Ile Arg Tyr Ala Asn Pro
610     615     620

Asn Ser Asn Thr Gln Ile Gly Val Arg Ile Thr Gln Asn Gly Ser Leu
625     630     635     640

Ile Ser Ser Ser Asn Leu Thr Leu Tyr Ser Thr Thr Asp Met Asn Asn
    645     650     655

Thr Leu Pro Leu Asn Val Tyr Val Ile Gly Glu Asn Gly Asn Tyr Thr
   660     665     670

Leu Gln Asp Leu Tyr Asn Thr Thr Asn Val Leu Ser Thr Gly Asp Ile
  675     680     685

Thr Leu Gln Ile Thr Gly Gly Asp Gln Lys Ile Phe Ile Asp Arg Ile
690     695     700

Glu Phe Val Pro Thr Met Pro Val Pro Gly Asn
705     710     715

<210> SEQ ID NO 11
<211> LENGTH: 2160
<212> TYPE: DNA
<213> ORGANISM: Artificial Sequence
<220> FEATURE:
<223> OTHER INFORMATION: synaxmi-031(ER)
<220> FEATURE:
<221> NAME/KEY: CDS
<222> LOCATION: (1)...(2160)

<400> SEQUENCE: 11 atg ggg tac tcc agc ttc gtt gct atc gct ctt ctt atg agc gtg gtt  48
Met Gly Tyr Ser Ser Phe Val Ala Ile Ala Leu Leu Met Ser Val Val

```
       1               5                    10                   15
gtt gtt tgc aat ggg ggc aag acg tcc acc tac gtg cgt aat ctg gat       96
Val Val Cys Asn Gly Gly Lys Thr Ser Thr Tyr Val Arg Asn Leu Asp
                20                   25                   30 tgc aat ctc cag agc cag cag aat atc cca tac aat gtg ctt gct atc      144
Cys Asn Leu Gln Ser Gln Gln Asn Ile Pro Tyr Asn Val Leu Ala Ile
         35                   40                   45 cct gtt agc aat gtt aat agc ctt acg gat acg gtt ggc gat cta aag      192
Pro Val Ser Asn Val Asn Ser Leu Thr Asp Thr Val Gly Asp Leu Lys
     50                   55                   60 aag gca tgg gaa gag ttc cag aag acg ggc agc ttc tcc ctt acc gca      240
Lys Ala Trp Glu Glu Phe Gln Lys Thr Gly Ser Phe Ser Leu Thr Ala
 65                   70                   75                   80 ctc cag cag ggc ttc agc gct tcc cag ggc ggg acg ttc aat tac ctc      288
Leu Gln Gln Gly Phe Ser Ala Ser Gln Gly Gly Thr Phe Asn Tyr Leu
                 85                   90                   95 acc ctc ctc cag tcc ggg atc tcc ctg gct ggc agc ttc gtg cct ggc      336
Thr Leu Leu Gln Ser Gly Ile Ser Leu Ala Gly Ser Phe Val Pro Gly
                100                  105                  110 ggc acc ttc gtt gct cca atc atc aat atg gtg atc ggc tgg ctc tgg      384
Gly Thr Phe Val Ala Pro Ile Ile Asn Met Val Ile Gly Trp Leu Trp
            115                  120                  125 cct cat aag aat aag aat gca gat acg gaa aat ctg atc aat ctg atc      432
Pro His Lys Asn Lys Asn Ala Asp Thr Glu Asn Leu Ile Asn Leu Ile
        130                  135                  140 gat tca gaa atc cag aag cag ctg aat aag gct ctg ctg gat gct gat      480
Asp Ser Glu Ile Gln Lys Gln Leu Asn Lys Ala Leu Leu Asp Ala Asp
145                  150                  155                  160 cgc aat gaa tgg agc agc tac ctc gag tcc atc ttc gat agc agc aat      528
Arg Asn Glu Trp Ser Ser Tyr Leu Glu Ser Ile Phe Asp Ser Ser Asn
                 165                  170                  175 aat ctg aat ggc gca atc gtt gat gct cag tgg tcc ggc acc gtg aat      576
Asn Leu Asn Gly Ala Ile Val Asp Ala Gln Trp Ser Gly Thr Val Asn
            180                  185                  190 acg acc aat cgt acg ctt cgt aat cct acg gaa tca gat tac acc aat      624
Thr Thr Asn Arg Thr Leu Arg Asn Pro Thr Glu Ser Asp Tyr Thr Asn
        195                  200                  205 gtg gtg acg aat ttc atc gca gca gat ggg gat atc gct aat aat gaa      672
Val Val Thr Asn Phe Ile Ala Ala Asp Gly Asp Ile Ala Asn Asn Glu
    210                  215                  220 aat cat atc atg aat ggg aat ttc gat gtg gca gca gct cca tac ttc      720
Asn His Ile Met Asn Gly Asn Phe Asp Val Ala Ala Ala Pro Tyr Phe
225                  230                  235                  240 gtt atc ggg gct acc gct aga ttc gca gct atg cag tcc tac atc aag      768
Val Ile Gly Ala Thr Ala Arg Phe Ala Ala Met Gln Ser Tyr Ile Lys
                245                  250                  255 ttc tgc aat gca tgg atc gat aag gtt ggg ctg tca gat gct cag ctg      816
Phe Cys Asn Ala Trp Ile Asp Lys Val Gly Leu Ser Asp Ala Gln Leu
            260                  265                  270 acc acg cag aag gct aat ctg gat aga acg aag cag aat atg cgt aat      864
Thr Thr Gln Lys Ala Asn Leu Asp Arg Thr Lys Gln Asn Met Arg Asn
        275                  280                  285 gct atc ctt aat tac acc cag cag gtt atg aag gtt ttc aag gat tcc      912
Ala Ile Leu Asn Tyr Thr Gln Gln Val Met Lys Val Phe Lys Asp Ser
    290                  295                  300 aag aat atg cca acg atc ggc acg aat aag ttc agc gtt gat acc tac      960
Lys Asn Met Pro Thr Ile Gly Thr Asn Lys Phe Ser Val Asp Thr Tyr
305                  310                  315                  320 aat gtt tac atc aag ggg atg acg ctt aat gtg ctt gat atc gtt gct     1008
Asn Val Tyr Ile Lys Gly Met Thr Leu Asn Val Leu Asp Ile Val Ala
```

```
                       325                 330                 335
atc tgg cca agc ctg tac cca gat gat tac acg tca cag acg gct ctg         1056
Ile Trp Pro Ser Leu Tyr Pro Asp Asp Tyr Thr Ser Gln Thr Ala Leu
            340                 345                 350 gaa cag acc cgc gtg acg ttc tcc aat atg gtg ggg cag gaa gaa ggc         1104
Glu Gln Thr Arg Val Thr Phe Ser Asn Met Val Gly Gln Glu Glu Gly
                355                 360                 365 acg gat ggc agc ctc aga atc tac aat acc ttc gat agc ttc tcc tac         1152
Thr Asp Gly Ser Leu Arg Ile Tyr Asn Thr Phe Asp Ser Phe Ser Tyr
        370                 375                 380 cag cat agc cct atc cct aat aat aat gtg aat ctc atc agc tac tac         1200
Gln His Ser Pro Ile Pro Asn Asn Asn Val Asn Leu Ile Ser Tyr Tyr
385                 390                 395                 400 aat gat gaa ctt cag aat ctg gaa ctc ggg gtt tac acc cca cca aag         1248
Asn Asp Glu Leu Gln Asn Leu Glu Leu Gly Val Tyr Thr Pro Pro Lys
                405                 410                 415 aag ggc tca ggc tac agc tac cca tac ggg ttc gtg ctg aat tac gca         1296
Lys Gly Ser Gly Tyr Ser Tyr Pro Tyr Gly Phe Val Leu Asn Tyr Ala
            420                 425                 430 aat agc aag tac aag tac ggc gat tcc aat gat cca gaa tcc ctc ggc         1344
Asn Ser Lys Tyr Lys Tyr Gly Asp Ser Asn Asp Pro Glu Ser Leu Gly
        435                 440                 445 ggg ctt tcc acc ctt agc gct cca atc caa cag gtt aat gct gct acc         1392
Gly Leu Ser Thr Leu Ser Ala Pro Ile Gln Gln Val Asn Ala Ala Thr
450                 455                 460 cag aat agc aag tac ctt gat ggc gaa atc ctg aat ggg atc ggc gca         1440
Gln Asn Ser Lys Tyr Leu Asp Gly Glu Ile Leu Asn Gly Ile Gly Ala
465                 470                 475                 480 agc ctg cct ggc tac tgc acg acc ggg tgc tca cct acc gaa cca cca         1488
Ser Leu Pro Gly Tyr Cys Thr Thr Gly Cys Ser Pro Thr Glu Pro Pro
                485                 490                 495 ttc agc tgc acg agc acg gca aat ggg tac aag gca agc tgc aat cca         1536
Phe Ser Cys Thr Ser Thr Ala Asn Gly Tyr Lys Ala Ser Cys Asn Pro
            500                 505                 510 agc gat acc aat cag aag atc aat gct ctc tac cca ttc acg cag gca         1584
Ser Asp Thr Asn Gln Lys Ile Asn Ala Leu Tyr Pro Phe Thr Gln Ala
        515                 520                 525 aat gtg aag ggg aat acc ggg aag ctg ggc gtt ctc gca agc ctt gtt         1632
Asn Val Lys Gly Asn Thr Gly Lys Leu Gly Val Leu Ala Ser Leu Val
    530                 535                 540 agc tac gat ctg aat cct aag aat gtt ttc ggg gaa ctc gat tca gat         1680
Ser Tyr Asp Leu Asn Pro Lys Asn Val Phe Gly Glu Leu Asp Ser Asp
545                 550                 555                 560 acc aat aat gtt atc ctt aag ggc atc cca gca gaa aag ggc tac ttc         1728
Thr Asn Asn Val Ile Leu Lys Gly Ile Pro Ala Glu Lys Gly Tyr Phe
                565                 570                 575 cca aat aat gca aga cca acc gtt gtg aag gaa tgg atc aat ggg gct         1776
Pro Asn Asn Ala Arg Pro Thr Val Val Lys Glu Trp Ile Asn Gly Ala
            580                 585                 590 tcc gca gtt cca ctt gat tcc ggc aat acc ctg ttc atg acg gct acg         1824
Ser Ala Val Pro Leu Asp Ser Gly Asn Thr Leu Phe Met Thr Ala Thr
        595                 600                 605 aac ctg acg gct acc cag tac aga atc cgc atc cgt tac gct aac cca         1872
Asn Leu Thr Ala Thr Gln Tyr Arg Ile Arg Ile Arg Tyr Ala Asn Pro
    610                 615                 620 aac tca aac acg cag atc ggc gtt aga atc acg cag aac ggg agc ctc         1920
Asn Ser Asn Thr Gln Ile Gly Val Arg Ile Thr Gln Asn Gly Ser Leu
625                 630                 635                 640 atc tcc tcc tcc aac ctc acg ctg tac tca acc acc gat atg aac aac         1968
Ile Ser Ser Ser Asn Leu Thr Leu Tyr Ser Thr Thr Asp Met Asn Asn
```

```
                       645                 650                 655
acc ctg cca ctg aac gtt tac gtg atc ggg gaa aac ggg aac tac acc    2016
Thr Leu Pro Leu Asn Val Tyr Val Ile Gly Glu Asn Gly Asn Tyr Thr
            660                 665                 670 ctc cag gat ctc tac aac acg acg aac gtt ctg tcc acg ggc gat atc    2064
Leu Gln Asp Leu Tyr Asn Thr Thr Asn Val Leu Ser Thr Gly Asp Ile
        675                 680                 685 acc ctg cag atc acc ggc ggg gat cag aag ata ttc atc gat cgc atc    2112
Thr Leu Gln Ile Thr Gly Gly Asp Gln Lys Ile Phe Ile Asp Arg Ile
690                 695                 700 gag ttc gtg cct acg atg cca gtg cca ggc aac aag gat gaa ctg taa    2160
Glu Phe Val Pro Thr Met Pro Val Pro Gly Asn Lys Asp Glu Leu  *
705                 710                 715

<210> SEQ ID NO 12
<211> LENGTH: 719
<212> TYPE: PRT
<213> ORGANISM: Artificial Sequence
<220> FEATURE:
<223> OTHER INFORMATION: SYNAXMI-031(ER)

<400> SEQUENCE: 12

Met Gly Tyr Ser Ser Phe Val Ala Ile Ala Leu Leu Met Ser Val Val
 1               5                  10                  15

Val Val Cys Asn Gly Gly Lys Thr Ser Thr Tyr Val Arg Asn Leu Asp
                20                  25                  30

Cys Asn Leu Gln Ser Gln Gln Asn Ile Pro Tyr Asn Val Leu Ala Ile
            35                  40                  45

Pro Val Ser Asn Val Asn Ser Leu Thr Asp Thr Val Gly Asp Leu Lys
        50                  55                  60

Lys Ala Trp Glu Glu Phe Gln Lys Thr Gly Ser Phe Ser Leu Thr Ala
65                  70                  75                  80

Leu Gln Gln Gly Phe Ser Ala Ser Gln Gly Gly Thr Phe Asn Tyr Leu
                85                  90                  95

Thr Leu Leu Gln Ser Gly Ile Ser Leu Ala Gly Ser Phe Val Pro Gly
            100                 105                 110

Gly Thr Phe Val Ala Pro Ile Ile Asn Met Val Ile Gly Trp Leu Trp
        115                 120                 125

Pro His Lys Asn Lys Asn Ala Asp Thr Glu Asn Leu Ile Asn Leu Ile
    130                 135                 140

Asp Ser Glu Ile Gln Lys Gln Leu Asn Lys Ala Leu Leu Asp Ala Asp
145                 150                 155                 160

Arg Asn Glu Trp Ser Ser Tyr Leu Glu Ser Ile Phe Asp Ser Ser Asn
                165                 170                 175

Asn Leu Asn Gly Ala Ile Val Asp Ala Gln Trp Ser Gly Thr Val Asn
            180                 185                 190

Thr Thr Asn Arg Thr Leu Arg Asn Pro Thr Glu Ser Asp Tyr Thr Asn
        195                 200                 205

Val Val Thr Asn Phe Ile Ala Ala Asp Gly Asp Ile Ala Asn Asn Glu
    210                 215                 220

Asn His Ile Met Asn Gly Asn Phe Asp Val Ala Ala Pro Tyr Phe
225                 230                 235                 240

Val Ile Gly Ala Thr Ala Arg Phe Ala Ala Met Gln Ser Tyr Ile Lys
                245                 250                 255

Phe Cys Asn Ala Trp Ile Asp Lys Val Gly Leu Ser Asp Ala Gln Leu
            260                 265                 270

Thr Thr Gln Lys Ala Asn Leu Asp Arg Thr Lys Gln Asn Met Arg Asn
```

```
            275                 280                 285
Ala Ile Leu Asn Tyr Thr Gln Gln Val Met Lys Val Phe Lys Asp Ser
290                 295                 300
Lys Asn Met Pro Thr Ile Gly Thr Asn Lys Phe Ser Val Asp Thr Tyr
305                 310                 315                 320
Asn Val Tyr Ile Lys Gly Met Thr Leu Asn Val Leu Asp Ile Val Ala
                325                 330                 335
Ile Trp Pro Ser Leu Tyr Pro Asp Asp Tyr Thr Ser Gln Thr Ala Leu
                340                 345                 350
Glu Gln Thr Arg Val Thr Phe Ser Asn Met Val Gly Gln Glu Glu Gly
                355                 360                 365
Thr Asp Gly Ser Leu Arg Ile Tyr Asn Thr Phe Asp Ser Phe Ser Tyr
370                 375                 380
Gln His Ser Pro Ile Pro Asn Asn Asn Val Asn Leu Ile Ser Tyr Tyr
385                 390                 395                 400
Asn Asp Glu Leu Gln Asn Leu Glu Leu Gly Val Tyr Thr Pro Pro Lys
                405                 410                 415
Lys Gly Ser Gly Tyr Ser Tyr Pro Tyr Gly Phe Val Leu Asn Tyr Ala
                420                 425                 430
Asn Ser Lys Tyr Lys Tyr Gly Asp Ser Asn Asp Pro Glu Ser Leu Gly
                435                 440                 445
Gly Leu Ser Thr Leu Ser Ala Pro Ile Gln Gln Val Asn Ala Ala Thr
450                 455                 460
Gln Asn Ser Lys Tyr Leu Asp Gly Glu Ile Leu Asn Gly Ile Gly Ala
465                 470                 475                 480
Ser Leu Pro Gly Tyr Cys Thr Thr Gly Cys Ser Pro Thr Glu Pro Pro
                485                 490                 495
Phe Ser Cys Thr Ser Thr Ala Asn Gly Tyr Lys Ala Ser Cys Asn Pro
                500                 505                 510
Ser Asp Thr Asn Gln Lys Ile Asn Ala Leu Tyr Pro Phe Thr Gln Ala
                515                 520                 525
Asn Val Lys Gly Asn Thr Gly Lys Leu Gly Val Leu Ala Ser Leu Val
530                 535                 540
Ser Tyr Asp Leu Asn Pro Lys Asn Val Phe Gly Glu Leu Asp Ser Asp
545                 550                 555                 560
Thr Asn Asn Val Ile Leu Lys Gly Ile Pro Ala Glu Lys Gly Tyr Phe
                565                 570                 575
Pro Asn Asn Ala Arg Pro Thr Val Val Lys Glu Trp Ile Asn Gly Ala
                580                 585                 590
Ser Ala Val Pro Leu Asp Ser Gly Asn Thr Leu Phe Met Thr Ala Thr
                595                 600                 605
Asn Leu Thr Ala Thr Gln Tyr Arg Ile Arg Ile Arg Tyr Ala Asn Pro
610                 615                 620
Asn Ser Asn Thr Gln Ile Gly Val Arg Ile Thr Gln Asn Gly Ser Leu
625                 630                 635                 640
Ile Ser Ser Ser Asn Leu Thr Leu Tyr Ser Thr Thr Asp Met Asn Asn
                645                 650                 655
Thr Leu Pro Leu Asn Val Tyr Val Ile Gly Glu Asn Gly Asn Tyr Thr
                660                 665                 670
Leu Gln Asp Leu Tyr Asn Thr Thr Asn Val Leu Ser Thr Gly Asp Ile
                675                 680                 685
Thr Leu Gln Ile Thr Gly Gly Asp Gln Lys Ile Phe Ile Asp Arg Ile
690                 695                 700
```

```
Glu Phe Val Pro Thr Met Pro Val Pro Gly Asn Lys Asp Glu Leu
705                 710                 715

<210> SEQ ID NO 13
<211> LENGTH: 1186
<212> TYPE: PRT
<213> ORGANISM: Bacillus thuringiensis

<400> SEQUENCE: 13

Met Asp Cys Asn Leu Gln Ser Gln Gln Asn Ile Pro Tyr Asn Val Leu
 1               5                  10                  15

Ala Ile Pro Val Ser Asn Val Asn Ala Leu Val Asp Thr Ala Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Ala Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Val Asn Met Val Ile Gly Trp
                85                  90                  95

Leu Trp Pro His Lys Asn Lys Thr Ala Asp Thr Glu Asn Leu Ile Lys
            100                 105                 110

Leu Ile Asp Glu Glu Ile Gln Lys Gln Leu Asn Lys Ala Leu Leu Asp
        115                 120                 125

Gln Asp Arg Asn Asn Trp Thr Ser Phe Leu Glu Ser Ile Phe Asp Thr
    130                 135                 140

Ser Ala Thr Val Ser Asn Ala Ile Ile Asp Ala Gln Trp Ser Gly Thr
145                 150                 155                 160

Val Asp Thr Thr Asn Arg Gln Gln Lys Thr Pro Thr Thr Ser Asp Tyr
                165                 170                 175

Leu Asn Val Val Gly Lys Phe Asp Ser Ala Asp Ser Ser Ile Ile Thr
            180                 185                 190

Asn Glu Asn Gln Ile Met Asn Gly Asn Phe Asp Val Ala Ala Ala Pro
        195                 200                 205

Tyr Phe Val Ile Gly Ala Thr Leu Arg Leu Ser Leu Tyr Gln Ser Tyr
    210                 215                 220

Ile Lys Phe Cys Asn Ser Trp Ile Asp Ala Val Gly Phe Ser Thr Asn
225                 230                 235                 240

Asp Ala Asn Thr Gln Lys Ala Asn Leu Ala Arg Thr Lys Leu Thr Met
                245                 250                 255

Arg Thr Thr Ile Asn Glu Tyr Thr Gln Arg Val Met Lys Val Phe Lys
            260                 265                 270

Asp Ser Lys Asn Met Pro Thr Ile Gly Thr Asn Lys Phe Ser Val Asp
        275                 280                 285

Ala Tyr Asn Val Tyr Val Lys Gly Met Thr Leu Asn Val Leu Asp Met
    290                 295                 300

Val Ala Ile Trp Ser Ser Leu Tyr Pro Asn Asp Tyr Thr Ser Gln Thr
305                 310                 315                 320

Ala Ile Glu Gln Thr Arg Val Thr Phe Ser Asn Met Val Gly Gln Glu
                325                 330                 335

Glu Gly Thr Asp Gly Thr Leu Lys Ile Tyr Asn Thr Phe Asp Ser Leu
            340                 345                 350

Ser Tyr Gln His Ser Leu Ile Pro Asn Asn Asn Val Asn Leu Ile Ser
        355                 360                 365
```

```
Tyr Tyr Thr Asp Glu Leu Gln Asn Leu Glu Leu Ala Val Tyr Thr Pro
    370                 375                 380
Lys Gly Gly Ser Gly Tyr Ala Tyr Pro Tyr Gly Phe Ile Leu Asn Tyr
385                 390                 395                 400
Ala Asn Ser Asn Tyr Lys Tyr Gly Asp Asn Asp Pro Thr Gly Lys Pro
                405                 410                 415
Leu Asn Lys Gln Asp Gly Pro Ile Gln Gln Ile Asn Ala Ala Thr Gln
            420                 425                 430
Asn Ser Lys Tyr Leu Asp Gly Glu Thr Ile Asn Gly Ile Gly Ala Ser
        435                 440                 445
Leu Pro Gly Tyr Cys Thr Thr Gly Cys Ser Ala Thr Glu Gln Pro Phe
    450                 455                 460
Ser Cys Thr Ser Thr Ala Asn Ser Tyr Lys Ala Ser Cys Asn Pro Ser
465                 470                 475                 480
Asp Thr Asn Gln Lys Ile Asn Ala Leu Tyr Ala Phe Thr Gln Thr Asn
                485                 490                 495
Val Lys Gly Ser Thr Gly Lys Leu Gly Val Leu Ala Ser Leu Val Pro
            500                 505                 510
Tyr Asp Leu Asn Pro Lys Asn Val Phe Gly Glu Leu Asp Ser Asp Thr
        515                 520                 525
Asn Asn Val Ile Leu Lys Gly Ile Pro Ala Glu Lys Gly Tyr Phe Pro
    530                 535                 540
Asn Asn Ala Arg Pro Thr Val Val Lys Glu Trp Ile Asn Gly Ala Ser
545                 550                 555                 560
Ala Val Pro Phe Tyr Ser Gly Asn Thr Leu Phe Met Thr Ala Thr Asn
                565                 570                 575
Leu Thr Ala Thr Gln Tyr Lys Ile Arg Ile Arg Tyr Ala Asn Pro Asn
            580                 585                 590
Ser Asp Thr Gln Ile Gly Val Leu Ile Thr Gln Asn Gly Ser Gln Ile
        595                 600                 605
Ser Asn Ser Asn Leu Thr Leu Tyr Ser Thr Thr Asp Ser Ser Met Ser
    610                 615                 620
Ser Asn Leu Pro Gln Asn Val Tyr Val Thr Gly Glu Asn Gly Asn Tyr
625                 630                 635                 640
Thr Leu Leu Asp Leu Tyr Ser Thr Thr Asn Val Leu Ser Thr Gly Asp
                645                 650                 655
Ile Thr Leu Lys Leu Thr Gly Gly Asn Gln Lys Ile Phe Ile Asp Arg
            660                 665                 670
Ile Glu Phe Ile Pro Thr Met Pro Val Pro Ala Pro Thr Asn Asn Thr
        675                 680                 685
Asn Asn Asn Asn Gly Asp Asn Gly Asn Asn Pro Pro His His Gly
    690                 695                 700
Cys Ala Ile Ala Gly Thr Gln Gln Leu Cys Ser Gly Pro Pro Lys Phe
705                 710                 715                 720
Glu Gln Val Ser Asp Leu Glu Lys Ile Thr Thr Gln Val Tyr Met Leu
                725                 730                 735
Phe Lys Ser Ser Ser Tyr Glu Glu Leu Ala Leu Lys Val Ser Ser Tyr
            740                 745                 750
Gln Ile Asn Gln Val Ala Leu Lys Val Met Ala Leu Ser Asp Glu Lys
        755                 760                 765
Phe Cys Glu Glu Lys Arg Leu Leu Arg Lys Leu Val Asn Lys Ala Asn
    770                 775                 780
Gln Leu Leu Glu Ala Arg Asn Leu Leu Val Gly Gly Asn Phe Glu Thr
785                 790                 795                 800
```

```
Thr Gln Asn Trp Val Leu Gly Thr Asn Ala Tyr Ile Asn Tyr Asp Ser
            805                 810                 815
Phe Leu Phe Asn Gly Asn Tyr Leu Ser Leu Gln Pro Ala Ser Gly Phe
        820                 825                 830
Phe Thr Ser Tyr Ala Tyr Gln Lys Ile Asp Glu Ser Thr Leu Lys Pro
    835                 840                 845
Tyr Thr Arg Tyr Lys Val Ser Gly Phe Ile Gly Gln Ser Asn Gln Val
850                 855                 860
Glu Leu Ile Ile Ser Arg Tyr Gly Lys Glu Ile Asp Lys Ile Leu Asn
865                 870                 875                 880
Val Pro Tyr Ala Gly Pro Leu Pro Ile Thr Ala Asp Ala Ser Ile Thr
                885                 890                 895
Cys Cys Ala Pro Glu Ile Asp Gln Cys Asp Gly Gln Ser Asp Ser
            900                 905                 910
His Phe Phe Asn Tyr Ser Ile Asp Val Gly Ala Leu His Pro Glu Leu
        915                 920                 925
Asn Pro Gly Ile Glu Ile Gly Leu Lys Ile Val Gln Ser Asn Gly Tyr
    930                 935                 940
Ile Thr Ile Ser Asn Leu Glu Ile Ile Glu Glu Arg Pro Leu Thr Glu
945                 950                 955                 960
Met Glu Ile Gln Ala Val Asn Arg Lys Asp Gln Lys Trp Lys Arg Glu
                965                 970                 975
Lys Leu Leu Glu Cys Ala Ser Val Ser Glu Leu Leu Gln Pro Ile Ile
            980                 985                 990
Asn Gln Ile Asp Ser Leu Phe Lys Asp Ala Asn Trp Tyr Asn Asp Ile
        995                 1000                1005
Leu Pro His Val Thr Tyr Gln Thr Leu Lys Asn Ile Ile Val Pro Asp
    1010                1015                1020
Leu Pro Lys Leu Lys His Trp Phe Ile Asp His Leu Pro Gly Glu Tyr
1025                1030                1035                1040
His Glu Ile Glu Gln Lys Met Lys Glu Ala Leu Lys His Ala Phe Thr
                1045                1050                1055
Gln Leu Asp Glu Lys Asn Leu Ile His Asn Gly His Phe Ala Thr Asn
            1060                1065                1070
Leu Ile Asp Trp Gln Val Glu Gly Asp Ala Arg Met Lys Val Leu Glu
        1075                1080                1085
Asn Asn Ala Leu Ala Leu Gln Leu Ser Asn Trp Asp Ser Ser Val Ser
    1090                1095                1100
Gln Ser Ile Asp Ile Leu Glu Phe Asp Glu Asp Lys Ala Tyr Lys Leu
1105                1110                1115                1120
Arg Val Tyr Ala Gln Gly Ser Gly Thr Ile Gln Phe Gly Asn Cys Glu
                1125                1130                1135
Asp Glu Ala Ile Gln Phe Asn Thr Asn Ser Phe Val Tyr Lys Glu Lys
            1140                1145                1150
Ile Ile Tyr Phe Asp Thr Pro Ser Ile Asn Leu His Ile Gln Ser Glu
        1155                1160                1165
Gly Ser Glu Phe Val Val Ser Ser Ile Asp Leu Val Glu Leu Ser Asp
    1170                1175                1180
Asp Glu
1185

<210> SEQ ID NO 14
<211> LENGTH: 2190
<212> TYPE: DNA
```

```
<213> ORGANISM: Artificial Sequence
<220> FEATURE:
<223> OTHER INFORMATION: axmi-031(truncated)
<220> FEATURE:
<221> NAME/KEY: CDS
<222> LOCATION: (1)...(2190)

<400> SEQUENCE: 14 atg tcg tac tac cat cac cat cac cac ctc gaa tca aca agt ttg        48
Met Ser Tyr Tyr His His His His His Leu Glu Ser Thr Ser Leu
 1               5                  10                  15 tac aaa aaa gca ggc ttc att gaa gga cgt atg gat tgt aat tta caa    96
Tyr Lys Lys Ala Gly Phe Ile Glu Gly Arg Met Asp Cys Asn Leu Gln
                20                  25                  30 tca caa caa aat att cca tat aat gta tta gca ata cca gta tct aat    144
Ser Gln Gln Asn Ile Pro Tyr Asn Val Leu Ala Ile Pro Val Ser Asn
            35                  40                  45 gtt aat tcg ttg act gat aca gtt gga gat tta aaa aaa gca tgg gaa    192
Val Asn Ser Leu Thr Asp Thr Val Gly Asp Leu Lys Lys Ala Trp Glu
 50                  55                  60 gaa ttt caa aaa act ggt tct ttt tca tta aca gct tta caa caa gga    240
Glu Phe Gln Lys Thr Gly Ser Phe Ser Leu Thr Ala Leu Gln Gln Gly
 65                  70                  75                  80 ttt tct gct tca caa gga gga aca ttc aat tat tta aca tta cta caa    288
Phe Ser Ala Ser Gln Gly Gly Thr Phe Asn Tyr Leu Thr Leu Leu Gln
                 85                  90                  95 tca gga ata tca tta gct ggt tct ttt gtt cct gga ggt act ttt gta    336
Ser Gly Ile Ser Leu Ala Gly Ser Phe Val Pro Gly Gly Thr Phe Val
            100                 105                 110 gca cct att att aat atg gtt att ggt tgg tta tgg cca cat aaa aac    384
Ala Pro Ile Ile Asn Met Val Ile Gly Trp Leu Trp Pro His Lys Asn
        115                 120                 125 aaa aat gcg gat aca gaa aat tta ata aat tta att gat tca gaa att    432
Lys Asn Ala Asp Thr Glu Asn Leu Ile Asn Leu Ile Asp Ser Glu Ile
130                 135                 140 caa aaa caa tta aac aaa gct tta tta gat gca gat aga aat gag tgg    480
Gln Lys Gln Leu Asn Lys Ala Leu Leu Asp Ala Asp Arg Asn Glu Trp
145                 150                 155                 160 agc tct tat tta gaa tct ata ttt gat tct tca aat aac cta aat ggt    528
Ser Ser Tyr Leu Glu Ser Ile Phe Asp Ser Ser Asn Asn Leu Asn Gly
                165                 170                 175 gca att gta gat gca cag tgg tca ggc act gta aat act aca aat aga    576
Ala Ile Val Asp Ala Gln Trp Ser Gly Thr Val Asn Thr Thr Asn Arg
            180                 185                 190 aca cta aga aat cca aca gaa tca gat tat aca aat gtt gtt aca aat    624
Thr Leu Arg Asn Pro Thr Glu Ser Asp Tyr Thr Asn Val Val Thr Asn
        195                 200                 205 ttt att gca gcg gat ggt gac att gca aat aat gaa aat cac ata atg    672
Phe Ile Ala Ala Asp Gly Asp Ile Ala Asn Asn Glu Asn His Ile Met
210                 215                 220 aat ggc aac ttt gac gta gct gca cct tat ttt gtt ata gga gca        720
Asn Gly Asn Phe Asp Val Ala Ala Pro Tyr Phe Val Ile Gly Ala
225                 230                 235                 240 aca gca cgt ttt gca gca atg caa tct tat att aaa ttt tgt aat gct    768
Thr Ala Arg Phe Ala Ala Met Gln Ser Tyr Ile Lys Phe Cys Asn Ala
                245                 250                 255 tgg att gat aaa gtt gga ttg agt gac gca cag ctt act aca caa aag    816
Trp Ile Asp Lys Val Gly Leu Ser Asp Ala Gln Leu Thr Thr Gln Lys
            260                 265                 270 gct aat tta gat cgc acg aaa caa aat atg cgt aat gca att ctt aac    864
Ala Asn Leu Asp Arg Thr Lys Gln Asn Met Arg Asn Ala Ile Leu Asn
        275                 280                 285
```

| | | | | | | | | | | | | | | | |
|---|---|---|---|---|---|---|---|---|---|---|---|---|---|---|---|
| tat | aca | caa | caa | gtt | atg | aaa | gtt | ttt | aaa | gat | tcc | aaa | aat | atg | cct | 912 |
| Tyr | Thr | Gln | Gln | Val | Met | Lys | Val | Phe | Lys | Asp | Ser | Lys | Asn | Met | Pro |
| 290 | | | | 295 | | | | | 300 | | | | | | |

| aca | ata | ggt | act | aat | aaa | ttt | agt | gtt | gat | acc | tat | aat | gta | tat | att | 960 |
| Thr | Ile | Gly | Thr | Asn | Lys | Phe | Ser | Val | Asp | Thr | Tyr | Asn | Val | Tyr | Ile |
| 305 | | | | | 310 | | | | | 315 | | | | | 320 |

| aaa | gga | atg | aca | tta | aat | gtt | tta | gat | att | gta | gca | ata | tgg | cct | tca | 1008 |
| Lys | Gly | Met | Thr | Leu | Asn | Val | Leu | Asp | Ile | Val | Ala | Ile | Trp | Pro | Ser |
| | | | | 325 | | | | | 330 | | | | | 335 | |

| tta | tat | cca | gat | gat | tat | act | tca | caa | aca | gcc | tta | gaa | caa | aca | cgt | 1056 |
| Leu | Tyr | Pro | Asp | Asp | Tyr | Thr | Ser | Gln | Thr | Ala | Leu | Glu | Gln | Thr | Arg |
| | | | 340 | | | | | 345 | | | | | 350 | | |

| gtc | act | ttt | tca | aat | atg | gtt | ggc | caa | gaa | gaa | ggt | aca | gat | gga | agc | 1104 |
| Val | Thr | Phe | Ser | Asn | Met | Val | Gly | Gln | Glu | Glu | Gly | Thr | Asp | Gly | Ser |
| | | | 355 | | | | | 360 | | | | | 365 | | |

| cta | aga | att | tac | aat | act | ttt | gat | tct | ttt | agt | tat | caa | cat | agt | cca | 1152 |
| Leu | Arg | Ile | Tyr | Asn | Thr | Phe | Asp | Ser | Phe | Ser | Tyr | Gln | His | Ser | Pro |
| 370 | | | | | 375 | | | | | 380 | | | | | |

| ata | cct | aat | aat | aat | gtt | aat | tta | att | tct | tat | tat | aat | gat | gaa | tta | 1200 |
| Ile | Pro | Asn | Asn | Asn | Val | Asn | Leu | Ile | Ser | Tyr | Tyr | Asn | Asp | Glu | Leu |
| 385 | | | | | 390 | | | | | 395 | | | | | 400 |

| caa | aat | cta | gaa | tta | gga | gta | tat | acc | cct | cct | aaa | aaa | gga | agt | gga | 1248 |
| Gln | Asn | Leu | Glu | Leu | Gly | Val | Tyr | Thr | Pro | Pro | Lys | Lys | Gly | Ser | Gly |
| | | | | 405 | | | | | 410 | | | | | 415 | |

| tac | tct | tat | cct | tat | gga | ttt | gtt | tta | aat | tat | gca | aac | agt | aaa | tat | 1296 |
| Tyr | Ser | Tyr | Pro | Tyr | Gly | Phe | Val | Leu | Asn | Tyr | Ala | Asn | Ser | Lys | Tyr |
| | | | 420 | | | | | 425 | | | | | 430 | | |

| aaa | tat | ggt | gat | agc | aat | gat | cca | gaa | tct | cta | gga | gga | tta | tct | aca | 1344 |
| Lys | Tyr | Gly | Asp | Ser | Asn | Asp | Pro | Glu | Ser | Leu | Gly | Gly | Leu | Ser | Thr |
| | | | 435 | | | | | 440 | | | | | 445 | | |

| cta | tct | gca | cct | ata | caa | caa | gtt | aat | gca | gca | act | caa | aac | agt | aaa | 1392 |
| Leu | Ser | Ala | Pro | Ile | Gln | Gln | Val | Asn | Ala | Ala | Thr | Gln | Asn | Ser | Lys |
| | 450 | | | | | 455 | | | | | 460 | | | | |

| tat | cta | gat | gga | gaa | atc | cta | aat | gga | ata | gga | gca | tcc | tta | cct | ggt | 1440 |
| Tyr | Leu | Asp | Gly | Glu | Ile | Leu | Asn | Gly | Ile | Gly | Ala | Ser | Leu | Pro | Gly |
| 465 | | | | | 470 | | | | | 475 | | | | | 480 |

| tat | tgt | act | aca | gga | tgt | tca | cca | aca | gaa | cca | cct | ttt | agt | tgt | act | 1488 |
| Tyr | Cys | Thr | Thr | Gly | Cys | Ser | Pro | Thr | Glu | Pro | Pro | Phe | Ser | Cys | Thr |
| | | | | 485 | | | | | 490 | | | | | 495 | |

| tct | acc | gct | aat | ggc | tat | aaa | gca | agc | tgt | aat | cct | tca | gat | aca | aat | 1536 |
| Ser | Thr | Ala | Asn | Gly | Tyr | Lys | Ala | Ser | Cys | Asn | Pro | Ser | Asp | Thr | Asn |
| | | | 500 | | | | | 505 | | | | | 510 | | |

| caa | aaa | att | aac | gct | tta | tat | cct | ttt | aca | caa | gct | aat | gta | aag | gga | 1584 |
| Gln | Lys | Ile | Asn | Ala | Leu | Tyr | Pro | Phe | Thr | Gln | Ala | Asn | Val | Lys | Gly |
| | | 515 | | | | | 520 | | | | | 525 | | | |

| aac | aca | gga | aaa | tta | gga | gta | ctg | gca | agt | ctt | gtt | tca | tat | gat | tta | 1632 |
| Asn | Thr | Gly | Lys | Leu | Gly | Val | Leu | Ala | Ser | Leu | Val | Ser | Tyr | Asp | Leu |
| | 530 | | | | | 535 | | | | | 540 | | | | |

| aat | cct | aaa | aat | gta | ttt | ggt | gaa | tta | gat | tca | gat | aca | aat | aat | gtt | 1680 |
| Asn | Pro | Lys | Asn | Val | Phe | Gly | Glu | Leu | Asp | Ser | Asp | Thr | Asn | Asn | Val |
| 545 | | | | | 550 | | | | | 555 | | | | | 560 |

| atc | tta | aaa | gga | att | cct | gca | gaa | aaa | gga | tat | ttt | cct | aat | aat | gcg | 1728 |
| Ile | Leu | Lys | Gly | Ile | Pro | Ala | Glu | Lys | Gly | Tyr | Phe | Pro | Asn | Asn | Ala |
| | | | | 565 | | | | | 570 | | | | | 575 | |

| cgt | cct | act | gtt | gta | aaa | gaa | tgg | att | aat | ggt | gca | agt | gct | gta | cca | 1776 |
| Arg | Pro | Thr | Val | Val | Lys | Glu | Trp | Ile | Asn | Gly | Ala | Ser | Ala | Val | Pro |
| | | | 580 | | | | | 585 | | | | | 590 | | |

| ctt | gat | tca | gga | aat | acc | tta | ttt | atg | acg | gct | acg | aat | tta | aca | gct | 1824 |
| Leu | Asp | Ser | Gly | Asn | Thr | Leu | Phe | Met | Thr | Ala | Thr | Asn | Leu | Thr | Ala |
| | | | 595 | | | | | 600 | | | | | 605 | | |

-continued

| | | |
|---|---|---|
| act caa tat aga att aga ata cgt tat gca aat cca aat tca aat act<br>Thr Gln Tyr Arg Ile Arg Ile Arg Tyr Ala Asn Pro Asn Ser Asn Thr<br>610                      615                      620 | 1872 |
| caa atc ggt gta cga att aca caa aat ggt tct cta att tcc agt agt<br>Gln Ile Gly Val Arg Ile Thr Gln Asn Gly Ser Leu Ile Ser Ser Ser<br>625                      630                      635                      640 | 1920 |
| aat cta aca ctt tat agt act act gat atg aat aat act tta cca cta<br>Asn Leu Thr Leu Tyr Ser Thr Thr Asp Met Asn Asn Thr Leu Pro Leu<br>                      645                      650                      655 | 1968 |
| aat gta tat gta ata gga gaa aat gga aat tat aca ctt caa gat tta<br>Asn Val Tyr Val Ile Gly Glu Asn Gly Asn Tyr Thr Leu Gln Asp Leu<br>                660                      665                      670 | 2016 |
| tat aat act act aat gtt tta tca aca gga gat att aca tta caa att<br>Tyr Asn Thr Thr Asn Val Leu Ser Thr Gly Asp Ile Thr Leu Gln Ile<br>675                      680                      685 | 2064 |
| aca gga gga gat caa aaa ata ttt att gat cga ata gaa ttt gtt cct<br>Thr Gly Gly Asp Gln Lys Ile Phe Ile Asp Arg Ile Glu Phe Val Pro<br>            690                      695                      700 | 2112 |
| act atg cct gta cct ggt aat act aac aac aat aac ggt aat aat aac<br>Thr Met Pro Val Pro Gly Asn Thr Asn Asn Asn Asn Gly Asn Asn Asn<br>705                      710                      715                      720 | 2160 |
| ggt aat aat aat ccc cca cac cac gtc tag<br>Gly Asn Asn Asn Pro Pro His His Val *<br>                    725 | 2190 |

<210> SEQ ID NO 15
<211> LENGTH: 729
<212> TYPE: PRT
<213> ORGANISM: Artificial Sequence
<220> FEATURE:
<223> OTHER INFORMATION: AXMI-031(TRUNCATED)

<400> SEQUENCE: 15

Met Ser Tyr Tyr His His His His His Leu Glu Ser Thr Ser Leu
1               5                   10                  15

Tyr Lys Lys Ala Gly Phe Ile Glu Gly Arg Met Asp Cys Asn Leu Gln
            20                  25                  30

Ser Gln Gln Asn Ile Pro Tyr Asn Val Leu Ala Ile Pro Val Ser Asn
        35                  40                  45

Val Asn Ser Leu Thr Asp Thr Val Gly Asp Leu Lys Lys Ala Trp Glu
    50                  55                  60

Glu Phe Gln Lys Thr Gly Ser Phe Ser Leu Thr Ala Leu Gln Gln Gly
65                  70                  75                  80

Phe Ser Ala Ser Gln Gly Gly Thr Phe Asn Tyr Leu Thr Leu Leu Gln
                85                  90                  95

Ser Gly Ile Ser Leu Ala Gly Ser Phe Val Pro Gly Gly Thr Phe Val
            100                 105                 110

Ala Pro Ile Ile Asn Met Val Ile Gly Trp Leu Trp Pro His Lys Asn
        115                 120                 125

Lys Asn Ala Asp Thr Glu Asn Leu Ile Asn Leu Ile Asp Ser Glu Ile
    130                 135                 140

Gln Lys Gln Leu Asn Lys Ala Leu Leu Asp Ala Asp Arg Asn Glu Trp
145                 150                 155                 160

Ser Ser Tyr Leu Glu Ser Ile Phe Asp Ser Ser Asn Asn Leu Asn Gly
                165                 170                 175

Ala Ile Val Asp Ala Gln Trp Ser Gly Thr Val Asn Thr Thr Asn Arg
            180                 185                 190

Thr Leu Arg Asn Pro Thr Glu Ser Asp Tyr Thr Asn Val Val Thr Asn

```
                195                 200                 205
    Phe Ile Ala Ala Asp Gly Asp Ile Ala Asn Asn Glu Asn His Ile Met
    210                 215                 220

Asn Gly Asn Phe Asp Val Ala Ala Ala Pro Tyr Phe Val Ile Gly Ala
    225                 230                 235                 240

Thr Ala Arg Phe Ala Ala Met Gln Ser Tyr Ile Lys Phe Cys Asn Ala
                    245                 250                 255

Trp Ile Asp Lys Val Gly Leu Ser Asp Ala Gln Leu Thr Thr Gln Lys
                    260                 265                 270

Ala Asn Leu Asp Arg Thr Lys Gln Asn Met Arg Asn Ala Ile Leu Asn
                275                 280                 285

Tyr Thr Gln Gln Val Met Lys Val Phe Lys Asp Ser Lys Asn Met Pro
        290                 295                 300

Thr Ile Gly Thr Asn Lys Phe Ser Val Asp Thr Tyr Asn Val Tyr Ile
    305                 310                 315                 320

Lys Gly Met Thr Leu Asn Val Leu Asp Ile Val Ala Ile Trp Pro Ser
                    325                 330                 335

Leu Tyr Pro Asp Asp Tyr Thr Ser Gln Thr Ala Leu Glu Gln Thr Arg
                    340                 345                 350

Val Thr Phe Ser Asn Met Val Gly Gln Glu Glu Gly Thr Asp Gly Ser
                355                 360                 365

Leu Arg Ile Tyr Asn Thr Phe Asp Ser Phe Ser Tyr Gln His Ser Pro
    370                 375                 380

Ile Pro Asn Asn Asn Val Asn Leu Ile Ser Tyr Tyr Asn Asp Glu Leu
    385                 390                 395                 400

Gln Asn Leu Glu Leu Gly Val Tyr Thr Pro Pro Lys Lys Gly Ser Gly
                    405                 410                 415

Tyr Ser Tyr Pro Tyr Gly Phe Val Leu Asn Tyr Ala Asn Ser Lys Tyr
                    420                 425                 430

Lys Tyr Gly Asp Ser Asn Asp Pro Glu Ser Leu Gly Gly Leu Ser Thr
                435                 440                 445

Leu Ser Ala Pro Ile Gln Gln Val Asn Ala Ala Thr Gln Asn Ser Lys
    450                 455                 460

Tyr Leu Asp Gly Glu Ile Leu Asn Gly Ile Gly Ala Ser Leu Pro Gly
    465                 470                 475                 480

Tyr Cys Thr Thr Gly Cys Ser Pro Thr Glu Pro Phe Ser Cys Thr
                    485                 490                 495

Ser Thr Ala Asn Gly Tyr Lys Ala Ser Cys Asn Pro Ser Asp Thr Asn
                500                 505                 510

Gln Lys Ile Asn Ala Leu Tyr Pro Phe Thr Gln Ala Asn Val Lys Gly
        515                 520                 525

Asn Thr Gly Lys Leu Gly Val Leu Ala Ser Leu Val Ser Tyr Asp Leu
        530                 535                 540

Asn Pro Lys Asn Val Phe Gly Glu Leu Asp Ser Asp Thr Asn Asn Val
    545                 550                 555                 560

Ile Leu Lys Gly Ile Pro Ala Glu Lys Gly Tyr Phe Pro Asn Asn Ala
                    565                 570                 575

Arg Pro Thr Val Val Lys Glu Trp Ile Asn Gly Ala Ser Ala Val Pro
                580                 585                 590

Leu Asp Ser Gly Asn Thr Leu Phe Met Thr Ala Thr Asn Leu Thr Ala
                595                 600                 605

Thr Gln Tyr Arg Ile Arg Ile Arg Tyr Ala Asn Pro Asn Ser Asn Thr
        610                 615                 620
```

```
Gln Ile Gly Val Arg Ile Thr Gln Asn Gly Ser Leu Ile Ser Ser Ser
625                 630                 635                 640

Asn Leu Thr Leu Tyr Ser Thr Thr Asp Met Asn Asn Thr Leu Pro Leu
            645                 650                 655

Asn Val Tyr Val Ile Gly Glu Asn Gly Asn Tyr Thr Leu Gln Asp Leu
        660                 665                 670

Tyr Asn Thr Thr Asn Val Leu Ser Thr Gly Asp Ile Thr Leu Gln Ile
            675                 680                 685

Thr Gly Gly Asp Gln Lys Ile Phe Ile Asp Arg Ile Glu Phe Val Pro
        690                 695                 700

Thr Met Pro Val Pro Gly Asn Thr Asn Asn Asn Gly Asn Asn
705                 710                 715                 720

Gly Asn Asn Asn Pro Pro His His Val
            725

<210> SEQ ID NO 16
<211> LENGTH: 3558
<212> TYPE: DNA
<213> ORGANISM: Artificial Sequence
<220> FEATURE:
<223> OTHER INFORMATION: axmi-031(m1)
<220> FEATURE:
<221> NAME/KEY: CDS
<222> LOCATION: (1)...(3558)

<400> SEQUENCE: 16 atg gat tgt aat tta caa tca caa caa aat att cca tat aat gta tta      48
Met Asp Cys Asn Leu Gln Ser Gln Gln Asn Ile Pro Tyr Asn Val Leu
 1               5                  10                  15 gca ata cca gta tct aat gtt aat tcg ttg act gat aca gtt gga gat      96
Ala Ile Pro Val Ser Asn Val Asn Ser Leu Thr Asp Thr Val Gly Asp
            20                  25                  30 tta aaa aaa gca tgg gaa gaa ttt caa aaa act ggt tct ttt tca tta     144
Leu Lys Lys Ala Trp Glu Glu Phe Gln Lys Thr Gly Ser Phe Ser Leu
        35                  40                  45 aca gct tta caa caa gga ttt tct gct tca caa gga gga aca ttc aat     192
Thr Ala Leu Gln Gln Gly Phe Ser Ala Ser Gln Gly Gly Thr Phe Asn
    50                  55                  60 tat tta aca tta cta caa tca gga ata tca tta gct ggt tct ttt gtt     240
Tyr Leu Thr Leu Leu Gln Ser Gly Ile Ser Leu Ala Gly Ser Phe Val
65                  70                  75                  80 cct gga ggt act ttt gta gca cct att att aat atg gtt att ggt tgg     288
Pro Gly Gly Thr Phe Val Ala Pro Ile Ile Asn Met Val Ile Gly Trp
                85                  90                  95 tta tgg cca cat aaa aac aaa aat gcg gat aca gaa aat tta ata aat     336
Leu Trp Pro His Lys Asn Lys Asn Ala Asp Thr Glu Asn Leu Ile Asn
            100                 105                 110 tta att gat tca gaa att caa aaa caa tta aac aaa gct tta tta gat     384
Leu Ile Asp Ser Glu Ile Gln Lys Gln Leu Asn Lys Ala Leu Leu Asp
        115                 120                 125 gca gat aga aat gag tgg agc tct tat tta gaa tct ata ttt gat tct     432
Ala Asp Arg Asn Glu Trp Ser Ser Tyr Leu Glu Ser Ile Phe Asp Ser
    130                 135                 140 tca aat aac cta aat ggt gca att gta gat gca cag tgg tca ggc act     480
Ser Asn Asn Leu Asn Gly Ala Ile Val Asp Ala Gln Trp Ser Gly Thr
145                 150                 155                 160 gta aat act aca aat aga aca cta aga aat cca aca gaa tca gat tat     528
Val Asn Thr Thr Asn Arg Thr Leu Arg Asn Pro Thr Glu Ser Asp Tyr
                165                 170                 175 aca aat gtt gtt aca aat ttt att gca gcg gat ggt gac att gca aat     576
Thr Asn Val Val Thr Asn Phe Ile Ala Ala Asp Gly Asp Ile Ala Asn
```

-continued

|   |   |   | 180 |   |   |   | 185 |   |   |   | 190 |   |   |   |   |
|---|---|---|---|---|---|---|---|---|---|---|---|---|---|---|---|

```
aat gaa aat cac ata atg aat ggc aac ttt gac gta gct gca gca cct      624
Asn Glu Asn His Ile Met Asn Gly Asn Phe Asp Val Ala Ala Ala Pro
            195                 200                 205 tat ttt gct ata gga gca aca gca cgt ttt gca gca atg caa tct tat      672
Tyr Phe Ala Ile Gly Ala Thr Ala Arg Phe Ala Ala Met Gln Ser Tyr
210                 215                 220 att aaa ttt tgt aat gct tgg att gat aaa gtt gga ttg agt gac gca      720
Ile Lys Phe Cys Asn Ala Trp Ile Asp Lys Val Gly Leu Ser Asp Ala
225                 230                 235                 240 cag ctt act aca caa aag gct aat tta gat cgc acg aaa caa aat atg      768
Gln Leu Thr Thr Gln Lys Ala Asn Leu Asp Arg Thr Lys Gln Asn Met
            245                 250                 255 cgt aat gca att ctt aac tat aca caa caa gtt atg aaa gtt ttt aaa      816
Arg Asn Ala Ile Leu Asn Tyr Thr Gln Gln Val Met Lys Val Phe Lys
            260                 265                 270 gat tcc aaa aat atg cct aca ata ggt act aat aaa ttt agt gtt gat      864
Asp Ser Lys Asn Met Pro Thr Ile Gly Thr Asn Lys Phe Ser Val Asp
            275                 280                 285 acc tat aat gta tat att aaa gga atg aca tta aat gtt tta gat att      912
Thr Tyr Asn Val Tyr Ile Lys Gly Met Thr Leu Asn Val Leu Asp Ile
            290                 295                 300 gta gca ata tgg cct tca tta tat cca gat gat tat act tca caa aca      960
Val Ala Ile Trp Pro Ser Leu Tyr Pro Asp Asp Tyr Thr Ser Gln Thr
305                 310                 315                 320 gcc tta gaa caa aca cgt gtc act ttt tca aat atg gtt ggc caa gaa     1008
Ala Leu Glu Gln Thr Arg Val Thr Phe Ser Asn Met Val Gly Gln Glu
            325                 330                 335 gaa ggt aca gat gga agc cta aga att tac aat act ttt gat tct ttt     1056
Glu Gly Thr Asp Gly Ser Leu Arg Ile Tyr Asn Thr Phe Asp Ser Phe
            340                 345                 350 agt tat caa cat agt cca ata cct aat aat aat gtt aat tta att tct     1104
Ser Tyr Gln His Ser Pro Ile Pro Asn Asn Asn Val Asn Leu Ile Ser
            355                 360                 365 tat tat aat gat gaa tta caa aat cta gaa tta gga gta tat acc cct     1152
Tyr Tyr Asn Asp Glu Leu Gln Asn Leu Glu Leu Gly Val Tyr Thr Pro
370                 375                 380 cct aaa aaa gga agt gga tac tct tat cct tat gga ttt gtt tta aat     1200
Pro Lys Lys Gly Ser Gly Tyr Ser Tyr Pro Tyr Gly Phe Val Leu Asn
385                 390                 395                 400 tat gca aac agt aaa tat aaa tat ggt gat agc aat gat cca gaa tct     1248
Tyr Ala Asn Ser Lys Tyr Lys Tyr Gly Asp Ser Asn Asp Pro Glu Ser
            405                 410                 415 cta gga gga tta tct aca cta tct gca cct ata caa caa gtt aat gca     1296
Leu Gly Gly Leu Ser Thr Leu Ser Ala Pro Ile Gln Gln Val Asn Ala
            420                 425                 430 gca act caa aac agt aaa tat cta gat gga gaa atc cta aat gga ata     1344
Ala Thr Gln Asn Ser Lys Tyr Leu Asp Gly Glu Ile Leu Asn Gly Ile
            435                 440                 445 gga gca tcc tta cct ggt tat tgt act aca gga tgt tca cca aca gaa     1392
Gly Ala Ser Leu Pro Gly Tyr Cys Thr Thr Gly Cys Ser Pro Thr Glu
450                 455                 460 cca cct ttt agt tgt act tct acc gct aat ggc tat aaa gca agc tgt     1440
Pro Pro Phe Ser Cys Thr Ser Thr Ala Asn Gly Tyr Lys Ala Ser Cys
465                 470                 475                 480 aat cct tca gat aca aat caa aaa att aac gct tta tat cct ttt aca     1488
Asn Pro Ser Asp Thr Asn Gln Lys Ile Asn Ala Leu Tyr Pro Phe Thr
            485                 490                 495 caa gct aat gta aag gga aac aca gga aaa tta gga gta ctg gca agt     1536
Gln Ala Asn Val Lys Gly Asn Thr Gly Lys Leu Gly Val Leu Ala Ser
```

-continued

|  |  |  |  |  |  |  |  |  |  |  |  |  |  |  |  |
|---|---|---|---|---|---|---|---|---|---|---|---|---|---|---|---|

```
                       500                  505                  510
ctt gtt tca tat gat tta aat cct aaa aat gta ttt ggt gag tta gat       1584
Leu Val Ser Tyr Asp Leu Asn Pro Lys Asn Val Phe Gly Glu Leu Asp
            515                  520                  525 tca gat aca aat aat gtt atc tta aaa gga att cct gca gaa aaa gga       1632
Ser Asp Thr Asn Asn Val Ile Leu Lys Gly Ile Pro Ala Glu Lys Gly
        530                  535                  540 tat ttt cct aat aat gcg cgt cct act gtt gta aaa gaa tgg att aat       1680
Tyr Phe Pro Asn Asn Ala Arg Pro Thr Val Val Lys Glu Trp Ile Asn
545                  550                  555                  560 ggt gca agt gct gta cca ctt gat tca gga aat acc tta ttt atg acg       1728
Gly Ala Ser Ala Val Pro Leu Asp Ser Gly Asn Thr Leu Phe Met Thr
                565                  570                  575 gct acg aat tta aca gct act caa tat aga att aga ata cgt tat gca       1776
Ala Thr Asn Leu Thr Ala Thr Gln Tyr Arg Ile Arg Ile Arg Tyr Ala
            580                  585                  590 aat cca aat tca aat act caa atc ggt gta cga att aca caa aat ggt       1824
Asn Pro Asn Ser Asn Thr Gln Ile Gly Val Arg Ile Thr Gln Asn Gly
        595                  600                  605 tct cta att tcc agt agt aat cta aca ctt tat agt act act gat atg       1872
Ser Leu Ile Ser Ser Ser Asn Leu Thr Leu Tyr Ser Thr Thr Asp Met
610                  615                  620 aat aat act tta cca cta aat gta tat gta ata gga gaa aat gga aat       1920
Asn Asn Thr Leu Pro Leu Asn Val Tyr Val Ile Gly Glu Asn Gly Asn
625                  630                  635                  640 tat aca ctt caa gat tta tat aat act act aat gtt tta tca aca gga       1968
Tyr Thr Leu Gln Asp Leu Tyr Asn Thr Thr Asn Val Leu Ser Thr Gly
                645                  650                  655 gat att aca tta caa att aca gga gga gat caa aaa ata ttt att gat       2016
Asp Ile Thr Leu Gln Ile Thr Gly Gly Asp Gln Lys Ile Phe Ile Asp
            660                  665                  670 cga ata gaa ttt gtt cct act atg cct gta cct ggt aat act aac aac       2064
Arg Ile Glu Phe Val Pro Thr Met Pro Val Pro Gly Asn Thr Asn Asn
        675                  680                  685 aat aac ggt aat aat aac ggt aat aat aat ccc cca cac cac gtt tgt       2112
Asn Asn Gly Asn Asn Asn Gly Asn Asn Asn Pro Pro His His Val Cys
690                  695                  700 gca ata gct ggt aca caa caa tct tgt tct gga ccg ccc aaa ttt gaa       2160
Ala Ile Ala Gly Thr Gln Gln Ser Cys Ser Gly Pro Pro Lys Phe Glu
705                  710                  715                  720 caa gta agt gat tta gaa aaa att aca aca caa gta tat atg tta ttc       2208
Gln Val Ser Asp Leu Glu Lys Ile Thr Thr Gln Val Tyr Met Leu Phe
                725                  730                  735 aaa tct tct ccg tat gaa gaa tta gct cta gaa gtt tcc agc tat caa       2256
Lys Ser Ser Pro Tyr Glu Glu Leu Ala Leu Glu Val Ser Ser Tyr Gln
            740                  745                  750 att agt caa gta gca tta aaa gtt atg gca tta tct gat gaa cta ttt       2304
Ile Ser Gln Val Ala Leu Lys Val Met Ala Leu Ser Asp Glu Leu Phe
        755                  760                  765 tgt gaa gaa aaa aac gta tta cga aaa tta gtc aat aaa gca aaa caa       2352
Cys Glu Glu Lys Asn Val Leu Arg Lys Leu Val Asn Lys Ala Lys Gln
770                  775                  780 tta tta gaa gca agt aac tta cta gta ggt gga aat ttt gaa aca act       2400
Leu Leu Glu Ala Ser Asn Leu Leu Val Gly Gly Asn Phe Glu Thr Thr
785                  790                  795                  800 caa aat tgg gta ctt gga aca aat gct tat ata aat tat gat tcg ttt       2448
Gln Asn Trp Val Leu Gly Thr Asn Ala Tyr Ile Asn Tyr Asp Ser Phe
                805                  810                  815 tta ttt aat gga aat tat tta tct tta caa cca gca agt gga ttt ttc       2496
Leu Phe Asn Gly Asn Tyr Leu Ser Leu Gln Pro Ala Ser Gly Phe Phe
```

-continued

```
               820             825             830
aca tct tat gct tat caa aaa ata gat gag tca aca tta aaa cca tat    2544
Thr Ser Tyr Ala Tyr Gln Lys Ile Asp Glu Ser Thr Leu Lys Pro Tyr
        835             840             845 aca cga tat aaa gtt tct ggg ttc att ggg caa agt aat caa gta gaa    2592
Thr Arg Tyr Lys Val Ser Gly Phe Ile Gly Gln Ser Asn Gln Val Glu
850             855             860 ctt att att tct cgt tat gga aaa gaa att gat aaa ata tta aat gtt    2640
Leu Ile Ile Ser Arg Tyr Gly Lys Glu Ile Asp Lys Ile Leu Asn Val
865             870             875             880 cca tat gca gga cct ctt cct atc act gct gat gca tca ata act tgt    2688
Pro Tyr Ala Gly Pro Leu Pro Ile Thr Ala Asp Ala Ser Ile Thr Cys
            885             890             895 tgt gca cca gaa ata ggc caa tgt gat ggg gaa caa tct gat tct cat    2736
Cys Ala Pro Glu Ile Gly Gln Cys Asp Gly Glu Gln Ser Asp Ser His
        900             905             910 ttc ttt aac tat agc atc gat gta ggt gca ctt cac cca gaa tta aac    2784
Phe Phe Asn Tyr Ser Ile Asp Val Gly Ala Leu His Pro Glu Leu Asn
    915             920             925 cct ggc att gaa att ggt ctt aaa att gtg caa tca aat ggt tat ata    2832
Pro Gly Ile Glu Ile Gly Leu Lys Ile Val Gln Ser Asn Gly Tyr Ile
930             935             940 aca att agt aat cta gaa att att gaa gaa cgt cca ctt aca gaa atg    2880
Thr Ile Ser Asn Leu Glu Ile Ile Glu Glu Arg Pro Leu Thr Glu Met
945             950             955             960 gaa att caa gca gtc aat cga aaa aat caa aaa tgg gaa aga gaa aaa    2928
Glu Ile Gln Ala Val Asn Arg Lys Asn Gln Lys Trp Glu Arg Glu Lys
            965             970             975 ctt cta gaa tgt gca agt att agt gaa ctt tta caa cca att att aat    2976
Leu Leu Glu Cys Ala Ser Ile Ser Glu Leu Leu Gln Pro Ile Ile Asn
        980             985             990 caa atc gat tca ttg ttt aaa gat gga aac tgg tat aat gat att ctt    3024
Gln Ile Asp Ser Leu Phe Lys Asp Gly Asn Trp Tyr Asn Asp Ile Leu
    995             1000            1005 cct cat gtc aca tat caa gat tta aaa aat att ata ata ccc gag tta    3072
Pro His Val Thr Tyr Gln Asp Leu Lys Asn Ile Ile Ile Pro Glu Leu
1010            1015            1020 cca aaa tta aaa cat tgg ttc ata gag aat ctc cca ggt gaa tat cat    3120
Pro Lys Leu Lys His Trp Phe Ile Glu Asn Leu Pro Gly Glu Tyr His
1025            1030            1035            1040 gaa att gaa caa aaa atg aaa gaa gct cta aaa tat gca ttt aca caa    3168
Glu Ile Glu Gln Lys Met Lys Glu Ala Leu Lys Tyr Ala Phe Thr Gln
            1045            1050            1055 tta gac gag aaa aat tta atc cac aat ggt cac ttt aca act aac tta    3216
Leu Asp Glu Lys Asn Leu Ile His Asn Gly His Phe Thr Thr Asn Leu
        1060            1065            1070 ata gat tgg caa gta gaa ggt gat gct caa atg aaa gta tta gaa aat    3264
Ile Asp Trp Gln Val Glu Gly Asp Ala Gln Met Lys Val Leu Glu Asn
    1075            1080            1085 gat gct ctt gca tta caa ctt ttc aac tgg gat gct aat gct tca caa    3312
Asp Ala Leu Ala Leu Gln Leu Phe Asn Trp Asp Ala Asn Ala Ser Gln
1090            1095            1100 tct ata aat ata tta gaa ttt gat gaa gat aag gca tat aaa ctt cgc    3360
Ser Ile Asn Ile Leu Glu Phe Asp Glu Asp Lys Ala Tyr Lys Leu Arg
1105            1110            1115            1120 gta tat gct caa gga agc gga aca atc caa ttt gga aac tgt gaa gat    3408
Val Tyr Ala Gln Gly Ser Gly Thr Ile Gln Phe Gly Asn Cys Glu Asp
            1125            1130            1135 gaa gct atc caa ttt aat aca aac tca ttc ata tat caa gaa aaa ata    3456
Glu Ala Ile Gln Phe Asn Thr Asn Ser Phe Ile Tyr Gln Glu Lys Ile
```

|  | 1140 |  |  |  | 1145 |  |  |  | 1150 |  |  |  |  |
|---|---|---|---|---|---|---|---|---|---|---|---|---|---|
| gtc | tat | ttc | gat | acc | cca | tca | gtt | aat | tta | cac | ata | caa tca gaa ggt | 3504 |
| Val | Tyr | Phe | Asp | Thr | Pro | Ser | Val | Asn | Leu | His | Ile | Gln Ser Glu Gly |  |
|  | 1155 |  |  |  | 1160 |  |  |  | 1165 |  |  |  |  | tct gaa ttt att gta agt agt atc gat cta att gaa tta tca gac gac    3552
Ser Glu Phe Ile Val Ser Ser Ile Asp Leu Ile Glu Leu Ser Asp Asp
    1170                1175                1180 caa taa                                                             3558
Gln *
1185

<210> SEQ ID NO 17
<211> LENGTH: 1185
<212> TYPE: PRT
<213> ORGANISM: Artificial Sequence
<220> FEATURE:
<223> OTHER INFORMATION: AXMI-031(M1)

<400> SEQUENCE: 17

Met Asp Cys Asn Leu Gln Ser Gln Gln Asn Ile Pro Tyr Asn Val Leu
 1               5                  10                  15

Ala Ile Pro Val Ser Asn Val Asn Ser Leu Thr Asp Thr Val Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Thr Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
    130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Ala Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
    290                 295                 300

```
Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Val Asn Leu Ile Ser
        355                 360                 365

Tyr Tyr Asn Asp Glu Leu Gln Asn Leu Glu Leu Gly Val Tyr Thr Pro
    370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Val Asn Ala
            420                 425                 430

Ala Thr Gln Asn Ser Lys Tyr Leu Asp Gly Glu Ile Leu Asn Gly Ile
        435                 440                 445

Gly Ala Ser Leu Pro Gly Tyr Cys Thr Thr Gly Cys Ser Pro Thr Glu
450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
                485                 490                 495

Gln Ala Asn Val Lys Gly Asn Thr Gly Lys Leu Gly Val Leu Ala Ser
                500                 505                 510

Leu Val Ser Tyr Asp Leu Asn Pro Lys Asn Val Phe Gly Glu Leu Asp
        515                 520                 525

Ser Asp Thr Asn Asn Val Ile Leu Lys Gly Ile Pro Ala Glu Lys Gly
    530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575

Ala Thr Asn Leu Thr Ala Thr Gln Tyr Arg Ile Arg Ile Arg Tyr Ala
        580                 585                 590

Asn Pro Asn Ser Asn Thr Gln Ile Gly Val Arg Ile Thr Gln Asn Gly
    595                 600                 605

Ser Leu Ile Ser Ser Ser Asn Leu Thr Leu Tyr Ser Thr Thr Asp Met
610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Asn Val Leu Ser Thr Gly
                645                 650                 655

Asp Ile Thr Leu Gln Ile Thr Gly Gly Asp Gln Lys Ile Phe Ile Asp
        660                 665                 670

Arg Ile Glu Phe Val Pro Thr Met Pro Val Pro Gly Asn Thr Asn Asn
    675                 680                 685

Asn Asn Gly Asn Asn Asn Gly Asn Asn Asn Pro His His Val Cys
690                 695                 700

Ala Ile Ala Gly Thr Gln Gln Ser Cys Ser Gly Pro Pro Lys Phe Glu
705                 710                 715                 720

Gln Val Ser Asp Leu Glu Lys Ile Thr Thr Gln Val Tyr Met Leu Phe
```

```
                    725                 730                 735
Lys Ser Ser Pro Tyr Glu Glu Leu Ala Leu Glu Val Ser Ser Tyr Gln
                740                 745                 750

Ile Ser Gln Val Ala Leu Lys Val Met Ala Leu Ser Asp Glu Leu Phe
                755                 760                 765

Cys Glu Glu Lys Asn Val Leu Arg Lys Leu Val Asn Lys Ala Lys Gln
                770                 775                 780

Leu Leu Glu Ala Ser Asn Leu Leu Val Gly Gly Asn Phe Glu Thr Thr
785                 790                 795                 800

Gln Asn Trp Val Leu Gly Thr Asn Ala Tyr Ile Asn Tyr Asp Ser Phe
                805                 810                 815

Leu Phe Asn Gly Asn Tyr Leu Ser Leu Gln Pro Ala Ser Gly Phe Phe
                820                 825                 830

Thr Ser Tyr Ala Tyr Gln Lys Ile Asp Glu Ser Thr Leu Lys Pro Tyr
                835                 840                 845

Thr Arg Tyr Lys Val Ser Gly Phe Ile Gly Gln Ser Asn Gln Val Glu
                850                 855                 860

Leu Ile Ile Ser Arg Tyr Gly Lys Glu Ile Asp Lys Ile Leu Asn Val
865                 870                 875                 880

Pro Tyr Ala Gly Pro Leu Pro Ile Thr Ala Asp Ala Ser Ile Thr Cys
                885                 890                 895

Cys Ala Pro Glu Ile Gly Gln Cys Asp Gly Glu Gln Ser Asp Ser His
                900                 905                 910

Phe Phe Asn Tyr Ser Ile Asp Val Gly Ala Leu His Pro Glu Leu Asn
                915                 920                 925

Pro Gly Ile Glu Ile Gly Leu Lys Ile Val Gln Ser Asn Gly Tyr Ile
                930                 935                 940

Thr Ile Ser Asn Leu Glu Ile Ile Glu Arg Pro Leu Thr Glu Met
945                 950                 955                 960

Glu Ile Gln Ala Val Asn Arg Lys Asn Gln Lys Trp Glu Arg Glu Lys
                965                 970                 975

Leu Leu Glu Cys Ala Ser Ile Ser Glu Leu Leu Gln Pro Ile Ile Asn
                980                 985                 990

Gln Ile Asp Ser Leu Phe Lys Asp Gly Asn Trp Tyr Asn Asp Ile Leu
                995                 1000                1005

Pro His Val Thr Tyr Gln Asp Leu Lys Asn Ile Ile Ile Pro Glu Leu
                1010                1015                1020

Pro Lys Leu Lys His Trp Phe Ile Glu Asn Leu Pro Gly Glu Tyr His
1025                1030                1035                1040

Glu Ile Glu Gln Lys Met Lys Glu Ala Leu Lys Tyr Ala Phe Thr Gln
                1045                1050                1055

Leu Asp Glu Lys Asn Leu Ile His Asn Gly His Phe Thr Thr Asn Leu
                1060                1065                1070

Ile Asp Trp Gln Val Gly Asp Ala Gln Met Lys Val Leu Glu Asn
                1075                1080                1085

Asp Ala Leu Ala Leu Gln Leu Phe Asn Trp Asp Ala Asn Ala Ser Gln
                1090                1095                1100

Ser Ile Asn Ile Leu Glu Phe Asp Glu Asp Lys Ala Tyr Lys Leu Arg
1105                1110                1115                1120

Val Tyr Ala Gln Gly Ser Gly Thr Ile Gln Phe Gly Asn Cys Glu Asp
                1125                1130                1135

Glu Ala Ile Gln Phe Asn Thr Asn Ser Phe Ile Tyr Gln Glu Lys Ile
                1140                1145                1150
```

```
Val Tyr Phe Asp Thr Pro Ser Val Asn Leu His Ile Gln Ser Glu Gly
        1155                1160                1165

Ser Glu Phe Ile Val Ser Ser Ile Asp Leu Ile Glu Leu Ser Asp Asp
    1170                1175                1180

Gln
1185

<210> SEQ ID NO 18
<211> LENGTH: 2112
<212> TYPE: DNA
<213> ORGANISM: Artificial Sequence
<220> FEATURE:
<223> OTHER INFORMATION: axmi-031(m1)truncated
<220> FEATURE:
<221> NAME/KEY: CDS
<222> LOCATION: (1)...(2112)

<400> SEQUENCE: 18 atg gat tgt aat tta caa tca caa caa aat att cca tat aat gta tta      48
Met Asp Cys Asn Leu Gln Ser Gln Gln Asn Ile Pro Tyr Asn Val Leu
  1               5                  10                  15 gca ata cca gta tct aat gtt aat tcg ttg act gat aca gtt gga gat      96
Ala Ile Pro Val Ser Asn Val Asn Ser Leu Thr Asp Thr Val Gly Asp
             20                  25                  30 tta aaa aaa gca tgg gaa gaa ttt caa aaa act ggt tct ttt tca tta     144
Leu Lys Lys Ala Trp Glu Glu Phe Gln Lys Thr Gly Ser Phe Ser Leu
         35                  40                  45 aca gct tta caa caa gga ttt tct gct tca caa gga gga aca ttc aat     192
Thr Ala Leu Gln Gln Gly Phe Ser Ala Ser Gln Gly Gly Thr Phe Asn
     50                  55                  60 tat tta aca tta cta caa tca gga ata tca tta gct ggt tct ttt gtt     240
Tyr Leu Thr Leu Leu Gln Ser Gly Ile Ser Leu Ala Gly Ser Phe Val
 65                  70                  75                  80 cct gga ggt act ttt gta gca cct att att aat atg gtt att ggt tgg     288
Pro Gly Gly Thr Phe Val Ala Pro Ile Ile Asn Met Val Ile Gly Trp
                 85                  90                  95 tta tgg cca cat aaa aac aaa aat gcg gat aca gaa aat tta ata aat     336
Leu Trp Pro His Lys Asn Lys Asn Ala Asp Thr Glu Asn Leu Ile Asn
            100                 105                 110 tta att gat tca gaa att caa aaa caa tta aac aaa gct tta tta gat     384
Leu Ile Asp Ser Glu Ile Gln Lys Gln Leu Asn Lys Ala Leu Leu Asp
        115                 120                 125 gca gat aga aat gag tgg agc tct tat tta gaa tct ata ttt gat tct     432
Ala Asp Arg Asn Glu Trp Ser Ser Tyr Leu Glu Ser Ile Phe Asp Ser
    130                 135                 140 tca aat aac cta aat ggt gca att gta gat gca cag tgg tca ggc act     480
Ser Asn Asn Leu Asn Gly Ala Ile Val Asp Ala Gln Trp Ser Gly Thr
145                 150                 155                 160 gta aat act aca aat aga aca cta aga aat cca aca gaa tca gat tat     528
Val Asn Thr Thr Asn Arg Thr Leu Arg Asn Pro Thr Glu Ser Asp Tyr
                165                 170                 175 aca aat gtt gtt aca aat ttt att gca gcg gat ggt gac att gca aat     576
Thr Asn Val Val Thr Asn Phe Ile Ala Ala Asp Gly Asp Ile Ala Asn
            180                 185                 190 aat gaa aat cac ata atg aat ggc aac ttt gac gta gct gca gca cct     624
Asn Glu Asn His Ile Met Asn Gly Asn Phe Asp Val Ala Ala Ala Pro
        195                 200                 205 tat ttt gct ata gga gca aca gca cgt ttt gca gca atg caa tct tat     672
Tyr Phe Ala Ile Gly Ala Thr Ala Arg Phe Ala Ala Met Gln Ser Tyr
    210                 215                 220 att aaa ttt tgt aat gct tgg att gat aaa gtt gga ttg agt gac gca     720
Ile Lys Phe Cys Asn Ala Trp Ile Asp Lys Val Gly Leu Ser Asp Ala
```

```
                225                 230                 235                 240
cag ctt act aca caa aag gct aat tta gat cgc acg aaa caa aat atg       768
Gln Leu Thr Thr Gln Lys Ala Asn Leu Asp Arg Thr Lys Gln Asn Met
                    245                 250                 255 cgt aat gca att ctt aac tat aca caa caa gtt atg aaa gtt ttt aaa       816
Arg Asn Ala Ile Leu Asn Tyr Thr Gln Gln Val Met Lys Val Phe Lys
                260                 265                 270 gat tcc aaa aat atg cct aca ata ggt act aat aaa ttt agt gtt gat       864
Asp Ser Lys Asn Met Pro Thr Ile Gly Thr Asn Lys Phe Ser Val Asp
            275                 280                 285 acc tat aat gta tat att aaa gga atg aca tta aat gtt tta gat att       912
Thr Tyr Asn Val Tyr Ile Lys Gly Met Thr Leu Asn Val Leu Asp Ile
        290                 295                 300 gta gca ata tgg cct tca tta tat cca gat gat tat act tca caa aca       960
Val Ala Ile Trp Pro Ser Leu Tyr Pro Asp Asp Tyr Thr Ser Gln Thr
305                 310                 315                 320 gcc tta gaa caa aca cgt gtc act ttt tca aat atg gtt ggc caa gaa      1008
Ala Leu Glu Gln Thr Arg Val Thr Phe Ser Asn Met Val Gly Gln Glu
                    325                 330                 335 gaa ggt aca gat gga agc cta aga att tac aat act ttt gat tct ttt      1056
Glu Gly Thr Asp Gly Ser Leu Arg Ile Tyr Asn Thr Phe Asp Ser Phe
                340                 345                 350 agt tat caa cat agt cca ata cct aat aat aat gtt aat tta att tct      1104
Ser Tyr Gln His Ser Pro Ile Pro Asn Asn Asn Val Asn Leu Ile Ser
            355                 360                 365 tat tat aat gat gaa tta caa aat cta gaa tta gga gta tat acc cct      1152
Tyr Tyr Asn Asp Glu Leu Gln Asn Leu Glu Leu Gly Val Tyr Thr Pro
        370                 375                 380 cct aaa aaa gga agt gga tac tct tat cct tat gga ttt gtt tta aat      1200
Pro Lys Lys Gly Ser Gly Tyr Ser Tyr Pro Tyr Gly Phe Val Leu Asn
385                 390                 395                 400 tat gca aac agt aaa tat aaa tat ggt gat agc aat gat cca gaa tct      1248
Tyr Ala Asn Ser Lys Tyr Lys Tyr Gly Asp Ser Asn Asp Pro Glu Ser
                    405                 410                 415 cta gga gga tta tct aca cta tct gca cct ata caa caa gtt aat gca      1296
Leu Gly Gly Leu Ser Thr Leu Ser Ala Pro Ile Gln Gln Val Asn Ala
                420                 425                 430 gca act caa aac agt aaa tat cta gat gga gaa atc cta aat gga ata      1344
Ala Thr Gln Asn Ser Lys Tyr Leu Asp Gly Glu Ile Leu Asn Gly Ile
            435                 440                 445 gga gca tcc tta cct ggt tat tgt act aca gga tgt tca cca aca gaa      1392
Gly Ala Ser Leu Pro Gly Tyr Cys Thr Thr Gly Cys Ser Pro Thr Glu
        450                 455                 460 cca cct ttt agt tgt act tct acc gct aat ggc tat aaa gca agc tgt      1440
Pro Pro Phe Ser Cys Thr Ser Thr Ala Asn Gly Tyr Lys Ala Ser Cys
465                 470                 475                 480 aat cct tca gat aca aat caa aaa att aac gct tta tat cct ttt aca      1488
Asn Pro Ser Asp Thr Asn Gln Lys Ile Asn Ala Leu Tyr Pro Phe Thr
                    485                 490                 495 caa gct aat gta aag gga aac aca gga aaa tta gga gta ctg gca agt      1536
Gln Ala Asn Val Lys Gly Asn Thr Gly Lys Leu Gly Val Leu Ala Ser
                500                 505                 510 ctt gtt tca tat gat tta aat cct aaa aat gta ttt ggt gag tta gat      1584
Leu Val Ser Tyr Asp Leu Asn Pro Lys Asn Val Phe Gly Glu Leu Asp
            515                 520                 525 tca gat aca aat aat gtt atc tta aaa gga att cct gca gaa aaa gga      1632
Ser Asp Thr Asn Asn Val Ile Leu Lys Gly Ile Pro Ala Glu Lys Gly
        530                 535                 540 tat ttt cct aat aat gcg cgt cct act gtt gta aaa gaa tgg att aat      1680
Tyr Phe Pro Asn Asn Ala Arg Pro Thr Val Val Lys Glu Trp Ile Asn
```

-continued

```
           545                 550                 555                 560
ggt gca agt gct gta cca ctt gat tca gga aat acc tta ttt atg acg       1728
Gly Ala Ser Ala Val Pro Leu Asp Ser Gly Asn Thr Leu Phe Met Thr
                565                 570                 575 gct acg aat tta aca gct act caa tat aga att aga ata cgt tat gca       1776
Ala Thr Asn Leu Thr Ala Thr Gln Tyr Arg Ile Arg Ile Arg Tyr Ala
                580                 585                 590 aat cca aat tca aat act caa atc ggt gta cga att aca caa aat ggt       1824
Asn Pro Asn Ser Asn Thr Gln Ile Gly Val Arg Ile Thr Gln Asn Gly
                595                 600                 605 tct cta att tcc agt agt aat cta aca ctt tat agt act act gat atg       1872
Ser Leu Ile Ser Ser Ser Asn Leu Thr Leu Tyr Ser Thr Thr Asp Met
        610                 615                 620 aat aat act tta cca cta aat gta tat gta ata gga gaa aat gga aat       1920
Asn Asn Thr Leu Pro Leu Asn Val Tyr Val Ile Gly Glu Asn Gly Asn
625                 630                 635                 640 tat aca ctt caa gat tta tat aat act act aat gtt tta tca aca gga       1968
Tyr Thr Leu Gln Asp Leu Tyr Asn Thr Thr Asn Val Leu Ser Thr Gly
                645                 650                 655 gat att aca tta caa att aca gga gga gat caa aaa ata ttt att gat       2016
Asp Ile Thr Leu Gln Ile Thr Gly Gly Asp Gln Lys Ile Phe Ile Asp
                660                 665                 670 cga ata gaa ttt gtt cct act atg cct gta cct ggt aat act aac aac       2064
Arg Ile Glu Phe Val Pro Thr Met Pro Val Pro Gly Asn Thr Asn Asn
                675                 680                 685 aat aac ggt aat aat aac ggt aat aat aat ccc cca cac cac gtc tag       2112
Asn Asn Gly Asn Asn Asn Gly Asn Asn Asn Pro Pro His His Val *
        690                 695                 700

<210> SEQ ID NO 19
<211> LENGTH: 703
<212> TYPE: PRT
<213> ORGANISM: Artificial Sequence
<220> FEATURE:
<223> OTHER INFORMATION: AXMI-031(M1)TRUNCATED

<400> SEQUENCE: 19

Met Asp Cys Asn Leu Gln Ser Gln Gln Asn Ile Pro Tyr Asn Val Leu
1               5                   10                  15

Ala Ile Pro Val Ser Asn Val Asn Ser Leu Thr Asp Thr Val Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Thr Phe Asn
    50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
    130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175
```

```
Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
            195                 200                 205

Tyr Phe Ala Ile Gly Ala Thr Ala Arg Phe Ala Ala Met Gln Ser Tyr
210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
            245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
            275                 280                 285

Thr Tyr Asn Val Tyr Ile Lys Gly Met Thr Leu Asn Val Leu Asp Ile
            290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
            325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Asn Val Asn Leu Ile Ser
            355                 360                 365

Tyr Tyr Asn Asp Glu Leu Gln Asn Leu Glu Leu Gly Val Tyr Thr Pro
            370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
            405                 410                 415

Leu Gly Gly Leu Ser Thr Leu Ser Ala Pro Ile Gln Gln Val Asn Ala
            420                 425                 430

Ala Thr Gln Asn Ser Lys Tyr Leu Asp Gly Glu Ile Leu Asn Gly Ile
            435                 440                 445

Gly Ala Ser Leu Pro Gly Tyr Cys Thr Thr Gly Cys Ser Pro Thr Glu
            450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
            485                 490                 495

Gln Ala Asn Val Lys Gly Asn Thr Gly Lys Leu Gly Val Leu Ala Ser
            500                 505                 510

Leu Val Ser Tyr Asp Leu Asn Pro Lys Asn Val Phe Gly Glu Leu Asp
            515                 520                 525

Ser Asp Thr Asn Asn Val Ile Leu Lys Gly Ile Pro Ala Glu Lys Gly
            530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
            565                 570                 575

Ala Thr Asn Leu Thr Ala Thr Gln Tyr Arg Ile Arg Ile Arg Tyr Ala
            580                 585                 590

Asn Pro Asn Ser Asn Thr Gln Ile Gly Val Arg Ile Thr Gln Asn Gly
```

-continued

```
                 595                 600                 605
Ser Leu Ile Ser Ser Ser Asn Leu Thr Leu Tyr Ser Thr Thr Asp Met
    610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Thr Asn Val Leu Ser Thr Gly
                645                 650                 655

Asp Ile Thr Leu Gln Ile Thr Gly Gly Asp Gln Lys Ile Phe Ile Asp
            660                 665                 670

Arg Ile Glu Phe Val Pro Thr Met Pro Val Pro Gly Asn Thr Asn Asn
        675                 680                 685

Asn Asn Gly Asn Asn Asn Gly Asn Asn Asn Pro Pro His His Val
    690                 695                 700

<210> SEQ ID NO 20
<211> LENGTH: 2219
<212> TYPE: DNA
<213> ORGANISM: Artificial Sequence
<220> FEATURE:
<223> OTHER INFORMATION: axmi-031(A-D)
<220> FEATURE:
<221> NAME/KEY: CDS
<222> LOCATION: (1)...(2216)

<400> SEQUENCE: 20 atg gat tgt aat tta caa tca caa caa aat att cca tat aat gta tta          48
Met Asp Cys Asn Leu Gln Ser Gln Gln Asn Ile Pro Tyr Asn Val Leu
 1               5                  10                  15 gca ata cca gta tct aat gtt aat tcg ttg act gat aca gtt gga gat          96
Ala Ile Pro Val Ser Asn Val Asn Ser Leu Thr Asp Thr Val Gly Asp
                20                  25                  30 tta aaa aaa gca tgg gaa gaa ttt caa aaa act ggt tct ttt tca tta         144
Leu Lys Lys Ala Trp Glu Glu Phe Gln Lys Thr Gly Ser Phe Ser Leu
            35                  40                  45 aca gct tta caa caa gga ttt tct gct tca caa gga gga aca ttc aat         192
Thr Ala Leu Gln Gln Gly Phe Ser Ala Ser Gln Gly Gly Thr Phe Asn
        50                  55                  60 tat tta aca tta cta caa tca gga ata tca tta gct ggt tct ttt gtt         240
Tyr Leu Thr Leu Leu Gln Ser Gly Ile Ser Leu Ala Gly Ser Phe Val
 65                  70                  75                  80 cct gga ggt act ttt gta gca cct att att aat atg gtt att ggt tgg         288
Pro Gly Gly Thr Phe Val Ala Pro Ile Ile Asn Met Val Ile Gly Trp
                85                  90                  95 tta tgg cca cat aaa aac aaa aat gcg gat aca gaa aat tta ata aat         336
Leu Trp Pro His Lys Asn Lys Asn Ala Asp Thr Glu Asn Leu Ile Asn
            100                 105                 110 tta att gat tca gaa att caa aaa caa tta aac aaa gct tta tta gat         384
Leu Ile Asp Ser Glu Ile Gln Lys Gln Leu Asn Lys Ala Leu Leu Asp
        115                 120                 125 gca gat aga aat gag tgg agc tct tat tta gaa tct ata ttt gat tct         432
Ala Asp Arg Asn Glu Trp Ser Ser Tyr Leu Glu Ser Ile Phe Asp Ser
130                 135                 140 tca aat aac cta aat ggt gca att gta gat gca cag tgg tca ggc act         480
Ser Asn Asn Leu Asn Gly Ala Ile Val Asp Ala Gln Trp Ser Gly Thr
145                 150                 155                 160 gta aat act aca aat aga aca cta aga aat cca aca gaa tca gat tat         528
Val Asn Thr Thr Asn Arg Thr Leu Arg Asn Pro Thr Glu Ser Asp Tyr
                165                 170                 175 aca aat gtt gtt aca aat ttt att gca gcg gat ggt gac att gca aat         576
Thr Asn Val Val Thr Asn Phe Ile Ala Ala Asp Gly Asp Ile Ala Asn
            180                 185                 190
```

```
aat gaa aat cac ata atg aat ggc aac ttt gac gta gct gca gca cct      624
Asn Glu Asn His Ile Met Asn Gly Asn Phe Asp Val Ala Ala Ala Pro
        195                 200                 205 tat ttt gtt ata gga gca aca gca cgt ttt gca gca atg caa tct tat      672
Tyr Phe Val Ile Gly Ala Thr Ala Arg Phe Ala Ala Met Gln Ser Tyr
    210                 215                 220 att aaa ttt tgt aat gct tgg att gat aaa gtt gga ttg agt gac gca      720
Ile Lys Phe Cys Asn Ala Trp Ile Asp Lys Val Gly Leu Ser Asp Ala
225                 230                 235                 240 cag ctt act aca caa aag gct aat tta gat cgc acg aaa caa aat atg      768
Gln Leu Thr Thr Gln Lys Ala Asn Leu Asp Arg Thr Lys Gln Asn Met
            245                 250                 255 cgt aat gca att ctt aac tat aca caa caa gtt atg aaa gtt ttt aaa      816
Arg Asn Ala Ile Leu Asn Tyr Thr Gln Gln Val Met Lys Val Phe Lys
        260                 265                 270 gat tcc aaa aat atg cct aca ata ggt act aat aaa ttt agt gtt gat      864
Asp Ser Lys Asn Met Pro Thr Ile Gly Thr Asn Lys Phe Ser Val Asp
    275                 280                 285 acc tat aat gta tat att aaa gga atg aca tta aat gtt tta gat att      912
Thr Tyr Asn Val Tyr Ile Lys Gly Met Thr Leu Asn Val Leu Asp Ile
290                 295                 300 gta gca ata tgg cct tca tta tat cca gat gat tat act tca caa aca      960
Val Ala Ile Trp Pro Ser Leu Tyr Pro Asp Asp Tyr Thr Ser Gln Thr
305                 310                 315                 320 gcc tta gaa caa aca cgt gtc act ttt tca aat atg gtt ggc caa gaa     1008
Ala Leu Glu Gln Thr Arg Val Thr Phe Ser Asn Met Val Gly Gln Glu
            325                 330                 335 gaa ggt aca gat gga agc cta aga att tac aat act ttt gat tct ttt     1056
Glu Gly Thr Asp Gly Ser Leu Arg Ile Tyr Asn Thr Phe Asp Ser Phe
        340                 345                 350 agt tat caa cat agt cca ata cct aat aat aat gtt aat tta att tct     1104
Ser Tyr Gln His Ser Pro Ile Pro Asn Asn Asn Val Asn Leu Ile Ser
    355                 360                 365 tat tat aat gat gaa tta caa aat cta gaa tta gga gta tat acc cct     1152
Tyr Tyr Asn Asp Glu Leu Gln Asn Leu Glu Leu Gly Val Tyr Thr Pro
370                 375                 380 cct aaa aaa gga agt gga tac tct tat cct tat gga ttt gtt tta aat     1200
Pro Lys Lys Gly Ser Gly Tyr Ser Tyr Pro Tyr Gly Phe Val Leu Asn
385                 390                 395                 400 tat gca aac agt aaa tat aaa tat ggt gat agc aat gat cca gaa tct     1248
Tyr Ala Asn Ser Lys Tyr Lys Tyr Gly Asp Ser Asn Asp Pro Glu Ser
            405                 410                 415 cta gga gga tta tct aca cta tct gca cct ata caa caa gtt aat gca     1296
Leu Gly Gly Leu Ser Thr Leu Ser Ala Pro Ile Gln Gln Val Asn Ala
        420                 425                 430 gca act caa aac agt aaa tat cta gat gga gaa atc cta aat gga ata     1344
Ala Thr Gln Asn Ser Lys Tyr Leu Asp Gly Glu Ile Leu Asn Gly Ile
    435                 440                 445 gga gca tcc tta cct ggt tat tgt act aca gga tgt tca cca aca gaa     1392
Gly Ala Ser Leu Pro Gly Tyr Cys Thr Thr Gly Cys Ser Pro Thr Glu
450                 455                 460 cca cct ttt agt tgt act tct acc gct aat ggc tat aaa gca agc tgt     1440
Pro Pro Phe Ser Cys Thr Ser Thr Ala Asn Gly Tyr Lys Ala Ser Cys
465                 470                 475                 480 aat cct tca gat aca aat caa aaa att aac gct tta tat cct ttt aca     1488
Asn Pro Ser Asp Thr Asn Gln Lys Ile Asn Ala Leu Tyr Pro Phe Thr
            485                 490                 495 caa gct aat gta aag gga aac aca gga aaa tta gga gta ctg gca agt     1536
Gln Ala Asn Val Lys Gly Asn Thr Gly Lys Leu Gly Val Leu Ala Ser
        500                 505                 510
```

| | | | | | | | | | | | | | | | |
|---|---|---|---|---|---|---|---|---|---|---|---|---|---|---|---|
| ctt | gtt | tca | tat | gat | tta | aat | cct | aaa | aat | gta | ttt | ggt | gaa | tta | gat | 1584 |
| Leu | Val | Ser | Tyr | Asp | Leu | Asn | Pro | Lys | Asn | Val | Phe | Gly | Glu | Leu | Asp | |
| | | | 515 | | | | | 520 | | | | | 525 | | | |

```
ctt gtt tca tat gat tta aat cct aaa aat gta ttt ggt gaa tta gat    1584
Leu Val Ser Tyr Asp Leu Asn Pro Lys Asn Val Phe Gly Glu Leu Asp
            515                 520                 525 tca gat aca aat aat gtt atc tta aaa gga att cct gca gaa aaa gga    1632
Ser Asp Thr Asn Asn Val Ile Leu Lys Gly Ile Pro Ala Glu Lys Gly
        530                 535                 540 tat ttt cct aat aat gcg cgt cct act gtt gta aaa gaa tgg att aat    1680
Tyr Phe Pro Asn Asn Ala Arg Pro Thr Val Val Lys Glu Trp Ile Asn
545                 550                 555                 560 ggt gca agt gct gta cca ctt gat tca gga aat acc tta ttt atg acg    1728
Gly Ala Ser Ala Val Pro Leu Asp Ser Gly Asn Thr Leu Phe Met Thr
                565                 570                 575 gct acg aat tta aca gct act caa tat aga att aga ata cgt tat gca    1776
Ala Thr Asn Leu Thr Ala Thr Gln Tyr Arg Ile Arg Ile Arg Tyr Ala
            580                 585                 590 aat cca aat tca aat act caa atc ggt gta cga att aca caa aat ggt    1824
Asn Pro Asn Ser Asn Thr Gln Ile Gly Val Arg Ile Thr Gln Asn Gly
        595                 600                 605 tct cta att tcc agt agt aat cta aca ctt tat agt act act gat atg    1872
Ser Leu Ile Ser Ser Ser Asn Leu Thr Leu Tyr Ser Thr Thr Asp Met
610                 615                 620 aat aat act tta cca cta aat gta tat gta ata gga gaa aat gga aat    1920
Asn Asn Thr Leu Pro Leu Asn Val Tyr Val Ile Gly Glu Asn Gly Asn
625                 630                 635                 640 tat aca ctt caa gat tta tat aat act act aat gtt tta tca aca gga    1968
Tyr Thr Leu Gln Asp Leu Tyr Asn Thr Thr Asn Val Leu Ser Thr Gly
                645                 650                 655 gat att aca tta caa att aca gga gga gat caa aaa ata ttt att gat    2016
Asp Ile Thr Leu Gln Ile Thr Gly Gly Asp Gln Lys Ile Phe Ile Asp
            660                 665                 670 cga ata gaa ttt gtt cct act atg cct gta cct ggt aat act aac aac    2064
Arg Ile Glu Phe Val Pro Thr Met Pro Val Pro Gly Asn Thr Asn Asn
        675                 680                 685 aat aac ggt aat aat aac ggt aat aat aat ccc cca cac cac gtt tgt    2112
Asn Asn Gly Asn Asn Asn Gly Asn Asn Asn Pro Pro His His Val Cys
690                 695                 700 gca ata gct ggt aca caa caa tct tgt tct gga ccg ccc aaa ttt gaa    2160
Ala Ile Ala Gly Thr Gln Gln Ser Cys Ser Gly Pro Pro Lys Phe Glu
705                 710                 715                 720 caa gta agt gat tta gaa aaa att aca aca caa gta tat atg tta ttc    2208
Gln Val Ser Asp Leu Glu Lys Ile Thr Thr Gln Val Tyr Met Leu Phe
                725                 730                 735 aaa tct ta tag                                                     2219
Lys Ser

<210> SEQ ID NO 21
<211> LENGTH: 738
<212> TYPE: PRT
<213> ORGANISM: Artificial Sequence
<220> FEATURE:
<223> OTHER INFORMATION: AXMI-031(A-D)

<400> SEQUENCE: 21

Met Asp Cys Asn Leu Gln Ser Gln Gln Asn Ile Pro Tyr Asn Val Leu
 1               5                  10                  15

Ala Ile Pro Val Ser Asn Val Asn Ser Leu Thr Asp Thr Val Gly Asp
                20                  25                  30

Leu Lys Lys Ala Trp Glu Glu Phe Gln Lys Thr Gly Ser Phe Ser Leu
            35                  40                  45

Thr Ala Leu Gln Gln Gly Phe Ser Ala Ser Gln Gly Gly Thr Phe Asn
```

```
              50                  55                  60
Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Val Ile Gly Ala Thr Ala Arg Phe Ala Ala Met Gln Ser Tyr
210                 215                 220

Ile Lys Phe Cys Asn Ala Trp Ile Asp Lys Val Gly Leu Ser Asp Ala
225                 230                 235                 240

Gln Leu Thr Thr Gln Lys Ala Asn Leu Asp Arg Thr Lys Gln Asn Met
                245                 250                 255

Arg Asn Ala Ile Leu Asn Tyr Thr Gln Gln Val Met Lys Val Phe Lys
            260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
290                 295                 300

Val Ala Ile Trp Pro Ser Leu Tyr Pro Asp Asp Tyr Thr Ser Gln Thr
305                 310                 315                 320

Ala Leu Glu Gln Thr Arg Val Thr Phe Ser Asn Met Val Gly Gln Glu
                325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Val Asn Leu Ile Ser
        355                 360                 365

Tyr Tyr Asn Asp Glu Leu Gln Asn Leu Glu Leu Gly Val Tyr Thr Pro
370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
                405                 410                 415

Leu Gly Gly Leu Ser Thr Leu Ser Ala Pro Ile Gln Gln Val Asn Ala
            420                 425                 430

Ala Thr Gln Asn Ser Lys Tyr Leu Asp Gly Glu Ile Leu Asn Gly Ile
        435                 440                 445

Gly Ala Ser Leu Pro Gly Tyr Cys Thr Thr Gly Cys Ser Pro Thr Glu
450                 455                 460

Pro Pro Phe Ser Cys Thr Ser Thr Ala Asn Gly Tyr Lys Ala Ser Cys
465                 470                 475                 480
```

```
Asn Pro Ser Asp Thr Asn Gln Lys Ile Asn Ala Leu Tyr Pro Phe Thr
            485                 490                 495

Gln Ala Asn Val Lys Gly Asn Thr Gly Lys Leu Gly Val Leu Ala Ser
            500                 505                 510

Leu Val Ser Tyr Asp Leu Asn Pro Lys Asn Val Phe Gly Glu Leu Asp
            515                 520                 525

Ser Asp Thr Asn Asn Val Ile Leu Lys Gly Ile Pro Ala Glu Lys Gly
            530                 535                 540

Tyr Phe Pro Asn Asn Ala Arg Pro Thr Val Val Lys Glu Trp Ile Asn
545                 550                 555                 560

Gly Ala Ser Ala Val Pro Leu Asp Ser Gly Asn Thr Leu Phe Met Thr
                565                 570                 575

Ala Thr Asn Leu Thr Ala Thr Gln Tyr Arg Ile Arg Ile Arg Tyr Ala
            580                 585                 590

Asn Pro Asn Ser Asn Thr Gln Ile Gly Val Arg Ile Thr Gln Asn Gly
            595                 600                 605

Ser Leu Ile Ser Ser Ser Asn Leu Thr Leu Tyr Ser Thr Thr Asp Met
            610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Asn Val Leu Ser Thr Gly
                645                 650                 655

Asp Ile Thr Leu Gln Ile Thr Gly Gly Asp Gln Lys Ile Phe Ile Asp
            660                 665                 670

Arg Ile Glu Phe Val Pro Thr Met Pro Val Pro Gly Asn Thr Asn Asn
            675                 680                 685

Asn Asn Gly Asn Asn Asn Gly Asn Asn Asn Pro His His Val Cys
690                 695                 700

Ala Ile Ala Gly Thr Gln Gln Ser Cys Ser Gly Pro Pro Lys Phe Glu
705                 710                 715                 720

Gln Val Ser Asp Leu Glu Lys Ile Thr Thr Gln Val Tyr Met Leu Phe
                725                 730                 735

Lys Ser

<210> SEQ ID NO 22
<211> LENGTH: 2015
<212> TYPE: DNA
<213> ORGANISM: Artificial Sequence
<220> FEATURE:
<223> OTHER INFORMATION: axmi-031(B-C)
<220> FEATURE:
<221> NAME/KEY: CDS
<222> LOCATION: (1)...(2012)

<400> SEQUENCE: 22 atg gca ata cca gta tct aat gtt aat tcg ttg act gat aca gtt gga      48
Met Ala Ile Pro Val Ser Asn Val Asn Ser Leu Thr Asp Thr Val Gly
 1               5                  10                  15 gat tta aaa aaa gca tgg gaa gaa ttt caa aaa act ggt tct ttt tca      96
Asp Leu Lys Lys Ala Trp Glu Glu Phe Gln Lys Thr Gly Ser Phe Ser
                20                  25                  30 tta aca gct tta caa caa gga ttt tct gct tca caa gga gga aca ttc     144
Leu Thr Ala Leu Gln Gln Gly Phe Ser Ala Ser Gln Gly Gly Thr Phe
            35                  40                  45 aat tat tta aca tta cta caa tca gga ata tca tta gct ggt tct ttt     192
Asn Tyr Leu Thr Leu Leu Gln Ser Gly Ile Ser Leu Ala Gly Ser Phe
        50                  55                  60 gtt cct gga ggt act ttt gta gca cct att att aat atg gtt att ggt     240
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Val | Pro | Gly | Gly | Thr | Phe | Val | Ala | Pro | Ile | Ile | Asn | Met | Val | Ile | Gly |      |
| 65  |     |     |     | 70  |     |     |     |     | 75  |     |     |     |     | 80  |     |      |
| tgg | tta | tgg | cca | cat | aaa | aac | aaa | aat | gcg | gat | aca | gaa | aat | tta | ata | 288  |
| Trp | Leu | Trp | Pro | His | Lys | Asn | Lys | Asn | Ala | Asp | Thr | Glu | Asn | Leu | Ile |      |
|     |     |     |     | 85  |     |     |     |     | 90  |     |     |     |     | 95  |     |      |
| aat | tta | att | gat | tca | gaa | att | caa | aaa | caa | tta | aac | aaa | gct | tta | tta | 336  |
| Asn | Leu | Ile | Asp | Ser | Glu | Ile | Gln | Lys | Gln | Leu | Asn | Lys | Ala | Leu | Leu |      |
|     |     |     | 100 |     |     |     |     | 105 |     |     |     |     | 110 |     |     |      |
| gat | gca | gat | aga | aat | gag | tgg | agc | tct | tat | tta | gaa | tct | ata | ttt | gat | 384  |
| Asp | Ala | Asp | Arg | Asn | Glu | Trp | Ser | Ser | Tyr | Leu | Glu | Ser | Ile | Phe | Asp |      |
|     |     | 115 |     |     |     |     | 120 |     |     |     |     | 125 |     |     |     |      |
| tct | tca | aat | aac | cta | aat | ggt | gca | att | gta | gat | gca | cag | tgg | tca | ggc | 432  |
| Ser | Ser | Asn | Asn | Leu | Asn | Gly | Ala | Ile | Val | Asp | Ala | Gln | Trp | Ser | Gly |      |
|     | 130 |     |     |     |     | 135 |     |     |     |     | 140 |     |     |     |     |      |
| act | gta | aat | act | aca | aat | aga | aca | cta | aga | aat | cca | aca | gaa | tca | gat | 480  |
| Thr | Val | Asn | Thr | Thr | Asn | Arg | Thr | Leu | Arg | Asn | Pro | Thr | Glu | Ser | Asp |      |
| 145 |     |     |     |     | 150 |     |     |     |     | 155 |     |     |     |     | 160 |      |
| tat | aca | aat | gtt | gtt | aca | aat | ttt | att | gca | gcg | gat | ggt | gac | att | gca | 528  |
| Tyr | Thr | Asn | Val | Val | Thr | Asn | Phe | Ile | Ala | Ala | Asp | Gly | Asp | Ile | Ala |      |
|     |     |     |     | 165 |     |     |     |     | 170 |     |     |     |     | 175 |     |      |
| aat | aat | gaa | aat | cac | ata | atg | aat | ggc | aac | ttt | gac | gta | gct | gca | gca | 576  |
| Asn | Asn | Glu | Asn | His | Ile | Met | Asn | Gly | Asn | Phe | Asp | Val | Ala | Ala | Ala |      |
|     |     |     | 180 |     |     |     |     | 185 |     |     |     |     | 190 |     |     |      |
| cct | tat | ttt | gtt | ata | gga | gca | aca | gca | cgt | ttt | gca | gca | atg | caa | tct | 624  |
| Pro | Tyr | Phe | Val | Ile | Gly | Ala | Thr | Ala | Arg | Phe | Ala | Ala | Met | Gln | Ser |      |
|     |     | 195 |     |     |     |     | 200 |     |     |     |     | 205 |     |     |     |      |
| tat | att | aaa | ttt | tgt | aat | gct | tgg | att | gat | aaa | gtt | gga | ttg | agt | gac | 672  |
| Tyr | Ile | Lys | Phe | Cys | Asn | Ala | Trp | Ile | Asp | Lys | Val | Gly | Leu | Ser | Asp |      |
|     | 210 |     |     |     |     | 215 |     |     |     |     | 220 |     |     |     |     |      |
| gca | cag | ctt | act | aca | caa | aag | gct | aat | tta | gat | cgc | acg | aaa | caa | aat | 720  |
| Ala | Gln | Leu | Thr | Thr | Gln | Lys | Ala | Asn | Leu | Asp | Arg | Thr | Lys | Gln | Asn |      |
| 225 |     |     |     |     | 230 |     |     |     |     | 235 |     |     |     |     | 240 |      |
| atg | cgt | aat | gca | att | ctt | aac | tat | aca | caa | caa | gtt | atg | aaa | gtt | ttt | 768  |
| Met | Arg | Asn | Ala | Ile | Leu | Asn | Tyr | Thr | Gln | Gln | Val | Met | Lys | Val | Phe |      |
|     |     |     |     | 245 |     |     |     |     | 250 |     |     |     |     | 255 |     |      |
| aaa | gat | tcc | aaa | aat | atg | cct | aca | ata | ggt | act | aat | aaa | ttt | agt | gtt | 816  |
| Lys | Asp | Ser | Lys | Asn | Met | Pro | Thr | Ile | Gly | Thr | Asn | Lys | Phe | Ser | Val |      |
|     |     |     | 260 |     |     |     |     | 265 |     |     |     |     | 270 |     |     |      |
| gat | acc | tat | aat | gta | tat | att | aaa | gga | atg | aca | tta | aat | gtt | tta | gat | 864  |
| Asp | Thr | Tyr | Asn | Val | Tyr | Ile | Lys | Gly | Met | Thr | Leu | Asn | Val | Leu | Asp |      |
|     |     | 275 |     |     |     |     | 280 |     |     |     |     | 285 |     |     |     |      |
| att | gta | gca | ata | tgg | cct | tca | tta | tat | cca | gat | gat | tat | act | tca | caa | 912  |
| Ile | Val | Ala | Ile | Trp | Pro | Ser | Leu | Tyr | Pro | Asp | Asp | Tyr | Thr | Ser | Gln |      |
|     | 290 |     |     |     |     | 295 |     |     |     |     | 300 |     |     |     |     |      |
| aca | gcc | tta | gaa | caa | aca | cgt | gtc | act | ttt | tca | aat | atg | gtt | ggc | caa | 960  |
| Thr | Ala | Leu | Glu | Gln | Thr | Arg | Val | Thr | Phe | Ser | Asn | Met | Val | Gly | Gln |      |
| 305 |     |     |     |     | 310 |     |     |     |     | 315 |     |     |     |     | 320 |      |
| gaa | gaa | ggt | aca | gat | gga | agc | cta | aga | att | tac | aat | act | ttt | gat | tct | 1008 |
| Glu | Glu | Gly | Thr | Asp | Gly | Ser | Leu | Arg | Ile | Tyr | Asn | Thr | Phe | Asp | Ser |      |
|     |     |     |     | 325 |     |     |     |     | 330 |     |     |     |     | 335 |     |      |
| ttt | agt | tat | caa | cat | agt | cca | ata | cct | aat | aat | aat | gtt | aat | tta | att | 1056 |
| Phe | Ser | Tyr | Gln | His | Ser | Pro | Ile | Pro | Asn | Asn | Asn | Val | Asn | Leu | Ile |      |
|     |     |     | 340 |     |     |     |     | 345 |     |     |     |     | 350 |     |     |      |
| tct | tat | tat | aat | gat | gaa | tta | caa | aat | cta | gaa | tta | gga | gta | tat | acc | 1104 |
| Ser | Tyr | Tyr | Asn | Asp | Glu | Leu | Gln | Asn | Leu | Glu | Leu | Gly | Val | Tyr | Thr |      |
|     |     | 355 |     |     |     |     | 360 |     |     |     |     | 365 |     |     |     |      |
| cct | cct | aaa | aaa | gga | agt | gga | tac | tct | tat | cct | tat | gga | ttt | gtt | tta | 1152 |
| Pro | Pro | Lys | Lys | Gly | Ser | Gly | Tyr | Ser | Tyr | Pro | Tyr | Gly | Phe | Val | Leu |      |
|     | 370 |     |     |     |     | 375 |     |     |     |     | 380 |     |     |     |     |      |
| aat | tat | gca | aac | agt | aaa | tat | aaa | tat | ggt | gat | agc | aat | gat | cca | gaa | 1200 |

```
Asn Tyr Ala Asn Ser Lys Tyr Lys Tyr Gly Asp Ser Asn Asp Pro Glu
385                 390                 395                 400 tct cta gga gga tta tct aca cta tct gca cct ata caa caa gtt aat    1248
Ser Leu Gly Gly Leu Ser Thr Leu Ser Ala Pro Ile Gln Gln Val Asn
                405                 410                 415 gca gca act caa aac agt aaa tat cta gat gga gaa atc cta aat gga    1296
Ala Ala Thr Gln Asn Ser Lys Tyr Leu Asp Gly Glu Ile Leu Asn Gly
            420                 425                 430 ata gga gca tcc tta cct ggt tat tgt act aca gga tgt tca cca aca    1344
Ile Gly Ala Ser Leu Pro Gly Tyr Cys Thr Thr Gly Cys Ser Pro Thr
        435                 440                 445 gaa cca cct ttt agt tgt act tct acc gct aat ggc tat aaa gca agc    1392
Glu Pro Pro Phe Ser Cys Thr Ser Thr Ala Asn Gly Tyr Lys Ala Ser
    450                 455                 460 tgt aat cct tca gat aca aat caa aaa att aac gct tta tat cct ttt    1440
Cys Asn Pro Ser Asp Thr Asn Gln Lys Ile Asn Ala Leu Tyr Pro Phe
465                 470                 475                 480 aca caa gct aat gta aag gga aac aca gga aaa tta gga gta ctg gca    1488
Thr Gln Ala Asn Val Lys Gly Asn Thr Gly Lys Leu Gly Val Leu Ala
                485                 490                 495 agt ctt gtt tca tat gat tta aat cct aaa aat gta ttt ggt gaa tta    1536
Ser Leu Val Ser Tyr Asp Leu Asn Pro Lys Asn Val Phe Gly Glu Leu
                500                 505                 510 gat tca gat aca aat aat gtt atc tta aaa gga att cct gca gaa aaa    1584
Asp Ser Asp Thr Asn Asn Val Ile Leu Lys Gly Ile Pro Ala Glu Lys
            515                 520                 525 gga tat ttt cct aat aat gcg cgt cct act gtt gta aaa gaa tgg att    1632
Gly Tyr Phe Pro Asn Asn Ala Arg Pro Thr Val Val Lys Glu Trp Ile
        530                 535                 540 aat ggt gca agt gct gta cca ctt gat tca gga aat acc tta ttt atg    1680
Asn Gly Ala Ser Ala Val Pro Leu Asp Ser Gly Asn Thr Leu Phe Met
545                 550                 555                 560 acg gct acg aat tta aca gct act caa tat aga att aga ata cgt tat    1728
Thr Ala Thr Asn Leu Thr Ala Thr Gln Tyr Arg Ile Arg Ile Arg Tyr
                565                 570                 575 gca aat cca aat tca aat act caa atc ggt gta cga att aca caa aat    1776
Ala Asn Pro Asn Ser Asn Thr Gln Ile Gly Val Arg Ile Thr Gln Asn
            580                 585                 590 ggt tct cta att tcc agt agt aat cta aca ctt tat agt act act gat    1824
Gly Ser Leu Ile Ser Ser Ser Asn Leu Thr Leu Tyr Ser Thr Thr Asp
        595                 600                 605 atg aat aat act tta cca cta aat gta tat gta ata gga gaa aat gga    1872
Met Asn Asn Thr Leu Pro Leu Asn Val Tyr Val Ile Gly Glu Asn Gly
    610                 615                 620 aat tat aca ctt caa gat tta tat aat act act aat gtt tta tca aca    1920
Asn Tyr Thr Leu Gln Asp Leu Tyr Asn Thr Thr Asn Val Leu Ser Thr
625                 630                 635                 640 gga gat att aca tta caa att aca gga gat caa aaa ata ttt att        1968
Gly Asp Ile Thr Leu Gln Ile Thr Gly Asp Gln Lys Ile Phe Ile
                645                 650                 655 gat cga ata gaa ttt gtt cct act atg cct gta cct ggt aat ta         2012
Asp Arg Ile Glu Phe Val Pro Thr Met Pro Val Pro Gly Asn
            660                 665                 670 tag                                                                 2015
```

<210> SEQ ID NO 23
<211> LENGTH: 670
<212> TYPE: PRT
<213> ORGANISM: Artificial Sequence
<220> FEATURE:
<223> OTHER INFORMATION: AXMI-031(B-C)

<400> SEQUENCE: 23

```
Met Ala Ile Pro Val Ser Asn Val Asn Ser Leu Thr Asp Thr Val Gly
  1               5                  10                  15

Asp Leu Lys Lys Ala Trp Glu Glu Phe Gln Lys Thr Gly Ser Phe Ser
             20                  25                  30

Leu Thr Ala Leu Gln Gln Gly Phe Ser Ala Ser Gln Gly Gly Thr Phe
         35                  40                  45

Asn Tyr Leu Thr Leu Leu Gln Ser Gly Ile Ser Leu Ala Gly Ser Phe
     50                  55                  60

Val Pro Gly Gly Thr Phe Val Ala Pro Ile Ile Asn Met Val Ile Gly
 65                  70                  75                  80

Trp Leu Trp Pro His Lys Asn Lys Asn Ala Asp Thr Glu Asn Leu Ile
                 85                  90                  95

Asn Leu Ile Asp Ser Glu Ile Gln Lys Gln Leu Asn Lys Ala Leu Leu
            100                 105                 110

Asp Ala Asp Arg Asn Glu Trp Ser Ser Tyr Leu Glu Ser Ile Phe Asp
        115                 120                 125

Ser Ser Asn Asn Leu Asn Gly Ala Ile Val Asp Ala Gln Trp Ser Gly
130                 135                 140

Thr Val Asn Thr Thr Asn Arg Thr Leu Arg Asn Pro Thr Glu Ser Asp
145                 150                 155                 160

Tyr Thr Asn Val Val Thr Asn Phe Ile Ala Ala Asp Gly Asp Ile Ala
                165                 170                 175

Asn Asn Glu Asn His Ile Met Asn Gly Asn Phe Asp Val Ala Ala Ala
            180                 185                 190

Pro Tyr Phe Val Ile Gly Ala Thr Ala Arg Phe Ala Ala Met Gln Ser
        195                 200                 205

Tyr Ile Lys Phe Cys Asn Ala Trp Ile Asp Lys Val Gly Leu Ser Asp
    210                 215                 220

Ala Gln Leu Thr Thr Gln Lys Ala Asn Leu Asp Arg Thr Lys Gln Asn
225                 230                 235                 240

Met Arg Asn Ala Ile Leu Asn Tyr Thr Gln Gln Val Met Lys Val Phe
                245                 250                 255

Lys Asp Ser Lys Asn Met Pro Thr Ile Gly Thr Asn Lys Phe Ser Val
            260                 265                 270

Asp Thr Tyr Asn Val Tyr Ile Lys Gly Met Thr Leu Asn Val Leu Asp
        275                 280                 285

Ile Val Ala Ile Trp Pro Ser Leu Tyr Pro Asp Asp Tyr Thr Ser Gln
    290                 295                 300

Thr Ala Leu Glu Gln Thr Arg Val Thr Phe Ser Asn Met Val Gly Gln
305                 310                 315                 320

Glu Glu Gly Thr Asp Gly Ser Leu Arg Ile Tyr Asn Thr Phe Asp Ser
                325                 330                 335

Phe Ser Tyr Gln His Ser Pro Ile Pro Asn Asn Val Asn Leu Ile
            340                 345                 350

Ser Tyr Tyr Asn Asp Glu Leu Gln Asn Leu Glu Leu Gly Val Tyr Thr
        355                 360                 365

Pro Pro Lys Lys Gly Ser Gly Tyr Ser Tyr Pro Tyr Gly Phe Val Leu
    370                 375                 380

Asn Tyr Ala Asn Ser Lys Tyr Lys Tyr Gly Asp Ser Asn Asp Pro Glu
385                 390                 395                 400

Ser Leu Gly Gly Leu Ser Thr Leu Ser Ala Pro Ile Gln Gln Val Asn
                405                 410                 415
```

```
Ala Ala Thr Gln Asn Ser Lys Tyr Leu Asp Gly Glu Ile Leu Asn Gly
            420                 425                 430

Ile Gly Ala Ser Leu Pro Gly Tyr Cys Thr Thr Gly Cys Ser Pro Thr
            435                 440                 445

Glu Pro Pro Phe Ser Cys Thr Ser Thr Ala Asn Gly Tyr Lys Ala Ser
450                 455                 460

Cys Asn Pro Ser Asp Thr Asn Gln Lys Ile Asn Ala Leu Tyr Pro Phe
465                 470                 475                 480

Thr Gln Ala Asn Val Lys Gly Asn Thr Gly Lys Leu Gly Val Leu Ala
                485                 490                 495

Ser Leu Val Ser Tyr Asp Leu Asn Pro Lys Asn Val Phe Gly Glu Leu
            500                 505                 510

Asp Ser Asp Thr Asn Asn Val Ile Leu Lys Gly Ile Pro Ala Glu Lys
            515                 520                 525

Gly Tyr Phe Pro Asn Asn Ala Arg Pro Thr Val Val Lys Glu Trp Ile
            530                 535                 540

Asn Gly Ala Ser Ala Val Pro Leu Asp Ser Gly Asn Thr Leu Phe Met
545                 550                 555                 560

Thr Ala Thr Asn Leu Thr Ala Thr Gln Tyr Arg Ile Arg Ile Arg Tyr
                565                 570                 575

Ala Asn Pro Asn Ser Asn Thr Gln Ile Gly Val Arg Ile Thr Gln Asn
            580                 585                 590

Gly Ser Leu Ile Ser Ser Ser Asn Leu Thr Leu Tyr Ser Thr Thr Asp
            595                 600                 605

Met Asn Asn Thr Leu Pro Leu Asn Val Tyr Val Ile Gly Glu Asn Gly
610                 615                 620

Asn Tyr Thr Leu Gln Asp Leu Tyr Asn Thr Thr Asn Val Leu Ser Thr
625                 630                 635                 640

Gly Asp Ile Thr Leu Gln Ile Thr Gly Gly Asp Gln Lys Ile Phe Ile
                645                 650                 655

Asp Arg Ile Glu Phe Val Pro Thr Met Pro Val Pro Gly Asn
            660                 665                 670

<210> SEQ ID NO 24
<211> LENGTH: 2174
<212> TYPE: DNA
<213> ORGANISM: Artificial Sequence
<220> FEATURE:
<223> OTHER INFORMATION: axmi-031(B-D)
<220> FEATURE:
<221> NAME/KEY: CDS
<222> LOCATION: (1)...(2171)

<400> SEQUENCE: 24 atg gca ata cca gta tct aat gtt aat tcg ttg act gat aca gtt gga    48
Met Ala Ile Pro Val Ser Asn Val Asn Ser Leu Thr Asp Thr Val Gly
1               5                   10                  15 gat tta aaa aaa gca tgg gaa gaa ttt caa aaa act ggt tct ttt tca    96
Asp Leu Lys Lys Ala Trp Glu Glu Phe Gln Lys Thr Gly Ser Phe Ser
                20                  25                  30 tta aca gct tta caa caa gga ttt tct gct tca caa gga gga aca ttc   144
Leu Thr Ala Leu Gln Gln Gly Phe Ser Ala Ser Gln Gly Gly Thr Phe
            35                  40                  45 aat tat tta aca tta cta caa tca gga ata tca tta gct ggt tct ttt   192
Asn Tyr Leu Thr Leu Leu Gln Ser Gly Ile Ser Leu Ala Gly Ser Phe
        50                  55                  60 gtt cct gga ggt act ttt gta gca cct att att aat atg gtt att ggt   240
Val Pro Gly Gly Thr Phe Val Ala Pro Ile Ile Asn Met Val Ile Gly
```

```
              65                  70                  75                  80
tgg tta tgg cca cat aaa aac aaa aat gcg gat aca gaa aat tta ata          288
Trp Leu Trp Pro His Lys Asn Lys Asn Ala Asp Thr Glu Asn Leu Ile
                    85                  90                  95 aat tta att gat tca gaa att caa aaa caa tta aac aaa gct tta tta          336
Asn Leu Ile Asp Ser Glu Ile Gln Lys Gln Leu Asn Lys Ala Leu Leu
                100                 105                 110 gat gca gat aga aat gag tgg agc tct tat tta gaa tct ata ttt gat          384
Asp Ala Asp Arg Asn Glu Trp Ser Ser Tyr Leu Glu Ser Ile Phe Asp
                115                 120                 125 tct tca aat aac cta aat ggt gca att gta gat gca cag tgg tca ggc          432
Ser Ser Asn Asn Leu Asn Gly Ala Ile Val Asp Ala Gln Trp Ser Gly
            130                 135                 140 act gta aat act aca aat aga aca cta aga aat cca aca gaa tca gat          480
Thr Val Asn Thr Thr Asn Arg Thr Leu Arg Asn Pro Thr Glu Ser Asp
145                 150                 155                 160 tat aca aat gtt gtt aca aat ttt att gca gcg gat ggt gac att gca          528
Tyr Thr Asn Val Val Thr Asn Phe Ile Ala Ala Asp Gly Asp Ile Ala
                165                 170                 175 aat aat gaa aat cac ata atg aat ggc aac ttt gac gta gct gca gca          576
Asn Asn Glu Asn His Ile Met Asn Gly Asn Phe Asp Val Ala Ala Ala
                180                 185                 190 cct tat ttt gtt ata gga gca aca gca cgt ttt gca gca atg caa tct          624
Pro Tyr Phe Val Ile Gly Ala Thr Ala Arg Phe Ala Ala Met Gln Ser
                195                 200                 205 tat att aaa ttt tgt aat gct tgg att gat aaa gtt gga ttg agt gac          672
Tyr Ile Lys Phe Cys Asn Ala Trp Ile Asp Lys Val Gly Leu Ser Asp
                210                 215                 220 gca cag ctt act aca caa aag gct aat tta gat cgc acg aaa caa aat          720
Ala Gln Leu Thr Thr Gln Lys Ala Asn Leu Asp Arg Thr Lys Gln Asn
225                 230                 235                 240 atg cgt aat gca att ctt aac tat aca caa caa gtt atg aaa gtt ttt          768
Met Arg Asn Ala Ile Leu Asn Tyr Thr Gln Gln Val Met Lys Val Phe
                245                 250                 255 aaa gat tcc aaa aat atg cct aca ata ggt act aat aaa ttt agt gtt          816
Lys Asp Ser Lys Asn Met Pro Thr Ile Gly Thr Asn Lys Phe Ser Val
                260                 265                 270 gat acc tat aat gta tat att aaa gga atg aca tta aat gtt tta gat          864
Asp Thr Tyr Asn Val Tyr Ile Lys Gly Met Thr Leu Asn Val Leu Asp
                275                 280                 285 att gta gca ata tgg cct tca tta tat cca gat gat tat act tca caa          912
Ile Val Ala Ile Trp Pro Ser Leu Tyr Pro Asp Asp Tyr Thr Ser Gln
                290                 295                 300 aca gcc tta gaa caa aca cgt gtc act ttt tca aat atg gtt ggc caa          960
Thr Ala Leu Glu Gln Thr Arg Val Thr Phe Ser Asn Met Val Gly Gln
305                 310                 315                 320 gaa gaa ggt aca gat gga agc cta aga att tac aat act ttt gat tct         1008
Glu Glu Gly Thr Asp Gly Ser Leu Arg Ile Tyr Asn Thr Phe Asp Ser
                325                 330                 335 ttt agt tat caa cat agt cca ata cct aat aat aat gtt aat tta att         1056
Phe Ser Tyr Gln His Ser Pro Ile Pro Asn Asn Asn Val Asn Leu Ile
                340                 345                 350 tct tat tat aat gat gaa tta caa aat cta gaa tta gga gta tat acc         1104
Ser Tyr Tyr Asn Asp Glu Leu Gln Asn Leu Glu Leu Gly Val Tyr Thr
                355                 360                 365 cct cct aaa aaa gga agt gga tac tct tat cct tat gga ttt gtt tta         1152
Pro Pro Lys Lys Gly Ser Gly Tyr Ser Tyr Pro Tyr Gly Phe Val Leu
370                 375                 380 aat tat gca aac agt aaa tat aaa tat ggt gat agc aat gat cca gaa         1200
Asn Tyr Ala Asn Ser Lys Tyr Lys Tyr Gly Asp Ser Asn Asp Pro Glu
```

```
                       385                 390                 395                 400
tct cta gga gga tta tct aca cta tct gca cct ata caa caa gtt aat        1248
Ser Leu Gly Gly Leu Ser Thr Leu Ser Ala Pro Ile Gln Gln Val Asn
                405                 410                 415 gca gca act caa aac agt aaa tat cta gat gga gaa atc cta aat gga        1296
Ala Ala Thr Gln Asn Ser Lys Tyr Leu Asp Gly Glu Ile Leu Asn Gly
                420                 425                 430 ata gga gca tcc tta cct ggt tat tgt act aca gga tgt tca cca aca        1344
Ile Gly Ala Ser Leu Pro Gly Tyr Cys Thr Thr Gly Cys Ser Pro Thr
                435                 440                 445 gaa cca cct ttt agt tgt act tct acc gct aat ggc tat aaa gca agc        1392
Glu Pro Pro Phe Ser Cys Thr Ser Thr Ala Asn Gly Tyr Lys Ala Ser
        450                 455                 460 tgt aat cct tca gat aca aat caa aaa att aac gct tta tat cct ttt        1440
Cys Asn Pro Ser Asp Thr Asn Gln Lys Ile Asn Ala Leu Tyr Pro Phe
465                 470                 475                 480 aca caa gct aat gta aag gga aac aca gga aaa tta gga gta ctg gca        1488
Thr Gln Ala Asn Val Lys Gly Asn Thr Gly Lys Leu Gly Val Leu Ala
                485                 490                 495 agt ctt gtt tca tat gat tta aat cct aaa aat gta ttt ggt gaa tta        1536
Ser Leu Val Ser Tyr Asp Leu Asn Pro Lys Asn Val Phe Gly Glu Leu
                500                 505                 510 gat tca gat aca aat aat gtt atc tta aaa gga att cct gca gaa aaa        1584
Asp Ser Asp Thr Asn Asn Val Ile Leu Lys Gly Ile Pro Ala Glu Lys
                515                 520                 525 gga tat ttt cct aat aat gcg cgt cct act gtt gta aaa gaa tgg att        1632
Gly Tyr Phe Pro Asn Asn Ala Arg Pro Thr Val Val Lys Glu Trp Ile
        530                 535                 540 aat ggt gca agt gct gta cca ctt gat tca gga aat acc tta ttt atg        1680
Asn Gly Ala Ser Ala Val Pro Leu Asp Ser Gly Asn Thr Leu Phe Met
545                 550                 555                 560 acg gct acg aat tta aca gct act caa tat aga att aga ata cgt tat        1728
Thr Ala Thr Asn Leu Thr Ala Thr Gln Tyr Arg Ile Arg Ile Arg Tyr
                565                 570                 575 gca aat cca aat tca aat act caa atc ggt gta cga att aca caa aat        1776
Ala Asn Pro Asn Ser Asn Thr Gln Ile Gly Val Arg Ile Thr Gln Asn
                580                 585                 590 ggt tct cta att tcc agt agt aat cta aca ctt tat agt act act gat        1824
Gly Ser Leu Ile Ser Ser Ser Asn Leu Thr Leu Tyr Ser Thr Thr Asp
                595                 600                 605 atg aat aat act tta cca cta aat gta tat gta ata gga gaa aat gga        1872
Met Asn Asn Thr Leu Pro Leu Asn Val Tyr Val Ile Gly Glu Asn Gly
        610                 615                 620 aat tat aca ctt caa gat tta tat aat act act aat gtt tta tca aca        1920
Asn Tyr Thr Leu Gln Asp Leu Tyr Asn Thr Thr Asn Val Leu Ser Thr
625                 630                 635                 640 gga gat att aca tta caa att aca gga gga gat caa aaa ata ttt att        1968
Gly Asp Ile Thr Leu Gln Ile Thr Gly Gly Asp Gln Lys Ile Phe Ile
                645                 650                 655 gat cga ata gaa ttt gtt cct act atg cct gta cct ggt aat act aac        2016
Asp Arg Ile Glu Phe Val Pro Thr Met Pro Val Pro Gly Asn Thr Asn
                660                 665                 670 aac aat aac ggt aat aat aac ggt aat aat aat ccc cca cac cac gtt        2064
Asn Asn Asn Gly Asn Asn Asn Gly Asn Asn Asn Pro Pro His His Val
                675                 680                 685 tgt gca ata gct ggt aca caa caa tct tgt tct gga ccg ccc aaa ttt        2112
Cys Ala Ile Ala Gly Thr Gln Gln Ser Cys Ser Gly Pro Pro Lys Phe
        690                 695                 700 gaa caa gta agt gat tta gaa aaa att aca aca caa gta tat atg tta        2160
Glu Gln Val Ser Asp Leu Glu Lys Ile Thr Thr Gln Val Tyr Met Leu
```

```
                705            710            715            720
ttc aaa tct ta tag                                                      2174
Phe Lys Ser
```

<210> SEQ ID NO 25
<211> LENGTH: 723
<212> TYPE: PRT
<213> ORGANISM: Artificial Sequence
<220> FEATURE:
<223> OTHER INFORMATION: AXMI-031(B-D)

<400> SEQUENCE: 25

```
Met Ala Ile Pro Val Ser Asn Val Asn Ser Leu Thr Asp Thr Val Gly
 1               5                  10                  15

Asp Leu Lys Lys Ala Trp Glu Glu Phe Gln Lys Thr Gly Ser Phe Ser
             20                  25                  30

Leu Thr Ala Leu Gln Gln Gly Phe Ser Ala Ser Gln Gly Gly Thr Phe
         35                  40                  45

Asn Tyr Leu Thr Leu Leu Gln Ser Gly Ile Ser Leu Ala Gly Ser Phe
     50                  55                  60

Val Pro Gly Gly Thr Phe Val Ala Pro Ile Ile Asn Met Val Ile Gly
 65                  70                  75                  80

Trp Leu Trp Pro His Lys Asn Lys Asn Ala Asp Thr Glu Asn Leu Ile
                 85                  90                  95

Asn Leu Ile Asp Ser Glu Ile Gln Lys Gln Leu Asn Lys Ala Leu Leu
            100                 105                 110

Asp Ala Asp Arg Asn Glu Trp Ser Ser Tyr Leu Glu Ser Ile Phe Asp
        115                 120                 125

Ser Ser Asn Asn Leu Asn Gly Ala Ile Val Asp Ala Gln Trp Ser Gly
    130                 135                 140

Thr Val Asn Thr Thr Asn Arg Thr Leu Arg Asn Pro Thr Glu Ser Asp
145                 150                 155                 160

Tyr Thr Asn Val Val Thr Asn Phe Ile Ala Ala Asp Gly Asp Ile Ala
                165                 170                 175

Asn Asn Glu Asn His Ile Met Asn Gly Asn Phe Asp Val Ala Ala Ala
            180                 185                 190

Pro Tyr Phe Val Ile Gly Ala Thr Ala Arg Phe Ala Ala Met Gln Ser
        195                 200                 205

Tyr Ile Lys Phe Cys Asn Ala Trp Ile Asp Lys Val Gly Leu Ser Asp
    210                 215                 220

Ala Gln Leu Thr Thr Gln Lys Ala Asn Leu Asp Arg Thr Lys Gln Asn
225                 230                 235                 240

Met Arg Asn Ala Ile Leu Asn Tyr Thr Gln Gln Val Met Lys Val Phe
                245                 250                 255

Lys Asp Ser Lys Asn Met Pro Thr Ile Gly Thr Asn Lys Phe Ser Val
            260                 265                 270

Asp Thr Tyr Asn Val Tyr Ile Lys Gly Met Thr Leu Asn Val Leu Asp
        275                 280                 285

Ile Val Ala Ile Trp Pro Ser Leu Tyr Pro Asp Tyr Thr Ser Gln
    290                 295                 300

Thr Ala Leu Glu Gln Thr Arg Val Thr Phe Ser Asn Met Val Gly Gln
305                 310                 315                 320

Glu Glu Gly Thr Asp Gly Ser Leu Arg Ile Tyr Asn Thr Phe Asp Ser
                325                 330                 335

Phe Ser Tyr Gln His Ser Pro Ile Pro Asn Asn Val Asn Leu Ile
            340                 345                 350
```

Ser Tyr Tyr Asn Asp Glu Leu Gln Asn Leu Glu Leu Gly Val Tyr Thr
            355                 360                 365

Pro Pro Lys Lys Gly Ser Gly Tyr Ser Tyr Pro Tyr Gly Phe Val Leu
    370                 375                 380

Asn Tyr Ala Asn Ser Lys Tyr Lys Tyr Gly Asp Ser Asn Asp Pro Glu
385                 390                 395                 400

Ser Leu Gly Gly Leu Ser Thr Leu Ser Ala Pro Ile Gln Gln Val Asn
            405                 410                 415

Ala Ala Thr Gln Asn Ser Lys Tyr Leu Asp Gly Glu Ile Leu Asn Gly
            420                 425                 430

Ile Gly Ala Ser Leu Pro Gly Tyr Cys Thr Thr Gly Cys Ser Pro Thr
            435                 440                 445

Glu Pro Pro Phe Ser Cys Thr Ser Thr Ala Asn Gly Tyr Lys Ala Ser
            450                 455                 460

Cys Asn Pro Ser Asp Thr Asn Gln Lys Ile Asn Ala Leu Tyr Pro Phe
465                 470                 475                 480

Thr Gln Ala Asn Val Lys Gly Asn Thr Gly Lys Leu Gly Val Leu Ala
            485                 490                 495

Ser Leu Val Ser Tyr Asp Leu Asn Pro Lys Asn Val Phe Gly Glu Leu
            500                 505                 510

Asp Ser Asp Thr Asn Asn Val Ile Leu Lys Gly Ile Pro Ala Glu Lys
            515                 520                 525

Gly Tyr Phe Pro Asn Asn Ala Arg Pro Thr Val Val Lys Glu Trp Ile
            530                 535                 540

Asn Gly Ala Ser Ala Val Pro Leu Asp Ser Gly Asn Thr Leu Phe Met
545                 550                 555                 560

Thr Ala Thr Asn Leu Thr Ala Thr Gln Tyr Arg Ile Arg Ile Arg Tyr
            565                 570                 575

Ala Asn Pro Asn Ser Asn Thr Gln Ile Gly Val Arg Ile Thr Gln Asn
            580                 585                 590

Gly Ser Leu Ile Ser Ser Ser Asn Leu Thr Leu Tyr Ser Thr Thr Asp
            595                 600                 605

Met Asn Asn Thr Leu Pro Leu Asn Val Tyr Val Ile Gly Glu Asn Gly
            610                 615                 620

Asn Tyr Thr Leu Gln Asp Leu Tyr Asn Thr Thr Asn Val Leu Ser Thr
625                 630                 635                 640

Gly Asp Ile Thr Leu Gln Ile Thr Gly Gly Asp Gln Lys Ile Phe Ile
            645                 650                 655

Asp Arg Ile Glu Phe Val Pro Thr Met Pro Val Pro Gly Asn Thr Asn
            660                 665                 670

Asn Asn Asn Gly Asn Asn Asn Gly Asn Asn Pro Pro His His Val
            675                 680                 685

Cys Ala Ile Ala Gly Thr Gln Gln Ser Cys Ser Gly Pro Pro Lys Phe
690                 695                 700

Glu Gln Val Ser Asp Leu Glu Lys Ile Thr Thr Gln Val Tyr Met Leu
705                 710                 715                 720

Phe Lys Ser

<210> SEQ ID NO 26
<211> LENGTH: 2226
<212> TYPE: DNA
<213> ORGANISM: Artificial Sequence
<220> FEATURE:
<223> OTHER INFORMATION: synaxmi-031(A-D)
<220> FEATURE:

```
<221> NAME/KEY: CDS
<222> LOCATION: (1)...(2226)

<400> SEQUENCE: 26 atg cag atc ctt gat tgc aat ctc cag agc cag cag aat atc cca tac      48
Met Gln Ile Leu Asp Cys Asn Leu Gln Ser Gln Gln Asn Ile Pro Tyr
 1               5                  10                  15 aat gtg ctt gct atc cct gtt agc aat gtt aat agc ctt acg gat acg      96
Asn Val Leu Ala Ile Pro Val Ser Asn Val Asn Ser Leu Thr Asp Thr
             20                  25                  30 gtt ggc gat cta aag aag gca tgg gaa gag ttc cag aag acg ggc agc     144
Val Gly Asp Leu Lys Lys Ala Trp Glu Glu Phe Gln Lys Thr Gly Ser
         35                  40                  45 ttc tcc ctt acc gca ctc cag cag ggc ttc agc gct tcc cag ggc ggg     192
Phe Ser Leu Thr Ala Leu Gln Gln Gly Phe Ser Ala Ser Gln Gly Gly
     50                  55                  60 acg ttc aat tac ctc acc ctc ctc cag tcc ggg atc tcc ctg gct ggc     240
Thr Phe Asn Tyr Leu Thr Leu Leu Gln Ser Gly Ile Ser Leu Ala Gly
 65                  70                  75                  80 agc ttc gtg cct ggc ggc acc ttc gtt gct cca atc atc aat atg gtg     288
Ser Phe Val Pro Gly Gly Thr Phe Val Ala Pro Ile Ile Asn Met Val
                 85                  90                  95 atc ggc tgg ctc tgg cct cat aag aat aag aat gca gat acg gaa aat     336
Ile Gly Trp Leu Trp Pro His Lys Asn Lys Asn Ala Asp Thr Glu Asn
            100                 105                 110 ctg atc aat ctg atc gat tca gaa atc cag aag cag ctg aat aag gct     384
Leu Ile Asn Leu Ile Asp Ser Glu Ile Gln Lys Gln Leu Asn Lys Ala
        115                 120                 125 ctg ctg gat gct gat cgc aat gaa tgg agc agc tac ctc gag tcc atc     432
Leu Leu Asp Ala Asp Arg Asn Glu Trp Ser Ser Tyr Leu Glu Ser Ile
    130                 135                 140 ttc gat agc agc aat aat ctg aat ggc gca atc gtt gat gct cag tgg     480
Phe Asp Ser Ser Asn Asn Leu Asn Gly Ala Ile Val Asp Ala Gln Trp
145                 150                 155                 160 tcc ggc acc gtg aat acg acc aat cgt acg ctt cgt aat cct acg gaa     528
Ser Gly Thr Val Asn Thr Thr Asn Arg Thr Leu Arg Asn Pro Thr Glu
                165                 170                 175 tca gat tac acc aat gtg gtg acg aat ttc atc gca gca gat ggg gat     576
Ser Asp Tyr Thr Asn Val Val Thr Asn Phe Ile Ala Ala Asp Gly Asp
            180                 185                 190 atc gct aat aat gaa aat cat atc atg aat ggg aat ttc gat gtg gca     624
Ile Ala Asn Asn Glu Asn His Ile Met Asn Gly Asn Phe Asp Val Ala
        195                 200                 205 gca gct cca tac ttc gtt atc ggg gct acc gct aga ttc gca gct atg     672
Ala Ala Pro Tyr Phe Val Ile Gly Ala Thr Ala Arg Phe Ala Ala Met
    210                 215                 220 cag tcc tac atc aag ttc tgc aat gca tgg atc gat aag gtt ggg ctg     720
Gln Ser Tyr Ile Lys Phe Cys Asn Ala Trp Ile Asp Lys Val Gly Leu
225                 230                 235                 240 tca gat gct cag ctg acc acg cag aag gct aat ctg gat aga acg aag     768
Ser Asp Ala Gln Leu Thr Thr Gln Lys Ala Asn Leu Asp Arg Thr Lys
                245                 250                 255 cag aat atg cgt aat gct atc ctt aat tac acc cag cag gtt atg aag     816
Gln Asn Met Arg Asn Ala Ile Leu Asn Tyr Thr Gln Gln Val Met Lys
            260                 265                 270 gtt ttc aag gat tcc aag aat atg cca acg atc ggc acg aat aag ttc     864
Val Phe Lys Asp Ser Lys Asn Met Pro Thr Ile Gly Thr Asn Lys Phe
        275                 280                 285 agc gtt gat acc tac aat gtt tac atc aag ggg atg acg ctt aat gtg     912
Ser Val Asp Thr Tyr Asn Val Tyr Ile Lys Gly Met Thr Leu Asn Val
    290                 295                 300
```

```
ctt gat atc gtt gct atc tgg cca agc ctg tac cca gat gat tac acg      960
Leu Asp Ile Val Ala Ile Trp Pro Ser Leu Tyr Pro Asp Asp Tyr Thr
305                 310                 315                 320 tca cag acg gct ctg gaa cag acc cgc gtg acg ttc tcc aat atg gtg     1008
Ser Gln Thr Ala Leu Glu Gln Thr Arg Val Thr Phe Ser Asn Met Val
            325                 330                 335 ggg cag gaa gaa ggc acg gat ggc agc ctc aga atc tac aat acc ttc     1056
Gly Gln Glu Glu Gly Thr Asp Gly Ser Leu Arg Ile Tyr Asn Thr Phe
        340                 345                 350 gat agc ttc tcc tac cag cat agc cct atc cct aat aat aat gtg aat     1104
Asp Ser Phe Ser Tyr Gln His Ser Pro Ile Pro Asn Asn Asn Val Asn
    355                 360                 365 ctc atc agc tac tac aat gat gaa ctt cag aat ctg gaa ctc ggg gtt     1152
Leu Ile Ser Tyr Tyr Asn Asp Glu Leu Gln Asn Leu Glu Leu Gly Val
370                 375                 380 tac acc cca cca aag aag ggc tca ggc tac agc tac cca tac ggg ttc     1200
Tyr Thr Pro Pro Lys Lys Gly Ser Gly Tyr Ser Tyr Pro Tyr Gly Phe
385                 390                 395                 400 gtg ctg aat tac gca aat agc aag tac aag tac ggt gat tcc aat gat     1248
Val Leu Asn Tyr Ala Asn Ser Lys Tyr Lys Tyr Gly Asp Ser Asn Asp
            405                 410                 415 cca gaa tcc ctc ggc ggg ctt tcc acc ctt agc gct cca atc caa cag     1296
Pro Glu Ser Leu Gly Gly Leu Ser Thr Leu Ser Ala Pro Ile Gln Gln
        420                 425                 430 gtt aat gct gct acc cag aat agc aag tac ctt gat ggc gaa atc ctg     1344
Val Asn Ala Ala Thr Gln Asn Ser Lys Tyr Leu Asp Gly Glu Ile Leu
    435                 440                 445 aat ggg atc ggc gca agc ctg cct ggc tac tgc acg acc ggg tgc tca     1392
Asn Gly Ile Gly Ala Ser Leu Pro Gly Tyr Cys Thr Thr Gly Cys Ser
450                 455                 460 cct acc gaa cca cca ttc agc tgc acg agc acg gca aat ggg tac aag     1440
Pro Thr Glu Pro Pro Phe Ser Cys Thr Ser Thr Ala Asn Gly Tyr Lys
465                 470                 475                 480 gca agc tgc aat cca agc gat acc aat cag aag atc aat gct ctc tac     1488
Ala Ser Cys Asn Pro Ser Asp Thr Asn Gln Lys Ile Asn Ala Leu Tyr
            485                 490                 495 cca ttc acg cag gca aat gtg aag ggg aat acc ggg aag ctg ggc gtt     1536
Pro Phe Thr Gln Ala Asn Val Lys Gly Asn Thr Gly Lys Leu Gly Val
        500                 505                 510 ctc gca agc ctt gtt agc tac gat ctg aat cct aag aat gtt ttc ggg     1584
Leu Ala Ser Leu Val Ser Tyr Asp Leu Asn Pro Lys Asn Val Phe Gly
    515                 520                 525 gaa ctc gat tca gat acc aat aat gtt atc ctt aag ggc atc cca gca     1632
Glu Leu Asp Ser Asp Thr Asn Asn Val Ile Leu Lys Gly Ile Pro Ala
530                 535                 540 gaa aag ggc tac ttc cca aat aat gca aga cca acc gtt gtg aag gaa     1680
Glu Lys Gly Tyr Phe Pro Asn Asn Ala Arg Pro Thr Val Val Lys Glu
545                 550                 555                 560 tgg atc aat ggg gct tcc gca gtt cca ctt gat tcc ggc aat acc ctg     1728
Trp Ile Asn Gly Ala Ser Ala Val Pro Leu Asp Ser Gly Asn Thr Leu
            565                 570                 575 ttc atg acg gct acg aac ctg acg gct acc cag tac aga atc cgc atc     1776
Phe Met Thr Ala Thr Asn Leu Thr Ala Thr Gln Tyr Arg Ile Arg Ile
        580                 585                 590 cgt tac gct aac cca aac tca aac acg cag atc ggc gtt aga atc acg     1824
Arg Tyr Ala Asn Pro Asn Ser Asn Thr Gln Ile Gly Val Arg Ile Thr
    595                 600                 605 cag aac ggg agc ctc atc tcc tcc tcc aac ctc acg ctg tac tca acc     1872
Gln Asn Gly Ser Leu Ile Ser Ser Ser Asn Leu Thr Leu Tyr Ser Thr
610                 615                 620
```

```
acc gat atg aac aac acc ctg cca ctg aac gtt tac gtg atc ggg gaa    1920
Thr Asp Met Asn Asn Thr Leu Pro Leu Asn Val Tyr Val Ile Gly Glu
625                 630                 635                 640 aac ggg aac tac acc ctc cag gat ctc tac aac acg acg aac gtt ctg    1968
Asn Gly Asn Tyr Thr Leu Gln Asp Leu Tyr Asn Thr Thr Asn Val Leu
            645                 650                 655 tcc acg ggc gat atc acc ctg cag atc acc ggc ggg gat cag aag ata    2016
Ser Thr Gly Asp Ile Thr Leu Gln Ile Thr Gly Gly Asp Gln Lys Ile
            660                 665                 670 ttc atc gat cgc atc gag ttc gtg cct acg atg cca gtg cca ggc aac    2064
Phe Ile Asp Arg Ile Glu Phe Val Pro Thr Met Pro Val Pro Gly Asn
            675                 680                 685 acc aac aac aac aac ggc aac aac ggc aac aac aac ccc ccc cat        2112
Thr Asn Asn Asn Asn Gly Asn Asn Gly Asn Asn Asn Pro Pro His
690                 695                 700 cat gtc tgc gct ata gct ggt act cag cag tct tgc tca ggt cct cct    2160
His Val Cys Ala Ile Ala Gly Thr Gln Gln Ser Cys Ser Gly Pro Pro
705                 710                 715                 720 aag ttc gag cag gtt tct gat ctc gag aag atc acc acc cag gtc tac    2208
Lys Phe Glu Gln Val Ser Asp Leu Glu Lys Ile Thr Thr Gln Val Tyr
                725                 730                 735 atg ctg ttc aag tcc taa                                            2226
Met Leu Phe Lys Ser *
740

<210> SEQ ID NO 27
<211> LENGTH: 741
<212> TYPE: PRT
<213> ORGANISM: Artificial Sequence
<220> FEATURE:
<223> OTHER INFORMATION: SYNAXMI-031(A-D)

<400> SEQUENCE: 27

Met Gln Ile Leu Asp Cys Asn Leu Gln Ser Gln Gln Asn Ile Pro Tyr
1               5                   10                  15

Asn Val Leu Ala Ile Pro Val Ser Asn Val Asn Ser Leu Thr Asp Thr
            20                  25                  30

Val Gly Asp Leu Lys Lys Ala Trp Glu Glu Phe Gln Lys Thr Gly Ser
        35                  40                  45

Phe Ser Leu Thr Ala Leu Gln Gln Gly Phe Ser Ala Ser Gln Gly Gly
    50                  55                  60

Thr Phe Asn Tyr Leu Thr Leu Leu Gln Ser Gly Ile Ser Leu Ala Gly
65                  70                  75                  80

Ser Phe Val Pro Gly Gly Thr Phe Val Ala Pro Ile Ile Asn Met Val
                85                  90                  95

Ile Gly Trp Leu Trp Pro His Lys Asn Lys Asn Ala Asp Thr Glu Asn
            100                 105                 110

Leu Ile Asn Leu Ile Asp Ser Glu Ile Gln Lys Gln Leu Asn Lys Ala
        115                 120                 125

Leu Leu Asp Ala Asp Arg Asn Glu Trp Ser Ser Tyr Leu Glu Ser Ile
    130                 135                 140

Phe Asp Ser Ser Asn Asn Leu Asn Gly Ala Ile Val Asp Ala Gln Trp
145                 150                 155                 160

Ser Gly Thr Val Asn Thr Thr Asn Arg Thr Leu Arg Asn Pro Thr Glu
                165                 170                 175

Ser Asp Tyr Thr Asn Val Val Thr Asn Phe Ile Ala Ala Asp Gly Asp
            180                 185                 190

Ile Ala Asn Asn Glu Asn His Ile Met Asn Gly Asn Phe Asp Val Ala
```

-continued

```
           195                 200                 205
Ala Ala Pro Tyr Phe Val Ile Gly Ala Thr Ala Arg Phe Ala Ala Met
210                 215                 220

Gln Ser Tyr Ile Lys Phe Cys Asn Ala Trp Ile Asp Lys Val Gly Leu
225                 230                 235                 240

Ser Asp Ala Gln Leu Thr Thr Gln Lys Ala Asn Leu Asp Arg Thr Lys
                245                 250                 255

Gln Asn Met Arg Asn Ala Ile Leu Asn Tyr Thr Gln Gln Val Met Lys
                260                 265                 270

Val Phe Lys Asp Ser Lys Asn Met Pro Thr Ile Gly Thr Asn Lys Phe
            275                 280                 285

Ser Val Asp Thr Tyr Asn Val Tyr Ile Lys Gly Met Thr Leu Asn Val
        290                 295                 300

Leu Asp Ile Val Ala Ile Trp Pro Ser Leu Tyr Pro Asp Asp Tyr Thr
305                 310                 315                 320

Ser Gln Thr Ala Leu Glu Gln Thr Arg Val Thr Phe Ser Asn Met Val
                325                 330                 335

Gly Gln Glu Glu Gly Thr Asp Gly Ser Leu Arg Ile Tyr Asn Thr Phe
                340                 345                 350

Asp Ser Phe Ser Tyr Gln His Ser Pro Ile Pro Asn Asn Asn Val Asn
            355                 360                 365

Leu Ile Ser Tyr Tyr Asn Asp Glu Leu Gln Asn Leu Glu Leu Gly Val
        370                 375                 380

Tyr Thr Pro Pro Lys Lys Gly Ser Gly Tyr Ser Tyr Pro Tyr Gly Phe
385                 390                 395                 400

Val Leu Asn Tyr Ala Asn Ser Lys Tyr Lys Tyr Gly Asp Ser Asn Asp
                405                 410                 415

Pro Glu Ser Leu Gly Gly Leu Ser Thr Leu Ser Ala Pro Ile Gln Gln
                420                 425                 430

Val Asn Ala Ala Thr Gln Asn Ser Lys Tyr Leu Asp Gly Glu Ile Leu
            435                 440                 445

Asn Gly Ile Gly Ala Ser Leu Pro Gly Tyr Cys Thr Thr Gly Cys Ser
        450                 455                 460

Pro Thr Glu Pro Pro Phe Ser Cys Thr Ser Thr Ala Asn Gly Tyr Lys
465                 470                 475                 480

Ala Ser Cys Asn Pro Ser Asp Thr Asn Gln Lys Ile Asn Ala Leu Tyr
                485                 490                 495

Pro Phe Thr Gln Ala Asn Val Lys Gly Asn Thr Gly Lys Leu Gly Val
                500                 505                 510

Leu Ala Ser Leu Val Ser Tyr Asp Leu Asn Pro Lys Asn Val Phe Gly
            515                 520                 525

Glu Leu Asp Ser Asp Thr Asn Asn Val Ile Leu Lys Gly Ile Pro Ala
        530                 535                 540

Glu Lys Gly Tyr Phe Pro Asn Asn Ala Arg Pro Thr Val Val Lys Glu
545                 550                 555                 560

Trp Ile Asn Gly Ala Ser Ala Val Pro Leu Asp Ser Gly Asn Thr Leu
                565                 570                 575

Phe Met Thr Ala Thr Asn Leu Thr Ala Thr Gln Tyr Arg Ile Arg Ile
                580                 585                 590

Arg Tyr Ala Asn Pro Asn Ser Asn Thr Gln Ile Gly Val Arg Ile Thr
            595                 600                 605

Gln Asn Gly Ser Leu Ile Ser Ser Ser Asn Leu Thr Leu Tyr Ser Thr
        610                 615                 620
```

-continued

```
Thr Asp Met Asn Asn Thr Leu Pro Leu Asn Val Tyr Val Ile Gly Glu
625                 630                 635                 640

Asn Gly Asn Tyr Thr Leu Gln Asp Leu Tyr Asn Thr Thr Asn Val Leu
            645                 650                 655

Ser Thr Gly Asp Ile Thr Leu Gln Ile Thr Gly Gly Asp Gln Lys Ile
            660                 665                 670

Phe Ile Asp Arg Ile Glu Phe Val Pro Thr Met Pro Val Pro Gly Asn
            675                 680                 685

Thr Asn Asn Asn Asn Gly Asn Asn Gly Asn Asn Asn Pro Pro His
            690                 695                 700

His Val Cys Ala Ile Ala Gly Thr Gln Gln Ser Cys Ser Gly Pro Pro
705                 710                 715                 720

Lys Phe Glu Gln Val Ser Asp Leu Glu Lys Ile Thr Thr Gln Val Tyr
                725                 730                 735

Met Leu Phe Lys Ser
            740
```

```
<210> SEQ ID NO 28
<211> LENGTH: 2316
<212> TYPE: DNA
<213> ORGANISM: Artificial Sequence
<220> FEATURE:
<223> OTHER INFORMATION: aposynaxmi-031(A-D)
<220> FEATURE:
<221> NAME/KEY: CDS
<222> LOCATION: (1)...(2316)

<400> SEQUENCE: 28 atg cag atc ctt ggg tac tcc agc ttc gtt gct atc gct ctt ctt atg      48
Met Gln Ile Leu Gly Tyr Ser Ser Phe Val Ala Ile Ala Leu Leu Met
1               5                   10                  15 agc gtg gtt gtt gtt tgc aat ggg ggc aag acg tcc acc tac gtg cgt      96
Ser Val Val Val Val Cys Asn Gly Gly Lys Thr Ser Thr Tyr Val Arg
            20                  25                  30 aat ctg gat tgc aat ctc cag agc cag cag aat atc cca tac aat gtg     144
Asn Leu Asp Cys Asn Leu Gln Ser Gln Gln Asn Ile Pro Tyr Asn Val
        35                  40                  45 ctt gct atc cct gtt agc aat gtt aat agc ctt acg gat acg gtt ggc     192
Leu Ala Ile Pro Val Ser Asn Val Asn Ser Leu Thr Asp Thr Val Gly
    50                  55                  60 gat cta aag aag gca tgg gaa gag ttc cag aag acg ggc agc ttc tcc     240
Asp Leu Lys Lys Ala Trp Glu Glu Phe Gln Lys Thr Gly Ser Phe Ser
65                  70                  75                  80 ctt acc gca ctc cag cag ggc ttc agc gct tcc cag ggc ggg acg ttc     288
Leu Thr Ala Leu Gln Gln Gly Phe Ser Ala Ser Gln Gly Gly Thr Phe
                85                  90                  95 aat tac ctc acc ctc ctc cag tcc ggg atc tcc ctg gct ggc agc ttc     336
Asn Tyr Leu Thr Leu Leu Gln Ser Gly Ile Ser Leu Ala Gly Ser Phe
            100                 105                 110 gtg cct ggc ggc acc ttc gtt gct cca atc atc aat atg gtg atc ggc     384
Val Pro Gly Gly Thr Phe Val Ala Pro Ile Ile Asn Met Val Ile Gly
        115                 120                 125 tgg ctc tgg cct cat aag aat aag aat gca gat acg gaa aat ctg atc     432
Trp Leu Trp Pro His Lys Asn Lys Asn Ala Asp Thr Glu Asn Leu Ile
    130                 135                 140 aat ctg atc gat tca gaa atc cag aag cag ctg aat aag gct ctg ctg     480
Asn Leu Ile Asp Ser Glu Ile Gln Lys Gln Leu Asn Lys Ala Leu Leu
145                 150                 155                 160 gat gct gat cgc aat gaa tgg agc agc tac ctc gag tcc atc ttc gat     528
Asp Ala Asp Arg Asn Glu Trp Ser Ser Tyr Leu Glu Ser Ile Phe Asp
                165                 170                 175
```

```
agc agc aat aat ctg aat ggc gca atc gtt gat gct cag tgg tcc ggc       576
Ser Ser Asn Asn Leu Asn Gly Ala Ile Val Asp Ala Gln Trp Ser Gly
        180                 185                 190 acc gtg aat acg acc aat cgt acg ctt cgt aat cct acg gaa tca gat       624
Thr Val Asn Thr Thr Asn Arg Thr Leu Arg Asn Pro Thr Glu Ser Asp
            195                 200                 205 tac acc aat gtg gtg acg aat ttc atc gca gca gat ggg gat atc gct       672
Tyr Thr Asn Val Val Thr Asn Phe Ile Ala Ala Asp Gly Asp Ile Ala
    210                 215                 220 aat aat gaa aat cat atc atg aat ggg aat ttc gat gtg gca gca gct       720
Asn Asn Glu Asn His Ile Met Asn Gly Asn Phe Asp Val Ala Ala Ala
225                 230                 235                 240 cca tac ttc gtt atc ggg gct acc gct aga ttc gca gct atg cag tcc       768
Pro Tyr Phe Val Ile Gly Ala Thr Ala Arg Phe Ala Ala Met Gln Ser
                245                 250                 255 tac atc aag ttc tgc aat gca tgg atc gat aag gtt ggg ctg tca gat       816
Tyr Ile Lys Phe Cys Asn Ala Trp Ile Asp Lys Val Gly Leu Ser Asp
            260                 265                 270 gct cag ctg acc acg cag aag gct aat ctg gat aga acg aag cag aat       864
Ala Gln Leu Thr Thr Gln Lys Ala Asn Leu Asp Arg Thr Lys Gln Asn
    275                 280                 285 atg cgt aat gct atc ctt aat tac acc cag cag gtt atg aag gtt ttc       912
Met Arg Asn Ala Ile Leu Asn Tyr Thr Gln Gln Val Met Lys Val Phe
290                 295                 300 aag gat tcc aag aat atg cca acg atc ggc acg aat aag ttc agc gtt       960
Lys Asp Ser Lys Asn Met Pro Thr Ile Gly Thr Asn Lys Phe Ser Val
305                 310                 315                 320 gat acc tac aat gtt tac atc aag ggg atg acg ctt aat gtg ctt gat      1008
Asp Thr Tyr Asn Val Tyr Ile Lys Gly Met Thr Leu Asn Val Leu Asp
                325                 330                 335 atc gtt gct atc tgg cca agc ctg tac cca gat gat tac acg tca cag      1056
Ile Val Ala Ile Trp Pro Ser Leu Tyr Pro Asp Asp Tyr Thr Ser Gln
            340                 345                 350 acg gct ctg gaa cag acc cgc gtg acg ttc tcc aat atg gtg ggg cag      1104
Thr Ala Leu Glu Gln Thr Arg Val Thr Phe Ser Asn Met Val Gly Gln
    355                 360                 365 gaa gaa ggc acg gat ggc agc ctc aga atc tac aat acc ttc gat agc      1152
Glu Glu Gly Thr Asp Gly Ser Leu Arg Ile Tyr Asn Thr Phe Asp Ser
370                 375                 380 ttc tcc tac cag cat agc cct atc cct aat aat aat gtg aat ctc atc      1200
Phe Ser Tyr Gln His Ser Pro Ile Pro Asn Asn Asn Val Asn Leu Ile
385                 390                 395                 400 agc tac tac aat gat gaa ctt cag aat ctg gaa ctc ggg gtt tac acc      1248
Ser Tyr Tyr Asn Asp Glu Leu Gln Asn Leu Glu Leu Gly Val Tyr Thr
                405                 410                 415 cca cca aag aag ggc tca ggc tac agc tac cca tac ggg ttc gtg ctg      1296
Pro Pro Lys Lys Gly Ser Gly Tyr Ser Tyr Pro Tyr Gly Phe Val Leu
            420                 425                 430 aat tac gca aat agc aag tac aag tac ggc gat tcc aat gat cca gaa      1344
Asn Tyr Ala Asn Ser Lys Tyr Lys Tyr Gly Asp Ser Asn Asp Pro Glu
    435                 440                 445 tcc ctc ggc ggg ctt tcc acc ctt agc gct cca atc caa cag gtt aat      1392
Ser Leu Gly Gly Leu Ser Thr Leu Ser Ala Pro Ile Gln Gln Val Asn
450                 455                 460 gct gct acc cag aat agc aag tac ctt gat ggc gaa atc ctg aat ggg      1440
Ala Ala Thr Gln Asn Ser Lys Tyr Leu Asp Gly Glu Ile Leu Asn Gly
465                 470                 475                 480 atc ggc gca agc ctg cct ggc tac tgc acg acc ggg tgc tca cct acc      1488
Ile Gly Ala Ser Leu Pro Gly Tyr Cys Thr Thr Gly Cys Ser Pro Thr
                485                 490                 495
```

```
gaa cca cca ttc agc tgc acg agc acg gca aat ggg tac aag gca agc    1536
Glu Pro Pro Phe Ser Cys Thr Ser Thr Ala Asn Gly Tyr Lys Ala Ser
        500                 505                 510 tgc aat cca agc gat acc aat cag aag atc aat gct ctc tac cca ttc    1584
Cys Asn Pro Ser Asp Thr Asn Gln Lys Ile Asn Ala Leu Tyr Pro Phe
    515                 520                 525 acg cag gca aat gtg aag ggg aat acc ggg aag ctg ggc gtt ctc gca    1632
Thr Gln Ala Asn Val Lys Gly Asn Thr Gly Lys Leu Gly Val Leu Ala
530                 535                 540 agc ctt gtt agc tac gat ctg aat cct aag aat gtt ttc ggg gaa ctc    1680
Ser Leu Val Ser Tyr Asp Leu Asn Pro Lys Asn Val Phe Gly Glu Leu
545                 550                 555                 560 gat tca gat acc aat aat gtt atc ctt aag ggc atc cca gca gaa aag    1728
Asp Ser Asp Thr Asn Asn Val Ile Leu Lys Gly Ile Pro Ala Glu Lys
                565                 570                 575 ggc tac ttc cca aat aat gca aga cca acc gtt gtg aag gaa tgg atc    1776
Gly Tyr Phe Pro Asn Asn Ala Arg Pro Thr Val Val Lys Glu Trp Ile
            580                 585                 590 aat ggg gct tcc gca gtt cca ctt gat tcc ggc aat acc ctg ttc atg    1824
Asn Gly Ala Ser Ala Val Pro Leu Asp Ser Gly Asn Thr Leu Phe Met
        595                 600                 605 acg gct acg aac ctg acg gct acc cag tac aga atc cgc atc cgt tac    1872
Thr Ala Thr Asn Leu Thr Ala Thr Gln Tyr Arg Ile Arg Ile Arg Tyr
    610                 615                 620 gct aac cca aac tca aac acg cag atc ggc gtt aga atc acg cag aac    1920
Ala Asn Pro Asn Ser Asn Thr Gln Ile Gly Val Arg Ile Thr Gln Asn
625                 630                 635                 640 ggg agc ctc atc tcc tcc tcc aac ctc acg ctg tac tca acc acc gat    1968
Gly Ser Leu Ile Ser Ser Ser Asn Leu Thr Leu Tyr Ser Thr Thr Asp
                645                 650                 655 atg aac aac acc ctg cca ctg aac gtt tac gtg atc ggg gaa aac ggg    2016
Met Asn Asn Thr Leu Pro Leu Asn Val Tyr Val Ile Gly Glu Asn Gly
            660                 665                 670 aac tac acc ctc cag gat ctc tac aac acg acg aac gtt ctg tcc acg    2064
Asn Tyr Thr Leu Gln Asp Leu Tyr Asn Thr Thr Asn Val Leu Ser Thr
        675                 680                 685 ggc gat atc acc ctg cag atc acc ggc ggg gat cag aag ata ttc atc    2112
Gly Asp Ile Thr Leu Gln Ile Thr Gly Gly Asp Gln Lys Ile Phe Ile
    690                 695                 700 gat cgc atc gag ttc gtg cct acg atg cca gtg cca ggc aac acc aac    2160
Asp Arg Ile Glu Phe Val Pro Thr Met Pro Val Pro Gly Asn Thr Asn
705                 710                 715                 720 aac aac aac ggc aac aac aac ggc aac aac aac ccc ccc cat cat gtc    2208
Asn Asn Asn Gly Asn Asn Asn Gly Asn Asn Asn Pro Pro His His Val
                725                 730                 735 tgc gct ata gct ggt act cag cag tct tgc tca ggt cct cct aag ttc    2256
Cys Ala Ile Ala Gly Thr Gln Gln Ser Cys Ser Gly Pro Pro Lys Phe
            740                 745                 750 gag cag gtt tct gat ctc gag aag atc acc acc cag gtc tac atg ctg    2304
Glu Gln Val Ser Asp Leu Glu Lys Ile Thr Thr Gln Val Tyr Met Leu
        755                 760                 765 ttc aag tcc taa                                                    2316
Phe Lys Ser *
    770

<210> SEQ ID NO 29
<211> LENGTH: 771
<212> TYPE: PRT
<213> ORGANISM: Artificial Sequence
<220> FEATURE:
<223> OTHER INFORMATION: APOSYNAXMI-031(A-D)
```

<400> SEQUENCE: 29

```
Met Gln Ile Leu Gly Tyr Ser Ser Phe Val Ala Ile Ala Leu Leu Met
 1               5                  10                  15

Ser Val Val Val Cys Asn Gly Gly Lys Thr Ser Thr Tyr Val Arg
            20                  25                  30

Asn Leu Asp Cys Asn Leu Gln Ser Gln Gln Asn Ile Pro Tyr Asn Val
            35                  40                  45

Leu Ala Ile Pro Val Ser Asn Val Asn Ser Leu Thr Asp Thr Val Gly
        50                  55                  60

Asp Leu Lys Lys Ala Trp Glu Glu Phe Gln Lys Thr Gly Ser Phe Ser
65                  70                  75                  80

Leu Thr Ala Leu Gln Gln Gly Phe Ser Ala Ser Gln Gly Gly Thr Phe
                85                  90                  95

Asn Tyr Leu Thr Leu Leu Gln Ser Gly Ile Ser Leu Ala Gly Ser Phe
            100                 105                 110

Val Pro Gly Gly Thr Phe Val Ala Pro Ile Ile Asn Met Val Ile Gly
        115                 120                 125

Trp Leu Trp Pro His Lys Asn Lys Asn Ala Asp Thr Glu Asn Leu Ile
130                 135                 140

Asn Leu Ile Asp Ser Glu Ile Gln Lys Gln Leu Asn Lys Ala Leu Leu
145                 150                 155                 160

Asp Ala Asp Arg Asn Glu Trp Ser Ser Tyr Leu Glu Ser Ile Phe Asp
                165                 170                 175

Ser Ser Asn Asn Leu Asn Gly Ala Ile Val Asp Ala Gln Trp Ser Gly
            180                 185                 190

Thr Val Asn Thr Thr Asn Arg Thr Leu Arg Asn Pro Thr Glu Ser Asp
        195                 200                 205

Tyr Thr Asn Val Val Thr Asn Phe Ile Ala Ala Asp Gly Asp Ile Ala
        210                 215                 220

Asn Asn Glu Asn His Ile Met Asn Gly Asn Phe Asp Val Ala Ala Ala
225                 230                 235                 240

Pro Tyr Phe Val Ile Gly Ala Thr Ala Arg Phe Ala Ala Met Gln Ser
                245                 250                 255

Tyr Ile Lys Phe Cys Asn Ala Trp Ile Asp Lys Val Gly Leu Ser Asp
            260                 265                 270

Ala Gln Leu Thr Thr Gln Lys Ala Asn Leu Asp Arg Thr Lys Gln Asn
        275                 280                 285

Met Arg Asn Ala Ile Leu Asn Tyr Thr Gln Val Met Lys Val Phe
        290                 295                 300

Lys Asp Ser Lys Asn Met Pro Thr Ile Gly Thr Asn Lys Phe Ser Val
305                 310                 315                 320

Asp Thr Tyr Asn Val Tyr Ile Lys Gly Met Thr Leu Asn Val Leu Asp
                325                 330                 335

Ile Val Ala Ile Trp Pro Ser Leu Tyr Pro Asp Asp Tyr Thr Ser Gln
            340                 345                 350

Thr Ala Leu Glu Gln Thr Arg Val Thr Phe Ser Asn Met Val Gly Gln
        355                 360                 365

Glu Glu Gly Thr Asp Gly Ser Leu Arg Ile Tyr Asn Thr Phe Asp Ser
    370                 375                 380

Phe Ser Tyr Gln His Ser Pro Ile Pro Asn Asn Asn Val Asn Leu Ile
385                 390                 395                 400

Ser Tyr Tyr Asn Asp Glu Leu Gln Asn Leu Glu Leu Gly Val Tyr Thr
                405                 410                 415
```

```
Pro Pro Lys Lys Gly Ser Gly Tyr Ser Tyr Pro Tyr Gly Phe Val Leu
        420                 425                 430
Asn Tyr Ala Asn Ser Lys Tyr Lys Tyr Gly Asp Ser Asn Asp Pro Glu
        435                 440                 445
Ser Leu Gly Gly Leu Ser Thr Leu Ser Ala Pro Ile Gln Gln Val Asn
450                 455                 460
Ala Ala Thr Gln Asn Ser Lys Tyr Leu Asp Gly Glu Ile Leu Asn Gly
465                 470                 475                 480
Ile Gly Ala Ser Leu Pro Gly Tyr Cys Thr Gly Cys Ser Pro Thr
                485                 490                 495
Glu Pro Pro Phe Ser Cys Thr Ser Thr Ala Asn Gly Tyr Lys Ala Ser
                500                 505                 510
Cys Asn Pro Ser Asp Thr Asn Gln Lys Ile Asn Ala Leu Tyr Pro Phe
                515                 520                 525
Thr Gln Ala Asn Val Lys Gly Asn Thr Gly Lys Leu Gly Val Leu Ala
                530                 535                 540
Ser Leu Val Ser Tyr Asp Leu Asn Pro Lys Asn Val Phe Gly Glu Leu
545                 550                 555                 560
Asp Ser Asp Thr Asn Asn Val Ile Leu Lys Gly Ile Pro Ala Glu Lys
                565                 570                 575
Gly Tyr Phe Pro Asn Asn Ala Arg Pro Thr Val Val Lys Glu Trp Ile
                580                 585                 590
Asn Gly Ala Ser Ala Val Pro Leu Asp Ser Gly Asn Thr Leu Phe Met
                595                 600                 605
Thr Ala Thr Asn Leu Thr Ala Thr Gln Tyr Arg Ile Arg Ile Arg Tyr
                610                 615                 620
Ala Asn Pro Asn Ser Asn Thr Gln Ile Gly Val Arg Ile Thr Gln Asn
625                 630                 635                 640
Gly Ser Leu Ile Ser Ser Ser Asn Leu Thr Leu Tyr Ser Thr Thr Asp
                645                 650                 655
Met Asn Asn Thr Leu Pro Leu Asn Val Tyr Val Ile Gly Glu Asn Gly
                660                 665                 670
Asn Tyr Thr Leu Gln Asp Leu Tyr Asn Thr Thr Asn Val Leu Ser Thr
                675                 680                 685
Gly Asp Ile Thr Leu Gln Ile Thr Gly Gly Asp Gln Lys Ile Phe Ile
                690                 695                 700
Asp Arg Ile Glu Phe Val Pro Thr Met Pro Val Pro Gly Asn Thr Asn
705                 710                 715                 720
Asn Asn Asn Gly Asn Asn Asn Gly Asn Asn Asn Pro Pro His His Val
                725                 730                 735
Cys Ala Ile Ala Gly Thr Gln Gln Ser Cys Ser Gly Pro Pro Lys Phe
                740                 745                 750
Glu Gln Val Ser Asp Leu Glu Lys Ile Thr Thr Gln Val Tyr Met Leu
                755                 760                 765
Phe Lys Ser
    770

<210> SEQ ID NO 30
<211> LENGTH: 2307
<212> TYPE: DNA
<213> ORGANISM: Artificial Sequence
<220> FEATURE:
<223> OTHER INFORMATION: aposyn2axmi-031(A-D)
<220> FEATURE:
<221> NAME/KEY: CDS
<222> LOCATION: (1)...(2307)
```

<400> SEQUENCE: 30

```
atg ggc tac agc agc ttc gtc gcc atc gcg ctg ctg atg agc gtg gtg      48
Met Gly Tyr Ser Ser Phe Val Ala Ile Ala Leu Leu Met Ser Val Val
 1               5                  10                  15 gtg gtg tgc aac ggc ggc aag aca agc acc tat gtg agg aac ctg gac      96
Val Val Cys Asn Gly Gly Lys Thr Ser Thr Tyr Val Arg Asn Leu Asp
             20                  25                  30 tgc aac ctc cag agc cag cag aac atc ccc tac aat gtg ctg gcc atc     144
Cys Asn Leu Gln Ser Gln Gln Asn Ile Pro Tyr Asn Val Leu Ala Ile
         35                  40                  45 ccc gtc tca aat gtc aac agc ttg aca gat act gtt ggt gat ttg aag     192
Pro Val Ser Asn Val Asn Ser Leu Thr Asp Thr Val Gly Asp Leu Lys
     50                  55                  60 aag gca tgg gag gag ttc cag aag acc ggc agc ttc agc ttg acg gcg     240
Lys Ala Trp Glu Glu Phe Gln Lys Thr Gly Ser Phe Ser Leu Thr Ala
 65                  70                  75                  80 ctg caa caa ggc ttc tca gca agc caa gga ggc acc ttc aac tac ctc     288
Leu Gln Gln Gly Phe Ser Ala Ser Gln Gly Gly Thr Phe Asn Tyr Leu
                 85                  90                  95 acc ttg ctg caa agc ggc atc agc ttg gcc ggc agc ttc gtg ccc ggc     336
Thr Leu Leu Gln Ser Gly Ile Ser Leu Ala Gly Ser Phe Val Pro Gly
            100                 105                 110 ggc acc ttc gtg gcg ccc atc atc aac atg gtg att gga tgg ctg tgg     384
Gly Thr Phe Val Ala Pro Ile Ile Asn Met Val Ile Gly Trp Leu Trp
        115                 120                 125 ccg cac aag aac aag aat gct gac aca gaa aat ttg atc aac ctc att     432
Pro His Lys Asn Lys Asn Ala Asp Thr Glu Asn Leu Ile Asn Leu Ile
    130                 135                 140 gat tca gag atc cag aag cag ctc aac aag gcg ctg ctg gat gct gac     480
Asp Ser Glu Ile Gln Lys Gln Leu Asn Lys Ala Leu Leu Asp Ala Asp
145                 150                 155                 160 aga aat gaa tgg agc agc tac ctg gag agc atc ttt gat tca agc aac     528
Arg Asn Glu Trp Ser Ser Tyr Leu Glu Ser Ile Phe Asp Ser Ser Asn
                165                 170                 175 aac ctc aac ggc gcc atc gtg gat gct caa tgg tca ggc acc gtc aac     576
Asn Leu Asn Gly Ala Ile Val Asp Ala Gln Trp Ser Gly Thr Val Asn
            180                 185                 190 acc acc aac agg acg ctg agg aat cca aca gaa agt gac tac acc aat     624
Thr Thr Asn Arg Thr Leu Arg Asn Pro Thr Glu Ser Asp Tyr Thr Asn
        195                 200                 205 gtg gtg acc aac ttc att gct gct gat gga gac atc gcc aac aat gag     672
Val Val Thr Asn Phe Ile Ala Ala Asp Gly Asp Ile Ala Asn Asn Glu
    210                 215                 220 aac cac atc atg aat gga aat ttt gat gtt gct gct gct cca tat ttt     720
Asn His Ile Met Asn Gly Asn Phe Asp Val Ala Ala Ala Pro Tyr Phe
225                 230                 235                 240 gtg att gga gca aca gca aga ttt gct gcc atg caa tca tac atc aag     768
Val Ile Gly Ala Thr Ala Arg Phe Ala Ala Met Gln Ser Tyr Ile Lys
                245                 250                 255 ttc tgc aat gca tgg atc gac aag gtg ggc ctc tct gat gct cag ctc     816
Phe Cys Asn Ala Trp Ile Asp Lys Val Gly Leu Ser Asp Ala Gln Leu
            260                 265                 270 acc acc cag aag gcc aac ctg gac agg acc aag cag aac atg agg aat     864
Thr Thr Gln Lys Ala Asn Leu Asp Arg Thr Lys Gln Asn Met Arg Asn
        275                 280                 285 gcc atc ttg aat tac acc cag cag gtg atg aag gtg ttc aag gac agc     912
Ala Ile Leu Asn Tyr Thr Gln Gln Val Met Lys Val Phe Lys Asp Ser
    290                 295                 300 aag aac atg cca acc atc ggc acc aac aag ttc tca gtg gac acc tac     960
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Lys | Asn | Met | Pro | Thr | Ile | Gly | Thr | Asn | Lys | Phe | Ser | Val | Asp | Thr | Tyr |      |
| 305 |     |     |     |     | 310 |     |     |     |     | 315 |     |     |     |     | 320 |      |

| aat | gtc | tac | atc | aag | ggc | atg | acg | ctc | aat | gtg | ctg | gac | atc | gtc | gcc | 1008 |
|-----|-----|-----|-----|-----|-----|-----|-----|-----|-----|-----|-----|-----|-----|-----|-----|------|
| Asn | Val | Tyr | Ile | Lys | Gly | Met | Thr | Leu | Asn | Val | Leu | Asp | Ile | Val | Ala |      |
|     |     |     |     | 325 |     |     |     |     | 330 |     |     |     |     | 335 |     |      |

| atc | tgg | cca | agc | ctc | tac | cct | gat | gac | tac | acc | tca | cag | acg | gcg | ctg | 1056 |
|-----|-----|-----|-----|-----|-----|-----|-----|-----|-----|-----|-----|-----|-----|-----|-----|------|
| Ile | Trp | Pro | Ser | Leu | Tyr | Pro | Asp | Asp | Tyr | Thr | Ser | Gln | Thr | Ala | Leu |      |
|     |     |     |     | 340 |     |     |     |     | 345 |     |     |     |     | 350 |     |      |

| gag | caa | aca | agg | gtg | acc | ttc | agc | aac | atg | gtg | ggc | caa | gaa | gaa | gga | 1104 |
|-----|-----|-----|-----|-----|-----|-----|-----|-----|-----|-----|-----|-----|-----|-----|-----|------|
| Glu | Gln | Thr | Arg | Val | Thr | Phe | Ser | Asn | Met | Val | Gly | Gln | Glu | Glu | Gly |      |
|     |     |     | 355 |     |     |     |     | 360 |     |     |     |     | 365 |     |     |      |

| act | gat | ggc | agc | ttg | agg | atc | tac | aac | acc | ttc | gac | agc | ttc | agc | tac | 1152 |
|-----|-----|-----|-----|-----|-----|-----|-----|-----|-----|-----|-----|-----|-----|-----|-----|------|
| Thr | Asp | Gly | Ser | Leu | Arg | Ile | Tyr | Asn | Thr | Phe | Asp | Ser | Phe | Ser | Tyr |      |
| 370 |     |     |     |     | 375 |     |     |     |     | 380 |     |     |     |     |     |      |

| cag | cat | tct | ccc | atc | ccc | aac | aac | aat | gtc | aac | ctc | atc | agc | tac | tac | 1200 |
|-----|-----|-----|-----|-----|-----|-----|-----|-----|-----|-----|-----|-----|-----|-----|-----|------|
| Gln | His | Ser | Pro | Ile | Pro | Asn | Asn | Asn | Val | Asn | Leu | Ile | Ser | Tyr | Tyr |      |
| 385 |     |     |     |     | 390 |     |     |     |     | 395 |     |     |     |     | 400 |      |

| aat | gat | gag | ctg | caa | aat | ttg | gag | cta | gga | gtc | tac | acg | ccg | cca | aag | 1248 |
|-----|-----|-----|-----|-----|-----|-----|-----|-----|-----|-----|-----|-----|-----|-----|-----|------|
| Asn | Asp | Glu | Leu | Gln | Asn | Leu | Glu | Leu | Gly | Val | Tyr | Thr | Pro | Pro | Lys |      |
|     |     |     |     | 405 |     |     |     |     | 410 |     |     |     |     | 415 |     |      |

| aaa | gga | agt | gga | tat | tct | tat | cct | tat | ggc | ttc | gtg | ctc | aac | tac | gcc | 1296 |
|-----|-----|-----|-----|-----|-----|-----|-----|-----|-----|-----|-----|-----|-----|-----|-----|------|
| Lys | Gly | Ser | Gly | Tyr | Ser | Tyr | Pro | Tyr | Gly | Phe | Val | Leu | Asn | Tyr | Ala |      |
|     |     |     | 420 |     |     |     |     | 425 |     |     |     |     | 430 |     |     |      |

| aac | agc | aag | tac | aag | tat | gga | gat | tca | aat | gat | cca | gaa | agc | ctc | ggc | 1344 |
|-----|-----|-----|-----|-----|-----|-----|-----|-----|-----|-----|-----|-----|-----|-----|-----|------|
| Asn | Ser | Lys | Tyr | Lys | Tyr | Gly | Asp | Ser | Asn | Asp | Pro | Glu | Ser | Leu | Gly |      |
|     |     | 435 |     |     |     |     | 440 |     |     |     |     | 445 |     |     |     |      |

| ggc | ctc | tcc | acc | ttg | tcg | gcg | ccc | atc | cag | cag | gtg | aac | gcc | gcc | acc | 1392 |
|-----|-----|-----|-----|-----|-----|-----|-----|-----|-----|-----|-----|-----|-----|-----|-----|------|
| Gly | Leu | Ser | Thr | Leu | Ser | Ala | Pro | Ile | Gln | Gln | Val | Asn | Ala | Ala | Thr |      |
|     | 450 |     |     |     |     | 455 |     |     |     |     | 460 |     |     |     |     |      |

| cag | aac | agc | aag | tac | ctt | gat | gga | gag | atc | ctc | aat | ggc | att | gga | gct | 1440 |
|-----|-----|-----|-----|-----|-----|-----|-----|-----|-----|-----|-----|-----|-----|-----|-----|------|
| Gln | Asn | Ser | Lys | Tyr | Leu | Asp | Gly | Glu | Ile | Leu | Asn | Gly | Ile | Gly | Ala |      |
| 465 |     |     |     |     | 470 |     |     |     |     | 475 |     |     |     |     | 480 |      |

| tct | ctt | cct | ggc | tac | tgc | acc | acc | ggc | tgc | tcg | ccg | acg | gag | ccg | ccc | 1488 |
|-----|-----|-----|-----|-----|-----|-----|-----|-----|-----|-----|-----|-----|-----|-----|-----|------|
| Ser | Leu | Pro | Gly | Tyr | Cys | Thr | Thr | Gly | Cys | Ser | Pro | Thr | Glu | Pro | Pro |      |
|     |     |     |     | 485 |     |     |     |     | 490 |     |     |     |     | 495 |     |      |

| ttc | agc | tgc | acc | tca | aca | gca | aat | ggc | tac | aag | gca | agc | tgc | aac | ccc | 1536 |
|-----|-----|-----|-----|-----|-----|-----|-----|-----|-----|-----|-----|-----|-----|-----|-----|------|
| Phe | Ser | Cys | Thr | Ser | Thr | Ala | Asn | Gly | Tyr | Lys | Ala | Ser | Cys | Asn | Pro |      |
|     |     |     | 500 |     |     |     |     | 505 |     |     |     |     | 510 |     |     |      |

| tcc | gac | acc | aac | cag | aag | atc | aac | gcg | ctc | tac | ccc | ttc | acc | caa | gct | 1584 |
|-----|-----|-----|-----|-----|-----|-----|-----|-----|-----|-----|-----|-----|-----|-----|-----|------|
| Ser | Asp | Thr | Asn | Gln | Lys | Ile | Asn | Ala | Leu | Tyr | Pro | Phe | Thr | Gln | Ala |      |
|     |     |     | 515 |     |     |     |     | 520 |     |     |     |     | 525 |     |     |      |

| aat | gtg | aag | ggc | aac | acc | ggc | aag | ctc | ggc | gtg | ctg | gcc | agc | ttg | gtg | 1632 |
|-----|-----|-----|-----|-----|-----|-----|-----|-----|-----|-----|-----|-----|-----|-----|-----|------|
| Asn | Val | Lys | Gly | Asn | Thr | Gly | Lys | Leu | Gly | Val | Leu | Ala | Ser | Leu | Val |      |
|     |     | 530 |     |     |     |     | 535 |     |     |     |     | 540 |     |     |     |      |

| agc | tac | gac | ctc | aac | ccc | aag | aat | gtt | ttt | gga | gag | ctg | gac | agc | gac | 1680 |
|-----|-----|-----|-----|-----|-----|-----|-----|-----|-----|-----|-----|-----|-----|-----|-----|------|
| Ser | Tyr | Asp | Leu | Asn | Pro | Lys | Asn | Val | Phe | Gly | Glu | Leu | Asp | Ser | Asp |      |
| 545 |     |     |     |     | 550 |     |     |     |     | 555 |     |     |     |     | 560 |      |

| acc | aac | aat | gtc | atc | cta | aag | ggc | atc | ccg | gcg | gag | aag | ggc | tac | ttc | 1728 |
|-----|-----|-----|-----|-----|-----|-----|-----|-----|-----|-----|-----|-----|-----|-----|-----|------|
| Thr | Asn | Asn | Val | Ile | Leu | Lys | Gly | Ile | Pro | Ala | Glu | Lys | Gly | Tyr | Phe |      |
|     |     |     |     | 565 |     |     |     |     | 570 |     |     |     |     | 575 |     |      |

| ccc | aac | aat | gca | agg | ccg | acg | gtg | gtg | aag | gag | tgg | atc | aat | gga | gct | 1776 |
|-----|-----|-----|-----|-----|-----|-----|-----|-----|-----|-----|-----|-----|-----|-----|-----|------|
| Pro | Asn | Asn | Ala | Arg | Pro | Thr | Val | Val | Lys | Glu | Trp | Ile | Asn | Gly | Ala |      |
|     |     |     | 580 |     |     |     |     | 585 |     |     |     |     | 590 |     |     |      |

| tcg | gcg | gtg | cct | ctt | gat | tca | ggc | aac | acc | ttg | ttc | atg | aca | gca | aca | 1824 |
|-----|-----|-----|-----|-----|-----|-----|-----|-----|-----|-----|-----|-----|-----|-----|-----|------|
| Ser | Ala | Val | Pro | Leu | Asp | Ser | Gly | Asn | Thr | Leu | Phe | Met | Thr | Ala | Thr |      |
|     |     | 595 |     |     |     |     | 600 |     |     |     |     | 605 |     |     |     |      |

| aat | ttg | acg | gcg | acg | cag | tac | agg | atc | agg | atc | aga | tat | gcc | aac | ccc | 1872 |
|-----|-----|-----|-----|-----|-----|-----|-----|-----|-----|-----|-----|-----|-----|-----|-----|------|
| Asn | Leu | Thr | Ala | Thr | Gln | Tyr | Arg | Ile | Arg | Ile | Arg | Tyr | Ala | Asn | Pro |      |
| 610 |     |     |     |     | 615 |     |     |     |     | 620 |     |     |     |     |     |      |

| aac | agc | aac | acc | cag | atc | ggc | gtg | agg | atc | acc | caa | aat | gga | agc | ctc | 1920 |

```
Asn Ser Asn Thr Gln Ile Gly Val Arg Ile Thr Gln Asn Gly Ser Leu
625                 630                 635                 640 atc agc agc agc aac ctc acc ctc tac tca aca act gac atg aac aac      1968
Ile Ser Ser Ser Asn Leu Thr Leu Tyr Ser Thr Thr Asp Met Asn Asn
                    645                 650                 655 acc ttg ccg ctc aat gtt tat gtg att gga gaa aat ggc aac tac acc      2016
Thr Leu Pro Leu Asn Val Tyr Val Ile Gly Glu Asn Gly Asn Tyr Thr
                660                 665                 670 ttg caa gat ctc tac aac acc acc aac gtg ctg agc acc ggc gac atc      2064
Leu Gln Asp Leu Tyr Asn Thr Thr Asn Val Leu Ser Thr Gly Asp Ile
            675                 680                 685 acc cta cag atc act gga gga gat cag aag atc ttc atc gac agg att      2112
Thr Leu Gln Ile Thr Gly Gly Asp Gln Lys Ile Phe Ile Asp Arg Ile
        690                 695                 700 gaa ttt gtt cca aca atg cca gtt cct ggc aac acc aac aac aac aat      2160
Glu Phe Val Pro Thr Met Pro Val Pro Gly Asn Thr Asn Asn Asn Asn
705                 710                 715                 720 ggc aac aac aat ggc aac aac aac ccg ccg cac cat gtt tgt gcc ata      2208
Gly Asn Asn Asn Gly Asn Asn Asn Pro Pro His His Val Cys Ala Ile
                    725                 730                 735 gct gga act caa caa agc tgc tct ggg ccg cca aaa ttt gag caa gtt      2256
Ala Gly Thr Gln Gln Ser Cys Ser Gly Pro Pro Lys Phe Glu Gln Val
                740                 745                 750 tca gat ctg gag aag atc acc acc caa gtc tac atg ctc ttc aag agc      2304
Ser Asp Leu Glu Lys Ile Thr Thr Gln Val Tyr Met Leu Phe Lys Ser
            755                 760                 765 taa                                                                  2307
*

<210> SEQ ID NO 31
<211> LENGTH: 768
<212> TYPE: PRT
<213> ORGANISM: Artificial Sequence
<220> FEATURE:
<223> OTHER INFORMATION: APOSYN2AXMI-031(A-D)

<400> SEQUENCE: 31

Met Gly Tyr Ser Ser Phe Val Ala Ile Ala Leu Leu Met Ser Val Val
1               5                   10                  15

Val Val Cys Asn Gly Gly Lys Thr Ser Thr Tyr Val Arg Asn Leu Asp
                20                  25                  30

Cys Asn Leu Gln Ser Gln Gln Asn Ile Pro Tyr Asn Val Leu Ala Ile
            35                  40                  45

Pro Val Ser Asn Val Asn Ser Leu Thr Asp Thr Val Gly Asp Leu Lys
        50                  55                  60

Lys Ala Trp Glu Glu Phe Gln Lys Thr Gly Ser Phe Ser Leu Thr Ala
65                  70                  75                  80

Leu Gln Gln Gly Phe Ser Ala Ser Gln Gly Gly Thr Phe Asn Tyr Leu
                85                  90                  95

Thr Leu Leu Gln Ser Gly Ile Ser Leu Ala Gly Ser Phe Val Pro Gly
                100                 105                 110

Gly Thr Phe Val Ala Pro Ile Ile Asn Met Val Ile Gly Trp Leu Trp
            115                 120                 125

Pro His Lys Asn Lys Asn Ala Asp Thr Glu Asn Leu Ile Asn Leu Ile
        130                 135                 140

Asp Ser Glu Ile Gln Lys Gln Leu Asn Lys Ala Leu Leu Asp Ala Asp
145                 150                 155                 160

Arg Asn Glu Trp Ser Ser Tyr Leu Glu Ser Ile Phe Asp Ser Ser Asn
                165                 170                 175
```

```
Asn Leu Asn Gly Ala Ile Val Asp Ala Gln Trp Ser Gly Thr Val Asn
            180                 185                 190
Thr Thr Asn Arg Thr Leu Arg Asn Pro Thr Glu Ser Asp Tyr Thr Asn
            195                 200                 205
Val Val Thr Asn Phe Ile Ala Ala Asp Gly Asp Ile Ala Asn Asn Glu
210                 215                 220
Asn His Ile Met Asn Gly Asn Phe Asp Val Ala Ala Ala Pro Tyr Phe
225                 230                 235                 240
Val Ile Gly Ala Thr Ala Arg Phe Ala Ala Met Gln Ser Tyr Ile Lys
            245                 250                 255
Phe Cys Asn Ala Trp Ile Asp Lys Val Gly Leu Ser Asp Ala Gln Leu
            260                 265                 270
Thr Thr Gln Lys Ala Asn Leu Asp Arg Thr Lys Gln Asn Met Arg Asn
            275                 280                 285
Ala Ile Leu Asn Tyr Thr Gln Gln Val Met Lys Val Phe Lys Asp Ser
290                 295                 300
Lys Asn Met Pro Thr Ile Gly Thr Asn Lys Phe Ser Val Asp Thr Tyr
305                 310                 315                 320
Asn Val Tyr Ile Lys Gly Met Thr Leu Asn Val Leu Asp Ile Val Ala
            325                 330                 335
Ile Trp Pro Ser Leu Tyr Pro Asp Asp Tyr Thr Ser Gln Thr Ala Leu
            340                 345                 350
Glu Gln Thr Arg Val Thr Phe Ser Asn Met Val Gly Gln Glu Glu Gly
            355                 360                 365
Thr Asp Gly Ser Leu Arg Ile Tyr Asn Thr Phe Asp Ser Phe Ser Tyr
370                 375                 380
Gln His Ser Pro Ile Pro Asn Asn Asn Val Asn Leu Ile Ser Tyr Tyr
385                 390                 395                 400
Asn Asp Glu Leu Gln Asn Leu Glu Leu Gly Val Tyr Thr Pro Pro Lys
            405                 410                 415
Lys Gly Ser Gly Tyr Ser Tyr Pro Tyr Gly Phe Val Leu Asn Tyr Ala
            420                 425                 430
Asn Ser Lys Tyr Lys Tyr Gly Asp Ser Asn Asp Pro Glu Ser Leu Gly
            435                 440                 445
Gly Leu Ser Thr Leu Ser Ala Pro Ile Gln Gln Val Asn Ala Ala Thr
450                 455                 460
Gln Asn Ser Lys Tyr Leu Asp Gly Glu Ile Leu Asn Gly Ile Gly Ala
465                 470                 475                 480
Ser Leu Pro Gly Tyr Cys Thr Thr Gly Cys Ser Pro Thr Glu Pro Pro
            485                 490                 495
Phe Ser Cys Thr Ser Thr Ala Asn Gly Tyr Lys Ala Ser Cys Asn Pro
            500                 505                 510
Ser Asp Thr Asn Gln Lys Ile Asn Ala Leu Tyr Pro Phe Thr Gln Ala
            515                 520                 525
Asn Val Lys Gly Asn Thr Gly Lys Leu Gly Val Leu Ala Ser Leu Val
530                 535                 540
Ser Tyr Asp Leu Asn Pro Lys Asn Val Phe Gly Glu Leu Asp Ser Asp
545                 550                 555                 560
Thr Asn Asn Val Ile Leu Lys Gly Ile Pro Ala Glu Lys Gly Tyr Phe
            565                 570                 575
Pro Asn Asn Ala Arg Pro Thr Val Val Lys Glu Trp Ile Asn Gly Ala
            580                 585                 590
Ser Ala Val Pro Leu Asp Ser Gly Asn Thr Leu Phe Met Thr Ala Thr
```

```
                595                 600                 605
Asn Leu Thr Ala Thr Gln Tyr Arg Ile Arg Ile Arg Tyr Ala Asn Pro
    610                 615                 620

Asn Ser Asn Thr Gln Ile Gly Val Arg Ile Thr Gln Asn Gly Ser Leu
625                 630                 635                 640

Ile Ser Ser Ser Asn Leu Thr Leu Tyr Ser Thr Thr Asp Met Asn Asn
                    645                 650                 655

Thr Leu Pro Leu Asn Val Tyr Val Ile Gly Glu Asn Gly Asn Tyr Thr
                660                 665                 670

Leu Gln Asp Leu Tyr Asn Thr Thr Asn Val Leu Ser Thr Gly Asp Ile
            675                 680                 685

Thr Leu Gln Ile Thr Gly Gly Asp Gln Lys Ile Phe Ile Asp Arg Ile
        690                 695                 700

Glu Phe Val Pro Thr Met Pro Val Pro Gly Asn Thr Asn Asn Asn Asn
705                 710                 715                 720

Gly Asn Asn Asn Gly Asn Asn Asn Pro Pro His His Val Cys Ala Ile
                    725                 730                 735

Ala Gly Thr Gln Gln Ser Cys Ser Gly Pro Pro Lys Phe Glu Gln Val
                740                 745                 750

Ser Asp Leu Glu Lys Ile Thr Thr Gln Val Tyr Met Leu Phe Lys Ser
            755                 760                 765

<210> SEQ ID NO 32
<211> LENGTH: 3570
<212> TYPE: DNA
<213> ORGANISM: Artificial Sequence
<220> FEATURE:
<223> OTHER INFORMATION: synaxmi-031(fl)-ER
<220> FEATURE:
<221> NAME/KEY: CDS
<222> LOCATION: (1)...(3570)

<400> SEQUENCE: 32 atg gat tgc aat ctc cag agc cag cag aat atc cca tac aat gtg ctt      48
Met Asp Cys Asn Leu Gln Ser Gln Gln Asn Ile Pro Tyr Asn Val Leu
 1               5                  10                  15 gct atc cct gtt agc aat gtt aat agc ctt acg gat acg gtt ggc gat      96
Ala Ile Pro Val Ser Asn Val Asn Ser Leu Thr Asp Thr Val Gly Asp
            20                  25                  30 cta aag aag gca tgg gaa gag ttc cag aag acg ggc agc ttc tcc ctt     144
Leu Lys Lys Ala Trp Glu Glu Phe Gln Lys Thr Gly Ser Phe Ser Leu
        35                  40                  45 acc gca ctc cag cag ggc ttc agc gct tcc cag ggc ggg acg ttc aat     192
Thr Ala Leu Gln Gln Gly Phe Ser Ala Ser Gln Gly Gly Thr Phe Asn
    50                  55                  60 tac ctc acc ctc ctc cag tcc ggg atc tcc ctg gct ggc agc ttc gtg     240
Tyr Leu Thr Leu Leu Gln Ser Gly Ile Ser Leu Ala Gly Ser Phe Val
65                  70                  75                  80 cct ggc ggc acc ttc gtt gct cca atc atc aat atg gtg atc ggc tgg     288
Pro Gly Gly Thr Phe Val Ala Pro Ile Ile Asn Met Val Ile Gly Trp
                85                  90                  95 ctc tgg cct cat aag aat aag aat gca gat acg gaa aat ctg atc aat     336
Leu Trp Pro His Lys Asn Lys Asn Ala Asp Thr Glu Asn Leu Ile Asn
            100                 105                 110 ctg atc gat tca gaa atc cag aag cag ctg aat aag gct ctg ctg gat     384
Leu Ile Asp Ser Glu Ile Gln Lys Gln Leu Asn Lys Ala Leu Leu Asp
        115                 120                 125 gct gat cgc aat gaa tgg agc agc tac ctc gag tcc atc ttc gat agc     432
Ala Asp Arg Asn Glu Trp Ser Ser Tyr Leu Glu Ser Ile Phe Asp Ser
    130                 135                 140
```

| | | | | | | | | | | | | | | | | |
|---|---|---|---|---|---|---|---|---|---|---|---|---|---|---|---|---|
| agc | aat | aat | ctg | aat | ggc | gca | atc | gtt | gat | gct | cag | tgg | tcc | ggc | acc | 480 |
| Ser | Asn | Asn | Leu | Asn | Gly | Ala | Ile | Val | Asp | Ala | Gln | Trp | Ser | Gly | Thr | |
| 145 | | | | 150 | | | | | 155 | | | | | 160 | | |
| gtg | aat | acg | acc | aat | cgt | acg | ctt | cgt | aat | cct | acg | gaa | tca | gat | tac | 528 |
| Val | Asn | Thr | Thr | Asn | Arg | Thr | Leu | Arg | Asn | Pro | Thr | Glu | Ser | Asp | Tyr | |
| | | | | 165 | | | | | 170 | | | | | 175 | | |
| acc | aat | gtg | gtg | acg | aat | ttc | atc | gca | gca | gat | ggg | gat | atc | gct | aat | 576 |
| Thr | Asn | Val | Val | Thr | Asn | Phe | Ile | Ala | Ala | Asp | Gly | Asp | Ile | Ala | Asn | |
| | | | 180 | | | | | 185 | | | | | 190 | | | |
| aat | gaa | aat | cat | atc | atg | aat | ggg | aat | ttc | gat | gtg | gca | gca | gct | cca | 624 |
| Asn | Glu | Asn | His | Ile | Met | Asn | Gly | Asn | Phe | Asp | Val | Ala | Ala | Ala | Pro | |
| | | | | 195 | | | | | 200 | | | | | 205 | | |
| tac | ttc | gtt | atc | ggg | gct | acc | gct | aga | ttc | gca | gct | atg | cag | tcc | tac | 672 |
| Tyr | Phe | Val | Ile | Gly | Ala | Thr | Ala | Arg | Phe | Ala | Ala | Met | Gln | Ser | Tyr | |
| | | 210 | | | | | 215 | | | | | 220 | | | | |
| atc | aag | ttc | tgc | aat | gca | tgg | atc | gat | aag | gtt | ggg | ctg | tca | gat | gct | 720 |
| Ile | Lys | Phe | Cys | Asn | Ala | Trp | Ile | Asp | Lys | Val | Gly | Leu | Ser | Asp | Ala | |
| 225 | | | | 230 | | | | | 235 | | | | | 240 | | |
| cag | ctg | acc | acg | cag | aag | gct | aat | ctg | gat | aga | acg | aag | cag | aat | atg | 768 |
| Gln | Leu | Thr | Thr | Gln | Lys | Ala | Asn | Leu | Asp | Arg | Thr | Lys | Gln | Asn | Met | |
| | | | | 245 | | | | | 250 | | | | | 255 | | |
| cgt | aat | gct | atc | ctt | aat | tac | acc | cag | cag | gtt | atg | aag | gtt | ttc | aag | 816 |
| Arg | Asn | Ala | Ile | Leu | Asn | Tyr | Thr | Gln | Gln | Val | Met | Lys | Val | Phe | Lys | |
| | | | 260 | | | | | 265 | | | | | 270 | | | |
| gat | tcc | aag | aat | atg | cca | acg | atc | ggc | acg | aat | aag | ttc | agc | gtt | gat | 864 |
| Asp | Ser | Lys | Asn | Met | Pro | Thr | Ile | Gly | Thr | Asn | Lys | Phe | Ser | Val | Asp | |
| | | 275 | | | | | 280 | | | | | 285 | | | | |
| acc | tac | aat | gtt | tac | atc | aag | ggg | atg | acg | ctt | aat | gtg | ctt | gat | atc | 912 |
| Thr | Tyr | Asn | Val | Tyr | Ile | Lys | Gly | Met | Thr | Leu | Asn | Val | Leu | Asp | Ile | |
| | 290 | | | | | 295 | | | | | 300 | | | | | |
| gtt | gct | atc | tgg | cca | agc | ctg | tac | cca | gat | gat | tac | acg | tca | cag | acg | 960 |
| Val | Ala | Ile | Trp | Pro | Ser | Leu | Tyr | Pro | Asp | Asp | Tyr | Thr | Ser | Gln | Thr | |
| 305 | | | | 310 | | | | | 315 | | | | | 320 | | |
| gct | ctg | gaa | cag | acc | cgc | gtg | acg | ttc | tcc | aat | atg | gtg | ggg | cag | gaa | 1008 |
| Ala | Leu | Glu | Gln | Thr | Arg | Val | Thr | Phe | Ser | Asn | Met | Val | Gly | Gln | Glu | |
| | | | | 325 | | | | | 330 | | | | | 335 | | |
| gaa | ggc | acg | gat | ggc | agc | ctc | aga | atc | tac | aat | acc | ttc | gat | agc | ttc | 1056 |
| Glu | Gly | Thr | Asp | Gly | Ser | Leu | Arg | Ile | Tyr | Asn | Thr | Phe | Asp | Ser | Phe | |
| | | | 340 | | | | | 345 | | | | | 350 | | | |
| tcc | tac | cag | cat | agc | cct | atc | cct | aat | aat | aat | gtg | aat | ctc | atc | agc | 1104 |
| Ser | Tyr | Gln | His | Ser | Pro | Ile | Pro | Asn | Asn | Asn | Val | Asn | Leu | Ile | Ser | |
| | | | | 355 | | | | | 360 | | | | | 365 | | |
| tac | tac | aat | gat | gaa | ctt | cag | aat | ctg | gaa | ctc | ggg | gtt | tac | acc | cca | 1152 |
| Tyr | Tyr | Asn | Asp | Glu | Leu | Gln | Asn | Leu | Glu | Leu | Gly | Val | Tyr | Thr | Pro | |
| | 370 | | | | | 375 | | | | | 380 | | | | | |
| cca | aag | aag | ggc | tca | ggc | tac | agc | tac | cca | tac | ggg | ttc | gtg | ctg | aat | 1200 |
| Pro | Lys | Lys | Gly | Ser | Gly | Tyr | Ser | Tyr | Pro | Tyr | Gly | Phe | Val | Leu | Asn | |
| 385 | | | | 390 | | | | | 395 | | | | | 400 | | |
| tac | gca | aat | agc | aag | tac | aag | tac | ggc | gat | tcc | aat | gat | cca | gaa | tcc | 1248 |
| Tyr | Ala | Asn | Ser | Lys | Tyr | Lys | Tyr | Gly | Asp | Ser | Asn | Asp | Pro | Glu | Ser | |
| | | | | 405 | | | | | 410 | | | | | 415 | | |
| ctc | ggc | ggg | ctt | tcc | acc | ctt | agc | gct | cca | atc | caa | cag | gtt | aat | gct | 1296 |
| Leu | Gly | Gly | Leu | Ser | Thr | Leu | Ser | Ala | Pro | Ile | Gln | Gln | Val | Asn | Ala | |
| | | | 420 | | | | | 425 | | | | | 430 | | | |
| gct | acc | cag | aat | agc | aag | tac | ctt | gat | ggc | gaa | atc | ctg | aat | ggg | atc | 1344 |
| Ala | Thr | Gln | Asn | Ser | Lys | Tyr | Leu | Asp | Gly | Glu | Ile | Leu | Asn | Gly | Ile | |
| | | | | 435 | | | | | 440 | | | | | 445 | | |
| ggc | gca | agc | ctg | cct | ggc | tac | tgc | acg | acc | ggg | tgc | tca | cct | acc | gaa | 1392 |
| Gly | Ala | Ser | Leu | Pro | Gly | Tyr | Cys | Thr | Thr | Gly | Cys | Ser | Pro | Thr | Glu | |
| | 450 | | | | | 455 | | | | | 460 | | | | | |

-continued

| | | | | | | | | | | | | | | | |
|---|---|---|---|---|---|---|---|---|---|---|---|---|---|---|---|
| cca | cca | ttc | agc | tgc | acg | agc | acg | gca | aat | ggg | tac | aag | gca | agc | tgc | 1440 |
| Pro | Pro | Phe | Ser | Cys | Thr | Ser | Thr | Ala | Asn | Gly | Tyr | Lys | Ala | Ser | Cys |
| 465 | | | | 470 | | | | | 475 | | | | | 480 | |

Pro Pro Phe Ser Cys Thr Ser Thr Ala Asn Gly Tyr Lys Ala Ser Cys 1440
465 470 475 480 aat cca agc gat acc aat cag aag atc aat gct ctc tac cca ttc acg 1488
Asn Pro Ser Asp Thr Asn Gln Lys Ile Asn Ala Leu Tyr Pro Phe Thr
485 490 495 cag gca aat gtg aag ggg aat acc ggg aag ctg ggc gtt ctc gca agc 1536
Gln Ala Asn Val Lys Gly Asn Thr Gly Lys Leu Gly Val Leu Ala Ser
500 505 510 ctt gtt agc tac gat ctg aat cct aag aat gtt ttc ggg gaa ctc gat 1584
Leu Val Ser Tyr Asp Leu Asn Pro Lys Asn Val Phe Gly Glu Leu Asp
515 520 525 tca gat acc aat aat gtt atc ctt aag ggc atc cca gca gaa aag ggc 1632
Ser Asp Thr Asn Asn Val Ile Leu Lys Gly Ile Pro Ala Glu Lys Gly
530 535 540 tac ttc cca aat aat gca aga cca acc gtt gtg aag gaa tgg atc aat 1680
Tyr Phe Pro Asn Asn Ala Arg Pro Thr Val Val Lys Glu Trp Ile Asn
545 550 555 560 ggg gct tcc gca gtt cca ctt gat tcc ggc aat acc ctg ttc atg acg 1728
Gly Ala Ser Ala Val Pro Leu Asp Ser Gly Asn Thr Leu Phe Met Thr
565 570 575 gct acg aac ctg acg gct acc cag tac aga atc cgc atc cgt tac gct 1776
Ala Thr Asn Leu Thr Ala Thr Gln Tyr Arg Ile Arg Ile Arg Tyr Ala
580 585 590 aac cca aac tca aac acg cag atc ggc gtt aga atc acg cag aac ggg 1824
Asn Pro Asn Ser Asn Thr Gln Ile Gly Val Arg Ile Thr Gln Asn Gly
595 600 605 agc ctc atc tcc tcc tcc aac ctc acg ctg tac tca acc acc gat atg 1872
Ser Leu Ile Ser Ser Ser Asn Leu Thr Leu Tyr Ser Thr Thr Asp Met
610 615 620 aac aac acc ctg cca ctg aac gtt tac gtg atc ggg gaa aac ggg aac 1920
Asn Asn Thr Leu Pro Leu Asn Val Tyr Val Ile Gly Glu Asn Gly Asn
625 630 635 640 tac acc ctc cag gat ctc tac aac acg acg aac gtt ctg tcc acg ggc 1968
Tyr Thr Leu Gln Asp Leu Tyr Asn Thr Thr Asn Val Leu Ser Thr Gly
645 650 655 gat atc acc ctg cag atc acc ggc ggg gat cag aag ata ttc atc gat 2016
Asp Ile Thr Leu Gln Ile Thr Gly Gly Asp Gln Lys Ile Phe Ile Asp
660 665 670 cgc atc gag ttc gtg cct acg atg cca gtg cca ggc aac acc aac aac 2064
Arg Ile Glu Phe Val Pro Thr Met Pro Val Pro Gly Asn Thr Asn Asn
675 680 685 aac aac ggg aac aac aac ggc aac aac aac cct cct cat cat gtt tgc 2112
Asn Asn Gly Asn Asn Asn Gly Asn Asn Asn Pro Pro His His Val Cys
690 695 700 gct atc gca ggc acc cag cag tcc tgc tcc ggc cca cca aag ttc gag 2160
Ala Ile Ala Gly Thr Gln Gln Ser Cys Ser Gly Pro Pro Lys Phe Glu
705 710 715 720 cag gtg tcc gat tta gaa aag ata acc acg cag gtt tac atg ctc ttc 2208
Gln Val Ser Asp Leu Glu Lys Ile Thr Thr Gln Val Tyr Met Leu Phe
725 730 735 aag tcc tcc cca tac gaa gaa ctt gct ctt gaa gtt agc agc tac cag 2256
Lys Ser Ser Pro Tyr Glu Glu Leu Ala Leu Glu Val Ser Ser Tyr Gln
740 745 750 atc agc cag gtt gca ctg aag gtt atg gct ctc agc gat gaa cta ttc 2304
Ile Ser Gln Val Ala Leu Lys Val Met Ala Leu Ser Asp Glu Leu Phe
755 760 765 tgc gaa gaa aag aac gtg ctg aga aag ctc gtg aac aag gca aag cag 2352
Cys Glu Glu Lys Asn Val Leu Arg Lys Leu Val Asn Lys Ala Lys Gln
770 775 780

| | | |
|---|---|---|
| ctt ctc gaa gca agc aac ctt ctc gtt ggg ggg aac ttc gag acg act<br>Leu Leu Glu Ala Ser Asn Leu Leu Val Gly Gly Asn Phe Glu Thr Thr<br>785                  790                    795                  800 | | 2400 |
| cag aac tgg gtg ctc ggc acg aac gct tac atc aac tat gat tca ttc<br>Gln Asn Trp Val Leu Gly Thr Asn Ala Tyr Ile Asn Tyr Asp Ser Phe<br>                  805                    810                   815 | | 2448 |
| ctg ttc aac ggg aac tac ctg agc ctc cag cca gca tcc ggc ttc ttc<br>Leu Phe Asn Gly Asn Tyr Leu Ser Leu Gln Pro Ala Ser Gly Phe Phe<br>820                         825                     830 | | 2496 |
| acg agc tac gct tac cag aag atc gat gaa tcc acg ctt aag cct tac<br>Thr Ser Tyr Ala Tyr Gln Lys Ile Asp Glu Ser Thr Leu Lys Pro Tyr<br>                  835                    840                  845 | | 2544 |
| acg cgc tac aag gtg tcc ggg ttc atc ggg cag tca aac cag gtt gaa<br>Thr Arg Tyr Lys Val Ser Gly Phe Ile Gly Gln Ser Asn Gln Val Glu<br>850                       855                     860 | | 2592 |
| ctg atc atc agc cgc tac ggg aag gaa atc gat aag atc ctt aac gtg<br>Leu Ile Ile Ser Arg Tyr Gly Lys Glu Ile Asp Lys Ile Leu Asn Val<br>865                  870                   875                  880 | | 2640 |
| cca tac gca ggg cca ctc cca atc acc gca gat gca agc atc acc tgc<br>Pro Tyr Ala Gly Pro Leu Pro Ile Thr Ala Asp Ala Ser Ile Thr Cys<br>                  885                    890                  895 | | 2688 |
| tgc gct cca gaa ata ggg cag tgc gat ggg gaa cag tca gat tcc cat<br>Cys Ala Pro Glu Ile Gly Gln Cys Asp Gly Glu Gln Ser Asp Ser His<br>900                       905                     910 | | 2736 |
| ttc ttc aac tac agc atc gat gtt ggc gca ctc cat cca gaa ctt aac<br>Phe Phe Asn Tyr Ser Ile Asp Val Gly Ala Leu His Pro Glu Leu Asn<br>915                       920                    925 | | 2784 |
| cca ggg atc gaa atc ggg ctg aag atc gtt cag agc aac ggc tac atc<br>Pro Gly Ile Glu Ile Gly Leu Lys Ile Val Gln Ser Asn Gly Tyr Ile<br>                  930                    935                  940 | | 2832 |
| acc atc tcc aac ctt gaa atc atc gaa gaa aga cca tta acg gaa atg<br>Thr Ile Ser Asn Leu Glu Ile Ile Glu Glu Arg Pro Leu Thr Glu Met<br>945                      950                   955                  960 | | 2880 |
| gaa att caa gca gtg aac cgc aag aac cag aag tgg gaa cgc gaa aag<br>Glu Ile Gln Ala Val Asn Arg Lys Asn Gln Lys Trp Glu Arg Glu Lys<br>                  965                    970                  975 | | 2928 |
| ctg ctt gaa tgc gca tcc atc tcc gaa ctc ctc cag cct atc atc aac<br>Leu Leu Glu Cys Ala Ser Ile Ser Glu Leu Leu Gln Pro Ile Ile Asn<br>                  980                    985                  990 | | 2976 |
| cag ata gat agc ctc ttc aag gat ggc aac tgg tac aac gat atc cta<br>Gln Ile Asp Ser Leu Phe Lys Asp Gly Asn Trp Tyr Asn Asp Ile Leu<br>                  995                  1000               1005 | | 3024 |
| cca cat gtt acc tac cag gat ctt aag aac atc atc atc cca gaa ctt<br>Pro His Val Thr Tyr Gln Asp Leu Lys Asn Ile Ile Ile Pro Glu Leu<br>    1010                     1015                   1020 | | 3072 |
| cct aag ctc aag cat tgg ttc atc gaa aac ctg cct ggg gaa tac cat<br>Pro Lys Leu Lys His Trp Phe Ile Glu Asn Leu Pro Gly Glu Tyr His<br>1025                  1030                   1035                  1040 | | 3120 |
| gaa atc gaa cag aag atg aag gaa gca tta aag tac gca ttc act cag<br>Glu Ile Glu Gln Lys Met Lys Glu Ala Leu Lys Tyr Ala Phe Thr Gln<br>                  1045                   1050                  1055 | | 3168 |
| ctc gat gaa aag aac ctg atc cat aac ggc cat ttc acc acc aac ctc<br>Leu Asp Glu Lys Asn Leu Ile His Asn Gly His Phe Thr Thr Asn Leu<br>                  1060                   1065                  1070 | | 3216 |
| atc gat tgg cag gtg gaa ggc gat gct cag atg aag gtg ctt gaa aac<br>Ile Asp Trp Gln Val Glu Gly Asp Ala Gln Met Lys Val Leu Glu Asn<br>                  1075                   1080                  1085 | | 3264 |
| gat gca ctc gct ctc cag cta ttc aac tgg gat gct tcc gca tcc cag<br>Asp Ala Leu Ala Leu Gln Leu Phe Asn Trp Asp Ala Ser Ala Ser Gln<br>                  1090                   1095                  1100 | | 3312 |

```
agc atc aac atc cta gag ttc gat gaa gat aag gct tac aag ctg cgt    3360
Ser Ile Asn Ile Leu Glu Phe Asp Glu Asp Lys Ala Tyr Lys Leu Arg
1105                1110                1115                1120 gtg tac gca cag ggc tcc ggg acg atc cag ttc ggc aac tgc gaa gat    3408
Val Tyr Ala Gln Gly Ser Gly Thr Ile Gln Phe Gly Asn Cys Glu Asp
            1125                1130                1135 gaa gct atc cag ttc aac acc aac tca ttc atc tac cag gaa aag ata    3456
Glu Ala Ile Gln Phe Asn Thr Asn Ser Phe Ile Tyr Gln Glu Lys Ile
        1140                1145                1150 gtg tac ttc gat acg cca tcc gtt aac ctt cat atc cag agc gaa ggc    3504
Val Tyr Phe Asp Thr Pro Ser Val Asn Leu His Ile Gln Ser Glu Gly
    1155                1160                1165 tcc gag ttc atc gtg agc agc atc gat ctc atc gaa ctc agc gat gat    3552
Ser Glu Phe Ile Val Ser Ser Ile Asp Leu Ile Glu Leu Ser Asp Asp
1170                1175                1180 cag aag gat gaa ctg taa                                            3570
Gln Lys Asp Glu Leu *
1185
```

<210> SEQ ID NO 33
<211> LENGTH: 1189
<212> TYPE: PRT
<213> ORGANISM: Artificial Sequence
<220> FEATURE:
<223> OTHER INFORMATION: SYNAXMI-031(FL)-ER

<400> SEQUENCE: 33

```
Met Asp Cys Asn Leu Gln Ser Gln Gln Asn Ile Pro Tyr Asn Val Leu
 1               5                  10                  15

Ala Ile Pro Val Ser Asn Val Asn Ser Leu Thr Asp Thr Val Gly Asp
                20                  25                  30

Leu Lys Lys Ala Trp Glu Glu Phe Gln Lys Thr Gly Ser Phe Ser Leu
            35                  40                  45

Thr Ala Leu Gln Gln Gly Phe Ser Ala Ser Gln Gly Gly Thr Phe Asn
        50                  55                  60

Tyr Leu Thr Leu Leu Gln Ser Gly Ile Ser Leu Ala Gly Ser Phe Val
65                  70                  75                  80

Pro Gly Gly Thr Phe Val Ala Pro Ile Ile Asn Met Val Ile Gly Trp
                85                  90                  95

Leu Trp Pro His Lys Asn Lys Asn Ala Asp Thr Glu Asn Leu Ile Asn
            100                 105                 110

Leu Ile Asp Ser Glu Ile Gln Lys Gln Leu Asn Lys Ala Leu Leu Asp
        115                 120                 125

Ala Asp Arg Asn Glu Trp Ser Ser Tyr Leu Glu Ser Ile Phe Asp Ser
    130                 135                 140

Ser Asn Asn Leu Asn Gly Ala Ile Val Asp Ala Gln Trp Ser Gly Thr
145                 150                 155                 160

Val Asn Thr Thr Asn Arg Thr Leu Arg Asn Pro Thr Glu Ser Asp Tyr
                165                 170                 175

Thr Asn Val Val Thr Asn Phe Ile Ala Ala Asp Gly Asp Ile Ala Asn
            180                 185                 190

Asn Glu Asn His Ile Met Asn Gly Asn Phe Asp Val Ala Ala Ala Pro
        195                 200                 205

Tyr Phe Val Ile Gly Ala Thr Ala Arg Phe Ala Ala Met Gln Ser Tyr
    210                 215                 220

Ile Lys Phe Cys Asn Ala Trp Ile Asp Lys Val Gly Leu Ser Asp Ala
225                 230                 235                 240
```

-continued

```
Gln Leu Thr Thr Gln Lys Ala Asn Leu Asp Arg Thr Lys Gln Asn Met
            245                 250                 255

Arg Asn Ala Ile Leu Asn Tyr Thr Gln Gln Val Met Lys Val Phe Lys
        260                 265                 270

Asp Ser Lys Asn Met Pro Thr Ile Gly Thr Asn Lys Phe Ser Val Asp
        275                 280                 285

Thr Tyr Asn Val Tyr Ile Lys Gly Met Thr Leu Asn Val Leu Asp Ile
        290                 295                 300

Val Ala Ile Trp Pro Ser Leu Tyr Pro Asp Tyr Thr Ser Gln Thr
305                 310                 315                 320

Ala Leu Glu Gln Thr Arg Val Thr Phe Ser Asn Met Val Gly Gln Glu
            325                 330                 335

Glu Gly Thr Asp Gly Ser Leu Arg Ile Tyr Asn Thr Phe Asp Ser Phe
            340                 345                 350

Ser Tyr Gln His Ser Pro Ile Pro Asn Asn Asn Val Asn Leu Ile Ser
            355                 360                 365

Tyr Tyr Asn Asp Glu Leu Gln Asn Leu Glu Leu Gly Val Tyr Thr Pro
        370                 375                 380

Pro Lys Lys Gly Ser Gly Tyr Ser Tyr Pro Tyr Gly Phe Val Leu Asn
385                 390                 395                 400

Tyr Ala Asn Ser Lys Tyr Lys Tyr Gly Asp Ser Asn Asp Pro Glu Ser
            405                 410                 415

Leu Gly Gly Leu Ser Thr Leu Ser Ala Pro Ile Gln Gln Val Asn Ala
            420                 425                 430

Ala Thr Gln Asn Ser Lys Tyr Leu Asp Gly Ile Leu Asn Gly Ile
            435                 440                 445

Gly Ala Ser Leu Pro Gly Tyr Cys Thr Thr Gly Cys Ser Pro Thr Glu
        450                 455                 460

Pro Pro Phe Ser Cys Thr Ser Thr Ala Asn Gly Tyr Lys Ala Ser Cys
465                 470                 475                 480

Asn Pro Ser Asp Thr Asn Gln Lys Ile Asn Ala Leu Tyr Pro Phe Thr
            485                 490                 495

Gln Ala Asn Val Lys Gly Asn Thr Gly Lys Leu Gly Val Leu Ala Ser
            500                 505                 510

Leu Val Ser Tyr Asp Leu Asn Pro Lys Asn Val Phe Gly Glu Leu Asp
        515                 520                 525

Ser Asp Thr Asn Asn Val Ile Leu Lys Gly Ile Pro Ala Glu Lys Gly
        530                 535                 540

Tyr Phe Pro Asn Asn Ala Arg Pro Thr Val Lys Glu Trp Ile Asn
545                 550                 555                 560

Gly Ala Ser Ala Val Pro Leu Asp Ser Gly Asn Thr Leu Phe Met Thr
            565                 570                 575

Ala Thr Asn Leu Thr Ala Thr Gln Tyr Arg Ile Arg Ile Arg Tyr Ala
        580                 585                 590

Asn Pro Asn Ser Asn Thr Gln Ile Gly Val Arg Ile Thr Gln Asn Gly
        595                 600                 605

Ser Leu Ile Ser Ser Ser Asn Leu Thr Leu Tyr Ser Thr Thr Asp Met
        610                 615                 620

Asn Asn Thr Leu Pro Leu Asn Val Tyr Val Ile Gly Glu Asn Gly Asn
625                 630                 635                 640

Tyr Thr Leu Gln Asp Leu Tyr Asn Thr Asn Val Leu Ser Thr Gly
            645                 650                 655

Asp Ile Thr Leu Gln Ile Thr Gly Gly Asp Gln Lys Ile Phe Ile Asp
        660                 665                 670
```

```
Arg Ile Glu Phe Val Pro Thr Met Pro Val Pro Gly Asn Thr Asn Asn
            675                 680                 685

Asn Asn Gly Asn Asn Asn Gly Asn Asn Asn Pro Pro His His Val Cys
        690                 695                 700

Ala Ile Ala Gly Thr Gln Gln Ser Cys Ser Gly Pro Pro Lys Phe Glu
705                 710                 715                 720

Gln Val Ser Asp Leu Glu Lys Ile Thr Thr Gln Val Tyr Met Leu Phe
                725                 730                 735

Lys Ser Ser Pro Tyr Glu Glu Leu Ala Leu Glu Val Ser Ser Tyr Gln
            740                 745                 750

Ile Ser Gln Val Ala Leu Lys Val Met Ala Leu Ser Asp Glu Leu Phe
        755                 760                 765

Cys Glu Glu Lys Asn Val Leu Arg Lys Leu Val Asn Lys Ala Lys Gln
770                 775                 780

Leu Leu Glu Ala Ser Asn Leu Leu Val Gly Gly Asn Phe Glu Thr Thr
785                 790                 795                 800

Gln Asn Trp Val Leu Gly Thr Asn Ala Tyr Ile Asn Tyr Asp Ser Phe
                805                 810                 815

Leu Phe Asn Gly Asn Tyr Leu Ser Leu Gln Pro Ala Ser Gly Phe Phe
            820                 825                 830

Thr Ser Tyr Ala Tyr Gln Lys Ile Asp Glu Ser Thr Leu Lys Pro Tyr
        835                 840                 845

Thr Arg Tyr Lys Val Ser Gly Phe Ile Gly Gln Ser Asn Gln Val Glu
850                 855                 860

Leu Ile Ile Ser Arg Tyr Gly Lys Glu Ile Asp Lys Ile Leu Asn Val
865                 870                 875                 880

Pro Tyr Ala Gly Pro Leu Pro Ile Thr Ala Asp Ala Ser Ile Thr Cys
                885                 890                 895

Cys Ala Pro Glu Ile Gly Gln Cys Asp Gly Glu Gln Ser Asp Ser His
            900                 905                 910

Phe Phe Asn Tyr Ser Ile Asp Val Gly Ala Leu His Pro Glu Leu Asn
        915                 920                 925

Pro Gly Ile Glu Ile Gly Leu Lys Ile Val Gln Ser Asn Gly Tyr Ile
        930                 935                 940

Thr Ile Ser Asn Leu Glu Ile Ile Glu Glu Arg Pro Leu Thr Glu Met
945                 950                 955                 960

Glu Ile Gln Ala Val Asn Arg Lys Asn Gln Lys Trp Glu Arg Glu Lys
                965                 970                 975

Leu Leu Glu Cys Ala Ser Ile Ser Glu Leu Leu Gln Pro Ile Ile Asn
            980                 985                 990

Gln Ile Asp Ser Leu Phe Lys Asp Gly Asn Trp Tyr Asn Asp Ile Leu
        995                 1000                1005

Pro His Val Thr Tyr Gln Asp Leu Lys Asn Ile Ile Ile Pro Glu Leu
    1010                1015                1020

Pro Lys Leu Lys His Trp Phe Ile Glu Asn Leu Pro Gly Glu Tyr His
1025                1030                1035                1040

Glu Ile Glu Gln Lys Met Lys Glu Ala Leu Lys Tyr Ala Phe Thr Gln
                1045                1050                1055

Leu Asp Glu Lys Asn Leu Ile His Asn Gly His Phe Thr Thr Asn Leu
            1060                1065                1070

Ile Asp Trp Gln Val Glu Gly Asp Ala Gln Met Lys Val Leu Glu Asn
        1075                1080                1085

Asp Ala Leu Ala Leu Gln Leu Phe Asn Trp Asp Ala Ser Ala Ser Gln
```

-continued

```
                1090                1095                1100
Ser Ile Asn Ile Leu Glu Phe Asp Glu Asp Lys Ala Tyr Lys Leu Arg
1105                1110                1115                1120

Val Tyr Ala Gln Gly Ser Gly Thr Ile Gln Phe Gly Asn Cys Glu Asp
                1125                1130                1135

Glu Ala Ile Gln Phe Asn Thr Asn Ser Phe Ile Tyr Gln Glu Lys Ile
            1140                1145                1150

Val Tyr Phe Asp Thr Pro Ser Val Asn Leu His Ile Gln Ser Glu Gly
        1155                1160                1165

Ser Glu Phe Ile Val Ser Ser Ile Asp Leu Ile Glu Leu Ser Asp Asp
    1170                1175                1180

Gln Lys Asp Glu Leu
1185

<210> SEQ ID NO 34
<211> LENGTH: 3669
<212> TYPE: DNA
<213> ORGANISM: Unknown
<220> FEATURE:
<223> OTHER INFORMATION: isolated from soil sample (AXMI-049)
<220> FEATURE:
<221> NAME/KEY: CDS
<222> LOCATION: (1)...(3669)

<400> SEQUENCE: 34 atg gat gac atg aca aat tta tcc gat gta tat tca ccc gta cct tcc      48
Met Asp Asp Met Thr Asn Leu Ser Asp Val Tyr Ser Pro Val Pro Ser
  1               5                  10                  15 aat gta tta gca gct cca ctt att ctt gaa gaa aca aag aaa aaa aca      96
Asn Val Leu Ala Ala Pro Leu Ile Leu Glu Glu Thr Lys Lys Lys Thr
                 20                  25                  30 ccg gct gaa caa gca aaa gaa gat tta gaa aag gca ttg aga aca gga     144
Pro Ala Glu Gln Ala Lys Glu Asp Leu Glu Lys Ala Leu Arg Thr Gly
             35                  40                  45 aag ttt tcc gat gca att gca caa att tta aat gat gtt ctt att aac     192
Lys Phe Ser Asp Ala Ile Ala Gln Ile Leu Asn Asp Val Leu Ile Asn
         50                  55                  60 caa aag ttc agc tat caa aca gcg gtt aca gtt tcc tta tct ttg gct     240
Gln Lys Phe Ser Tyr Gln Thr Ala Val Thr Val Ser Leu Ser Leu Ala
 65                  70                  75                  80 agt ata gtt ctt cca gaa ata ggt ttt ttt gcc ccc ttt gtt ggt tta     288
Ser Ile Val Leu Pro Glu Ile Gly Phe Phe Ala Pro Phe Val Gly Leu
                 85                  90                  95 ttt ttt tct gct tta aat aaa tct caa aat ata cct acg act tca gat     336
Phe Phe Ser Ala Leu Asn Lys Ser Gln Asn Ile Pro Thr Thr Ser Asp
            100                 105                 110 att ttt gaa gcg atg aaa cca gct att caa aca atg att gat cgt agt     384
Ile Phe Glu Ala Met Lys Pro Ala Ile Gln Thr Met Ile Asp Arg Ser
        115                 120                 125 tta aca gat gct gaa aac aag gag atg gat gat cag gcg cac aac cta     432
Leu Thr Asp Ala Glu Asn Lys Glu Met Asp Asp Gln Ala His Asn Leu
    130                 135                 140 ttt acg cga tta caa act tat caa gag caa ata gat ctc tat aaa cat     480
Phe Thr Arg Leu Gln Thr Tyr Gln Glu Gln Ile Asp Leu Tyr Lys His
145                 150                 155                 160 att tta gat gca aaa caa aaa cca act ctt aac gat ata gga gat ctt     528
Ile Leu Asp Ala Lys Gln Lys Pro Thr Leu Asn Asp Ile Gly Asp Leu
                165                 170                 175 cac act tcg atc gac gaa act ctc aga aca tta gat tcc aat tta gca     576
His Thr Ser Ile Asp Glu Thr Leu Arg Thr Leu Asp Ser Asn Leu Ala
            180                 185                 190
```

| | | |
|---|---|---|
| ttt ttc caa aca gaa ggc tat caa gat ctc ggg tta cca tat tac aca<br>Phe Phe Gln Thr Glu Gly Tyr Gln Asp Leu Gly Leu Pro Tyr Tyr Thr<br>                195                      200                    205 | | 624 |
| att ttt gcc aca caa tat ttg tta atc ctt tca gat aaa att aaa act<br>Ile Phe Ala Thr Gln Tyr Leu Leu Ile Leu Ser Asp Lys Ile Lys Thr<br>210                      215                    220 | | 672 |
| ggt atc aca tgg gga tat aat cct att aac att cca gat ttt caa aac<br>Gly Ile Thr Trp Gly Tyr Asn Pro Ile Asn Ile Pro Asp Phe Gln Asn<br>225                      230                    235                    240 | | 720 |
| caa ttt aat aat aga ata ctt tta ttt aca aaa tac att agt ggt caa<br>Gln Phe Asn Asn Arg Ile Leu Leu Phe Thr Lys Tyr Ile Ser Gly Gln<br>                245                    250                    255 | | 768 |
| ctt aag aaa atg tat gac aac ggt gta cat cca gca ctt tta tat caa<br>Leu Lys Lys Met Tyr Asp Asn Gly Val His Pro Ala Leu Leu Tyr Gln<br>                260                    265                    270 | | 816 |
| aac tgt atc caa ttt gtt gct tta tgg cct act ttt tct ccc gca gat<br>Asn Cys Ile Gln Phe Val Ala Leu Trp Pro Thr Phe Ser Pro Ala Asp<br>                275                    280                    285 | | 864 |
| tat aac ctt agt aac agc aca gat tta gaa caa aca ata agt ttt aag<br>Tyr Asn Leu Ser Asn Ser Thr Asp Leu Glu Gln Thr Ile Ser Phe Lys<br>290                      295                    300 | | 912 |
| agt ttc atc tcc tat aag agt tta aat gat tat aat tat gca ctt cct<br>Ser Phe Ile Ser Tyr Lys Ser Leu Asn Asp Tyr Asn Tyr Ala Leu Pro<br>305                      310                    315                    320 | | 960 |
| gaa att aat aca tgg aca aat ttt gaa atg aca aaa tca ctt gat ttt<br>Glu Ile Asn Thr Trp Thr Asn Phe Glu Met Thr Lys Ser Leu Asp Phe<br>                      325                    330                    335 | | 1008 |
| aac aac tgt aga tcc atg gat aat tat ggt atc gcg ggt gac ctt cgt<br>Asn Asn Cys Arg Ser Met Asp Asn Tyr Gly Ile Ala Gly Asp Leu Arg<br>                      340                    345                    350 | | 1056 |
| ata aca aat cat aaa aat gaa atc cat gaa ata tct gct cct tcg gta<br>Ile Thr Asn His Lys Asn Glu Ile His Glu Ile Ser Ala Pro Ser Val<br>                355                    360                    365 | | 1104 |
| ctc tac atg aca tca aat cag tgt aac tca aga ctt gtt ttt cca ttc<br>Leu Tyr Met Thr Ser Asn Gln Cys Asn Ser Arg Leu Val Phe Pro Phe<br>                370                    375                    380 | | 1152 |
| gat gat cct att gtt aaa ttc gaa gga aca agt agt gtt ttc ata ggg<br>Asp Asp Pro Ile Val Lys Phe Glu Gly Thr Ser Ser Val Phe Ile Gly<br>385                      390                    395                    400 | | 1200 |
| aca cct gga tta cct caa ttt tat aca aat ttt cag ttg act tct ggt<br>Thr Pro Gly Leu Pro Gln Phe Tyr Thr Asn Phe Gln Leu Thr Ser Gly<br>                      405                    410                    415 | | 1248 |
| aaa agt tta ata ttc cct cct cct tca gga gtt aat caa caa ggt ttc<br>Lys Ser Leu Ile Phe Pro Pro Pro Ser Gly Val Asn Gln Gln Gly Phe<br>                      420                    425                    430 | | 1296 |
| aca caa aat tat tcg gta atc cct cat cct gga ttt aaa ata gca ggt<br>Thr Gln Asn Tyr Ser Val Ile Pro His Pro Gly Phe Lys Ile Ala Gly<br>                435                    440                    445 | | 1344 |
| att aca aat atg tca tat tta cct act cat cac gat agt aat gcg cgg<br>Ile Thr Asn Met Ser Tyr Leu Pro Thr His His Asp Ser Asn Ala Arg<br>                450                    455                    460 | | 1392 |
| aca caa ata gaa cat atc caa gtt cct gaa aaa atc ttt cca gaa aat<br>Thr Gln Ile Glu His Ile Gln Val Pro Glu Lys Ile Phe Pro Glu Asn<br>465                      470                    475                    480 | | 1440 |
| att atc ggg gtt cca gat cca gat aat aac aat cta atc cca atc aaa<br>Ile Ile Gly Val Pro Asp Pro Asp Asn Asn Asn Leu Ile Pro Ile Lys<br>                      485                    490                    495 | | 1488 |
| ggt att ccc gca gaa aaa gga tat ggt gac tca att gca tat gtg tca<br>Gly Ile Pro Ala Glu Lys Gly Tyr Gly Asp Ser Ile Ala Tyr Val Ser<br>                500                    505                    510 | | 1536 |

| | | | | | | | | | | | | | | |
|---|---|---|---|---|---|---|---|---|---|---|---|---|---|---|
| gaa | ccg | gta | aat | ggt | gcg | agt | gca | gtt | aaa | ctt | act | tca | aat | caa att |
| Glu | Pro | Val | Asn | Gly | Ala | Ser | Ala | Val | Lys | Leu | Thr | Ser | Asn | Gln Ile |
| | 515 | | | | 520 | | | | | 525 | | | | |

1584

| | | | | | | | | | | | | | | |
|---|---|---|---|---|---|---|---|---|---|---|---|---|---|---|
| ctc | caa | atg | gaa | att | aca | aat | gta | aca | act | caa | aaa | tat | caa | gtt cgc |
| Leu | Gln | Met | Glu | Ile | Thr | Asn | Val | Thr | Thr | Gln | Lys | Tyr | Gln | Val Arg |
| 530 | | | | | 535 | | | | | 540 | | | | |

1632

| | | | | | | | | | | | | | | |
|---|---|---|---|---|---|---|---|---|---|---|---|---|---|---|
| ata | cgt | tat | gct | aca | gct | gga | gat | aca | gag | gct | aat | ata | agg | ttc cat |
| Ile | Arg | Tyr | Ala | Thr | Ala | Gly | Asp | Thr | Glu | Ala | Asn | Ile | Arg | Phe His |
| 545 | | | | 550 | | | | | 555 | | | | | 560 |

1680

| | | | | | | | | | | | | | | |
|---|---|---|---|---|---|---|---|---|---|---|---|---|---|---|
| att | att | gat | cca | aat | gaa | aat | aat | tta | ata | aat | ggg | cct | aat | cat ttc |
| Ile | Ile | Asp | Pro | Asn | Glu | Asn | Asn | Leu | Ile | Asn | Gly | Pro | Asn | His Phe |
| | | | | 565 | | | | | 570 | | | | | 575 |

1728

| | | | | | | | | | | | | | | |
|---|---|---|---|---|---|---|---|---|---|---|---|---|---|---|
| aca | gct | gta | tct | aat | act | caa | acg | tct | gtc | caa | ggt | gaa | aat | gga aaa |
| Thr | Ala | Val | Ser | Asn | Thr | Gln | Thr | Ser | Val | Gln | Gly | Glu | Asn | Gly Lys |
| | | | 580 | | | | | 585 | | | | | 590 | |

1776

| | | | | | | | | | | | | | | |
|---|---|---|---|---|---|---|---|---|---|---|---|---|---|---|
| tat | gta | cta | aac | aca | ctt | gta | aat | tca | ata | ata | tta | cca | tca | gga aaa |
| Tyr | Val | Leu | Asn | Thr | Leu | Val | Asn | Ser | Ile | Ile | Leu | Pro | Ser | Gly Lys |
| | | | 595 | | | | | 600 | | | | | 605 | |

1824

| | | | | | | | | | | | | | | |
|---|---|---|---|---|---|---|---|---|---|---|---|---|---|---|
| caa | aag | gtc | ttt | att | caa | aac | act | ggt | tct | caa | gat | ctc | ttt | tta gac |
| Gln | Lys | Val | Phe | Ile | Gln | Asn | Thr | Gly | Ser | Gln | Asp | Leu | Phe | Leu Asp |
| | 610 | | | | | 615 | | | | | 620 | | | |

1872

| | | | | | | | | | | | | | | |
|---|---|---|---|---|---|---|---|---|---|---|---|---|---|---|
| cgt | att | gaa | ttt | att | cca | tta | caa | cta | gaa | ctt | cct | ttc | act | tca aaa |
| Arg | Ile | Glu | Phe | Ile | Pro | Leu | Gln | Leu | Glu | Leu | Pro | Phe | Thr | Ser Lys |
| 625 | | | | | 630 | | | | | 635 | | | | 640 |

1920

| | | | | | | | | | | | | | | |
|---|---|---|---|---|---|---|---|---|---|---|---|---|---|---|
| tta | cct | gaa | act | act | aca | caa | cca | aat | aca | aca | aaa | aca | att | tgg tca |
| Leu | Pro | Glu | Thr | Thr | Thr | Gln | Pro | Asn | Thr | Thr | Lys | Thr | Ile | Trp Ser |
| | | | | 645 | | | | | 650 | | | | | 655 |

1968

| | | | | | | | | | | | | | | |
|---|---|---|---|---|---|---|---|---|---|---|---|---|---|---|
| ggt | caa | aaa | cct | gct | aat | aca | ctt | tct | ctt | caa | ggt | aca | gtt | tat aat |
| Gly | Gln | Lys | Pro | Ala | Asn | Thr | Leu | Ser | Leu | Gln | Gly | Thr | Val | Tyr Asn |
| | | | 660 | | | | | 665 | | | | | 670 | |

2016

| | | | | | | | | | | | | | | |
|---|---|---|---|---|---|---|---|---|---|---|---|---|---|---|
| gat | gct | tct | atc | gaa | tta | caa | ctt | tat | atg | aac | gat | aac | tta | gtc caa |
| Asp | Ala | Ser | Ile | Glu | Leu | Gln | Leu | Tyr | Met | Asn | Asp | Asn | Leu | Val Gln |
| | | | 675 | | | | | 680 | | | | | 685 | |

2064

| | | | | | | | | | | | | | | |
|---|---|---|---|---|---|---|---|---|---|---|---|---|---|---|
| aaa | atc | cct | gca | caa | ggt | cct | ggt | cct | agt | ttt | gac | tgt | gac | gac caa |
| Lys | Ile | Pro | Ala | Gln | Gly | Pro | Gly | Pro | Ser | Phe | Asp | Cys | Asp | Asp Gln |
| | 690 | | | | | 695 | | | | | 700 | | | |

2112

| | | | | | | | | | | | | | | |
|---|---|---|---|---|---|---|---|---|---|---|---|---|---|---|
| tct | aaa | cct | att | aat | caa | cca | aat | ata | aaa | act | gaa | gaa | ttt | aac aaa |
| Ser | Lys | Pro | Ile | Asn | Gln | Pro | Asn | Ile | Lys | Thr | Glu | Glu | Phe | Asn Lys |
| 705 | | | | | 710 | | | | | 715 | | | | 720 |

2160

| | | | | | | | | | | | | | | |
|---|---|---|---|---|---|---|---|---|---|---|---|---|---|---|
| ctt | gtc | tta | aaa | gaa | tta | agt | agt | acc | tat | tcg | tat | tgt | atg | gga gga |
| Leu | Val | Leu | Lys | Glu | Leu | Ser | Ser | Thr | Tyr | Ser | Tyr | Cys | Met | Gly Gly |
| | | | 725 | | | | | 730 | | | | | 735 | |

2208

| | | | | | | | | | | | | | | |
|---|---|---|---|---|---|---|---|---|---|---|---|---|---|---|
| gct | ttt | gaa | aac | act | tac | caa | att | gat | att | aca | ata | gac | agc | aaa tcc |
| Ala | Phe | Glu | Asn | Thr | Tyr | Gln | Ile | Asp | Ile | Thr | Ile | Asp | Ser | Lys Ser |
| | | | 740 | | | | | 745 | | | | | 750 | |

2256

| | | | | | | | | | | | | | | |
|---|---|---|---|---|---|---|---|---|---|---|---|---|---|---|
| caa | tct | ttt | act | act | cca | gaa | gat | tta | gaa | aaa | atc | aca | aac | caa gtc |
| Gln | Ser | Phe | Thr | Thr | Pro | Glu | Asp | Leu | Glu | Lys | Ile | Thr | Asn | Gln Val |
| | | 755 | | | | | 760 | | | | | 765 | | |

2304

| | | | | | | | | | | | | | | |
|---|---|---|---|---|---|---|---|---|---|---|---|---|---|---|
| aac | cag | tta | ttt | act | tcc | tca | tcc | caa | aca | aaa | ttg | gtt | caa | acc gta |
| Asn | Gln | Leu | Phe | Thr | Ser | Ser | Gln | Thr | Lys | Leu | Val | Gln | Thr | Val |
| | 770 | | | | | 775 | | | | | 780 | | | |

2352

| | | | | | | | | | | | | | | |
|---|---|---|---|---|---|---|---|---|---|---|---|---|---|---|
| acg | gat | tat | gga | att | gat | caa | atg | gta | atg | aaa | gta | gat | gcg | tta tca |
| Thr | Asp | Tyr | Gly | Ile | Asp | Gln | Met | Val | Met | Lys | Val | Asp | Ala | Leu Ser |
| 785 | | | | | 790 | | | | | 795 | | | | 800 |

2400

| | | | | | | | | | | | | | | |
|---|---|---|---|---|---|---|---|---|---|---|---|---|---|---|
| gac | gat | gta | ttt | ggt | gtc | gag | aaa | aaa | gca | tta | cgt | aaa | ctt | gtc aat |
| Asp | Asp | Val | Phe | Gly | Val | Glu | Lys | Lys | Ala | Leu | Arg | Lys | Leu | Val Asn |
| | | | | 805 | | | | | 810 | | | | | 815 |

2448

| | | | | | | | | | | | | | | |
|---|---|---|---|---|---|---|---|---|---|---|---|---|---|---|
| cag | gcc | aaa | caa | tta | agt | aaa | gta | cga | aat | gta | ctg | gtc | ggt | gga aac |
| Gln | Ala | Lys | Gln | Leu | Ser | Lys | Val | Arg | Asn | Val | Leu | Val | Gly | Gly Asn |
| | | | 820 | | | | | 825 | | | | | 830 | |

2496

-continued

| | | |
|---|---|---|
| ttt gaa aaa ggt cat aaa tgg gta cta ggt cgt aaa gcg aca acg gta<br>Phe Glu Lys Gly His Lys Trp Val Leu Gly Arg Lys Ala Thr Thr Val<br>     835                       840                        845 | 2544 | |
| gcg gat cat gat tta ttc aaa ggg gat cat tta tta tta cca cca cca<br>Ala Asp His Asp Leu Phe Lys Gly Asp His Leu Leu Leu Pro Pro Pro<br>850                         855                       860 | 2592 | |
| acc ctg tat cca tcg tat gcg tat caa aaa atc gat gaa tct aaa tta<br>Thr Leu Tyr Pro Ser Tyr Ala Tyr Gln Lys Ile Asp Glu Ser Lys Leu<br>865                         870                       875                       880 | 2640 | |
| aaa tcc aat aca cgc tat acg gtt tcc ggt ttt gtt gcg caa agt gaa<br>Lys Ser Asn Thr Arg Tyr Thr Val Ser Gly Phe Val Ala Gln Ser Glu<br>                   885                       890                       895 | 2688 | |
| cat tta gaa gtt gtt gtt tct cgc tat ggg aaa gaa gta aat acc ctg<br>His Leu Glu Val Val Val Ser Arg Tyr Gly Lys Glu Val Asn Thr Leu<br>900                         905                       910 | 2736 | |
| tta cat gtc cct tat gaa gaa gca tta ccg att tct tcc gat gag cgt<br>Leu His Val Pro Tyr Glu Glu Ala Leu Pro Ile Ser Ser Asp Glu Arg<br>                 915                       920                       925 | 2784 | |
| cca aat tgc tgt aaa cca gct gct tgt cag tgt cca tct tgc aat ggt<br>Pro Asn Cys Cys Lys Pro Ala Ala Cys Gln Cys Pro Ser Cys Asn Gly<br>930                         935                       940 | 2832 | |
| gat gca cca gac tcc cat ttc ttt agc tat agt atc gat gtt ggt tcc<br>Asp Ala Pro Asp Ser His Phe Phe Ser Tyr Ser Ile Asp Val Gly Ser<br>945                         950                       955                       960 | 2880 | |
| tta caa gca gat gta aat tta gga att gag ttt ggt ctt cgt att gtg<br>Leu Gln Ala Asp Val Asn Leu Gly Ile Glu Phe Gly Leu Arg Ile Val<br>                 965                       970                       975 | 2928 | |
| aaa tcc aac gga ttt gca aaa atc agt aac cta gaa atc aaa gaa gac<br>Lys Ser Asn Gly Phe Ala Lys Ile Ser Asn Leu Glu Ile Lys Glu Asp<br>               980                       985                       990 | 2976 | |
| cgt cca tta aca gaa aaa gaa att aag aaa ata caa cgc aaa gaa caa<br>Arg Pro Leu Thr Glu Lys Glu Ile Lys Lys Ile Gln Arg Lys Glu Gln<br>               995                      1000                     1005 | 3024 | |
| aag tgg aaa aaa gca ttt gac aaa gaa cag gca gag tta acg gca aca<br>Lys Trp Lys Lys Ala Phe Asp Lys Glu Gln Ala Glu Leu Thr Ala Thr<br>1010                       1015                     1020 | 3072 | |
| ctc caa cca acc ctg aac caa atc aat gcc tta tat caa aat gaa gat<br>Leu Gln Pro Thr Leu Asn Gln Ile Asn Ala Leu Tyr Gln Asn Glu Asp<br>1025                       1030                     1035                    1040 | 3120 | |
| tgg aac ggt tcg att cac cct cat gta acg tat caa cat cta tcc gat<br>Trp Asn Gly Ser Ile His Pro His Val Thr Tyr Gln His Leu Ser Asp<br>                     1045                     1050                    1055 | 3168 | |
| gtt gtc gta cca gca tta cca aaa caa aga cat tgg ttt atg gaa gat<br>Val Val Val Pro Ala Leu Pro Lys Gln Arg His Trp Phe Met Glu Asp<br>                     1060                     1065                    1070 | 3216 | |
| cga caa ggt gaa cat tac aat gta aca caa caa ttc caa caa gca tta<br>Arg Gln Gly Glu His Tyr Asn Val Thr Gln Gln Phe Gln Gln Ala Leu<br>               1075                       1080                     1085 | 3264 | |
| gat cgt gct ttc caa caa atc gaa gaa caa aac tta att cac aat ggt<br>Asp Arg Ala Phe Gln Gln Ile Glu Glu Gln Asn Leu Ile His Asn Gly<br>1090                       1095                     1100 | 3312 | |
| agc ttt gcg aat gga ttg aca gat tgg act gtc aca ggg gat gca cat<br>Ser Phe Ala Asn Gly Leu Thr Asp Trp Thr Val Thr Gly Asp Ala His<br>1105                       1110                     1115                    1120 | 3360 | |
| gtt act atc cag gat gat gat caa gta tta gaa cta tct cat tgg gat<br>Val Thr Ile Gln Asp Asp Asp Gln Val Leu Glu Leu Ser His Trp Asp<br>                     1125                     1130                    1135 | 3408 | |
| gca agt gtc tct caa acg att gaa att att gat ttt gaa gaa gaa aaa<br>Ala Ser Val Ser Gln Thr Ile Glu Ile Ile Asp Phe Glu Glu Glu Lys<br>1140                       1145                     1150 | 3456 | |

| | | |
|---|---|---|
| gaa tac aaa ctt cgt gta cgt gga aaa ggt aaa gga acg gta acc gtt<br>Glu Tyr Lys Leu Arg Val Arg Gly Lys Gly Lys Gly Thr Val Thr Val<br>     1155                          1160                         1165 | 3504 |
| caa cat gga gaa gaa gag tta gaa aca atg aca ttt aat gca acg agt<br>Gln His Gly Glu Glu Glu Leu Glu Thr Met Thr Phe Asn Ala Thr Ser<br>1170                         1175                           1180 | 3552 |
| ttt aca acg caa gaa caa acc ttc tat ttc gaa gga aat aca gtg gat<br>Phe Thr Thr Gln Glu Gln Thr Phe Tyr Phe Glu Gly Asn Thr Val Asp<br>1185                         1190                       1195                   1200 | 3600 |
| ata cac gtt caa tca gag aat aat aca ttc ctg gta gac agt gta gaa<br>Ile His Val Gln Ser Glu Asn Asn Thr Phe Leu Val Asp Ser Val Glu<br>                       1205                         1210                       1215 | 3648 |
| ctc att gaa att ata gaa aag<br>Leu Ile Glu Ile Ile Glu Lys<br>1220 | 3669 |

<210> SEQ ID NO 35
<211> LENGTH: 1223
<212> TYPE: PRT
<213> ORGANISM: Unknown
<220> FEATURE:
<223> OTHER INFORMATION: isolated from soil sample (AXMI-049)

<400> SEQUENCE: 35

Met Asp Asp Met Thr Asn Leu Ser Asp Val Tyr Ser Pro Val Pro Ser
1               5                   10                  15

Asn Val Leu Ala Ala Pro Leu Ile Leu Glu Glu Thr Lys Lys Lys Thr
            20                  25                  30

Pro Ala Glu Gln Ala Lys Glu Asp Leu Glu Lys Ala Leu Arg Thr Gly
        35                  40                  45

Lys Phe Ser Asp Ala Ile Ala Gln Ile Leu Asn Asp Val Leu Ile Asn
50                  55                  60

Gln Lys Phe Ser Tyr Gln Thr Ala Val Thr Val Ser Leu Ser Leu Ala
65                  70                  75                  80

Ser Ile Val Leu Pro Glu Ile Gly Phe Phe Ala Pro Phe Val Gly Leu
                85                  90                  95

Phe Phe Ser Ala Leu Asn Lys Ser Gln Asn Ile Pro Thr Thr Ser Asp
            100                 105                 110

Ile Phe Glu Ala Met Lys Pro Ala Ile Gln Thr Met Ile Asp Arg Ser
        115                 120                 125

Leu Thr Asp Ala Glu Asn Lys Glu Met Asp Asp Gln Ala His Asn Leu
130                 135                 140

Phe Thr Arg Leu Gln Thr Tyr Gln Glu Gln Ile Asp Leu Tyr Lys His
145                 150                 155                 160

Ile Leu Asp Ala Lys Gln Lys Pro Thr Leu Asn Asp Ile Gly Asp Leu
                165                 170                 175

His Thr Ser Ile Asp Glu Thr Leu Arg Thr Leu Asp Ser Asn Leu Ala
            180                 185                 190

Phe Phe Gln Thr Glu Gly Tyr Gln Asp Leu Gly Leu Pro Tyr Tyr Thr
        195                 200                 205

Ile Phe Ala Thr Gln Tyr Leu Leu Ile Leu Ser Asp Lys Ile Lys Thr
210                 215                 220

Gly Ile Thr Trp Gly Tyr Asn Pro Ile Asn Ile Pro Asp Phe Gln Asn
225                 230                 235                 240

Gln Phe Asn Asn Arg Ile Leu Leu Phe Thr Lys Tyr Ile Ser Gly Gln
                245                 250                 255

Leu Lys Lys Met Tyr Asp Asn Gly Val His Pro Ala Leu Leu Tyr Gln

-continued

```
                260                 265                 270
Asn Cys Ile Gln Phe Val Ala Leu Trp Pro Thr Phe Ser Pro Ala Asp
            275                 280                 285
Tyr Asn Leu Ser Asn Ser Thr Asp Leu Glu Gln Thr Ile Ser Phe Lys
        290                 295                 300
Ser Phe Ile Ser Tyr Lys Ser Leu Asn Asp Tyr Asn Tyr Ala Leu Pro
305                 310                 315                 320
Glu Ile Asn Thr Trp Thr Asn Phe Glu Met Thr Lys Ser Leu Asp Phe
                325                 330                 335
Asn Asn Cys Arg Ser Met Asp Asn Tyr Gly Ile Ala Gly Asp Leu Arg
            340                 345                 350
Ile Thr Asn His Lys Asn Glu Ile His Glu Ile Ser Ala Pro Ser Val
        355                 360                 365
Leu Tyr Met Thr Ser Asn Gln Cys Asn Ser Arg Leu Val Phe Pro Phe
370                 375                 380
Asp Asp Pro Ile Val Lys Phe Glu Gly Thr Ser Ser Val Phe Ile Gly
385                 390                 395                 400
Thr Pro Gly Leu Pro Gln Phe Tyr Thr Asn Phe Gln Leu Thr Ser Gly
                405                 410                 415
Lys Ser Leu Ile Phe Pro Pro Ser Gly Val Asn Gln Gln Gly Phe
            420                 425                 430
Thr Gln Asn Tyr Ser Val Ile Pro His Pro Gly Phe Lys Ile Ala Gly
        435                 440                 445
Ile Thr Asn Met Ser Tyr Leu Pro Thr His His Asp Ser Asn Ala Arg
450                 455                 460
Thr Gln Ile Glu His Ile Gln Val Pro Glu Lys Ile Phe Pro Glu Asn
465                 470                 475                 480
Ile Ile Gly Val Pro Asp Pro Asp Asn Asn Asn Leu Ile Pro Ile Lys
                485                 490                 495
Gly Ile Pro Ala Glu Lys Gly Tyr Gly Asp Ser Ile Ala Tyr Val Ser
            500                 505                 510
Glu Pro Val Asn Gly Ala Ser Ala Val Lys Leu Thr Ser Asn Gln Ile
        515                 520                 525
Leu Gln Met Glu Ile Thr Asn Val Thr Thr Gln Lys Tyr Gln Val Arg
530                 535                 540
Ile Arg Tyr Ala Thr Ala Gly Asp Thr Glu Ala Asn Ile Arg Phe His
545                 550                 555                 560
Ile Ile Asp Pro Asn Glu Asn Leu Ile Asn Gly Pro Asn His Phe
                565                 570                 575
Thr Ala Val Ser Asn Thr Gln Thr Ser Val Gln Gly Glu Asn Gly Lys
            580                 585                 590
Tyr Val Leu Asn Thr Leu Val Asn Ser Ile Ile Leu Pro Ser Gly Lys
        595                 600                 605
Gln Lys Val Phe Ile Gln Asn Thr Gly Ser Gln Asp Leu Phe Leu Asp
610                 615                 620
Arg Ile Glu Phe Ile Pro Leu Gln Leu Glu Leu Pro Phe Thr Ser Lys
625                 630                 635                 640
Leu Pro Glu Thr Thr Thr Gln Pro Asn Thr Thr Lys Thr Ile Trp Ser
                645                 650                 655
Gly Gln Lys Pro Ala Asn Thr Leu Ser Leu Gln Gly Thr Val Tyr Asn
            660                 665                 670
Asp Ala Ser Ile Glu Leu Gln Leu Tyr Met Asn Asp Asn Leu Val Gln
        675                 680                 685
```

-continued

Lys Ile Pro Ala Gln Gly Pro Gly Pro Ser Phe Asp Cys Asp Asp Gln
            690                 695                 700

Ser Lys Pro Ile Asn Gln Pro Asn Ile Lys Thr Glu Glu Phe Asn Lys
705                 710                 715                 720

Leu Val Leu Lys Glu Leu Ser Ser Thr Tyr Ser Tyr Cys Met Gly Gly
                725                 730                 735

Ala Phe Glu Asn Thr Tyr Gln Ile Asp Ile Thr Ile Asp Ser Lys Ser
            740                 745                 750

Gln Ser Phe Thr Thr Pro Glu Asp Leu Glu Lys Ile Thr Asn Gln Val
        755                 760                 765

Asn Gln Leu Phe Thr Ser Ser Gln Thr Lys Leu Val Gln Thr Val
770                 775                 780

Thr Asp Tyr Gly Ile Asp Gln Met Val Met Lys Val Asp Ala Leu Ser
785                 790                 795                 800

Asp Asp Val Phe Gly Val Glu Lys Lys Ala Leu Arg Lys Leu Val Asn
            805                 810                 815

Gln Ala Lys Gln Leu Ser Lys Val Arg Asn Val Leu Val Gly Gly Asn
        820                 825                 830

Phe Glu Lys Gly His Lys Trp Val Leu Gly Arg Lys Ala Thr Thr Val
    835                 840                 845

Ala Asp His Asp Leu Phe Lys Gly Asp His Leu Leu Leu Pro Pro Pro
850                 855                 860

Thr Leu Tyr Pro Ser Tyr Ala Tyr Gln Lys Ile Asp Glu Ser Lys Leu
865                 870                 875                 880

Lys Ser Asn Thr Arg Tyr Thr Val Ser Gly Phe Val Ala Gln Ser Glu
            885                 890                 895

His Leu Glu Val Val Val Ser Arg Tyr Gly Lys Glu Val Asn Thr Leu
        900                 905                 910

Leu His Val Pro Tyr Glu Glu Ala Leu Pro Ile Ser Ser Asp Glu Arg
    915                 920                 925

Pro Asn Cys Cys Lys Pro Ala Ala Cys Gln Cys Pro Ser Cys Asn Gly
930                 935                 940

Asp Ala Pro Asp Ser His Phe Phe Ser Tyr Ser Ile Asp Val Gly Ser
945                 950                 955                 960

Leu Gln Ala Asp Val Asn Leu Gly Ile Glu Phe Gly Leu Arg Ile Val
            965                 970                 975

Lys Ser Asn Gly Phe Ala Lys Ile Ser Asn Leu Glu Ile Lys Glu Asp
        980                 985                 990

Arg Pro Leu Thr Glu Lys Glu Ile Lys Lys Ile Gln Arg Lys Glu Gln
    995                 1000                1005

Lys Trp Lys Lys Ala Phe Asp Lys Glu Gln Ala Glu Leu Thr Ala Thr
    1010                1015                1020

Leu Gln Pro Thr Leu Asn Gln Ile Asn Ala Leu Tyr Gln Asn Glu Asp
1025                1030                1035                1040

Trp Asn Gly Ser Ile His Pro His Val Thr Tyr Gln His Leu Ser Asp
                1045                1050                1055

Val Val Val Pro Ala Leu Pro Lys Gln Arg His Trp Phe Met Glu Asp
            1060                1065                1070

Arg Gln Gly Glu His Tyr Asn Val Thr Gln Gln Phe Gln Gln Ala Leu
        1075                1080                1085

Asp Arg Ala Phe Gln Gln Ile Glu Glu Gln Asn Leu Ile His Asn Gly
    1090                1095                1100

Ser Phe Ala Asn Gly Leu Thr Asp Trp Thr Val Thr Gly Asp Ala His
1105                1110                1115                1120

```
Val Thr Ile Gln Asp Asp Gln Val Leu Glu Leu Ser His Trp Asp
            1125                1130                1135

Ala Ser Val Ser Gln Thr Ile Glu Ile Ile Asp Phe Glu Glu Lys
            1140                1145                1150

Glu Tyr Lys Leu Arg Val Arg Gly Lys Gly Lys Gly Thr Val Thr Val
            1155                1160                1165

Gln His Gly Glu Glu Glu Leu Glu Thr Met Thr Phe Asn Ala Thr Ser
            1170                1175                1180

Phe Thr Thr Gln Glu Gln Thr Phe Tyr Phe Glu Gly Asn Thr Val Asp
1185                1190                1195                1200

Ile His Val Gln Ser Glu Asn Asn Thr Phe Leu Val Asp Ser Val Glu
            1205                1210                1215

Leu Ile Glu Ile Ile Glu Lys
            1220

<210> SEQ ID NO 36
<211> LENGTH: 4
<212> TYPE: PRT
<213> ORGANISM: Artificial Sequence
<220> FEATURE:
<223> OTHER INFORMATION: Targeting peptide

<400> SEQUENCE: 36

Lys Asp Glu Leu
 1

<210> SEQ ID NO 37
<211> LENGTH: 3657
<212> TYPE: DNA
<213> ORGANISM: Artificial Sequence
<220> FEATURE:
<223> OTHER INFORMATION: aposynaxmi-031(fl)
<220> FEATURE:
<221> NAME/KEY: CDS
<222> LOCATION: (1)...(3657)

<400> SEQUENCE: 37 atg cag atc ctt ggg tac tcc agc ttc gtt gct atc gct ctt ctt atg       48
Met Gln Ile Leu Gly Tyr Ser Ser Phe Val Ala Ile Ala Leu Leu Met
 1               5                  10                  15 agc gtg gtt gtt gtt tgc aat ggg ggc aag acg tcc acc tac gtg cgt       96
Ser Val Val Val Val Cys Asn Gly Gly Lys Thr Ser Thr Tyr Val Arg
                20                  25                  30 aat ctg gat tgc aat ctc cag agc cag cag aat atc cca tac aat gtg      144
Asn Leu Asp Cys Asn Leu Gln Ser Gln Gln Asn Ile Pro Tyr Asn Val
            35                  40                  45 ctt gct atc cct gtt agc aat gtt aat agc ctt acg gat acg gtt ggc      192
Leu Ala Ile Pro Val Ser Asn Val Asn Ser Leu Thr Asp Thr Val Gly
        50                  55                  60 gat cta aag aag gca tgg gaa gag ttc cag aag acg ggc agc ttc tcc      240
Asp Leu Lys Lys Ala Trp Glu Glu Phe Gln Lys Thr Gly Ser Phe Ser
 65                  70                  75                  80 ctt acc gca ctc cag cag ggc ttc agc gct tcc cag ggc ggg acg ttc      288
Leu Thr Ala Leu Gln Gln Gly Phe Ser Ala Ser Gln Gly Gly Thr Phe
                85                  90                  95 aat tac ctc acc ctc ctc cag tcc ggg atc tcc ctg gct ggc agc ttc      336
Asn Tyr Leu Thr Leu Leu Gln Ser Gly Ile Ser Leu Ala Gly Ser Phe
            100                 105                 110 gtg cct ggc ggc acc ttc gtt gct cca atc atc aat atg gtg atc ggc      384
Val Pro Gly Gly Thr Phe Val Ala Pro Ile Ile Asn Met Val Ile Gly
        115                 120                 125
```

```
tgg ctc tgg cct cat aag aat aag aat gca gat acg gaa aat ctg atc    432
Trp Leu Trp Pro His Lys Asn Lys Asn Ala Asp Thr Glu Asn Leu Ile
    130             135                 140 aat ctg atc gat tca gaa atc cag aag cag ctg aat aag gct ctg ctg    480
Asn Leu Ile Asp Ser Glu Ile Gln Lys Gln Leu Asn Lys Ala Leu Leu
145             150                 155                 160 gat gct gat cgc aat gaa tgg agc agc tac ctc gag tcc atc ttc gat    528
Asp Ala Asp Arg Asn Glu Trp Ser Ser Tyr Leu Glu Ser Ile Phe Asp
                165                 170                 175 agc agc aat aat ctg aat ggc gca atc gtt gat gct cag tgg tcc ggc    576
Ser Ser Asn Asn Leu Asn Gly Ala Ile Val Asp Ala Gln Trp Ser Gly
            180                 185                 190 acc gtg aat acg acc aat cgt acg ctt cgt aat cct acg gaa tca gat    624
Thr Val Asn Thr Thr Asn Arg Thr Leu Arg Asn Pro Thr Glu Ser Asp
        195                 200                 205 tac acc aat gtg gtg acg aat ttc atc gca gca gat ggg gat atc gct    672
Tyr Thr Asn Val Val Thr Asn Phe Ile Ala Ala Asp Gly Asp Ile Ala
    210                 215                 220 aat aat gaa aat cat atc atg aat ggg aat ttc gat gtg gca gca gct    720
Asn Asn Glu Asn His Ile Met Asn Gly Asn Phe Asp Val Ala Ala Ala
225             230                 235                 240 cca tac ttc gtt atc ggg gct acc gct aga ttc gca gct atg cag tcc    768
Pro Tyr Phe Val Ile Gly Ala Thr Ala Arg Phe Ala Ala Met Gln Ser
                245                 250                 255 tac atc aag ttc tgc aat gca tgg atc gat aag gtt ggg ctg tca gat    816
Tyr Ile Lys Phe Cys Asn Ala Trp Ile Asp Lys Val Gly Leu Ser Asp
            260                 265                 270 gct cag ctg acc acg cag aag gct aat ctg gat aga acg aag cag aat    864
Ala Gln Leu Thr Thr Gln Lys Ala Asn Leu Asp Arg Thr Lys Gln Asn
        275                 280                 285 atg cgt aat gct atc ctt aat tac acc cag cag gtt atg aag gtt ttc    912
Met Arg Asn Ala Ile Leu Asn Tyr Thr Gln Gln Val Met Lys Val Phe
    290                 295                 300 aag gat tcc aag aat atg cca acg atc ggc acg aat aag ttc agc gtt    960
Lys Asp Ser Lys Asn Met Pro Thr Ile Gly Thr Asn Lys Phe Ser Val
305             310                 315                 320 gat acc tac aat gtt tac atc aag ggg atg acg ctt aat gtg ctt gat   1008
Asp Thr Tyr Asn Val Tyr Ile Lys Gly Met Thr Leu Asn Val Leu Asp
                325                 330                 335 atc gtt gct atc tgg cca agc ctg tac cca gat gat tac acg tca cag   1056
Ile Val Ala Ile Trp Pro Ser Leu Tyr Pro Asp Asp Tyr Thr Ser Gln
            340                 345                 350 acg gct ctg gaa cag acc cgc gtg acg ttc tcc aat atg gtg ggg cag   1104
Thr Ala Leu Glu Gln Thr Arg Val Thr Phe Ser Asn Met Val Gly Gln
        355                 360                 365 gaa gaa ggc acg gat ggc agc ctc aga atc tac aat acc ttc gat agc   1152
Glu Glu Gly Thr Asp Gly Ser Leu Arg Ile Tyr Asn Thr Phe Asp Ser
    370                 375                 380 ttc tcc tac cag cat agc cct atc cct aat aat aat gtg aat ctc atc   1200
Phe Ser Tyr Gln His Ser Pro Ile Pro Asn Asn Asn Val Asn Leu Ile
385             390                 395                 400 agc tac tac aat gat gaa ctt cag aat ctg gaa ctc ggg gtt tac acc   1248
Ser Tyr Tyr Asn Asp Glu Leu Gln Asn Leu Glu Leu Gly Val Tyr Thr
                405                 410                 415 cca cca aag aag ggc tca ggc tac agc tac cca tac ggg ttc gtg ctg   1296
Pro Pro Lys Lys Gly Ser Gly Tyr Ser Tyr Pro Tyr Gly Phe Val Leu
            420                 425                 430 aat tac gca aat agc aag tac aag tac ggc gat tcc aat gat cca gaa   1344
Asn Tyr Ala Asn Ser Lys Tyr Lys Tyr Gly Asp Ser Asn Asp Pro Glu
        435                 440                 445
```

```
tcc ctc ggc ggg ctt tcc acc ctt agc gct cca atc caa cag gtt aat      1392
Ser Leu Gly Gly Leu Ser Thr Leu Ser Ala Pro Ile Gln Gln Val Asn
    450                 455                 460 gct gct acc cag aat agc aag tac ctt gat ggc gaa atc ctg aat ggg      1440
Ala Ala Thr Gln Asn Ser Lys Tyr Leu Asp Gly Glu Ile Leu Asn Gly
465                 470                 475                 480 atc ggc gca agc ctg cct ggc tac tgc acg acc ggg tgc tca cct acc      1488
Ile Gly Ala Ser Leu Pro Gly Tyr Cys Thr Thr Gly Cys Ser Pro Thr
                485                 490                 495 gaa cca cca ttc agc tgc acg agc acg gca aat ggg tac aag gca agc      1536
Glu Pro Pro Phe Ser Cys Thr Ser Thr Ala Asn Gly Tyr Lys Ala Ser
            500                 505                 510 tgc aat cca agc gat acc aat cag aag atc aat gct ctc tac cca ttc      1584
Cys Asn Pro Ser Asp Thr Asn Gln Lys Ile Asn Ala Leu Tyr Pro Phe
        515                 520                 525 acg cag gca aat gtg aag ggg aat acc ggg aag ctg ggc gtt ctc gca      1632
Thr Gln Ala Asn Val Lys Gly Asn Thr Gly Lys Leu Gly Val Leu Ala
    530                 535                 540 agc ctt gtt agc tac gat ctg aat cct aag aat gtt ttc ggg gaa ctc      1680
Ser Leu Val Ser Tyr Asp Leu Asn Pro Lys Asn Val Phe Gly Glu Leu
545                 550                 555                 560 gat tca gat acc aat aat gtt atc ctt aag ggc atc cca gca gaa aag      1728
Asp Ser Asp Thr Asn Asn Val Ile Leu Lys Gly Ile Pro Ala Glu Lys
                565                 570                 575 ggc tac ttc cca aat aat gca aga cca acc gtt gtg aag gaa tgg atc      1776
Gly Tyr Phe Pro Asn Asn Ala Arg Pro Thr Val Val Lys Glu Trp Ile
            580                 585                 590 aat ggg gct tcc gca gtt cca ctt gat tcc ggc aat acc ctg ttc atg      1824
Asn Gly Ala Ser Ala Val Pro Leu Asp Ser Gly Asn Thr Leu Phe Met
        595                 600                 605 acg gct acg aac ctg acg gct acc cag tac aga atc cgc atc cgt tac      1872
Thr Ala Thr Asn Leu Thr Ala Thr Gln Tyr Arg Ile Arg Ile Arg Tyr
    610                 615                 620 gct aac cca aac tca aac acg cag atc ggc gtt aga atc acg cag aac      1920
Ala Asn Pro Asn Ser Asn Thr Gln Ile Gly Val Arg Ile Thr Gln Asn
625                 630                 635                 640 ggg agc ctc atc tcc tcc tcc aac ctc acg ctg tac tca acc acc gat      1968
Gly Ser Leu Ile Ser Ser Ser Asn Leu Thr Leu Tyr Ser Thr Thr Asp
                645                 650                 655 atg aac aac acc ctg cca ctg aac gtt tac gtg atc ggg gaa aac ggg      2016
Met Asn Asn Thr Leu Pro Leu Asn Val Tyr Val Ile Gly Glu Asn Gly
            660                 665                 670 aac tac acc ctc cag gat ctc tac aac acg acg aac gtt ctg tcc acg      2064
Asn Tyr Thr Leu Gln Asp Leu Tyr Asn Thr Thr Asn Val Leu Ser Thr
        675                 680                 685 ggc gat atc acc ctg cag atc acc ggc ggg gat cag aag ata ttc atc      2112
Gly Asp Ile Thr Leu Gln Ile Thr Gly Gly Asp Gln Lys Ile Phe Ile
    690                 695                 700 gat cgc atc gag ttc gtg cct acg atg cca gtg cca ggc aac acc aac      2160
Asp Arg Ile Glu Phe Val Pro Thr Met Pro Val Pro Gly Asn Thr Asn
705                 710                 715                 720 aac aac aac ggg aac aac aac ggc aac aac aac cct cct cat cat gtt      2208
Asn Asn Asn Gly Asn Asn Asn Gly Asn Asn Asn Pro Pro His His Val
                725                 730                 735 tgc gct atc gca ggc acc cag cag tcc tgc tcc ggc cca cca aag ttc      2256
Cys Ala Ile Ala Gly Thr Gln Gln Ser Cys Ser Gly Pro Pro Lys Phe
            740                 745                 750 gag cag gtg tcc gat tta gaa aag ata acc acg cag gtt tac atg ctc      2304
Glu Gln Val Ser Asp Leu Glu Lys Ile Thr Thr Gln Val Tyr Met Leu
        755                 760                 765
```

```
ttc aag tcc tcc cca tac gaa gaa ctt gct ctt gaa gtt agc agc tac     2352
Phe Lys Ser Ser Pro Tyr Glu Glu Leu Ala Leu Glu Val Ser Ser Tyr
    770                 775                 780 cag atc agc cag gtt gca ctg aag gtt atg gct ctc agc gat gaa cta     2400
Gln Ile Ser Gln Val Ala Leu Lys Val Met Ala Leu Ser Asp Glu Leu
785                 790                 795                 800 ttc tgc gaa gaa aag aac gtg ctg aga aag ctc gtg aac aag gca aag     2448
Phe Cys Glu Glu Lys Asn Val Leu Arg Lys Leu Val Asn Lys Ala Lys
                805                 810                 815 cag ctt ctc gaa gca agc aac ctt ctc gtt ggg ggg aac ttc gag acg     2496
Gln Leu Leu Glu Ala Ser Asn Leu Leu Val Gly Gly Asn Phe Glu Thr
            820                 825                 830 act cag aac tgg gtg ctc ggc acg aac gct tac atc aac tat gat tca     2544
Thr Gln Asn Trp Val Leu Gly Thr Asn Ala Tyr Ile Asn Tyr Asp Ser
        835                 840                 845 ttc ctg ttc aac ggg aac tac ctg agc ctc cag cca gca tcc ggc ttc     2592
Phe Leu Phe Asn Gly Asn Tyr Leu Ser Leu Gln Pro Ala Ser Gly Phe
    850                 855                 860 ttc acg agc tac gct tac cag aag atc gat gaa tcc acg ctt aag cct     2640
Phe Thr Ser Tyr Ala Tyr Gln Lys Ile Asp Glu Ser Thr Leu Lys Pro
865                 870                 875                 880 tac acg cgc tac aag gtg tcc ggg ttc atc ggg cag tca aac cag gtt     2688
Tyr Thr Arg Tyr Lys Val Ser Gly Phe Ile Gly Gln Ser Asn Gln Val
                885                 890                 895 gaa ctg atc atc agc cgc tac ggg aag gaa atc gat aag atc ctt aac     2736
Glu Leu Ile Ile Ser Arg Tyr Gly Lys Glu Ile Asp Lys Ile Leu Asn
            900                 905                 910 gtg cca tac gca ggg cca ctc cca atc acc gca gat gca agc atc acc     2784
Val Pro Tyr Ala Gly Pro Leu Pro Ile Thr Ala Asp Ala Ser Ile Thr
        915                 920                 925 tgc tgc gct cca gaa ata ggg cag tgc gat ggg gaa cag tca gat tcc     2832
Cys Cys Ala Pro Glu Ile Gly Gln Cys Asp Gly Glu Gln Ser Asp Ser
    930                 935                 940 cat ttc ttc aac tac agc atc gat gtt ggc gca ctc cat cca gaa ctt     2880
His Phe Phe Asn Tyr Ser Ile Asp Val Gly Ala Leu His Pro Glu Leu
945                 950                 955                 960 aac cca ggg atc gaa atc ggg ctg aag atc gtt cag agc aac ggc tac     2928
Asn Pro Gly Ile Glu Ile Gly Leu Lys Ile Val Gln Ser Asn Gly Tyr
                965                 970                 975 atc acc atc tcc aac ctt gaa atc atc gaa gaa aga cca tta acg gaa     2976
Ile Thr Ile Ser Asn Leu Glu Ile Ile Glu Glu Arg Pro Leu Thr Glu
            980                 985                 990 atg gaa att caa gca gtg aac cgc aag aac cag aag tgg gaa cgc gaa     3024
Met Glu Ile Gln Ala Val Asn Arg Lys Asn Gln Lys Trp Glu Arg Glu
        995                 1000                1005 aag ctg ctt gaa tgc gca tcc atc tcc gaa ctc ctc cag cct atc atc     3072
Lys Leu Leu Glu Cys Ala Ser Ile Ser Glu Leu Leu Gln Pro Ile Ile
    1010                1015                1020 aac cag ata gat agc ctc ttc aag gat ggc aac tgg tac aac gat atc     3120
Asn Gln Ile Asp Ser Leu Phe Lys Asp Gly Asn Trp Tyr Asn Asp Ile
1025                1030                1035                1040 cta cca cat gtt acc tac cag gat ctt aag aac atc atc atc cca gaa     3168
Leu Pro His Val Thr Tyr Gln Asp Leu Lys Asn Ile Ile Ile Pro Glu
                1045                1050                1055 ctt cct aag ctc aag cat tgg ttc atc gaa aac ctg cct ggg gaa tac     3216
Leu Pro Lys Leu Lys His Trp Phe Ile Glu Asn Leu Pro Gly Glu Tyr
            1060                1065                1070 cat gaa atc gaa cag aag atg aag gaa gca tta aag tac gca ttc act     3264
His Glu Ile Glu Gln Lys Met Lys Glu Ala Leu Lys Tyr Ala Phe Thr
        1075                1080                1085
```

```
                                                    -continued cag ctc gat gaa aag aac ctg atc cat aac ggc cat ttc acc acc aac    3312
Gln Leu Asp Glu Lys Asn Leu Ile His Asn Gly His Phe Thr Thr Asn
    1090                1095                1100 ctc atc gat tgg cag gtg gaa ggc gat gct cag atg aag gtg ctt gaa    3360
Leu Ile Asp Trp Gln Val Glu Gly Asp Ala Gln Met Lys Val Leu Glu
1105                1110                1115                1120 aac gat gca ctc gct ctc cag cta ttc aac tgg gat gct tcc gca tcc    3408
Asn Asp Ala Leu Ala Leu Gln Leu Phe Asn Trp Asp Ala Ser Ala Ser
                1125                1130                1135 cag agc atc aac atc cta gag ttc gat gaa gat aag gct tac aag ctg    3456
Gln Ser Ile Asn Ile Leu Glu Phe Asp Glu Asp Lys Ala Tyr Lys Leu
            1140                1145                1150 cgt gtg tac gca cag ggc tcc ggg acg atc cag ttc ggc aac tgc gaa    3504
Arg Val Tyr Ala Gln Gly Ser Gly Thr Ile Gln Phe Gly Asn Cys Glu
        1155                1160                1165 gat gaa gct atc cag ttc aac acc aac tca ttc atc tac cag gaa aag    3552
Asp Glu Ala Ile Gln Phe Asn Thr Asn Ser Phe Ile Tyr Gln Glu Lys
    1170                1175                1180 ata gtg tac ttc gat acg cca tcc gtt aac ctt cat atc cag agc gaa    3600
Ile Val Tyr Phe Asp Thr Pro Ser Val Asn Leu His Ile Gln Ser Glu
1185                1190                1195                1200 ggc tcc gag ttc atc gtg agc agc atc gat ctc atc gaa ctc agc gat    3648
Gly Ser Glu Phe Ile Val Ser Ser Ile Asp Leu Ile Glu Leu Ser Asp
                1205                1210                1215 gat cag tag                                                        3657
Asp Gln *

<210> SEQ ID NO 38
<211> LENGTH: 1218
<212> TYPE: PRT
<213> ORGANISM: Artificial Sequence
<220> FEATURE:
<223> OTHER INFORMATION: APOSYNAXMI-031(FL)

<400> SEQUENCE: 38

Met Gln Ile Leu Gly Tyr Ser Ser Phe Val Ala Ile Ala Leu Leu Met
1               5                   10                  15

Ser Val Val Val Cys Asn Gly Gly Lys Thr Ser Thr Tyr Val Arg
            20                  25                  30

Asn Leu Asp Cys Asn Leu Gln Ser Gln Gln Asn Ile Pro Tyr Asn Val
        35                  40                  45

Leu Ala Ile Pro Val Ser Asn Val Asn Ser Leu Thr Asp Thr Val Gly
    50                  55                  60

Asp Leu Lys Lys Ala Trp Glu Glu Phe Gln Lys Thr Gly Ser Phe Ser
65                  70                  75                  80

Leu Thr Ala Leu Gln Gln Gly Phe Ser Ala Ser Gln Gly Gly Thr Phe
                85                  90                  95

Asn Tyr Leu Thr Leu Leu Gln Ser Gly Ile Ser Leu Ala Gly Ser Phe
            100                 105                 110

Val Pro Gly Gly Thr Phe Val Ala Pro Ile Ile Asn Met Val Ile Gly
        115                 120                 125

Trp Leu Trp Pro His Lys Asn Lys Asn Ala Asp Thr Glu Asn Leu Ile
    130                 135                 140

Asn Leu Ile Asp Ser Glu Ile Gln Lys Gln Leu Asn Lys Ala Leu Leu
145                 150                 155                 160

Asp Ala Asp Arg Asn Glu Trp Ser Ser Tyr Leu Glu Ser Ile Phe Asp
                165                 170                 175

Ser Ser Asn Asn Leu Asn Gly Ala Ile Val Asp Ala Gln Trp Ser Gly
            180                 185                 190
```

Thr Val Asn Thr Thr Asn Arg Thr Leu Arg Asn Pro Thr Glu Ser Asp
            195                 200                 205

Tyr Thr Asn Val Val Thr Asn Phe Ile Ala Ala Asp Gly Asp Ile Ala
        210                 215                 220

Asn Asn Glu Asn His Ile Met Asn Gly Asn Phe Asp Val Ala Ala Ala
225                 230                 235                 240

Pro Tyr Phe Val Ile Gly Ala Thr Ala Arg Phe Ala Ala Met Gln Ser
                245                 250                 255

Tyr Ile Lys Phe Cys Asn Ala Trp Ile Asp Lys Val Gly Leu Ser Asp
            260                 265                 270

Ala Gln Leu Thr Thr Gln Lys Ala Asn Leu Asp Arg Thr Lys Gln Asn
        275                 280                 285

Met Arg Asn Ala Ile Leu Asn Tyr Thr Gln Gln Val Met Lys Val Phe
    290                 295                 300

Lys Asp Ser Lys Asn Met Pro Thr Ile Gly Thr Asn Lys Phe Ser Val
305                 310                 315                 320

Asp Thr Tyr Asn Val Tyr Ile Lys Gly Met Thr Leu Asn Val Leu Asp
                325                 330                 335

Ile Val Ala Ile Trp Pro Ser Leu Tyr Pro Asp Tyr Thr Ser Gln
            340                 345                 350

Thr Ala Leu Glu Gln Thr Arg Val Thr Phe Ser Asn Met Val Gly Gln
        355                 360                 365

Glu Glu Gly Thr Asp Gly Ser Leu Arg Ile Tyr Asn Thr Phe Asp Ser
    370                 375                 380

Phe Ser Tyr Gln His Ser Pro Ile Pro Asn Asn Asn Val Asn Leu Ile
385                 390                 395                 400

Ser Tyr Tyr Asn Asp Glu Leu Gln Asn Leu Glu Leu Gly Val Tyr Thr
                405                 410                 415

Pro Pro Lys Lys Gly Ser Gly Tyr Ser Tyr Pro Tyr Gly Phe Val Leu
            420                 425                 430

Asn Tyr Ala Asn Ser Lys Tyr Lys Tyr Gly Asp Ser Asn Asp Pro Glu
        435                 440                 445

Ser Leu Gly Gly Leu Ser Thr Leu Ser Ala Pro Ile Gln Gln Val Asn
    450                 455                 460

Ala Ala Thr Gln Asn Ser Lys Tyr Leu Asp Gly Glu Ile Leu Asn Gly
465                 470                 475                 480

Ile Gly Ala Ser Leu Pro Gly Tyr Cys Thr Thr Gly Cys Ser Pro Thr
                485                 490                 495

Glu Pro Pro Phe Ser Cys Thr Ser Thr Ala Asn Gly Tyr Lys Ala Ser
            500                 505                 510

Cys Asn Pro Ser Asp Thr Asn Gln Lys Ile Asn Ala Leu Tyr Pro Phe
        515                 520                 525

Thr Gln Ala Asn Val Lys Gly Asn Thr Gly Lys Leu Gly Val Leu Ala
    530                 535                 540

Ser Leu Val Ser Tyr Asp Leu Asn Pro Lys Asn Val Phe Gly Glu Leu
545                 550                 555                 560

Asp Ser Asp Thr Asn Asn Val Ile Leu Lys Gly Ile Pro Ala Glu Lys
                565                 570                 575

Gly Tyr Phe Pro Asn Asn Ala Arg Pro Thr Val Val Lys Glu Trp Ile
            580                 585                 590

Asn Gly Ala Ser Ala Val Pro Leu Asp Ser Gly Asn Thr Leu Phe Met
        595                 600                 605

Thr Ala Thr Asn Leu Thr Ala Thr Gln Tyr Arg Ile Arg Ile Arg Tyr

```
            610                 615                 620
Ala Asn Pro Asn Ser Asn Thr Gln Ile Gly Val Arg Ile Thr Gln Asn
625                 630                 635                 640

Gly Ser Leu Ile Ser Ser Ser Asn Leu Thr Leu Tyr Ser Thr Thr Asp
                    645                 650                 655

Met Asn Asn Thr Leu Pro Leu Asn Val Tyr Val Ile Gly Glu Asn Gly
                660                 665                 670

Asn Tyr Thr Leu Gln Asp Leu Tyr Asn Thr Thr Asn Val Leu Ser Thr
                    675                 680                 685

Gly Asp Ile Thr Leu Gln Ile Thr Gly Gly Asp Gln Lys Ile Phe Ile
                690                 695                 700

Asp Arg Ile Glu Phe Val Pro Thr Met Pro Val Pro Gly Asn Thr Asn
705                 710                 715                 720

Asn Asn Asn Gly Asn Asn Asn Gly Asn Asn Asn Pro Pro His His Val
                    725                 730                 735

Cys Ala Ile Ala Gly Thr Gln Ser Cys Ser Gly Pro Pro Lys Phe
                740                 745                 750

Glu Gln Val Ser Asp Leu Glu Lys Ile Thr Thr Gln Val Tyr Met Leu
                    755                 760                 765

Phe Lys Ser Ser Pro Tyr Glu Glu Leu Ala Leu Glu Val Ser Ser Tyr
770                 775                 780

Gln Ile Ser Gln Val Ala Leu Lys Val Met Ala Leu Ser Asp Glu Leu
785                 790                 795                 800

Phe Cys Glu Glu Lys Asn Val Leu Arg Lys Leu Val Asn Lys Ala Lys
                    805                 810                 815

Gln Leu Leu Glu Ala Ser Asn Leu Leu Val Gly Gly Asn Phe Glu Thr
                820                 825                 830

Thr Gln Asn Trp Val Leu Gly Thr Asn Ala Tyr Ile Asn Tyr Asp Ser
            835                 840                 845

Phe Leu Phe Asn Gly Asn Tyr Leu Ser Leu Gln Pro Ala Ser Gly Phe
            850                 855                 860

Phe Thr Ser Tyr Ala Tyr Gln Lys Ile Asp Glu Ser Thr Leu Lys Pro
865                 870                 875                 880

Tyr Thr Arg Tyr Lys Val Ser Gly Phe Ile Gly Gln Ser Asn Gln Val
                    885                 890                 895

Glu Leu Ile Ile Ser Arg Tyr Gly Lys Glu Ile Asp Lys Ile Leu Asn
                900                 905                 910

Val Pro Tyr Ala Gly Pro Leu Pro Ile Thr Ala Asp Ala Ser Ile Thr
                    915                 920                 925

Cys Cys Ala Pro Glu Ile Gly Gln Cys Asp Gly Glu Gln Ser Asp Ser
930                 935                 940

His Phe Phe Asn Tyr Ser Ile Asp Val Gly Ala Leu His Pro Glu Leu
945                 950                 955                 960

Asn Pro Gly Ile Glu Ile Gly Leu Lys Ile Val Gln Ser Asn Gly Tyr
                965                 970                 975

Ile Thr Ile Ser Asn Leu Glu Ile Ile Glu Glu Arg Pro Leu Thr Glu
                980                 985                 990

Met Glu Ile Gln Ala Val Asn Arg Lys Asn Gln Lys Trp Glu Arg Glu
                995                 1000                1005

Lys Leu Leu Glu Cys Ala Ser Ile Ser Glu Leu Leu Gln Pro Ile Ile
            1010                1015                1020

Asn Gln Ile Asp Ser Leu Phe Lys Asp Gly Asn Trp Tyr Asn Asp Ile
1025                1030                1035                1040
```

-continued

```
Leu Pro His Val Thr Tyr Gln Asp Leu Lys Asn Ile Ile Ile Pro Glu
            1045                1050                1055

Leu Pro Lys Leu Lys His Trp Phe Ile Glu Asn Leu Pro Gly Glu Tyr
            1060                1065                1070

His Glu Ile Glu Gln Lys Met Lys Glu Ala Leu Lys Tyr Ala Phe Thr
        1075                1080                1085

Gln Leu Asp Glu Lys Asn Leu Ile His Asn Gly His Phe Thr Thr Asn
    1090                1095                1100

Leu Ile Asp Trp Gln Val Glu Gly Asp Ala Gln Met Lys Val Leu Glu
1105                1110                1115                1120

Asn Asp Ala Leu Ala Leu Gln Leu Phe Asn Trp Asp Ala Ser Ala Ser
            1125                1130                1135

Gln Ser Ile Asn Ile Leu Glu Phe Asp Glu Asp Lys Ala Tyr Lys Leu
            1140                1145                1150

Arg Val Tyr Ala Gln Gly Ser Gly Thr Ile Gln Phe Gly Asn Cys Glu
            1155                1160                1165

Asp Glu Ala Ile Gln Phe Asn Thr Asn Ser Phe Ile Tyr Gln Glu Lys
        1170                1175                1180

Ile Val Tyr Phe Asp Thr Pro Ser Val Asn Leu His Ile Gln Ser Glu
1185                1190                1195                1200

Gly Ser Glu Phe Ile Val Ser Ser Ile Asp Leu Ile Glu Leu Ser Asp
            1205                1210                1215

Asp Gln
```